US011318278B2

(12) United States Patent
Grossman et al.

(10) Patent No.: US 11,318,278 B2
(45) Date of Patent: May 3, 2022

(54) METHODS AND APPARATUS FOR INDUCING OR MODIFYING SLEEP

(71) Applicants: Massachusetts Institute of Technology, Cambridge, MA (US); Elemind Technologies, Inc, Cambridge, MA (US)

(72) Inventors: Nir Grossman, Lorrach (DE); David Wang, Cambridge, MA (US); Edward Boyden, Chestnut Hill, MA (US)

(73) Assignees: Massachusetts Institute of Technology, Cambridge, MA (US); Elemind Technologies, Inc., Cambridge, MA (US)

( * ) Notice: Subject to any disclaimer, the term of this patent is extended or adjusted under 35 U.S.C. 154(b) by 688 days.

(21) Appl. No.: 16/231,478

(22) Filed: Dec. 22, 2018

(65) Prior Publication Data
US 2019/0143073 A1     May 16, 2019

Related U.S. Application Data

(63) Continuation-in-part of application No. 16/131,022, filed on Sep. 13, 2018, now abandoned.
(Continued)

(51) Int. Cl.
*A61M 21/02* (2006.01)
*A61B 5/377* (2021.01)
(Continued)

(52) U.S. Cl.
CPC ............. *A61M 21/02* (2013.01); *A61B 5/316* (2021.01); *A61B 5/377* (2021.01); *A61B 5/4812* (2013.01);
(Continued)

(58) Field of Classification Search
CPC .................. A61M 21/00; A61M 21/02; A61M 2021/0005; A61M 2021/0027;
(Continued)

(56) References Cited

U.S. PATENT DOCUMENTS

| 5,213,562 A | 5/1993 | Monroe |
| 5,241,967 A | 9/1993 | Yasushi et al. |

(Continued)

FOREIGN PATENT DOCUMENTS

| WO | 2016110804 A1 | 7/2016 |
| WO | 2017015428 A1 | 1/2017 |

OTHER PUBLICATIONS

Cox, R., et al., Sound Asleep: Processing and Retention of Slow Oscillation Phase-Targeted Stimuli; published in PLoS One vol. 9 Issue 7, Jul. 2014.
(Continued)

*Primary Examiner* — Carrie R Dorna
(74) *Attorney, Agent, or Firm* — Smith Baluch LLP

(57) ABSTRACT

A neuromodulator may output stimuli that causes a user to fall asleep faster than the user would in the absence of the stimuli. Alternatively, the stimuli may modify a sleep state or behavior associated with a sleep state, or may cause or hinder a transition from a waking state to a sleep state or from a sleep state to another sleep state. The neuromodulator may take electroencephalography measurements. Based on these measurements, the neuromodulator may detect, in real time, instantaneous amplitude and instantaneous phase of an endogenous brain signal. The neuromodulator may output stimulation that is, or that causes sensations which are, phase-locked with the endogenous brain signal. In the course of calculating instantaneous phase and amplitude, the neuromodulator may perform an endpoint-corrected Hilbert
(Continued)

transform. The stimuli may comprise auditory, visual, electrical, magnetic, vibrotactile or haptic stimuli.

20 Claims, 51 Drawing Sheets

Related U.S. Application Data

(60) Provisional application No. 62/558,237, filed on Sep. 13, 2017.

(51) Int. Cl.
    *A61M 21/00*     (2006.01)
    *A61B 5/00*     (2006.01)
    *G16H 10/00*     (2018.01)
    *A61N 5/06*     (2006.01)
    *A61N 1/00*     (2006.01)
    *A61N 2/00*     (2006.01)
    *A61B 5/316*     (2021.01)

(52) U.S. Cl.
    CPC .............. *A61N 1/00* (2013.01); *A61N 2/006* (2013.01); *A61N 5/0622* (2013.01); *G16H 10/00* (2018.01); *A61B 5/4836* (2013.01); *A61B 5/7257* (2013.01); *A61M 2021/0022* (2013.01); *A61M 2021/0027* (2013.01); *A61M 2021/0038* (2013.01); *A61M 2021/0044* (2013.01); *A61M 2021/0055* (2013.01); *A61M 2021/0072* (2013.01); *A61M 2205/054* (2013.01); *A61M 2205/057* (2013.01); *A61M 2205/058* (2013.01); *A61M 2205/332* (2013.01); *A61M 2205/3306* (2013.01); *A61M 2205/3375* (2013.01); *A61M 2205/3584* (2013.01); *A61M 2205/3592* (2013.01); *A61M 2205/50* (2013.01); *A61M 2205/505* (2013.01); *A61M 2205/52* (2013.01); *A61M 2205/8206* (2013.01); *A61M 2210/0693* (2013.01); *A61M 2230/04* (2013.01); *A61M 2230/10* (2013.01); *A61M 2230/42* (2013.01); *A61M 2230/63* (2013.01); *A61N 2005/0626* (2013.01); *A61N 2005/0648* (2013.01); *A61N 2005/0662* (2013.01)

(58) Field of Classification Search
    CPC .. A61M 2021/0044; A61M 2021/0072; A61B 5/4806; A61B 5/4809; A61B 5/4812; A61B 5/4821
    See application file for complete search history.

(56) References Cited

U.S. PATENT DOCUMENTS

| | | | |
|---|---|---|---|
| 6,978,179 B1 | 12/2005 | Flagg et al. | |
| 10,448,883 B2 | 10/2019 | Grossman et al. | |
| 10,758,175 B2 | 9/2020 | Grossman et al. | |
| 2006/0205994 A1 | 9/2006 | Sunnen | |
| 2008/0081941 A1 | 4/2008 | Tonini | |
| 2011/0257556 A1* | 10/2011 | Guo ..................... | A61B 5/4812 600/544 |
| 2014/0316230 A1* | 10/2014 | Denison ................. | A61B 5/165 600/383 |
| 2014/0343354 A1 | 11/2014 | Larson et al. | |
| 2015/0343168 A1 | 12/2015 | Garcia Molina | |
| 2016/0128864 A1 | 5/2016 | Nofzinger et al. | |
| 2016/0220783 A1 | 8/2016 | Garcia Molina | |
| 2016/0302718 A1 | 10/2016 | Lapoint et al. | |
| 2016/0331307 A1 | 11/2016 | Purdon et al. | |
| 2017/0304587 A1 | 10/2017 | Santostasi et al. | |
| 2017/0323481 A1 | 11/2017 | Tran et al. | |
| 2017/0340855 A1 | 11/2017 | Soulet De Brugiere et al. | |
| 2019/0060602 A1 | 2/2019 | Tran et al. | |
| 2019/0125456 A1 | 5/2019 | Shelton, IV et al. | |
| 2019/0125457 A1 | 5/2019 | Parihar et al. | |
| 2019/0125459 A1 | 5/2019 | Shelton, IV et al. | |
| 2021/0059528 A1 | 3/2021 | Grossman et al. | |

OTHER PUBLICATIONS

Leminen, M., et al., Enhanced Memory Consolidation Via Automatic Sound Stimulation During Non-REM Sleep published in Sleep, vol. 40 No. 3, Mar. 2017.

Lustenberger, C., et al., Feedback-controlled transcranial alternating current stimulation reveals functional role of sleep spindles in motor memory consolidation; published in Current Biology, 26, pp. 2127-2136, Aug. 22, 2016.

Marshall, L., et al., Boosting slow oscillations during sleep potentiates memory; published in Nature, vol. 444, pp. 610-613, Nov. 2006.

Muzet, A., Environmental noise, sleep and health; published in Sleep Medicine Reviews, vol. 11, Issue 2, Apr. 2007, pp. 135-142.

Ngo, H., et al., Auditory closed-loop stimulation of the sleep slow oscillation enhances memory; published in Neuron, 78(3), pp. 545-553, May 2013.

Ong, J., et al., Effects of phase-locked acoustic stimulation during a nap on EEG spectra and declarative memory consolidation; published in Sleep Medicine, 20, 88-97, Nov. 2015.

Papalambros, N., et al., Acoustic Enhancement of Sleep Slow Oscillations and Concomitant Memory Improvement in Older Adults; published in Frontiers in Human Neuroscience, vol. 11, Article 109, Mar. 8, 2017.

Santostasi, G., et al., Phase-locked loop for precisely timed acoustic stimulation during sleep; published in Journal of Neuroscience Methods, vol. 259, pp. 101-114, Feb. 2016.

Westerberg, C., et al., Memory improvement via slow-oscillatory stimulation during sleep in older adults; published in Neurobiology of Aging vol. 36 issue 9, pp. 2577-2586, Sep. 2015.

Chen, L., et al., Real-Time Brain Oscillation Detection and Phase-Locked Stimulation Using Autoregressive Spectral Estimation and Time-Series Forward Prediction; published in IEEE Transactions on Biomedical Engineering, vol. 60, Issue 3, pp. 753-762, Mar. 2013.

Mansouri, F., et al., A Fast EEG Forecasting Algorithm for Phase-Locked Transcranial Electrical Stimulation of the Human Brain; published in Frontiers in Human Neuroscience, vol. 11, Article 401, Jul. 2017.

AASM Manual for the Scoring of Sleep and Associated Events Version 2.6 and Summary of Updates from Version 2.0. American Academy of Sleep Medicine Jan. 2020. Accessed at https://aasm.org/clinical-resources/scoring-manual/. 35 pages.

Ansari, "IIR discrete-time Hilbert transformers." IEEE Transactions on Acoustics, Speech, and Signal Processing 35.8 (1987): 1116-1119.

Freeman, "Hilbert transform for brain waves. Scholarpedia 2 (1): 1338." (2007). 9 pages.

Gross et al., "Dynamic imaging of coherent sources: studying neural interactions in the human brain." Proceedings of the National Academy of Sciences 98.2 (2001): 694-699.

International Search Report and Written Opinion in International Patent Application No. PCT/US18/50974 dated Dec. 10, 2018, 10 pages.

International Search Report and Written Opinion in International Patent Application No. PCT/US2018/067425 dated Apr. 1, 2019, 11 pages.

Ogilvie, "The process of falling asleep." Sleep medicine reviews 5.3 (2001): 247-270.

Olkkonen et al., "Complex hilbert transform filter." Journal of Signal and Information Processing 2.2 (2011): 112. 5 pages.

Sharbrough, "American Electroencephalographic Society guidelines for standard electrode position nomenclature." J clin Neurophysiol 8 (1991): 200-202.

\* cited by examiner

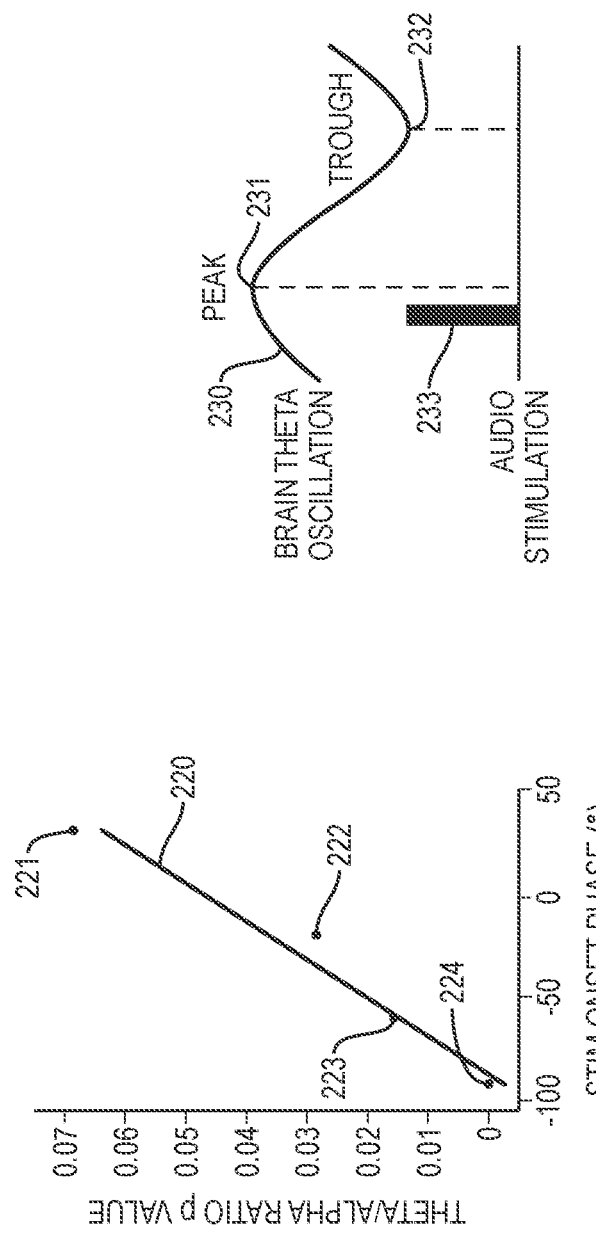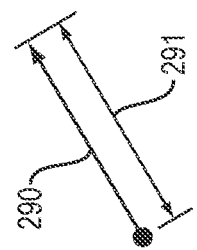

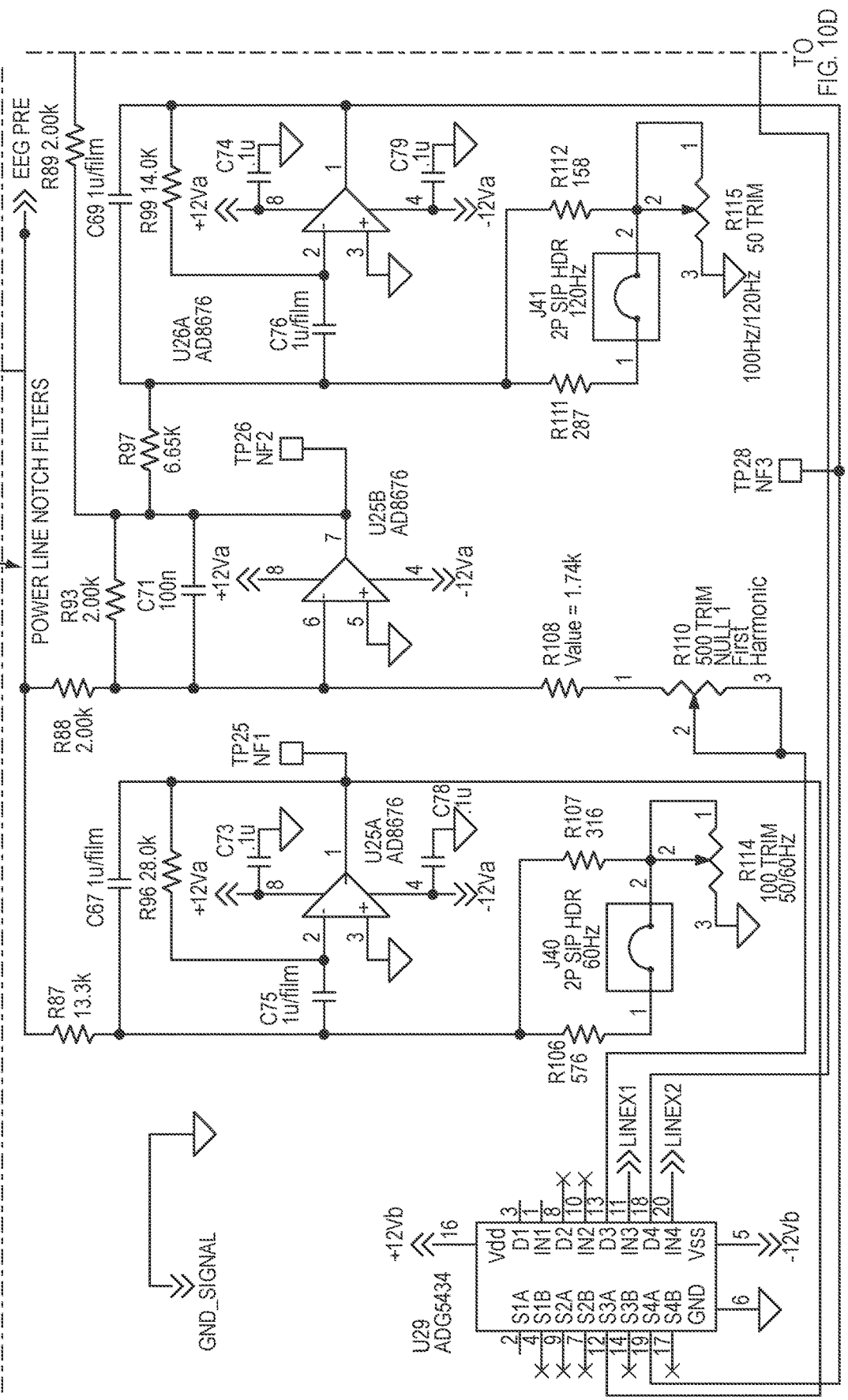

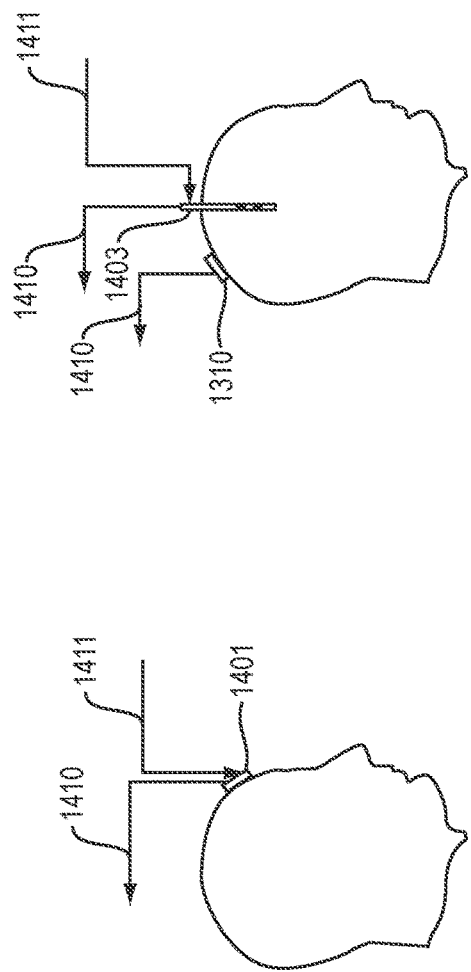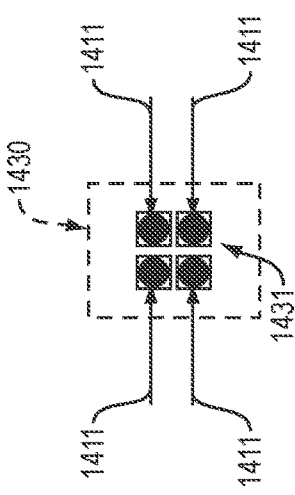
FIG. 14B
FIG. 14C
FIG. 14A

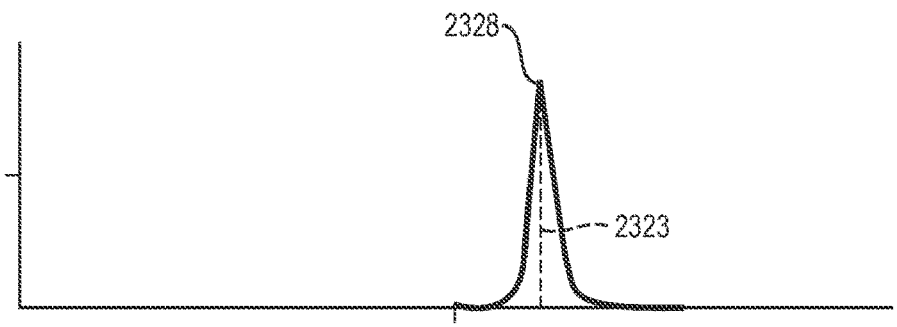
FIG. 23A
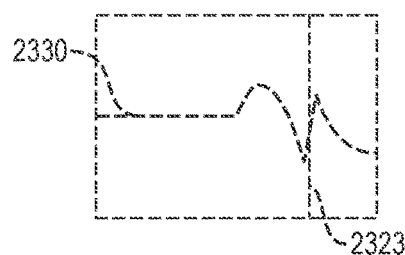
FIG. 23B
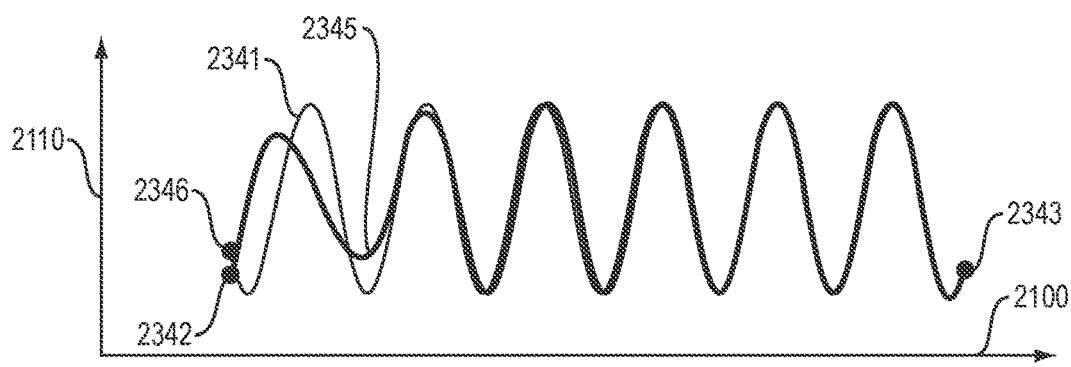
FIG. 23C
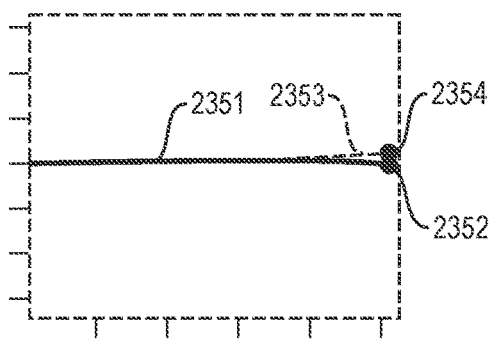 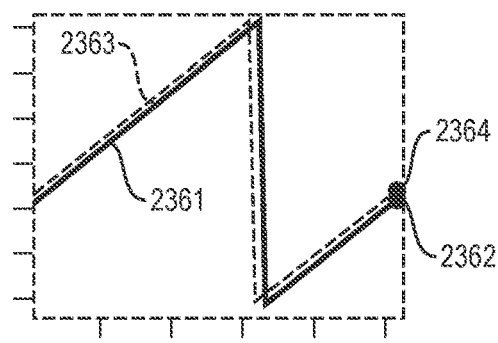
FIG. 23D          FIG. 23E

METHODS AND APPARATUS FOR INDUCING OR MODIFYING SLEEP

RELATED APPLICATIONS

This application is a continuation-in-part of U.S. application Ser. No. 16/131,022 filed Sep. 13, 2018 (the "'022 Application"), which claims the benefit of U.S. Provisional Application No. 62/558,237 filed Sep. 13, 2017 (the "Provisional").

FIELD OF TECHNOLOGY

The present invention relates generally to neuromodulation.

COMPUTER PROGRAM LISTING

The following 34 computer program files are incorporated by reference herein: (1) adc_LTC2442_h.txt with a size of about 8 KB; (2) ButterworthBandpass_v2_h.txt with a size of about 8 KB; (3) config_table_h.txt with a size of about 5 KB; (4) digital_pot_AD5290_h.txt with a size of about 2 KB; (5) display_LCM_S04004DSF_h.txt with a size of about 3 KB; (6) due_pin_config_h.txt with a size of about 2 KB; (7) DueFirmware_ino.txt with a size of about 91 KB; (8) DueTimer_cpp.txt with a size of about 8 KB; (9) DueTimer_h.txt with a size of about 3 KB; (10) EEGRegisterData_h.txt with a size of about 2 KB; (11) FFT_C.txt with a size of about 6 KB; (12) FFT_H.txt with a size of about 1 KB; (13) iir_c.txt with a size of about 17 KB; (14) iir_h.txt with a size of about 2 KB; (15) InputHandler_h.txt with a size of about 7 KB; (16) math_util_h.txt with a size of about 5 KB; (17) trigger_h.txt with a size of about 2 KB; (18) VarSizeSplitRadixRealP_cpp.txt with a size of about 10 KB; (19) VarSizeSplitRadixRealP_h.txt with a size of about 2 KB; (20) VirtualLiquidCrystal_h.txt with a size of about 3 KB; (21) waveconst_h.txt with a size of about 15 KB; (22) window_h.txt with a size of about 4 KB; (23) z_atan2_approximation_h.txt with a size of about 3 KB; (24) Adafruit_Soundboard_Mod_cpp.txt with a size of about 10 KB; (25) Adafruit_Soundboard_Mod_h.txt with a size of about 4 KB; (26) dac_AD5065_h.txt with a size of about 6 KB; (27) digital_pot_AD5122 h.txt with a size of about 2 KB; (28) EEGRegisterControl_h.txt with a size of about 2 KB; (29) EEGRegisterData_h.txt with a size of about 2 KB; (30) InputHandler_h.txt with a size of about 7 KB; (31) shift_reg_74HC595_h.txt with a size of about 2 KB; (32) teensy_pin_config_h.txt with a size of about 2 KB; (33) TeensyFirmware_ino.txt with a size of about 18 KB; and (34) time_utils_h.txt with a size of about 3 KB. Each of these 34 files were created as an ASCII .txt file on Sep. 13, 2018.

BACKGROUND

The transition from an wakefulness to sleep is a gradual and continuous process that that can be objectively determined with EEG (electroencephalography) or behavioral measurements.

Falling asleep involves passing through multiple stages of consciousness. For instance, the American Academy of Sleep Medicine defines five sleep/wake stages: StageW (wakefulness); Stage N1 (non-REM 1); Stage N2 (non-NREM 2); Stage N3 (non-REM 1); and Stage R (REM). See *AASM Manual for the Scoring of Sleep and Associated Events version* 2.1 ("AASM Manual") Likewise, the Hori nine-stage EEG-based system defines nine EEG stages of falling asleep: (1) alpha wave train; (2) alpha wave intermittent (≥50%); (3) alpha wave intermittent (<50%); (4) EEG flattening; (5) ripples; (6) vertex sharp wave solitary; (7) vertex sharp wave bursts; (8) vertex sharp wave and incomplete spindles; and (9) spindles. In the Hori EEG-based system: EEG stages 1 and 2 occur during wakefulness; EEG stages 3-8 occur during Stage 1 sleep; and EEG stage 9 occurs during Stage 2 sleep. See Robert Ogilvie, *The Process of Falling Asleep, Sleep Medicine Reviews*, Vol. 5, No. 3, pp 247-270, 2001.

The transition from wakefulness to deep sleep and through intermediate stages between is associated with frequency changes in EEG waves. Falling asleep is hallmarked by a progressive decrease in synchronous brain activity in the alpha band and a progressive increase in synchronous brain activity in the theta band and in the delta band. Furthermore, falling asleep is characterized by a significant increase in absolute theta band power accompanied by an increase in the theta to alpha ratio (i.e., the ratio of theta power to alpha power). EEG potentials and their spectral decomposed signals including alpha, theta and delta bands provide continuous physiologic metrics of transition from wake-to-sleep. A significant increase in the absolute power of theta is an indicator of sleep onset.

According to the AASM Manual, sleep onset is the start of the EEG epoch (i.e., 30 sec of EEG recording) that is scored as any stage other than awake stage (W). The common transition from awake stage is to non-REM stage 1 (N1). According to the AASM Manual, for persons who are alpha/PDR (posterior-dominant rhythm) producers in Stage W (i.e., most persons), Stage N1 is scored when alpha/PDR (which dominates Stage W) is replaced and more than 50% of the epoch contains a low-amplitude mixed-frequency (LAMF) activity particularly in a 4-7 Hz band. According the AASM Manual, for persons who are not alpha/PDR producers in Stage 2, Stage N1 is scored when any of the following appear: (a) 4-7 Hz activity with slowing of background by at least 1 Hz from those of Stage W; (b) vertex sharp waves; or (c) slow eye movements. This paragraph is rough, general summary of relevant sections of the AASM Manual; for the exact, full details see the AASM Manual.

The dominant alpha wave producing region of the brain changes spatial position as a person falls asleep, moving from posterior to anterior cortical regions.

The transition from wakefulness to sleep may also be characterized by behavioral changes. For instance, a person who is falling asleep may be asked to respond to an external stimuli (such as a faint audio tone or vibrotactile stimuli), which effectively asks "are you awake?" At a certain point in the sleep onset process, a person's response to the external response becomes slower and less likely to occur, and ultimately ceases. Or, for instance, a subject who is falling asleep may be asked to perform a behavior (such as holding an object, or applying pressure to a switch, or squeezing a ball each time the person inhales). After a certain point in the sleep onset process, the person's performance of the behavior becomes progressively less likely, and ultimately ceases. For example, if a person who is falling asleep is asked to squeeze a hand-held ball each time that she or he inhales, then, after a certain point in the sleep onset process, the pressure applied by the person on the ball may progressively decrease and the likelihood that the person will squeeze the ball during inhalation may decrease. After another point in the sleep onset process, the subject may drop the ball or may completely cease to squeeze the ball.

Behavioral measures of falling asleep may correlate well with EEG measures of falling asleep. In some cases, during sleep onset, a transition in EEG state may precede or follow a transition in behavior by a time interval (e.g., one to two minutes).

In addition to EEG signals, other biomarkers may be measured to help identify stages of sleep, including stages of sleep onset. For instance, polysomnography may be performed to detect stages of sleep. The polysomnography may include taking EEG measurements, EMG (electromyography) measurements, EOG (electrooculography) measurements, and measurements of blood oxygen level, heart rate, respiration rate, eye movements, leg movements, arm movements, body position, and may also include recording sounds (e.g., snoring) that the subject makes.

SUMMARY

In illustrative implementations, a neuromodulation system induces sleep onset. For instance, the neuromodulation system may produce stimulation that causes sleep onset to occur more quickly than would otherwise occur in the absence of the stimulation. Likewise, the neuromodulation system may produce stimulation that, for a given person, reduces the average time that it takes for the given person to transition from wakefulness to sleep onset (i.e., may reduce the person's average sleep latency.) This reduction in average sleep latency may occur regardless of how long the given person ordinarily (in the absence of stimulation by the neuromodulation system) takes to fall asleep.

To the inventors' knowledge, this ability to induce or accelerate sleep onset by non-pharmacological neuromodulation is novel. Some conventional neuromodulation devices enhance slow wave (delta) activity after the person is already in stage N2 or N3 sleep. But, in the present invention, the neuromodulation system may do something quite different—it may speed up sleep onset. That is, the present invention may cause a person to fall asleep faster in the first place, rather than merely modifying a person's sleep after the person is already asleep. (The present invention may also modify sleep after a person is already asleep, as discussed below).

In some implementations of this invention, a neuromodulation system: (a) filters, with a bandpass filter, a signal comprising measurements of endogenous brain electrical activity; and (b) then detects, in real time, instantaneous phase and amplitude of the filtered signal. The neuromodulation system may then produce stimulation that is phase-locked with the detected instantaneous phase. For instance, in some cases, the neuromodulation system produces pulsed stimulation, where pulses of stimulation each occur at, or shortly before, a peak (point of greatest magnitude in a period) of an endogenous wave (e.g., theta wave, alpha wave, or delta wave). In some other cases, the neuromodulation system produces pulsed stimulation, where pulses of stimulation each occur at, or shortly before, a trough (point of lowest magnitude in a period) of an endogenous wave (e.g., theta wave, alpha wave, or delta wave). In yet other cases, the neuromodulation system produces pulsed stimulation, where pulses of stimulation each occur at 90 degrees (or slightly more than 90 degrees) before a peak of an endogenous wave (e.g., theta wave, alpha wave, or delta wave). In other cases, the neuromodulation system produces pulsed stimulation, where pulses of stimulation each occur at 90 degrees (or slightly more than 90 degrees) before a trough of an endogenous wave (e.g., theta wave, alpha wave, or delta wave).

In illustrative implementations, phase-locked stimulation (e.g., phase-locked to detected phase of endogenous theta or alpha waves) is applied while the user is lying down (or sitting) with eyes closed. This phase-locked stimulation may cause a person to fall asleep faster than the person otherwise would. For instance, the phase-locked stimulation: (a) may cause the absolute spectral power in the theta band to increase faster than it otherwise would; and (b) may cause the ratio of theta band power to alpha band ratio to increase faster than it otherwise would.

As noted above, in illustrative implementations, the neuromodulation system: (a) detects, in real time, the instantaneous phase of endogenous electrical activity in the brain; and (b) produces, in real time, stimulation that is phase-locked with this detected instantaneous phase. This is quite different than conventional entrainment. In conventional entrainment, the stimulation device does not detect instantaneous phase of endogenous neural activity in the brain. In conventional entrainment: (a) the device produces stimulation at a frequency and phase which do not initially match the frequency and phase of a dominant endogenous neural signal; and (b) eventually, in some cases, the brain mimics the external stimulation by producing a dominant endogenous neural signal that has approximately the same frequency and phase as the external stimuli.

In some implementations, the neuromodulator detects instantaneous phase and amplitude of the most recent EEG sample by performing an algorithm that involves what we loosely call endpoint-corrected Hilbert transform ("ECHT"). ECHT may correct distortions due to Gibbs phenomenon that otherwise arise when calculating an analytic signal that is used in calculating instantaneous phase. In some cases, employing ECHT enables the neuromodulator to detect instantaneous phase of the endogenous neural signal with extreme accuracy (e.g., with an accuracy of 4 milliseconds or less). In some use scenarios, the neuromodulator detects the instantaneous phase with a 1-5 degrees phase error. In some cases, the neuromodulator computes instantaneous phase and instantaneous amplitude in real time and outputs, in real time, instructions for transducers to produce stimulation. In some cases, the amount of time that elapses while the neuromodulator takes, as an input, a sample window and outputs instantaneous phase and instantaneous amplitude of the most recent sample in the window is less than 10 milliseconds (ms), or less than 9 ms, or less than 8 ms, or less than 7 ms, or less than 6 ms, or less than 5 ms, or less than 4 ms, or less than 3 ms, or less than 2 ms. In some cases, the amount of time that elapses while the neuromodulator takes, as an input, a window of EEG measurements of an endogenous neural signal from a human brain, calculates instantaneous phase and instantaneous amplitude of the most recent sample in the window, and outputs instructions for a transducer to output stimulation (e.g., stimulation that is phase-locked with the endogenous signal) is less than 10 milliseconds, or less than 9 ms, or less than 8 ms, or less than 7 ms, or less than 6 ms, or less than 5 ms, or less than 4 ms, or less than 3 ms, or less than 2 ms.

In some implementations, the neuromodulator performs what we loosely call "frequency domain ECHT". Alternatively, in some implementations, the neuromodulator performs what we loosely call "front-padded time domain ECHT", or performs what we loosely call "end-padded time domain ECHT". These versions of ECHT are described in more detail below.

This invention is not limited to ECHT. The neuromodulator may perform any algorithm that: (a) takes, as an input, a signal comprising EEG measurements of endogenous brain activity; and (b) computes instantaneous phase and instantaneous amplitude of the most recent sample of that signal. For instance, in some cases, the neuromodulator accurately computes instantaneous phase and amplitude by performing an algorithm that involves a filtered Hilbert transform. In some other cases, the neuromodulator accurately computes instantaneous phase and amplitude by padding the EEG sample so that the most recent sample is in the middle of the padded sample window and thus furthest from ends of the window where distortion due to Gibbs phenomenon occurs. For instance, the neuromodulator may generate the padding: (a) by employing an autoregressive model of the sampled data to generate predictions of future values; or (b) by employing a trained recurrent neural network to predict values at future times.

In some implementations, the neuromodulator produces audio stimulation that is phase-locked with the detected instantaneous phase of an endogenous neural signal. The audio stimulus may comprise audible pulses that are delivered by an audio transducer, such as an earphone, earbud, bone conduction transducer or speaker (e.g., a speaker embedded or housed in a bed, pillow, chair or other item of furniture or bedding). For instance, a bone conduction transducer may be positioned in front of or behind the ear and may generate the audible pulses. In some cases, the audio stimulation comprises pulses of pink noise, or of synthetic music, or of another recorded or synthetic sound track. The audio stimulation may comprise sound at any tonal frequency that is perceptible to the subject. For instance, the center frequency or dominant fundamental frequency of the aural stimulation may be in a range between 20 and 20,000 Hz, or in a range between 32 and 10,000 Hz, or in a range between 100 and 8,000 Hz.

Alternatively, the stimulation may comprise light. For instance, in some cases: (a) light sources may be positioned near a user's eyes (e.g., in a sleeping mask worn over the user's eyes); (b) the light sources may emit pulses of light that are phase-locked with detected instantaneous phase of an endogenous neural signal; (c) an attenuated portion of the light pulses may pass through the user's closed eyelids; and (d) thus, the user may perceive the light pulses even though the user's eyes are closed. In some cases, the stimulation light may comprise red light or green light. Red light may be advantageous because red is often soothing. Green light may be advantageous because the retina is most sensitive to green light. In some cases, the light stimulation comprises phosphenes. For instance, in some cases: (a) electrodes positioned near a user's eyes (e.g., in a sleeping mask worn over the user's eyes) may electrically stimulate the retina of each eye; and (b) this electrical stimulation of the retina may cause the user to perceive phosphenes.

Alternatively, the stimulation may comprise electrical, magnetic, vibrotactile, or haptic stimulation that is phase-locked with detected instantaneous phase of an endogenous neural signal. For instance, electrical stimulation may be applied via surface electrodes (worn on the skin) or subdural electrodes. Likewise, magnetic stimulation may be applied via surface magnets (worn on or near the skin) or subdural magnets. In some cases, electrodes (for electrical stimulation) or magnets (for magnetic stimulation) may be positioned anywhere on or near the user's head.

This invention is not limited to cases where the stimulation itself is phase-locked to the endogenous neural signal. Alternatively, the stimulation may be performed in such a way that it causes the user to perceive a sensation (e.g., an induced or illusory sensation), which sensation is phase-locked with the endogenous neural signal. For instance, the stimulation may cause a user to perceive a binaural beat, which binaural beat is phase-locked with an endogenous neural signal of the user. In some cases: (a) stimulation may be performed by producing a first tone in a first ear of the user and a second tone in the other ear of the user, thereby causing the user to perceive an illusory binaural beat tone that has a frequency equal to the difference between the first and second tone; and (b) the beat tone may be phase-locked with an endogenous neural signal of the user. Or, for instance, the stimulation may cause the user to see a phosphene, which phosphene is phase-locked with an endogenous neural signal of the user. In some cases: (a) electrical stimulation of an eye or brain of a user may cause the user to see phosphenes; and (b) the phosphenes may be phase-locked with an endogenous neural signal of the user.

This invention is not limited to speeding up sleep onset. For instance, this invention may be employed to mitigate sleep arousal (wakening during sleep). For example, in some cases, the neuromodulator may produce stimulation that reduces sleep fragmentation and reduces the average number of times that a person wakes up each night. Also, in some cases, this invention may be employed to increase the amplitude of slow-wave rhythms. Increasing the amplitude of slow-wave rhythms may improve memory.

This invention is not limited to phase-locking with an endogenous signal in the alpha or theta bands. The stimulation may be in any frequency band, including delta, theta, alpha, beta and gamma.

The Summary and Abstract sections and the title of this document: (a) do not limit this invention; (b) are intended only to give a general introduction to some illustrative implementations of this invention; (c) do not describe all of the details of this invention; and (d) merely describe non-limiting examples of this invention. This invention may be implemented in many other ways. Likewise, the Field of Technology section is not limiting; instead it identifies, in a general, non-exclusive manner, a field of technology to which some implementations of this invention generally relate.

BRIEF DESCRIPTION OF THE DRAWINGS

FIG. 2D is a chart of theta/alpha ratio p value as a function of stimulation onset phase.

FIG. 2E shows a phase window for neuromodulation to accelerate sleep onset.

FIG. 2F shows a mean resultant vector.

FIGS. 8A, 8B, 8C, 8D, 8E, 8F, 8G, 8H, 9A, 9B, 9C, 9D, 9E, 10A, 10B, 10C, 10D, 11A, 11B, 11C, 11D and 11E are each a circuit schematic for a circuit in a prototype of this invention.

FIG. 14A shows an electrode that delivers a neuromodulation electrical signal and detects electrical activity produced by tissue.

FIG. 14B shows an implantable electrode and an external recording electrode.

FIG. 14C shows external electrodes for transcutaneous stimulation.

FIG. 21A shows a discrete signal that is a sampling of a natural signal; (b) FIG. 21B and FIG. 21C show the amplitude and phase, respectively, of the Fourier transform of the discrete signal; (c) FIG. 21D and FIG. 21E show the amplitude and phase, respectively, of the Fourier transform of the analytic signal; (d) FIG. 21F shows the correct and the computed Hilbert transform signal; (e) FIG. 21G shows the correct and the computed instantaneous amplitude A[n] values near the sample endpoint; and (f) FIG. 21H shows the correct and the computed instantaneous phase φ[n] values near the sample endpoint.

FIG. 22A shows a zero-padded signal before and after it is smoothed by a causal filter in the time domain; (b) FIG. 22B and FIG. 22C show the amplitude and phase, respectively, of the Fourier transform of the smoothed, padded signal; (c) FIG. 22D and FIG. 22E show the amplitude and phase, respectively, of the Fourier transform of the analytic signal; (d) FIG. 22F shows the correct and the computed Hilbert transform signal; (e) FIG. 22G shows the correct and the computed instantaneous amplitude A[n] values near the sample endpoint; and (f) FIG. 22H shows the correct and the computed instantaneous phase φ[n] values near the sample endpoint.

FIGS. 23A, 23B, 23C, 23D, and 23E illustrate aspects of a "frequency domain" version of ECHT, in an implementation of this invention. This version of ECHT accurately measures instantaneous amplitude and phase of a natural signal. For this "frequency domain" version of ECHT: (a) FIG. 23A and FIG. 23B show the amplitude and phase, respectively, of the Fourier transform of the analytic signal; (b) FIG. 23C shows the correct and the computed Hilbert transform signal; (e) FIG. 23D shows the correct and the computed instantaneous amplitude A[n] values near the sample endpoint; and (f) FIG. 23E shows the correct and the computed instantaneous phase φ[n] values near the sample endpoint.

Figure 1A:
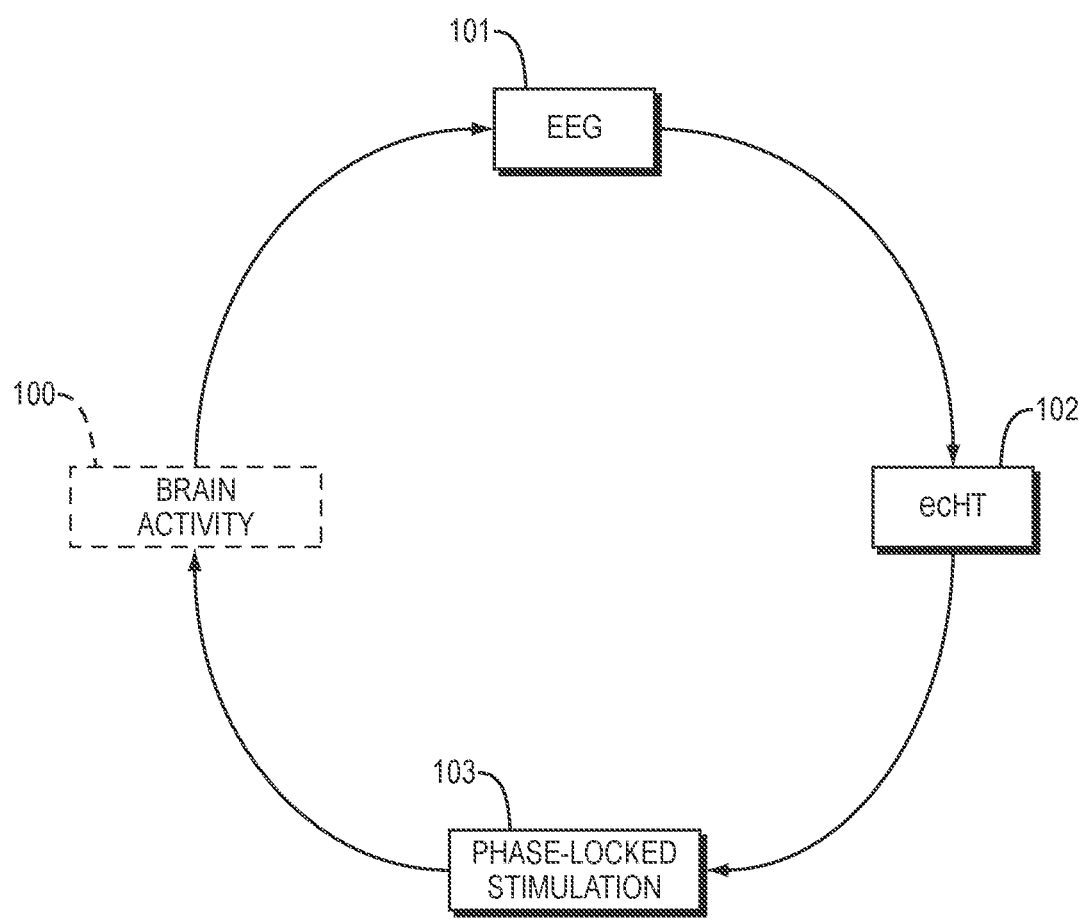
FIGS. 1A, 1B, 1C, 1D and 1E are each a flow-chart for a method of accelerating sleep onset.

The above Figures are not necessarily drawn to scale. The above Figures show some illustrative implementations of this invention, or provide information that relates to those implementations. The examples shown in the above Figures do not limit this invention. This invention may be implemented in many other ways.

DETAILED DESCRIPTION

General

The process of falling asleep is hallmarked by a progressive decrease in the synchronous brain activity at the 8-12 Hz band and a progressive increase in the synchronous brain activity at the 4-7 Hz band and at the 0.5-5 Hz band.

In some implementations of this invention, an apparatus accelerates the process of entering this state, when the eyes are closed, by delivering a stimulation that is phase-locked to the endogenous electrical oscillation of the brain, e.g., after the trough and before the peak of theta band oscillation, which shifts the brain synchronization from the alpha band to the theta band. The endogenous electrical activity of the brain may be measured via external electrodes (e.g., electroencephalography, EEG) or intracranial electrodes (e.g., electroencephalography, iEEG) and a recording amplifier. The phase of the endogenous electrical oscillation may be computed in real-time using the endpoint corrected Hilbert transformation (ecHT) method, with a bandpass filter that has a center frequency in the theta band, for example, 5 Hz. The stimulation that is delivered to the brain may be sensory (e.g., auditory, visual, or tactile), electric field or magnetic field.

In some implementations of this invention, an apparatus outputs stimulation that shifts brain synchronization from the alpha band to the theta band, thereby accelerating the sleep onset process, by measuring the oscillatory electrical brain activity, computing the instantaneous phase of the brain activity in real-time, and stimulating the brain after the trough and before the peak of theta band oscillation. In some cases, the optimal phase of stimulation is approximately −90 degree (i.e., a quarter of a period before the peak) shifted from the measured brain activity. The optimal phase shift may be specific for a particular setting (individual person and brain location) but may vary between brain locations and between people.

In some implementations of this invention, an apparatus measures oscillatory electrical brain activity, computes the instantaneous phase of the brain activity in real-time, and stimulates the brain at a specific phase. In some implementations, this apparatus operates in real-time, records and computes accurately, while minimizing the latency between the measurement of brain activity and the production of stimulus at the target phase. The apparatus may include electrodes, low-noise recording amplifier, analog-to-digital converter (ADC), computational hardware, digital-to-analog converter (DAC), and stimulation hardware. The recording electrode may be positioned for example above the frontal cortex, e.g., at the Fz location of the international 10-20 system (American Electroencephalographic Society. Guidelines for standard electrode position nomenclature. J Clin Neurophysiol, 8:200-202, 1991), and the reference electrode and the ground electrode may be positioned for example above the mastoid bone or the ear-lobe. The ecHT algorithm may be implemented in the computational hardware in order to compute the instantaneous phase and envelope amplitude of the recorded signal in real-time. In addition, a control algorithm may also be implemented in the computational hardware. The stimulation hardware may include audio amplifier for audio stimulation, light source (such as light emitting diode) for visual stimulation, vibrating mechanics for tactile stimulation and controlled voltage source to drive electric and magnetic fields.

In some implementations of this invention, a digital potentiometer rapidly attenuates a continuously playing audio source. This may allow the audio stimulus to start and stop at precise times by removing the latency common to starting and stopping audio sources which use a buffer. This may also minimize the 'popping' sound characteristic to the sudden start and stop of an audio source which can prevent falling asleep.

In some implementations of this invention, to reduce the latency and improve responsiveness of the apparatus, the measurement of electrical brain activity, computation of ecHT, and generation of stimulus, run in parallel.

Inducing Sleep Onset

As discussed in the Background section above, there are many different ways to measure and define sleep onset. In illustrative implementations of this invention, sleep onset is accelerated, regardless of which metric is used to measure or define sleep onset.

In some cases, the neuromodulation system produces stimulation that: (a) causes sleep onset (as defined in the AASM manual) to occur more rapidly than would otherwise occur in the absence of the stimulation; and (b) for a given person, reduces the average time that it takes for the given person to transition from wakefulness to sleep onset (as defined in the AASM manual).

In some cases, the neuromodulation system produces stimulation that: (a) causes sleep onset (as defined in the following sentence) to occur more rapidly than would otherwise occur in the absence of the stimulation; and (b) for a given person, reduces the average time that it takes for the given person to transition from wakefulness to sleep onset (as defined in the following sentence). For purposes of the preceding sentence: (a) wakefulness is the last 30-second epoch, before sleep onset, during which the theta/alpha ratio of a frontal cortex EEG is on average less than one; and (b) sleep onset is the start of the first 30-second epoch, after wakefulness, during which the theta/alpha ratio of a frontal cortex EEG is greater than or equal to one.

In some cases, the neuromodulation system produces stimulation that: (a) causes sleep onset (as defined in the following sentence) to occur more rapidly than would otherwise occur in the absence of the stimulation; and (b) for a given person, reduces the average time that it takes for the given person to transition from wakefulness to sleep onset (as defined in the following sentence). For purposes of the preceding sentence, sleep onset is the first 30-second epoch in which: (a) average absolute theta power during the epoch is at least 50% greater than an initial absolute theta power; and (b) average theta/alpha ratio during the epoch is at least 50% greater than an initial theta/alpha ratio, where the initial absolute theta power and the initial theta/alpha ratio are the absolute theta power and the theta/alpha ratio, respectively, during an initial 30-second period that starts when the user first lies down and closes his or her eyes.

In some cases, the neuromodulation system produces stimulation that: (a) causes sleep onset (as defined in the following sentence) to occur more rapidly than would otherwise occur in the absence of the stimulation; and (b) reduces the average time that it takes for a given person to transition from wakefulness to sleep onset (as defined in the following sentence). The preceding sentence is true for each of the following different definitions of sleep onset: (a) sleep onset occurs during the first 30-second epoch of Stage N1 sleep; (b) sleep onset occurs during the first 30-second epoch of Stage N2 sleep; (c) sleep onset occurs during the first of any three consecutive NREM 30-second epochs; (d) sleep onset occurs during the first of any ten consecutive NREM 30-second epochs; and (e) sleep onset occurs during first 5-second epoch of the third stage of the Hori nine-stage EEG-based system for identifying EEG changes during the sleep onset process (the third Hori stage occurring during a 5 second epoch that contains less than 50% alpha activity with a minimum amplitude of 20 microvolts).

In some cases, the neuromodulation system produces stimulation that: (a) causes sleep onset (as defined in the following sentence) to occur more rapidly than would otherwise occur in the absence of the stimulation; and (b) reduces the average time that it takes for a given person to transition from wakefulness to sleep onset (as defined in the following sentence). The preceding sentence is true for any definition of "sleep onset" (or any equivalent term) that: (a) on or before Sep. 13, 2017, was recognized, published or promulgated by any professional association, research association, sleep association or scientific association; or (b) was set forth in any peer-reviewed publication that was published on or before Sep. 13, 2017.

In illustrative implementations, the reduction in average sleep latency may occur regardless of how long the given person ordinarily (in the absence of stimulation by the neuromodulation system) takes to fall asleep.

In some use scenarios: (a) this invention may reduce the average amount of time that it takes for a given person to achieve sleep onset, and (b) the resulting reduced sleep latency may be in a normal range for a population.

Inducing Other Changes

In some implementations: (a) a neuromodulation system detects, in real time, instantaneous phase and amplitude of endogenous electrical activity in the brain of a human; (b) the neuromodulation system produces stimulation that is phase-locked with the detected instantaneous phase of the endogenous electrical activity; and (c) the stimulation produces one or more of the effects described in the following nine paragraphs.

In some cases, the stimulation causes a substantial increase in absolute theta power. In some cases, the stimulation causes absolute theta power to increase more rapidly than it would in the absence of the stimulation.

In some cases, the stimulation causes a substantial increase in theta/alpha ratio. In some cases, the stimulation causes theta/alpha ratio power to increase more rapidly than it would in the absence of the stimulation.

In some cases, the stimulation causes a substantial increase in absolute theta power and also causes a substantial increase in theta/alpha ratio. In some cases, the stimulation causes absolute theta power to increase more rapidly than it would in the absence of the stimulation and also causes theta/alpha ratio power to increase more rapidly than it would in the absence of the stimulation.

In some cases, the stimulation causes a substantial increase in delta/total spectrum ratio. In some cases, the stimulation causes delta/total spectrum ratio to increase more rapidly than it would in the absence of the stimulation.

In some cases, the stimulation causes a substantial increase in sleep spindles. In some cases, the stimulation causes the number of sleep spindles to increase more rapidly than it would in the absence of the stimulation.

In some cases, the stimulation causes a substantial increase in EEG K-complexes. In some cases, the stimulation causes the number of EEG K-complexes to increase more rapidly than it would in the absence of the stimulation.

In some cases, the stimulation causes a substantial increase in EEG vertex sharp waves. In some cases, the stimulation causes the number of EEG vertex sharp waves to increase more rapidly than it would in the absence of the stimulation.

In some cases, the stimulation causes a behavioral change that is positively correlated with a sleep onset process or with a sleep stage. In some cases, the stimulation causes a behavioral change to occur more rapidly than it would in the absence of the stimulation, where the behavioral change is positively correlated with a sleep onset process or with a sleep stage.

In some cases, the stimulation causes a physiological change (or physiological state) that is positively correlated with a sleep onset process or with a sleep stage. In some cases, the stimulation causes a physiological change (or physiological state) to occur more rapidly than it would in the absence of the stimulation, where the physiological change (or physiological state) is positively correlated with a sleep onset process or with a sleep stage. For instance, the physiological change (or physiological state) may comprise a change in, or state of, any one or more of the following: respiration, heart rate, other cardiac pulse parameter, eye movement, or movement of a body part.

In some cases, the stimulation causes one or more of the following: (a) a substantial increase in absolute theta power; (b) a substantial increase in theta/alpha ratio; (c) a substantial increase in delta/total spectrum ratio; (d) a substantial increase in sleep spindles; (e) a substantial increase in EEG K-complexes; (f) a substantial increase in EEG vertex sharp waves; (g) a behavioral change that is positively correlated with a sleep onset process or with a sleep stage; or (h) a physiological change (or physiological state) that is positively correlated with a sleep onset process or with a sleep stage. For instance, the physiological change (or physiological state) may comprise a change in, or state of, any one or more of the following: respiration, heart rate, other cardiac pulse parameter, eye movement, or movement of a body part.

In the preceding two paragraphs, a change in movement of a body part may, in some cases, comprise slowing of movement, cessation of movement, or decreasing regularity of movement.

Method

FIG. 1A is a flow-chart for a method of accelerating sleep onset. In the example shown in FIG. 1A, the method comprises at least the following steps: A brain of a human subject engages in brain activity which comprises an endogenous neural signal (Step 100). For instance, the endogenous neural activity may be synchronized neural activity of the brain in the theta band, in the alpha band, in the delta band, or in the gamma band, or in the beta band. This endogenous neural signal may (at least in some use scenarios and at some times) be the dominant (highest amplitude) neural signal in its frequency band (e.g., in the theta band). An EEG sensor may take EEG measurements of the endogenous neural signal (Step 101). A neuromodulator may, based on the EEG measurements, calculate instantaneous phase and instantaneous amplitude of the endogenous neural signal by a calculation that involves use of an endpoint-corrected Hilbert Transform (ECHT) (Step 102). A neuromodulator may, based on the detected instantaneous phase (e.g., instantaneous phase estimated based on the EEG measurements) calculate stimulation that is phase-locked with the endogenous neural signal and then physically output this stimulation in a manner perceptible to the human subject (Step 103). For instance: (a) the endogenous neural signal may comprise a theta wave; and (b) the stimulation may comprise pulses that each occur at or shortly before a peak of the theta wave. Or, for instance: (a) the endogenous neural signal may comprise a theta wave; and (b) the stimulation may comprise pulses that each occur at or shortly before a trough of the theta wave. The stimulation may be audio, visual, electrical, magnetic, vibrotactile, or haptic. The phase-locked stimulation may cause the brain activity to change in such a way that the person falls asleep more quickly than the person would in the absence of the stimulation.

Figure 1B:
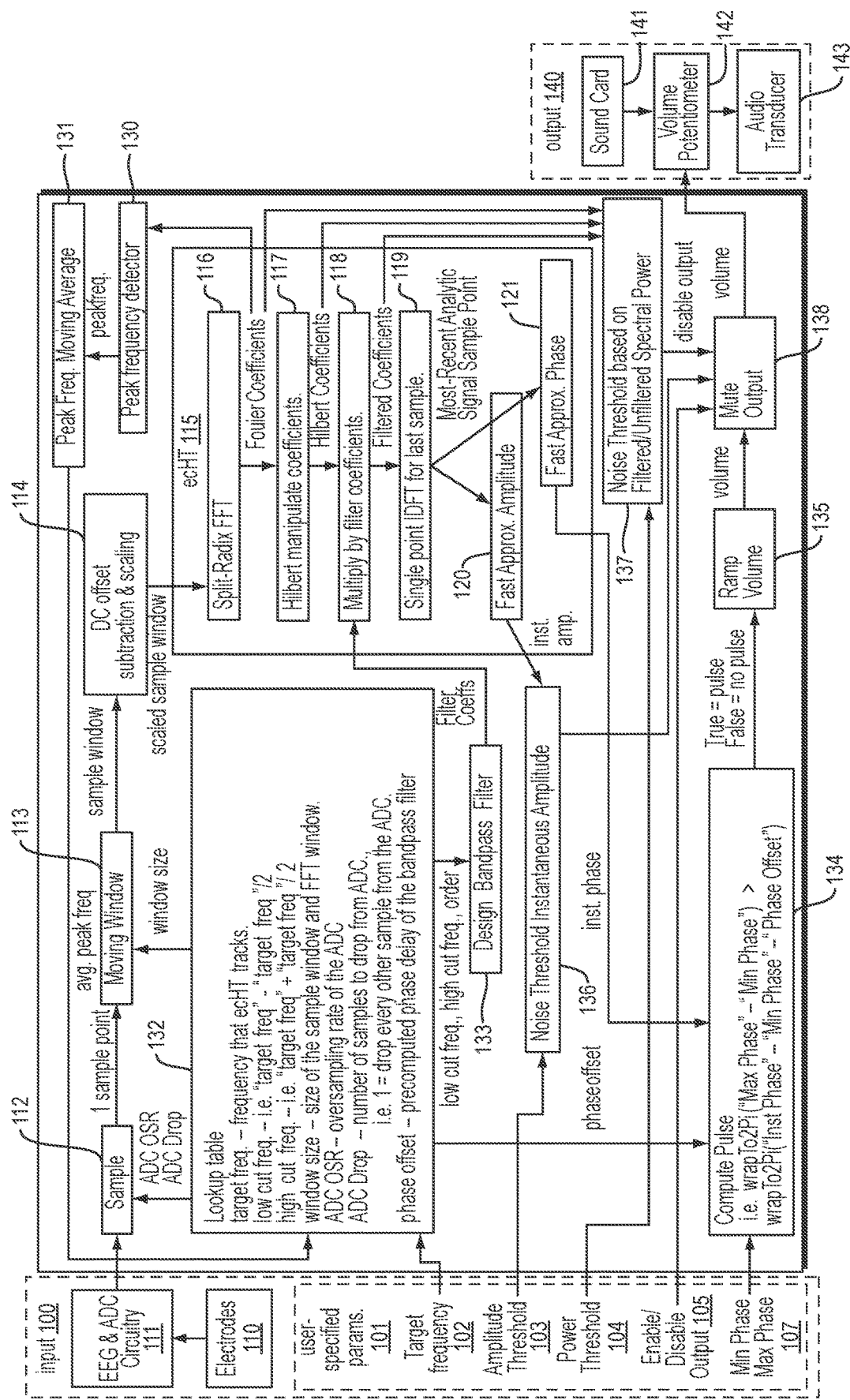
Figure 1C:
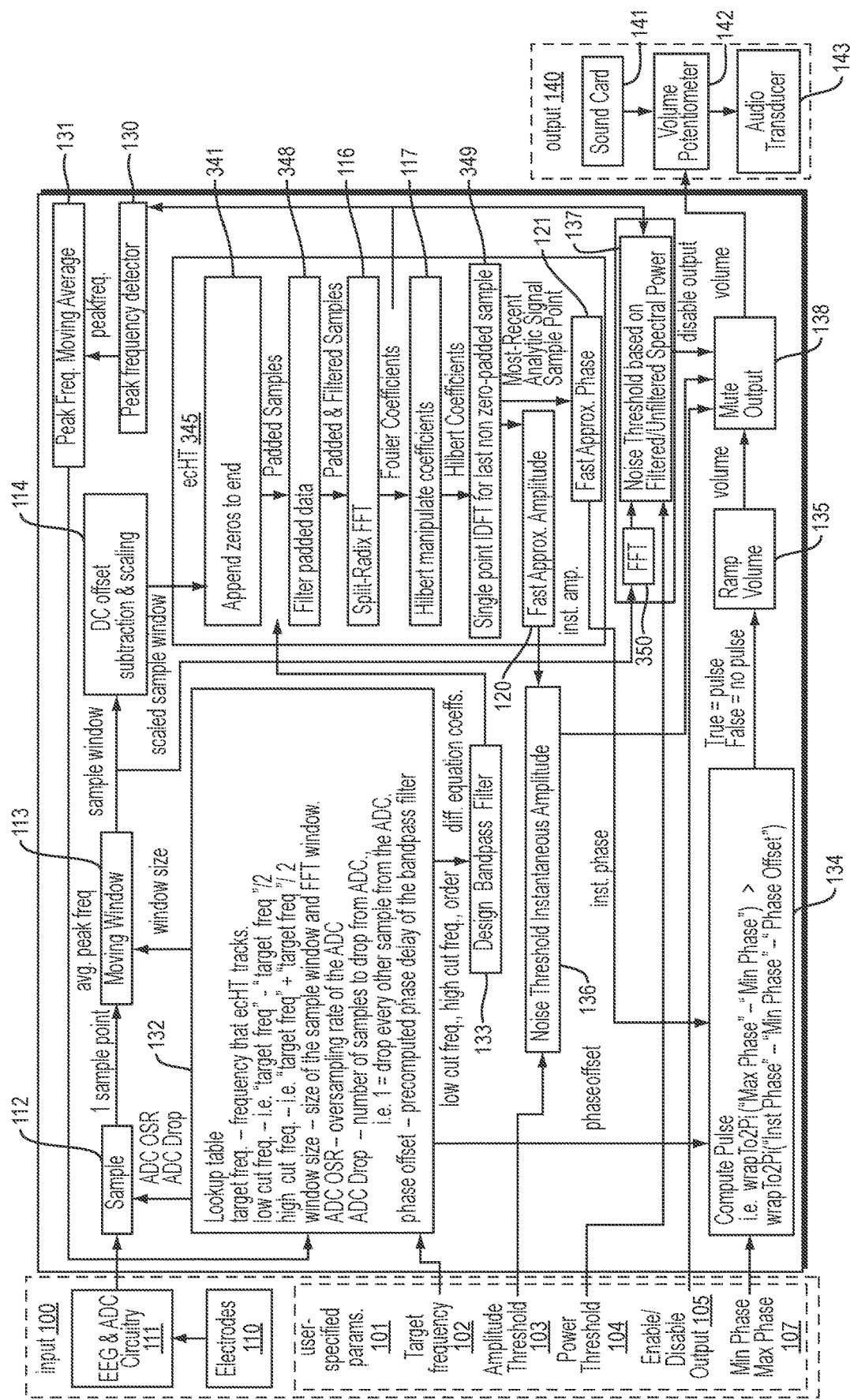
Figure 1D:
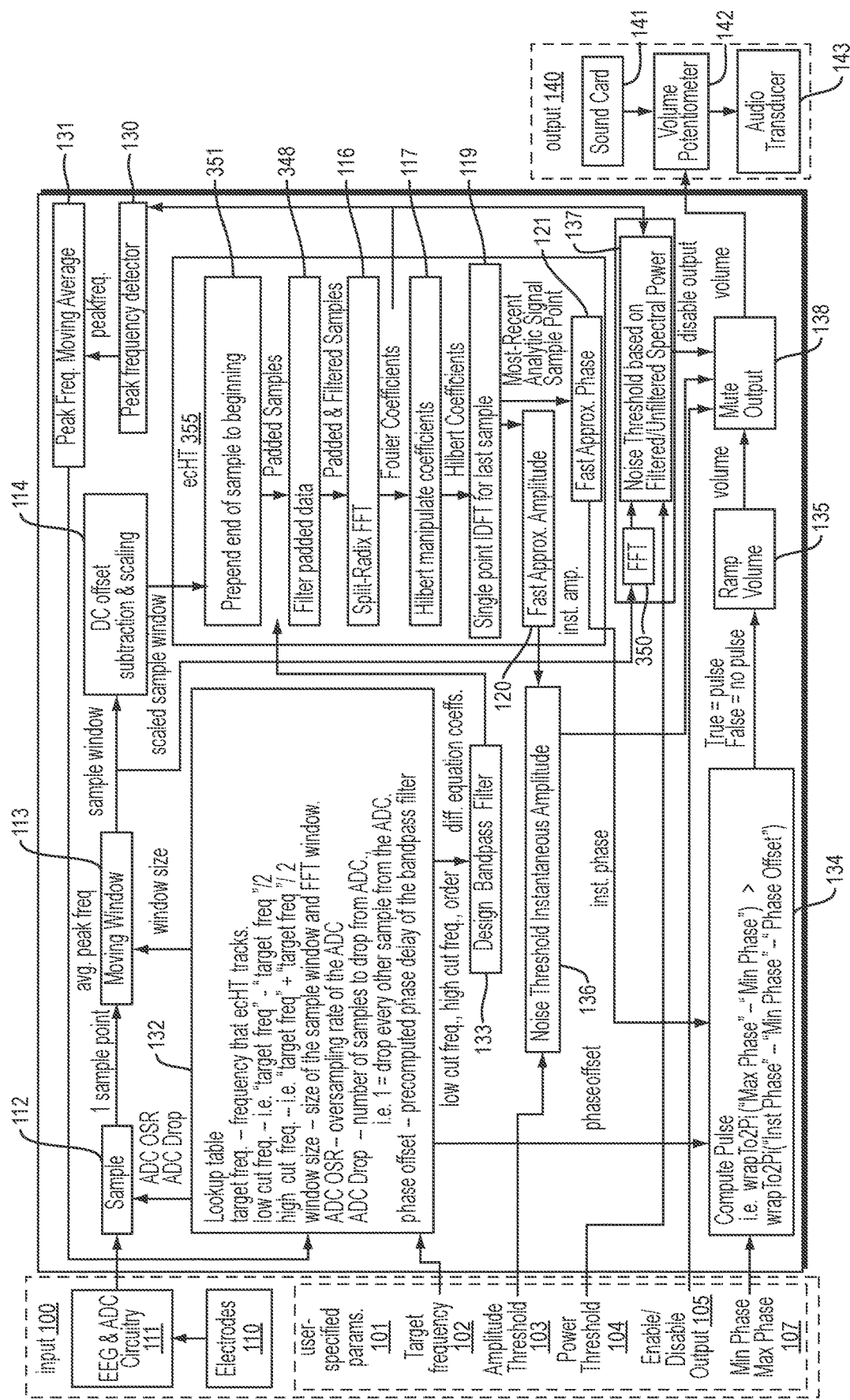

FIGS. 1B, 1C and 1D are each a flow-chart for a method of accelerating sleep onset using an ECHT algorithm. In FIG. 1B, a "frequency domain" version of ECHT is employed. In FIG. 1C, an "end-padded time domain" version of ECHT is employed. In FIG. 1D, a "front-padded time domain" version of ECHT is employed.

In FIGS. 1B, 1C and 1D, the ECHT algorithm (e.g., 115, 345, 355): (a) takes a scaled sample window as an input; and (b) outputs the instantaneous phase and instantaneous amplitude of the most recent sample in the scaled sample window.

In FIG. 1B, ECHT algorithm 115 comprises a "frequency domain" version of ECHT. In FIG. 1B, ECHT algorithm 115 includes the following steps: (a) performing a split-radix FFT (Fast Fourier Transform) 116 on the scaled sample window; (b) calculating Hilbert coefficients, by performing Hilbert transform manipulations 117 on the Fourier coefficients produced by the FFT; (c) calculating filtered coefficients, by multiplying the Hilbert coefficients by filter coefficients 118; and (d) performing a single-point IDFT (inverse discrete Fourier transform) 119 that estimates in real time the instantaneous phase (fast approximate phase 121) and instantaneous amplitude (fast approximate amplitude 120) of the most recent sample point.

In FIG. 1B, ECHT algorithm 115 may take filter coefficients as an input. These filter coefficients may be computed for a bandpass filter 133, one filter coefficient for each Fourier coefficient. In ECHT algorithm 115, the Fourier coefficients may be multiplied by the filter coefficients in an element-wise computation, in which each Fourier coefficient is multiplied by its corresponding filter coefficient.

In FIG. 1C, ECHT algorithm 345 comprises an "end-padded time domain" version of ECHT. In FIG. 1C, ECHT algorithm 345 includes the following steps: (a) appending zeros to the end of the sample window (e.g., in such a way that the zero padding has the same length as the sample window before padding) 341; (b) filtering the padded data in the time domain with a bandpass filter 348; (c) performing a split-radix FFT (Fast Fourier Transform) 116 on the scaled, filtered sample window; (d) calculating Hilbert coefficients, by performing Hilbert transform manipulations 117 on the Fourier coefficients produced by the FFT; and (e) performing a single-point IDFT 349 that estimates in real time the instantaneous phase (fast approximate phase 121) and instantaneous amplitude (fast approximate amplitude 120) of the most recent sample point that was not added by zero padding.

In FIG. 1D, ECHT algorithm 355 comprises a "front-padded time domain" version of ECHT. In FIG. 1D, ECHT algorithm 355 includes the following steps: (a) prepending an end region of the sample window to the beginning of the sample window 351; (b) filtering the padded data in the time domain with a bandpass filter 348; (c) performing a split-radix FFT 116 on the scaled, filtered sample window; (d) calculating Hilbert coefficients, by performing Hilbert transform manipulations 117 on the Fourier coefficients produced by the FFT; and (e) performing a single-point IDFT 119 that estimates in real time the instantaneous phase (fast approximate phase 121) and instantaneous amplitude (fast approximate amplitude 120) of the most recent sample point that was not added by zero padding.

In FIGS. 1B, 1C and 1D, a split-radix FFT 116 is desirable because it is very efficient. Alternatively, another type of FFT may be performed, instead of split-radix.

In FIGS. 1B, 1C and 1D, the Hilbert transform manipulations 117 may comprise calculating C[n] as described below. Thus, the resulting Hilbert coefficients may correspond to only positive frequencies of the FFT spectrum.

Alternatively, in FIGS. 1B, 1C and 1D, instead of disregarding Fourier coefficients that correspond to negative frequencies, the Hilbert Transform manipulation 117 may set these Fourier coefficients equal to zero. However, in many cases, it is computationally more efficient to disregard Fourier coefficients that correspond to negative frequencies, rather than setting them to zero.

In FIGS. 1B, 1C and 1D, a computational bandpass filter may be designed 133 to have a low cutoff frequency and a high cut-off frequency, where: (a) the low cutoff frequency is equal to one half of a target frequency; and (b) the high cutoff frequency is equal to the product of 1.5 and the target frequency. For instance, the cutoff frequencies may be selected in such a way that power at the cutoff frequencies is attenuated by a specified amount (e.g., by half, or by 3 decibels, or by 30 decibels) relative to nominal bandpass power. Look-up table 132 may store the cutoff frequencies for each different target frequency, in a set of target frequencies. As noted above, in FIG. 1B, filter coefficients for the bandpass filter may be multiplied by Fourier coefficients 118. In FIGS. 1C and 1D, differential equation coefficients for the bandpass filter may be used to filter the sample window in the time domain 348.

In FIGS. 1B and 1D, a single-point IDFT 119 may estimate in real time the instantaneous phase (fast approximate phase 121) and instantaneous amplitude (fast approximate amplitude 120) of the most recent sample point. Likewise, in FIG. 1C, a single-point IDFT (Inverse DFT) 349 may estimate in real time the instantaneous phase (fast approximate phase 121) and instantaneous amplitude (fast approximate amplitude 120) of the most recent sample point that was not added by zero padding.

In FIGS. 1B, 1C and 1D, the single-point IDFT is more efficient than a conventional IFFT (inverse FFT). This is due, in part, to the fact that a conventional IFFT would reconstruct each sample point in the original time domain window; whereas the single-point IDFT reconstructs only the most recent sample point.

Frequency domain ECHT may be more efficient than time domain versions of ECHT (e.g., front-padded or end-padded) for at least two reasons. First, if a noise threshold based on filtered/unfiltered spectral power 137 is computed, an FFT may be run anyway and the resulting Fourier coefficients may be employed for frequency domain ECHT. Second, even if front-padded or end-padded ECHT is performed in the time domain, it may be desirable to perform an FFT and Hilbert transform to create an analytic signal which in turn is used to determine instantaneous phase. Thus, front-padded or end-padded ECHT may involve extra computational steps that are not employed in frequency domain ECHT and may still involve calculating an FFT.

Figure 1E:
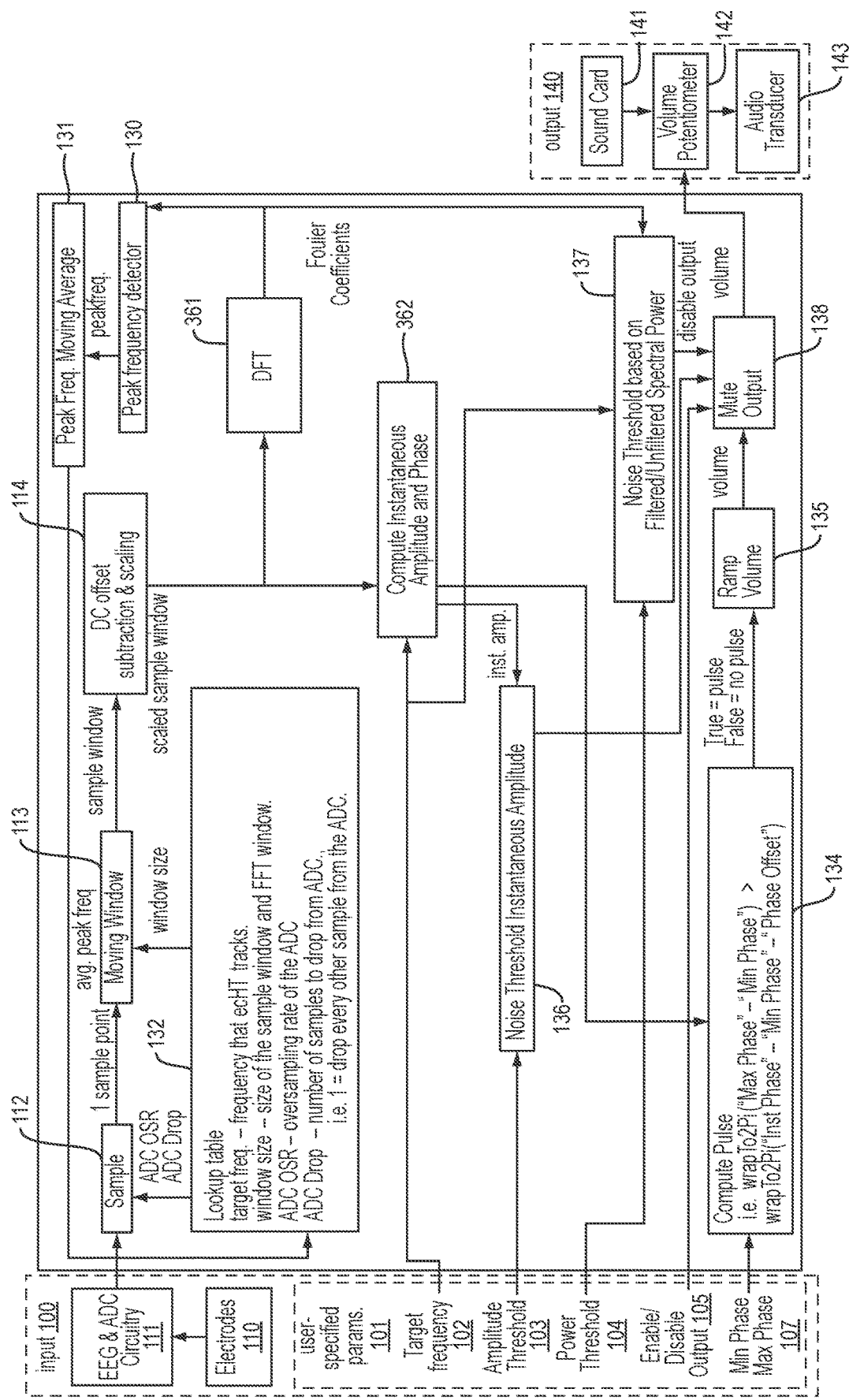

FIG. 1E is a flow-chart for a method of accelerating sleep onset, by using an algorithm that calculates instantaneous phase and instantaneous amplitude of the most recent time domain sample.

In FIG. 1E, a filter-based implementation of the Hilbert transform may be employed to compute the instantaneous phase and instantaneous amplitude of the most recent time domain sample. In some cases, filter-based implementations of the Hilbert transform are less precise than the FFT-based Hilbert transform described in ecHT, but may be more efficiently implemented. In a filter-based implementation of the Hilbert transform, the input signal (i.e. analog or sampled, digital) may be bandpass filtered. This bandpass filtering may be done with a variety of software and hardware implementations, including the implementation described in this application.

In some examples of the method shown in FIG. 1E, Hilbert transforms based on Infinite Impulse Response (IIR) filters are: (a) implemented in software; or (b) are implemented efficiently using analog circuitry, allowing continuous computation of the complex values of the analytic signal corresponding to the filtered input signal. When using an IIR based Hilbert transform implemented in analog circuitry, the real and imaginary values used in ECHT to compute the instantaneous amplitude and phase may be recovered by sampling the filtered input signal for the real value, and sampling the analytic signal for the imaginary value. The instantaneous amplitude and phase may then be computed by using these real and imaginary values, as they were computed in ECHT. See, e.g., Ansari, R., *IIR discrete-time Hilbert transformers, IEEE Transactions on Acoustics, Speech, and Signal Processing*, Volume 35, Issue 8, August 1987.

In some examples of the method shown in FIG. 1E, Hilbert transforms based on Finite Impulse Response (FIR) filters: (a) may take as inputs sampled, digitized data; and (b) may be efficiently implemented in digital logic, such as in an FPGA (field programmable gate array) or shift registers. When using an FIR based Hilbert transform: (a) the filtered input signal may be sampled; and (b) the sampled data may be fed into the FIR Hilbert transform to calculate the imaginary component of the analytic signal. The sample from the filtered input signal may be treated as the real value of the analytic signal. The instantaneous amplitude and phase may then be computed based on these real and imaginary values. A non-limiting example of an FIR Hilbert transform is described n in Olkkonen, Juuso T, Olkkonen, Hannu. *Complex Hilbert Transform Filter, Journal of Signal and Information Processing*, 2011, 2, 112-116.

Alternatively, in FIG. 1E: (a) prediction may be instead of a bandpass filter; (b) a Hilbert transform may be employed after prediction to compute the instantaneous amplitude and phase; and (c) a model may be built or trained on existing data prior to prediction. This approach (which involves prediction) may build upon the observation that the Hilbert transform most accurately computes the analytic signal (and thus the instantaneous amplitude and instantaneous phase) for the middle sample in a sequence of samples. This middle sample may be furthest away from either end of the sequence of samples and thus least susceptible to inaccuracies due to the Gibbs phenomenon or any windowing (e.g., Hamming window) approach used to reduce the impact of the Gibbs phenomenon. Since the instantaneous amplitude and phase for the most-recent sample point may be desired, this approach (which involves prediction), may pad the end of the sampled data with an equal length of generated (or predicted) data. This may ensure that the most-recent sample point is in the middle of the sequence of samples.

There are many ways to generate this padding data. In some cases, the padding is generated by computing an autoregressive model of the sampled data and then using that model to predict, or generate samples for, future sample times. See, e.g., Chen, L Leon and Madhavan, Radhika and Rapoport, Benjamin I and Anderson, William S., *Real-time brain oscillation detection and phase-locked stimulation using autoregressive spectral estimation and time-series forward prediction, IEEE transactions on Biomedical Engineering*, 60, 3, pages 753-762, 2013.

In some other cases, the padding is generated by building and training a neural network (e.g., a recurrent neural network) on the sampled data and then using that model to predict values at future sample times. Training the recurrent neural network may require a large data set. In some cases: (a) the desired length of the input data is n; and (b) each datum in the set consists of 2*n samples. Half of the datum may be employed to train the neural network, and the other half may be used to compare against the output.

In FIG. 1E: (a) a DFT is computed 361; and (b) the resulting Fourier coefficients are used as inputs for peak frequency detection 130. Also: (a) the resulting Fourier coefficients may be filtered to produce filtered coefficients; and (b) both the unfiltered Fourier coefficients and the filtered coefficients may be inputs for a noise threshold test based on filtered/unfiltered spectral power 137.

Alternatively, in FIG. 1E, an algorithm that employs recursive polynomial fitting, such as the Box-Jenkins model, may be employed to take a signal (e.g., a scaled sample window) as an input and to compute an instantaneous phase and instantaneous amplitude 362 of the most recent sample point.

In FIGS. 1B, 1C, 1D and 1E, an analog electrical signal is created by endogenous brain activity and is measured at electrodes 110 (e.g. surface, subdural or transcranial electrodes positioned on or in a subject's head). For instance, the analog electrical signal may comprise electric potential difference (specifically, difference between voltage at a measurement electrode and voltage at a reference electrode) as a function of time. EEG and ADC circuitry 111 may convert this analog signal into a digital signal. This digital signal may encode samples (e.g., sample 112) of the EEG measurements of the analog electrical signal. In some cases, the ADC's sampling rate is faster than the maximum rate (samples per second) at which the neuromodulator calculates instantaneous phase using an ECHT algorithm. Thus, in some cases, the ECHT algorithm is run at its maximum speed, and the ADC sampling rate is effectively reduced to the maximum rate of samples that the ECHT algorithm can process in real time. A lookup table 132 may store (i) ADC oversampling rate and (ii) ADC Drop, where ADC Drop is the number of samples to drop from the ADC. For instance, if ADC Drop is "1", then every other sample may be dropped from the ADC. Lookup table 132 may also store window size (size of sample window and FFT window). Based on the window size stored in lookup table 132, a moving window 113 may be identified (e.g., the current sample plus x samples before the current sample). DC offset subtraction (to eliminate DC offset) and scaling 114 may be performed to produce a scaled sample window.

In FIGS. 1B, 1C, 1D and 1E, a peak frequency may be detected 130. The detected peak frequency is the highest amplitude frequency (e.g., is located in the highest amplitude frequency bin) in a specific frequency band (e.g., theta band, or alpha band, or delta band). A moving average of the peak frequency 131 may be computed.

In FIGS. 1B, 1C, 1D and 1E, the EEG target frequency that is tracked by ECHT algorithm may be dynamically adjusted during a stimulation session to match the moving average peak frequency. For instance, the EEG target frequency that is tracked by ECHT algorithm may be the center frequency for a bandpass filter whose filter coefficients are employed in ECHT algorithm. Look-up table 132 may be accessed to determine the low cutoff frequency and high cutoff frequency (and thus bandpass filter 133) that would result from setting the moving average peak frequency as the target frequency. For instance, in some cases: (a) the default target frequency for the theta band is 5 Hz; and (b) if a moving average peak frequency for the theta band is measured to be 4.5 Hz, then the target frequency for the theta band may be dynamically adjusted to 4.5 Hz and ECHT algorithm 115 may then track a target frequency of 4.5 Hz.

In FIGS. 1B, 1C, 1D and 1E, a causal filter (e.g., bandpass filter 133) may be employed. This causal filter may create a slight time delay—or equivalently, create a slight phase delay. (This is because a causal filter cannot act on a future input, and the output comes after the input). Lookup table 132 may store a phase offset that is the pre-computed phase delay due to the causal filter (e.g., bandpass filter 133). For instance, in some cases, the look-up table stores a different phase offset for each target frequency.

In FIGS. 1B, 1C, and 1D, and in some cases in FIG. 1E, pulse computation 134: (a) may take, as inputs, instantaneous phase (calculated by an ECHT algorithm or otherwise) and phase offset (from look-up table 132); and (b) may effectively determine whether the detected instantaneous phase (minus the phase offset due to the bandpass filter) is within a phase range in which a pulse should be outputted. Specifically, pulse computation 134 may determine whether the detected instantaneous phase (minus the phase offset due to a causal filter) is within a phase range bounded by the start phase (i.e., so-called minimum phase) and the end phase (i.e., so-called maximum phase) for a stimulation pulse. The start phase may be the phase at which the pulse starts and the end phase may be the phase at which the pulse ends. In some cases, pulse computation 134 includes: (a) determining whether wrapTo2Pi(MaxPhase−MinPhase) is greater than wrapTo2Pi(InstPhase−MinPhase−PhaseOffset), where InstPhase is the instantaneous phase detected by ECHT algorithm 115, MinPhase is the start phase, MaxPhase is the end phase, and PhaseOffset is the phase offset (for the bandpass filter) from the lookup table; and (b) if the answer is yes, outputting "True" and if the answer is no, outputting "False". In pulse computation 134, the range (i.e., image) of function wrapTo2Pi is [0, 2π]—that is, wrapTo2Pi outputs only positive phases. Specifically, the function wrapTo2Pi may calculate a modulo version of its argument (with a modulus of 2π), and, if the result is negative, add 2π. This is advantageous, because the argument InstPhase−MinPhase−PhaseOffset may be negative. In some cases in FIG. 1E, a causal filter is employed and thus a phase offset is stored in the look-up table and is taken into account in the pulse computation, as described above in this paragraph. In some other cases in FIG. 1E, a causal filter is not employed and thus: (a) phase offset is not stored in the look-up table and is not taken into account in the pulse computation; or (b) the phase offset stored in the look-up table and used in the pulse computation is zero.

In FIGS. 1B, 1C, 1D, and 1E and in all other examples herein: (a) the units of phase may be radians; (b) phase may be expressed in radians; and (c) phase may be inputted, computed and outputted in radians.

In FIGS. 1B, 1C, 1D, and 1E, in many cases: (a) if the output of pulse computation 134 is "True", this indicates that stimulation should currently be produced as part of a pulse; and (b) if the output of pulse computation 134 is "False", this indicates that stimulation should not be produced currently.

In FIGS. 1B, 1C, 1D, and 1E, volume of audio stimulus may be ramped 135. For instance, if the output of pulse computation 134 is "True", then volume of a pulse of audio stimulus may (if not already at the pulse's maximum volume) be increased in a ramp that is sufficiently gradual to prevent a popping or clicking noise that may otherwise occur if volume were instantly (or in a single jump) increased to maximum. Likewise, if the output of pulse computation 134 is "False", then volume of audio stimulus may (if not already at the pulse's maximum volume) be decreased in a ramp that is sufficiently gradual to prevent a popping or clicking noise that may otherwise occur if volume were instantly (or in a single jump) decreased to zero.

In some implementations: (a) the neuromodulator outputs audio stimulation; and (b) the audio is started and stopped with low latency relative to the frequency of brain wave being targeted. In some cases, the latency is so low that the time between outputting a digital instruction (to start or stop the audio) and the speaker driver (e.g., headphones) responding is within 1% of the target frequency's period. For example, in some use scenarios: (a) a 5 Hz brain wave is being tracked and 5 Hz is the target frequency; (b) the brain wave has a period of ⅕ Hz=200 ms; and (c) the latency is less than or equal to 2 ms.

However, unless a corrective step is taken, the abrupt starting and stopping of an audio source may lead to a popping noise which is disruptive to sleep onset. The popping sound may result from the speaker driver starting from rest and suddenly reacting to an audio signal with non-zero mean, or starting from an audio signal with non-zero mean and returning to rest.

In some implementations of this invention, volume ramping 135: (a) is performed to eliminate the popping noise; and (b) comprises a gradual increase to, or gradual decrease from, a given audio signal volume. For instance, in some cases, a sound card generates audio by continuously play pre-recorded audio files, such as pink noise. The audio signal may be fed through an amplifier whose gain is controlled by a digital potentiometer, allowing for fast, programmatic gain control over the volume of the audio signal.

Conventional sound cards use a buffer whose data is consumed continuously as audio is played. For a conventional sound card: (a) data is refilled in the buffer by retrieving audio data from memory; and (b) the buffer helps ensure the playback is seamless despite delays in the amount of time it takes to retrieve the audio data from memory. However, the use of the buffer for a conventional sound card has a disadvantage: when audio playback is started, it is delayed by the time it takes to retrieve audio data from memory.

In contrast, in some implementations of this invention: (a) a sound card plays audio continuously in a loop; and (b) the audio signal's volume is attenuated through the use of a digital potentiometer. In this arrangement, high quality audio may be played while still retaining the ability to start and stop the audio with low latency. To prevent the popping sound at the start of a pulse, the volume of the audio signal may be scaled linearly from 0% to 100% over a short duration, e.g., 0.5 ms. To prevent the popping sound when the pulse ends, the volume of the audio signal may be scaled linearly from 100% to 0% over a short duration, e.g., 0.5 ms. The precise duration of the pulse may be selected such that the subject does not hear or is not bothered by the popping. This may be done by playing a pulse train with the volume ramping for a subject and increasing the duration of the ramp if the subject says the popping sound is still audible.

This invention is not limited to a linear ramp for volume ramping. For instance, in some cases, the ramping curve is linear, exponential, logarithmic, or polynomial.

Alternatively, volume ramping may be achieved using different hardware and software configurations. If the speaker driver's frequency response and the audio stimulus frequency components are known ahead of time, then a high-pass filter may remove the lower frequencies of the audio signal, such as any non-zero mean, while still permitting frequencies within the response range of the speaker driver to pass. The filter may be implemented by using a resistor and capacitor in series with the audio source.

In some implementations, the audio source allows real-time manipulation of its buffer or output audio stream, allowing the output audio signal to be multiplied by a scaling factor prior to a digital to analog converter (DAC). In some cases: (a) the audio is completely synthesized; and (b) the synthesis is performed in such a way that the synthesized audio signal has zero mean or incorporates volume ramping.

In FIGS. 1B, 1C, 1D, and 1E, the stimulus output may be muted 138 entirely under certain circumstances. For instance, stimulus output may be muted 138 entirely while the recorded EEG signal is too noisy or while a user specifies that output be muted. In some cases, stimulus output is muted 138 is muted while one or more of the following states occurs: (1) a noise threshold based on instantaneous amplitude 136 is exceeded; (b) a noise threshold based on filtered/unfiltered spectral power 137 is exceeded; or (c) a user inputs an instruction to disable output.

In FIGS. 1B, 1C, 1D, and 1E, the first noise threshold test 136 may be based on the instantaneous amplitude calculated by the ECHT algorithm (or by any other algorithm). Specifically, if the detected instantaneous amplitude exceeds a specified threshold, then the first noise threshold test 136 may determine that the EEG signal is currently too noisy and may output an instruction to temporarily mute stimulus output 138 entirely. Thus, the first noise threshold test 136 may disable stimulus when large spikes occur in the EEG signal that are due to noise or other artifacts in the EEG signal. For instance, the large spike may be due to spectral leakage from a very large EEG spike that occurs in a different frequency band than that in which the ECHT algorithm is tracking. For example, in some cases, the large EEG spike may be due to a muscle movement.

In FIGS. 1B, 1C, 1D, and 1E, the second noise threshold test 137: (a) may determine a ratio (specifically, a ratio of spectral power in a specific frequency band to total spectral power); and (b) if the ratio is less than a specified amount (i) may determine that the EEG signal is currently too noisy, and (ii) may output an instruction to temporarily mute stimulus output 138 entirely. In some cases, spectral power in the frequency band of interest is computed based on filtered coefficients that are calculated in ECHT algorithm 115. In some cases, total spectral power is computed based on unfiltered coefficients (e.g., Fourier coefficients or Hilbert coefficients) that are calculated in an ECHT algorithm (e.g., 115, 345 or 355) or in a separate FFT algorithm (e.g., 350 or 361). In some cases, in the method shown in FIG. 1B, the second noise threshold test 137 includes the following steps: (a) calculate a filtered power by squaring each filtered coefficient and summing the squares; (b) calculate an unfiltered power by squaring each Fourier coefficient and summing the squares; and (c) if the ratio of filtered power to unfiltered power is less than a specified threshold, output an instruction to temporarily mute stimulus output 138 entirely.

Alternatively, in some cases, stimulus output is disabled due to a noisy EEG signal only if the EEG signal is noisy for a sufficiently long period of time. For instance, in some cases, the neuromodulator mutes its stimulus output 138 entirely if one or more of the noise thresholds tests (e.g., 136, 137) indicate that the EEG signal is too noisy for a time period that is longer than a specified threshold.

Alternatively, in some cases, when the EEG signal is too noisy (as indicated by one or more of the noise thresholds tests (e.g., 136, 137), the neuromodulator may: (a) temporarily cease to produce phase-locked stimulation in a specific frequency band (e.g., theta or alpha); and (b) may begin to produce another stimulus (e.g., such as slow wave stimulus to trigger entrainment). For instance, in some use scenarios: (a) the neuromodulator initially produces pulsed stimulation in the theta band with pulses each occurring at or shortly before the peak of an endogenous theta signal); and (b) then the neuromodulator detects that the EEG signal in the theta band is too noisy and begins tracking EEG signals in a different frequency band and providing phase-locked stimulation in the different frequency band. For instance: (a) the different frequency band may be alpha; and (b) pulses may each occur at (or shortly before) a trough of an endogenous alpha signal.

In FIGS. 1B, 1C, 1D, and 1E, sound card 141 may continuously output a signal that encodes sound at a constant volume. Digital volume potentiometer 142 may adjust the sound volume based on whether output is muted 138 entirely and based on the volume ramping 135. As noted above, this volume ramping prevent audible popping or clicks. Audio transducer 143 may output audio stimulation to the user. For instance, audio transducer 143 may comprise an earphone, earbud, bone conduction transducer or speaker.

Alternatively, in FIGS. 1B, 1C, 1D, and 1E, the neuromodulator output 140 may comprise pulsed visual, electrical, magnetic, vibrotactile or haptic stimuli. In some cases, where the neuromodulator output is not audio, the volume ramping 135 step may be omitted.

In FIGS. 1B, 1C, 1D, and 1E, a user may input one or more user-specified parameters 101 of the neuromodulator. For instance, the user-specified parameters 101 may include: (a) target frequency 102; (b) amplitude threshold 103; (c) power threshold 104; (d) minimum phase and maximum phase 107; and (e) commands to enable/disable output 105. The target frequency 102 may comprise a default target frequency that is employed to calculate cutoff frequencies of the bandpass filter. The amplitude threshold 103 may comprise the threshold for the noise threshold instantaneous amplitude 136 test. The power threshold 104 may comprise the threshold for the noise threshold based on filtered/unfiltered spectral power 137 test. The minimum phase and maximum phase 107 may comprise the start phase and end phase, respectively, for computing the pulse 134. Input 100 to the neuromodulator may also include other signals or data, such as other sensor data.

In some implementations, one or more parameters of the neuromodulator adjust dynamically and automatically in response to EEG measurements (e.g., theta/alpha ratio ratio) or to measurements by other sensors. Thus, in some cases, the neuromodulator performs closed loop control. In some cases, parameters of the neuromodulator may be adjusted over time (e.g., for a specific individual during a single session of inducing sleep).

In FIGS. 1B, 1C, 1D, and 1E, parameters of the neuromodulator may be customized for an individual person, for specific hardware, or for specific software (e.g., specific drivers).

In FIGS. 1B, 1C, 1D, and 1E, the method may be performed iteratively: (a) to calculate, in each iteration, the instantaneous phase and instantaneous amplitude for the most recent sample in the sample window; and (b) to control stimulation, based on the instantaneous phase and instantaneous amplitude. Furthermore, in FIGS. 1B, 1C, 1D, and 1E, the ADC and EEG circuitry may generate sample windows in such a way that each sample window is based on the most recent corresponding portion of the analog EEG signal being measured. Also, in FIGS. 1B, 1C, 1D, and 1E, an audio transducer or other transducer may output stimulation in accordance with then current control instructions.

In FIGS. 1B, 1C, 1D, and 1E, a low-pass filter may filter the EEG signal in the time domain to ensure that the resulting filtered signal is band-limited and that the maximum frequency of the filtered signal is less than one half of the sampling rate.

In some implementations of this invention, a neuromodulator generates pulsed stimulation that causes a user to fall asleep more quickly than the user would in the absence of the stimulation, all other factors being equal. Each stimulation pulse produced by the neuromodulator may start at a start phase and stop at an end phase, where the start phase and stop phase are each phases of an endogenous neural signal being measured by the neuromodulator.

In some use scenarios of this invention, the stimulation pulses produced by a neuromodulator occur, on average, at or near a peak of an endogenous signal produced by neurons in a brain of a human user. Stimulating at or near the peak of an endogenous neural signal may cause the amplitude of the signal to increase (similar to the effect of constructive wave interference).

For instance, in some cases, the stimulation pulses occur, on average, at or near a peak of a endogenous EEG theta signal. In some cases, stimulating at or near the peak of the endogenous theta signal may cause the amplitude of this signal to increase (similar to the effect of constructive wave interference). This enhancement of theta wave activity may cause, or help to cause, the user to fall asleep. (Recall that falling asleep may be associated with increases in absolute theta power and in theta/alpha ratio).

In some use scenarios of this invention, the stimulation pulses produced by a neuromodulator occur, on average, at or near the trough of an endogenous signal produced by neurons in a brain of a human user. In some cases, stimulating at or near the trough of the endogenous neural signal may suppress this signal—e.g., may cause the amplitude of the signal to decrease (similar to the effect of defective wave interference).

For instance, in some use scenarios, the stimulation pulses occur, on average, at or near the trough of an endogenous EEG alpha signal. Stimulating at or near the trough of the endogenous EEG alpha signal may suppress the alpha signal—e.g., may cause the amplitude of the signal to decrease (similar to the effect of destructive wave interference). This suppression of alpha wave activity may cause, or help to cause, the user to fall asleep. (Falling asleep may be associated with decreases in absolute alpha power).

In illustrative implementations, attributes of the target phase window (employed for stimulation) depend on the frequency band (e.g., theta, alpha, delta, gamma, or beta) being measured and stimulated by the neuromodulator.

In some cases, the default target frequency is 5 Hz for the theta band, 10 Hz for the alpha band, and 1 Hz or 0.75 Hz for the delta band. In some cases, the target frequency for an individual user is customized: (a) by measuring that user's theta, alpha and delta frequency (e.g., the peak at the FFT at the corresponding band's during a short 1 minute or less recording) before stimulating; and (b) by using these measured frequencies for phase-locking.

In some use scenarios, the duration of a single pulse is between 10-50 ms (e.g., 20 ms). The duration of the stimulation session depends on the application. For example, in some cases, the duration of the stimulation session may be: (a) between 5 minutes and 90 minutes for a nap; (b) between 5 minutes and 60 minutes to induce sleep onset for overnight sleep; (b) between 5 minutes and 60 minutes to mitigate or reduce wakefulness/arousal (e.g., sleep fragmentation) during overnight sleep; and (d) up to a few hours to maintain deep sleep. The duration of the stimulation session may also vary as a function of the user's age and health status.

In some cases, the neuromodulator stores (or accesses, or dynamically computes) parameters that specify a pulse's start phase, end phase, minimum duration and maximum duration. The start phase may be the phase of an endogenous neural signal when the pulse starts. The end phase may be the phase of an endogenous neural signal when the pulse ends. These parameters may be employed to control the timing of a pulse. For instance, if the end phase would otherwise cause a pulse to end before the minimum duration of a pulse, then the length of the pulse may be extended so that the pulse length is equal to the minimum duration. Similarly, if the end phase would otherwise cause a pulse to end after the maximum duration of a pulse, then the length of the pulse may be shortened so that the pulse length is equal to the maximum duration.

In some cases, the neuromodulator stores (or accesses or dynamically computes) other parameters, such as the type(s) of stimulation (e.g., aural or visual), location(s) of stimulation, maximum and minimum amplitude of stimulation (e.g., audio volume), and duration of stimulation session. Likewise, in some cases, the neuromodulator stores (or accesses, or dynamically computes) additional parameters (such as target frequency being tracked) that indirectly affect the computation of the pulse.

In some implementations, parameters of a neuromodulator (e.g., any one or more of the parameters mentioned in the preceding two paragraphs): (a) may be individually customized for different users; (b) may vary by brain region; and (c) may be dynamically adjusted in real time.

For instance, in some cases, one or more of the following parameters may by customized for individual users: (a) default target frequency being tracked by the neuromodulator; (b) start phase of pulse, (c) end phase of pulse; (c) minimum duration of pulse; (e) maximum duration of pulse; (f) location of stimuli; (g) type of stimuli (e.g., aural or visual); and (h) duration of stimulation session.

Likewise, in some cases, one or more of the following parameters may vary depending on the location at which the stimuli are being applied: (a) default target frequency being tracked by the neuromodulator; (b) start phase of pulse, (c) end phase of pulse; (c) minimum duration of pulse; (e) maximum duration of pulse; (f) type of stimuli (e.g., aural or visual); and (g) duration of stimulation session.

Likewise, in some cases, one or more of the following parameters may be dynamically adjusted in real time (e.g., in response to feedback from one or more sensors): (a) target frequency being tracked by the neuromodulator; (b) start phase of pulse, (c) end phase of pulse; (c) minimum duration of pulse; (e) maximum duration of pulse; (f) location of stimuli; (g) type of stimuli (e.g., aural or visual); and (h) duration of stimulation session.

In some cases, "phase" is treated as having a range of: (a) [−180 degrees, 180 degrees] or equivalently [−π radians, π radians]; (b) [0 degrees, 360 degrees] or equivalently [0 radians, 2π radians]; or (c) any other closed interval with a length of 360 degrees or 2π radians. Phase values that would be out of this range may be converted into a phase that is in this range by performing a modulo operation that wraps with a modulus of 2π.

In some use scenarios, the neuromodulator generates an exogenous signal that has a precisely controlled phase (e.g., an exogenous signal that comprises pulses that occur only in a certain phase window of neural activity). Due to this phase, the exogenous signal may tend to excite the neural tissue during refractory portions of the neural activity, and thus tend to inhibit the recharging of the neural tissue during the refractory portions, and thus tend to the reduce the excitability of the neural tissue in subsequent (excitable) portions of the periodic neural activity. Thus, the exogenous signal may cause a decrease in amplitude of a brain signal or otherwise cause neural activity to no longer be hyper-synchronized.

In some use scenarios, a neuromodulator enhances a target pattern of physiological activity. Again, the neuromodulator may do so by generating an exogenous signal that has a precisely controlled phase (e.g., an exogenous signal that comprises pulses that occur only in a certain phase window of neural activity). For instance, the neuromodulator may generate an exogenous signal that has the identical phase as a physiological signal. Or, for instance, the neuromodulator may generate an exogenous signal with a phase such that the exogenous signal tends to stimulate the neural tissue during peak (excitable) portions of a periodic physiological signal, and thus tends to make the neural tissue more excitable. An effect of this exogenous signal may be to increase the amplitude of the physiological signal.

Unless the context clearly indicates otherwise: (a) zero degrees phase occurs at a peak; (b) "peak" means the largest value of a signal during a period of the signal; and (c) "trough" means the smallest value of a signal during a period of the signal.

In some use scenarios, a stimulation pulse is centered on, or includes, a time at which a peak or a trough of an endogenous signal occurs.

For instance, in some cases, a stimulation pulse produced by a neuromodulator: (a) starts when an endogenous theta signal being measured has a phase that is less than or equal to zero degrees; and (b) stops when the theta signal has a phase that is greater than or equal to zero degrees. Similarly, in some cases, a stimulation pulse produced by a neuromodulator: (a) starts when an endogenous theta signal being measured has a phase that is less than or equal to 180 degrees; and (b) stops when the theta signal has a phase that is greater than or equal to 180 degrees.

Likewise, in some cases, a stimulation pulse produced by a neuromodulator: (a) starts when an endogenous alpha signal being measured has a phase that is less than or equal to zero degrees; and (b) stops when the alpha signal has a phase that is greater than or equal to zero degrees. In some cases, a stimulation pulse produced by a neuromodulator: (a) starts when an endogenous alpha signal being measured has a phase that is less than or equal to 180 degrees; and (b) stops when the alpha signal has a phase that is greater than or equal to 180 degrees.

Likewise, in some cases, a stimulation pulse produced by a neuromodulator: (a) starts when an endogenous signal (e.g., delta signal, gamma signal, or beta signal) being measured has a phase that is less than or equal to zero degrees; and (b) stops when the endogenous signal has a phase that is greater than or equal to zero degrees. In some cases, a stimulation pulse produced by a neuromodulator: (a) starts when an endogenous signal (e.g., delta signal, gamma signal, or beta signal) being measured has a phase that is less than or equal to 180 degrees; and (b) stops when the endogenous signal has a phase that is greater than or equal to 180 degrees.

In some use scenarios, a stimulation pulse is centered on, or includes, a time that is 90 degrees before a peak or a trough of an endogenous signal.

In some cases, a stimulation pulse produced by a neuromodulator: (a) starts at a time when an endogenous theta signal being measured has a phase that is less than or equal to 90 degrees; and (b) stops at a time when the theta signal has a phase that is greater than or equal to 90 degrees. In some cases, a stimulation pulse produced by a neuromodulator: (a) starts at a time when an endogenous alpha signal being measured has a phase that is less than or equal to 90 degrees; and (b) stops at a time when the alpha signal has a phase that is greater than or equal to 90 degrees. In some cases, a stimulation pulse produced by a neuromodulator: (a) starts at a time when an endogenous signal (e.g., delta signal, gamma signal or beta signal) being measured has a phase that is less than or equal to 90 degrees; and (b) stops at a time when the endogenous signal has a phase that is greater than or equal to 90 degrees.

In some use scenarios, it is advantageous to stimulate right before a peak or a trough of an endogenous neural signal. This may compensate for latency that may in some cases otherwise occur.

For instance, in some cases, a stimulation pulse produced by a neuromodulator: (a) starts when an endogenous theta signal being measured has a phase that is less than or equal to −10 degrees; and (b) stops when the theta signal has a phase that is greater than or equal to zero degrees. Similarly, in some cases, a stimulation pulse produced by a neuromodulator: (a) starts when an endogenous theta signal being measured has a phase that is less than or equal to 170 degrees; and (b) stops when the theta signal has a phase that is greater than or equal to 180 degrees.

Likewise, in some cases, a stimulation pulse produced by a neuromodulator: (a) starts when an endogenous alpha signal being measured has a phase that is less than or equal to −10 degrees; and (b) stops when the alpha signal has a phase that is greater than or equal to zero degrees. In some cases, a stimulation pulse produced by a neuromodulator: (a) starts when an endogenous alpha signal being measured has a phase that is less than or equal to 170 degrees; and (b) stops when the alpha signal has a phase that is greater than or equal to 180 degrees.

Similarly, in some cases, a stimulation pulse produced by a neuromodulator: (a) starts when an endogenous signal (e.g., delta signal, gamma signal or beta signal) being measured has a phase that is less than or equal to −10 degrees; and (b) stops when the endogenous signal has a phase that is greater than or equal to zero degrees. In some cases, a stimulation pulse produced by a neuromodulator: (a) starts when an endogenous signal (e.g., delta signal, gamma signal or beta signal) being measured has a phase that is less than or equal to 170 degrees; and (b) stops when the endogenous signal has a phase that is greater than or equal to 180 degrees.

In some use scenarios, the pulses—on average—are centered on, or include, a time at which a peak or a trough of an endogenous signal occurs.

For instance, in some cases, stimulation pulses produced by a neuromodulator during a period of time: (a) start, on average, when an endogenous theta signal being measured has a phase that is less than or equal to zero degrees; and (b) stop, on average, when the theta signal has a phase that is greater than or equal to zero degrees. Similarly, in some cases, stimulation pulses produced by a neuromodulator during a period of time: (a) start, on average, when an endogenous theta signal being measured has a phase that is less than or equal to 180 degrees; and (b) stop, on average, when the theta signal has a phase that is greater than or equal to 180 degrees.

Likewise, in some cases, stimulation pulses produced by a neuromodulator during a period of time: (a) start, on average, when an endogenous alpha signal being measured has a phase that is less than or equal to zero degrees; and (b) stop, on average, when the alpha signal has a phase that is greater than or equal to zero degrees. Likewise, in some cases, stimulation pulses produced by a neuromodulator during a period of time: (a) start, on average, when an endogenous alpha signal being measured has a phase that is less than or equal to 180 degrees; and (b) stop, on average, when the alpha signal has a phase that is greater than or equal to 180 degrees.

Likewise, in some cases, stimulation pulses produced by a neuromodulator during a period of time: (a) start, on average, when an endogenous signal (e.g., delta signal, gamma signal or beta signal) being measured has a phase that is less than or equal to zero degrees; and (b) stop, on average, when the endogenous signal has a phase that is greater than or equal to zero degrees. Likewise, in some cases, stimulation pulses produced by a neuromodulator during a period of time: (a) start, on average, when an endogenous signal (e.g., delta signal, gamma signal or beta signal) being measured has a phase that is less than or equal to 180 degrees; and (b) stop, on average, when the endogenous signal has a phase that is greater than or equal to 180 degrees.

In some use scenarios, the pulses—on average—are centered on, or include, a time that is 90 degrees before a peak or a trough of an endogenous signal.

For instance, in some cases, stimulation pulses produced by a neuromodulator during a period of time: (a) start, on average, when an endogenous theta signal being measured has a phase that is less than or equal to −90 degrees; and (b) stop, on average, when the theta signal has a phase that is greater than or equal to −90 degrees. In some cases, stimulation pulses produced by a neuromodulator during a period of time: (a) start, on average, when an endogenous theta signal being measured has a phase that is less than or equal to 90 degrees; and (b) stop, on average, when the theta signal has a phase that is greater than or equal to 90 degrees.

Likewise, in some cases, stimulation pulses produced by a neuromodulator during a period of time: (a) start, on average, when an endogenous alpha signal being measured has a phase that is less than or equal to −90 degrees; and (b) stop, on average, when the alpha signal has a phase that is greater than or equal to −90 degrees. In some cases, stimulation pulses produced by a neuromodulator during a period of time: (a) start, on average, when an endogenous alpha signal being measured has a phase that is less than or equal to 90 degrees; and (b) stop, on average, when the alpha signal has a phase that is greater than or equal to 90 degrees.

Likewise, in some cases, stimulation pulses produced by a neuromodulator during a period of time: (a) start, on average, when an endogenous signal (e.g., delta signal, gamma signal or beta signal) being measured has a phase that is less than or equal to −90 degrees; and (b) stop, on average, when the endogenous signal has a phase that is greater than or equal to −90 degrees. In some cases, stimulation pulses produced by a neuromodulator during a period of time: (a) start, on average, when an endogenous signal (e.g., delta signal, gamma signal or beta signal) being measured has a phase that is less than or equal to 90 degrees; and (b) stop, on average, when the endogenous signal has a phase that is greater than or equal to 90 degrees.

In some use scenarios, it is advantageous to stimulate—on average—right before a peak or a trough of an endogenous neural signal. This may compensate for latency that may in some cases otherwise occur.

For instance, in some cases, stimulation pulses produced by a neuromodulator during a period of time: (a) start, on average, when an endogenous theta signal being measured has a phase that is less than or equal to −10 degrees; and (b) stop, on average, when the theta signal has a phase that is greater than or equal to zero degrees. Likewise, in some cases, stimulation pulses produced by a neuromodulator during a period of time: (a) start, on average, when an endogenous theta signal being measured has a phase that is less than or equal to 170 degrees; and (b) stop, on average, when the theta signal has a phase that is greater than or equal to 180 degrees.

Likewise, in some cases, stimulation pulses produced by a neuromodulator during a period of time: (a) start, on average, when an endogenous alpha signal being measured has a phase that is less than or equal to −10 degrees; and (b) stop, on average, when the alpha signal has a phase that is greater than or equal to zero degrees. In some cases, stimulation pulses produced by a neuromodulator during a period of time: (a) start, on average, when an endogenous alpha signal being measured has a phase that is less than or equal to 170 degrees; and (b) stop, on average, when the alpha signal has a phase that is greater than or equal to 180 degrees.

Likewise, in some cases, stimulation pulses produced by a neuromodulator during a period of time: (a) start, on average, when an endogenous signal (e.g., delta signal, gamma signal or beta signal) being measured has a phase that is less than or equal to −10 degrees; and (b) stop, on average, when the endogenous signal has a phase that is greater than or equal to zero degrees. In some cases, stimulation pulses produced by a neuromodulator during a period of time: (a) start, on average, when an endogenous signal (e.g., delta signal, gamma signal or beta signal) being measured has a phase that is less than or equal to 170 degrees; and (b) stop, on average, when the endogenous signal has a phase that is greater than or equal to 180 degrees.

In some use scenarios, the actual phase of the stimulation pulses diverges by up to a specified threshold from a target.

For instance, in some use scenarios, a feature (e.g., peak or trough) of an endogenous signal is the target and the stimulation pulses may diverge by up to y degrees from the phase of the target.

For example, in some cases: (a) a feature (e.g., peak or trough) of an endogenous signal is the target; and (b) a stimulation pulse (i) may start at any time when the phase of the EEG signal is equal to phase of the signal at the target plus or minus y degrees, and (ii) may end at any later time when the phase of the EEG signal is equal to phase of the signal at the target plus or minus y degrees.

The same principle may apply where the stimulation pulses are averaged. For instance, in some cases: (a) a feature (e.g., peak or trough) of an endogenous signal is the target; and (b) stimulation pulses produced by a neuromodulator during a period of time: (i) may, on average, start at any time when the phase of the EEG signal is equal to phase of the signal at the target plus or minus y degrees, and (ii) may, on average, end at any later time when the phase of the EEG signal is equal to phase of the signal at the target plus or minus y degrees.

In some cases, in the preceding two paragraphs, the endogenous neural signal comprises an EEG theta signal, an EEG alpha signal; an EEG delta signal, an EEG beta signal, or an EEG gamma signal. In some cases, in the preceding two paragraphs, y is any real number in the range [0, 30].

Figure 2A:
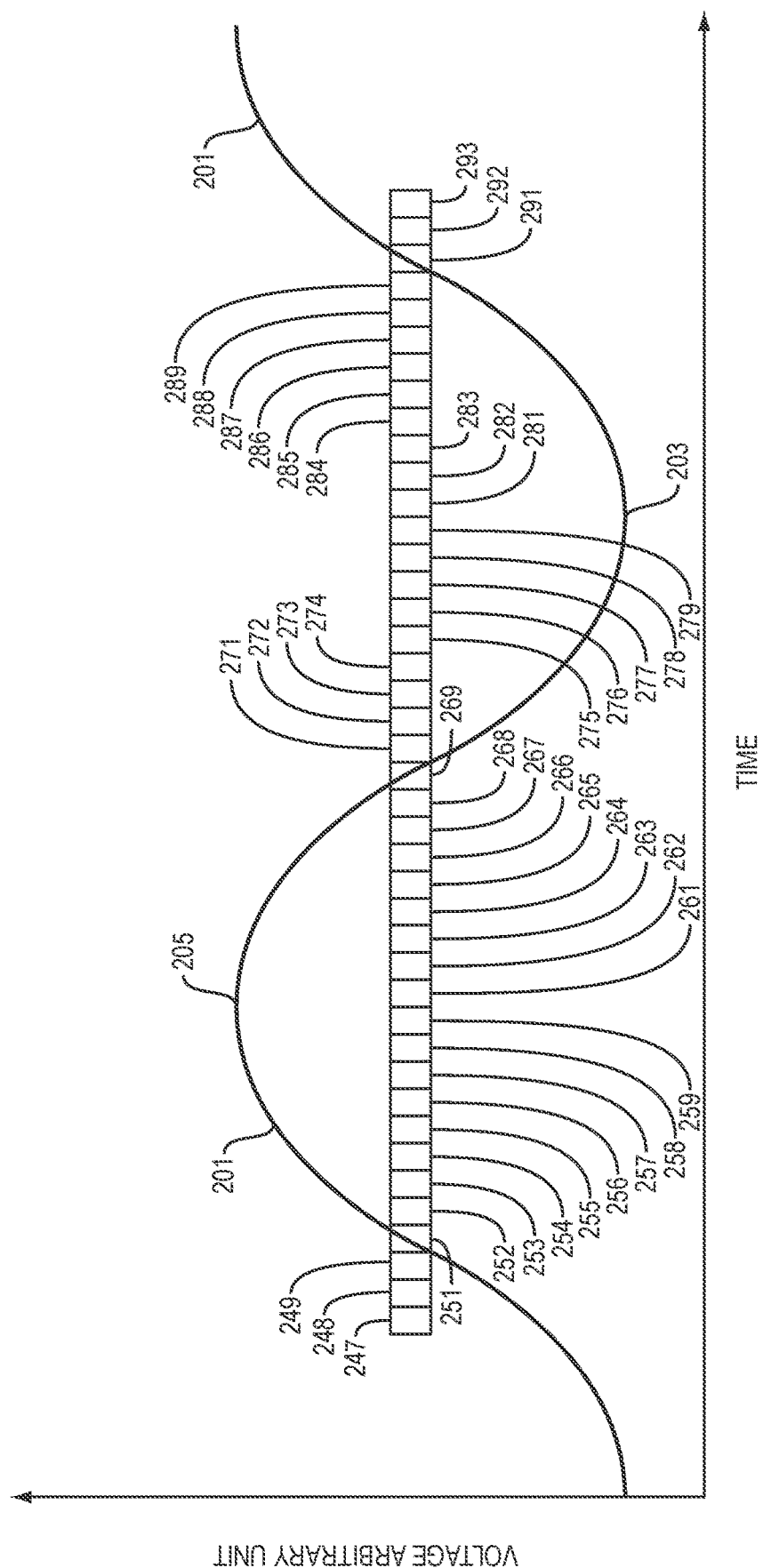
FIG. 2A shows phase windows during which a stimulation pulse may start or end.

FIG. 2A shows phase windows during which an event may start or end. In the example shown in FIG. 2A, an endogenous neural signal 201 varies as a function of time. In the time interval shown in FIG. 2A, signal has a peak 205 and a trough 203. Each of these occur at a particular phase relative to peak 205 (the trough is at 180 degrees relative to the peak and the peak is at 0 degrees relative to itself). In the example shown in FIG. 2A, peak 205 is treated as having a phase of zero degrees. The horizontal axis of FIG. 2A is time, or is equivalently phase (since the phase of signal 201 varies as a function of time).

In FIG. 2A, phase windows 247, 248, 249, 251, 252, 253, 254, 255, 256, 257, 258, 259, 261, 262, 263, 264, 265, 266, 267, 268, 269, 271, 272, 273, 274, 275, 276, 277, 278, 279, 281, 282, 283, 284, 285, 286, 287, 288, 289, 291, 292, 293 are shown. Each of these is a 10 degree phase window. For instance: (a) phase window 259 is a window from −10 degrees to zero degrees; and (b) phase window 279 is a window from 170 degrees to 180 degrees.

In the example shown in FIG. 2A, a stimulation pulse may start in any of these phase windows and may end in the same phase window or in any other of the phase windows. In the example shown in FIG. 2A, a sensation that is induced or created by stimulation may start in any of these phase windows and may end in the same phase window or in any other of the phase windows.

In some implementations of this invention, a stimulation pulse may start at any phase and may end at any phase. In some implementations of this invention, a sensation that is created or induced by pulse may start at any phase and may end at any phase.

Each of the above examples of timing of stimulation (e.g., simulation pulses) may also apply to timing of sensations caused by the stimulation. For instance, in some cases, the neuromodulation system produces stimulation that causes a user to perceive sensations that each occur at, or shortly before, a peak of an endogenous theta wave. Or, in some other cases, the neuromodulation system produces stimulation that causes a user to perceive sensations that each occur at, or shortly before, a trough of an endogenous wave (e.g., an alpha wave or theta wave).

Figure 2B:
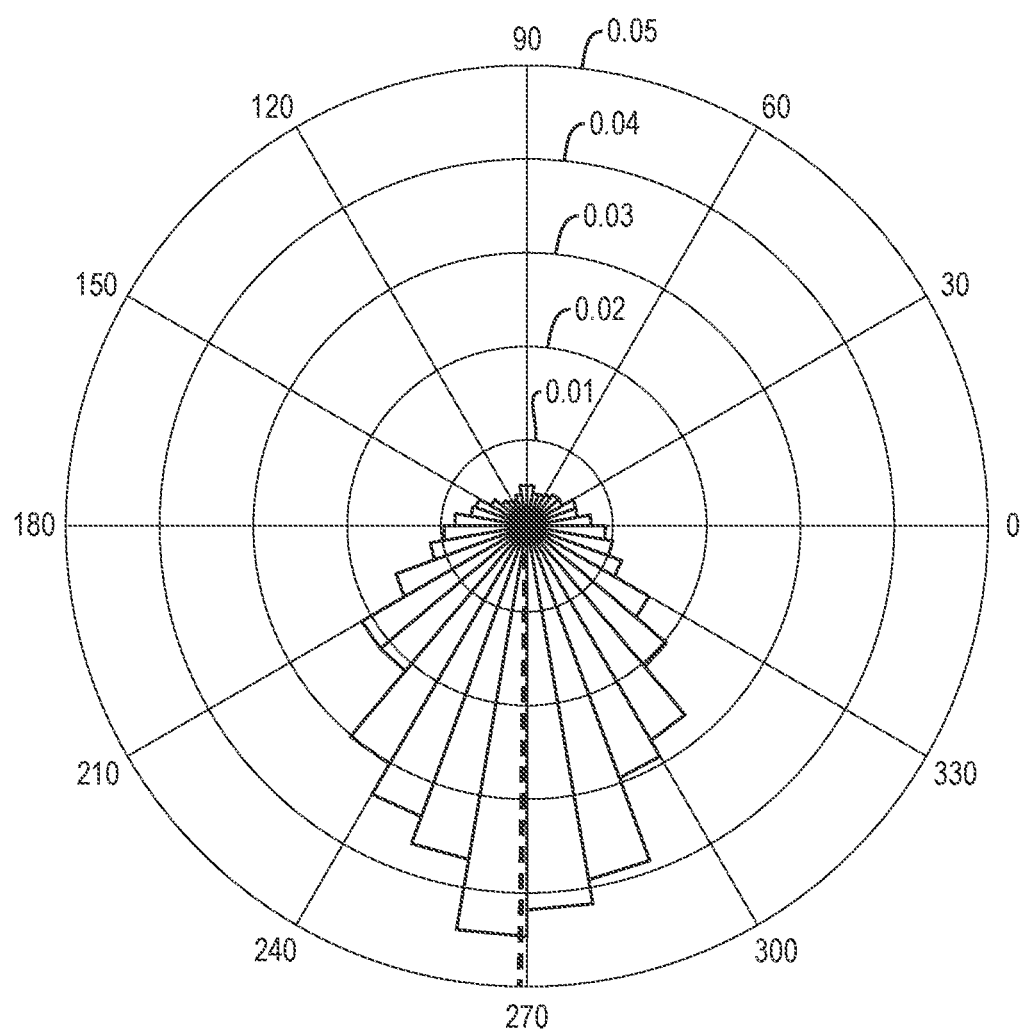
FIG. 2B is a phase histogram of starting phases for stimulation pulses.
Figure 2C:
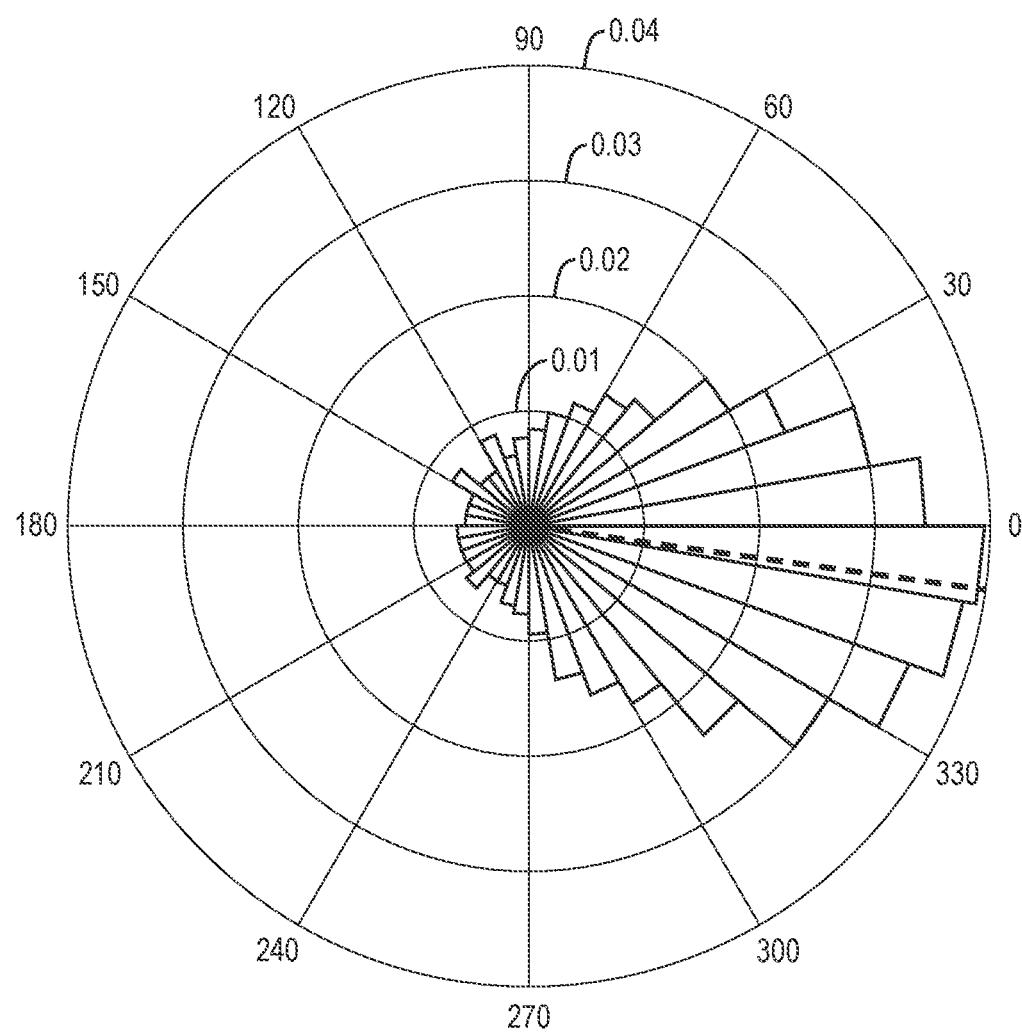
FIG. 2C is a phase histogram of ending phases for stimulation pulses.

FIG. 2B is a phase histogram of starting phases for stimulation pulses. FIG. 2C is a phase histogram of ending phases for stimulation pulses. These starting and ending phases were employed in a test of a prototype of this invention, to speed up the process of falling asleep. In FIGS. 2B and 2C, phase is relative to the peak of endogenous theta oscillation in the brain of the subject. The numbers 0.01, 0.02, 0.03, 0.04 in FIGS. 2B and 2C (and the number 0.05 in FIG. 2B), are each the fraction of samples (out of total samples) that occurred in a bin of the phase histogram. For example, in FIGS. 2B and 2C: (a) if the magnitude of a bin of the histogram is 0.04, then 4 percent of the phase samples were in that bin; (b) if the magnitude of a bin of the histogram is 0.03, then 3 percent of the phase samples were in that bin; (c) if the magnitude of a bin of the histogram is 0.02, then 2 percent of the phase samples were in that bin; and (d) if the magnitude of a bin of the histogram is 0.01, then 1 percent of the phase samples were in that bin. Likewise, in FIG. 2B, if the magnitude of a bin of the histogram is 0.05, then 5 percent of the phase samples were in that bin. In FIGS. 2B and 2C, the dashed line indicates mean phase.

FIG. 2D is a chart of theta/alpha ratio p value as a function of stimulation onset phase, during a test of a prototype of this invention. In the example shown in FIG. 2D, a linear fit 220 is shown for four sample points 221, 222, 223, 224. In FIG. 2D, each of these sample points is at a different phase of onset of stimulation.

FIG. 2E is a schematic of a phase-locking strategy employed in a test of a prototype of this invention. In the example shown in FIG. 2E, a pulse of audio stimulation 233 is applied shortly before the peak 231 of a subject's brain theta oscillation 230. This theta oscillation also has a trough 232. In FIG. 2E, the audio stimulus comprises pink noise pulses (50 ms duration; amplitude 60 dB SL). The phase-locking strategy shown in FIG. 2E was employed for all subjects in a test, except that the phase-locking strategy for one subject was to stimulate before the trough of alpha oscillation.

The prototype that was used for the tests summarized in FIGS. 2B, 2C, 2D and 2E is a non-limiting example of this invention. This invention may be implemented in other ways, and other test results may be obtained.

FIG. 2F shows a mean resultant vector 290 which has a length 291.

In some implementations of this invention, each algorithm described herein may be performed in part or in whole in hardware.

Single Point IDFT

In some implementations of this invention (e.g., the methods shown in FIGS. 1B, 1C and 1D), a single point Inverse Discrete Fourier Transform (IDFT) computes a single complex time domain value from a sequence of frequency domain values. As used herein, a "complex" number means a number that has an imaginary part and a real part.

In some implementations of this invention, an IDFT is defined by the equation ("IDFT Equation"):

$$x(n) = \frac{1}{N} \sum_{k=0}^{N-1} X(k) * e^{(2*i*\pi*n*k)/N}$$

where $X(k)$ are frequency domain samples (also known as Fourier coefficients), $x(n)$ are time domain samples, N is the number of time domain samples, n is an index of the time domain samples and may range over any integer value, and $k=0, 1, \ldots, N-1$, is an index into the frequency domain samples. Given that $F_s$ is the sampling frequency used to collect the time domain samples, the frequency corresponding to each frequency domain sample may be computed as follows. The frequencies for $k=0, 1, \ldots, N/2$, also known as positive frequencies, can be computed by the equation $f=F_s*k/N$. The frequencies for $$k = \frac{N}{2} + 1, \ldots, N-2, N-1,$$

also known as negative frequencies, can be computed by the equation $f=F_s*(N-k)/N$.

Conventionally, the IDFT equation is computed for each integer n starting with $n=0$ and ending with $n \leq (N-1)$.

In contrast, in some implementations of this invention: (a) a single point IDFT evaluates the IDFT Equation for only one value of n; and (b) the value of n is selected to correspond to the index of the most recent sample point.

In some implementations, a single-point IDFT may be employed with either "frequency domain" ECHT, "end-padded time domain" ECHT, or "front-padded time domain" ECHT.

Consider the following, non-limiting example. In this example, the time domain samples are $x=[s_0, s_1, s_2, s_3, s_4, s_5, s_6, s_7]$ where $s_i$ is a real-valued sample. Note that if a Fast Fourier Transform (FFT) is used in place of a DFT, then for many versions of FFT, it is desirable that the number of samples equal a power of 2 (e.g., because, in some cases, the FFT version requires that, or runs more efficiently if, the number of samples is a power of 2).

In this example, if "frequency domain" ECHT is performed, then: (a) the DFT of x may be computed and the resulting Fourier coefficients may be Hilbert transformed and multiplied by filter coefficients, resulting in $X=[f_0, f_1, f_2, f_3, f_4, 0, 0, 0]$ with $f_0$ corresponding to 0 frequency, $f_4$ corresponding to the Nyquist frequency, and $f_1$ through $f_3$ corresponding to positive frequencies; and (b) the single point IDFT may compute the complex-valued $x(n=7)$ given X and $N=8$.

In this example, if "end-padded time domain" ECHT is performed, then: (a) zeros may be added to the end of x, where the sequence of zeroes being added has the same length as x, resulting in $x=[s_0, s_1, s_2, s_3, s_4, s_5, s_6, s_7, 0, 0, 0, 0, 0, 0, 0, 0]$; (b) the resulting value after time domain filtering then DFT is $X=[f_0, f_1, f_2, f_3, f_4, f_5, f_6, f_7, f_8, 0, 0, 0, 0, 0, 0, 0]$, with $f_0$ corresponding to 0 frequency, $f_8$ corresponding to the Nyquist frequency, and $f_1$ through $f_7$ corresponding to the positive frequencies; and (c) the single point IDFT may compute the complex-valued $x(n=7)$ given X and $N=16$.

Alternatively, in this example, if "end-padded time domain" ECHT is performed, then: (a) zeros may be added to the end of x, and the same number of sample points as zeros added may be removed from the beginning of x, resulting in $x=[s_3, s_4, s_5, s_6, s_7, 0, 0, 0]$; (b) the resulting value after time domain filtering then DFT is $X=[f_0, f_1, f_2, f_3, f_4, 0, 0, 0]$, with $f_0$ corresponding to 0 frequency, $f_4$ corresponding to the Nyquist frequency, and $f_1$ through $f_3$ corresponding to the positive frequencies; and (c) the single point IDFT may compute the complex-valued $x(n=4)$ given X and $N=8$.

In this example, if "front-padded time domain" ECHT is performed, then: (a) a copy of an end segment of the time domain samples may be added to the beginning of x, resulting in $x=[s_0, s_1, s_2, s_3, s_4, s_5, s_6, s_7, s_0, s_1, s_2, s_3, s_4, s_5, s_6, s_7]$; (b) the resulting value after time domain filtering then DFT is $x=[f_0, f_1, f_2, f_3, f_4, f_5, f_6, f_7, f_8, 0, 0, 0, 0, 0, 0, 0]$, with $f_0$ corresponding to 0 frequency, $f_8$ corresponding to the Nyquist frequency, and $f_1$ through $f_7$ corresponding to the positive frequencies; and (c) the single point IDFT may compute the complex-valued $x(n=7)$ given X and $N=16$.

Alternatively, in this example, if "front-padded time domain" ECHT is performed, then: (a) a copy of an end segment of the time domain samples may be added to the beginning of x, and the same number of sample points as sample points added may be removed from the end of x resulting in $x=[s_4, s_5, s_6, s_7, s_0, s_1, s_2, s_3]$; (b) the resulting value after time domain filtering then DFT is $X=[f_0, f_1, f_2' f_3, f_4, 0, 0, 0]$, with $f_0$ corresponding to 0 frequency, $f_4$ corresponding to the Nyquist frequency, and $f_1$ through $f_3$ corresponding to the positive frequencies; and (c) the single point IDFT may compute the complex-valued $x(n=3)$ given X and $N=8$.

In some implementations of this invention, employing a single point IDFT causes ECHT to run faster, reducing the latency from electrode sampling to stimulus. The computational efficiency of the single-point IDFT may arise, at least in part, from computing only the instantaneous phase and amplitude of the most-recent time domain sample. However, this invention may be implemented with any type of IDFT or IFFT.

A conventional application of the IDFT, using the IDFT equation, computes N time domain samples given N frequency domain samples with an asymptotic running time of $O(n*n)$.

An IFFT (Inverse FFT) is an efficient implementation of IDFT. A conventional IFFT where $n=k$ and n is a power of 2, has an asymptotic running time of $O(N*log(N))$.

In comparison, in some implementations of this invention, a single point IDFT has an asymptotic running time of $O(N)$, and calculates only a single time domain value that encodes the instantaneous amplitude and phase of the most recent sample point. For instance, a single point IDFT (e.g., 119, 349, 359) may be performed in the methods shown in FIGS. 1B, 1C and 1D.

Hardware

FIGS. 3, 4, 5, 6 and 7 each show hardware that may be employed to accelerate sleep onset, in illustrative implementations of this invention.

Figure 3:
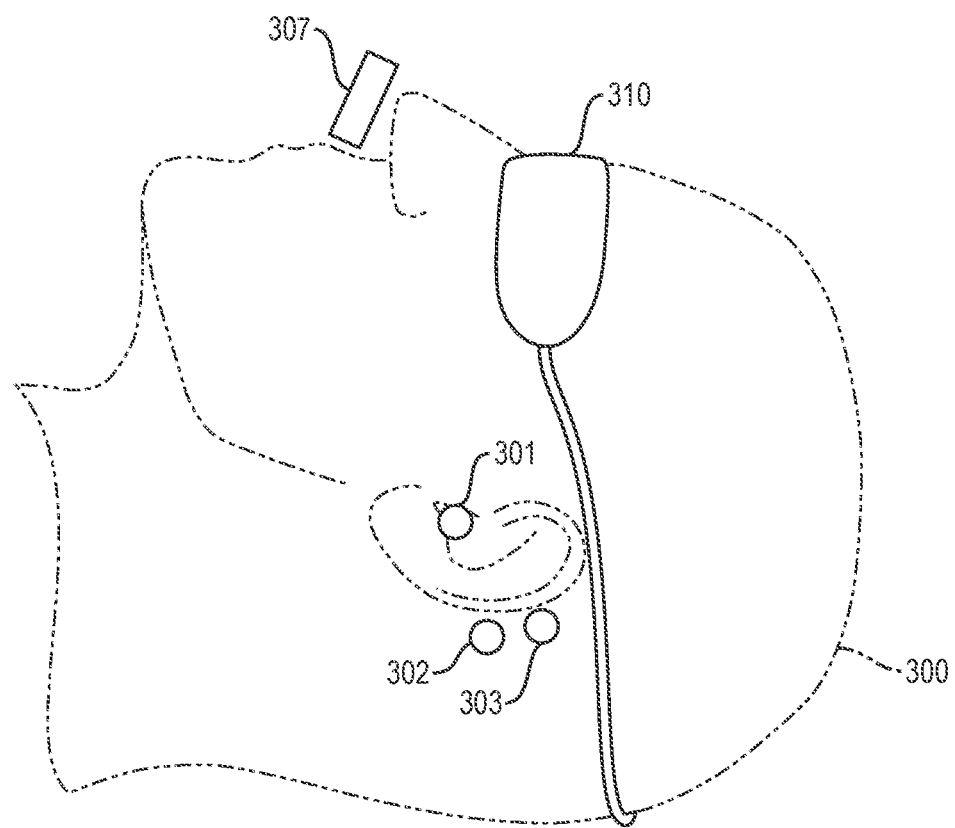
FIGS. 3, 4, 5, 6 and 7 each show hardware that may be employed to accelerate sleep onset.

In the example shown in FIG. 3, a user 300 wears an eye mask 308 while lying down in a supine position (e.g., on a bed) or while sitting (e.g., in a reclining chair). An EEG channel may utilize measurement electrode 310, reference electrode 302 and ground electrode 303. This EEG channel may measure electric potential difference (voltage difference) between the measurement electrode 310 and reference electrode 302. Measurement electrode 310 may be located at position FpZ or position FZ. Unless the context clearly indicates otherwise, electrode positions are named herein in accordance with the International 10-20 System for electrode position nomenclature. Reference electrode 302 and ground electrode 303 may be located behind the ear against the skin (e.g., superficial to the mastoid part of the temporal bone). Earphone (or earbud) 301 may be positioned in an ear. A breath sensor 307 may be positioned near the nose to measure respiration (e.g., respiration rate).

Alternatively: (a) one or more measurement electrodes may be located at any position on the head, including any electrode position described by the International 10-20 System; and (b) reference and ground electrodes may be located at any position on the human body, including head, ear or earlobe.

In some implementations, multiple EEG channels are employed (e.g., each with different measurement, reference and ground electrodes). Each different EEG channel may record a signal in a different frequency band or in a different spatial region. In each EEG channel, the measurement, reference and ground electrodes may be positioned in any spatial arrangement in which a brain EEG signal may be detected. In some cases: (a) a measure of central tendency (e.g., average) of voltages (e.g., reference voltages) from a set of EEG may be computed; and (b) the measure of central tendency is treated as the reference voltage for a particular EEG channel. In some cases: (a) alpha band activity is suppressed by stimulation, where each pulse of stimulation is at or shortly before the trough of an alpha band signal; and (b) different EEG channels with electrodes at different spatial locations are employed to record alpha band activity as the dominant brain region of alpha band activity changes spatial position during the process of falling asleep.

In some cases: (a) the neuromodulator outputs electrical stimulation; and (b) the stimulation electrode may be in the same position as a EEG measurement electrode. For instance: (a) the stimulation electrode may comprise a ring electrode around an EEG measurement electrode located at the FZ position or FpZ position; and (b) an EEG reference electrode may be positioned on the skin superficial to the inion.

Figure 4:
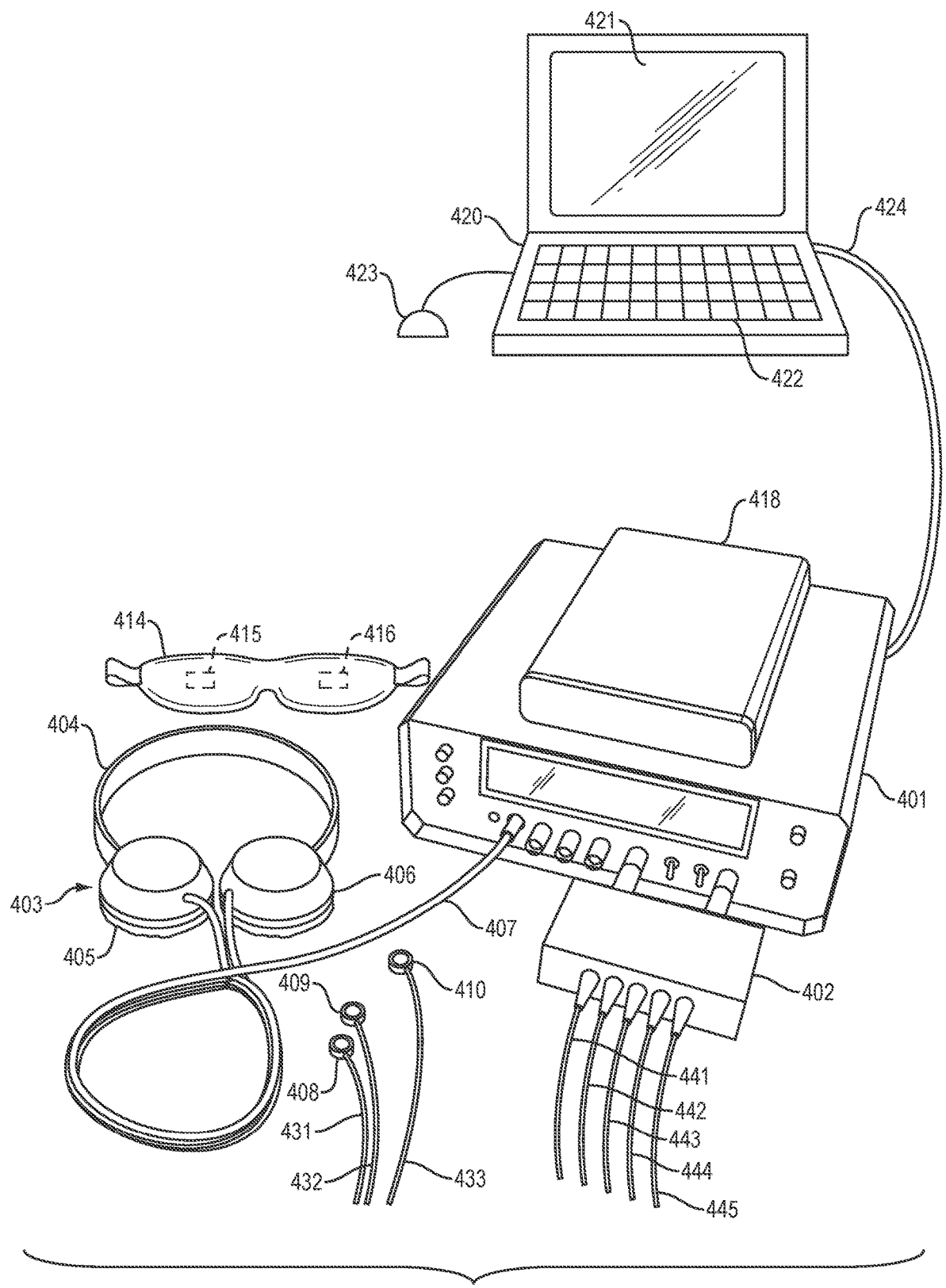

In the example shown in FIG. 4, a neuromodulation system includes a sleep modulation device 401, an adapter 402, headphones 403, an eye mask 414, electrodes 408, 409, 410, electrode leads 431, 432, 433, 441-445, a battery 418\*, a computer 420 and input/put devices such as a keyboard 422, computer mouse 423 and display screen 421. Computer 420 may be communicatively connected to sleep modulation device 401 by a wired connection 424. Headphones 404 include a headband 404 and earphones 405, 406. Headphones 404 may output audio stimulation that is phase-locked to endogenous brain electrical activity. Eye mask 414 may be worn to cover the user's eyes. In some cases, eye mask 414 includes stimulators 415, 416. For instance, stimulators 415, 416 may comprise light sources that output light which is perceived by the user, even when the user closes her or his eyes. Or, for instance, stimulators 415, 416 may comprise electrodes that electrically stimulate the retina of each eye of the user and thereby cause the user to perceive phosphenes.

In FIG. 4, electrodes 408 and 410 are shielded electrodes. Electrode leads 431 and 433 are electrically connected to these two electrodes and each have a co-axial metal jacket (shield) which is electrically connected to ground. For instance, the shielding in electrode lead 431 and 433 may be electrically connected to ground via one or more wires 442, 443, 444. Electrode leads 441 and 445 may be extensions of electrode lead wires 431 and 433, respectively, and may relay signals of interest from electrodes 408 and 410, respectively.

In FIG. 4, sleep modulation device 401 includes an internal EEG sensor, including amplifiers, filters, and an ADC (analog-to-digital converter). Sleep modulation device 401 also includes an external analog hookup for an external EEG sensor. Sleep modulation device 401 also includes an Arduino® Due microcontroller board and an Arduino® Teensy® development board. In FIG. 4, sleep modulation device 401 performs multiple functions, including: (a) reading EEG ADC; (b) reading and processing configuration commands; (c) computing instantaneous phase and instantaneous amplitude (e.g., using an EECH algorithm); (d) streaming data; and (e) controlling phase-locked stimulation outputs. Sleep modulation device 401 may include a sound card with high speed volume control and waveform generators. Sleep modulation device 401 may produce digital pulsed output that triggers external devices, and may perform multiple logic I/O (input/output) for digital interfacing. Sleep modulation device 401 includes on-board power regulation circuitry, and an Arduino® Due USB (universal serial bus) programming port. Jacks for an external EEG may be located in the rear of sleep modulation device 401.

Figure 5:
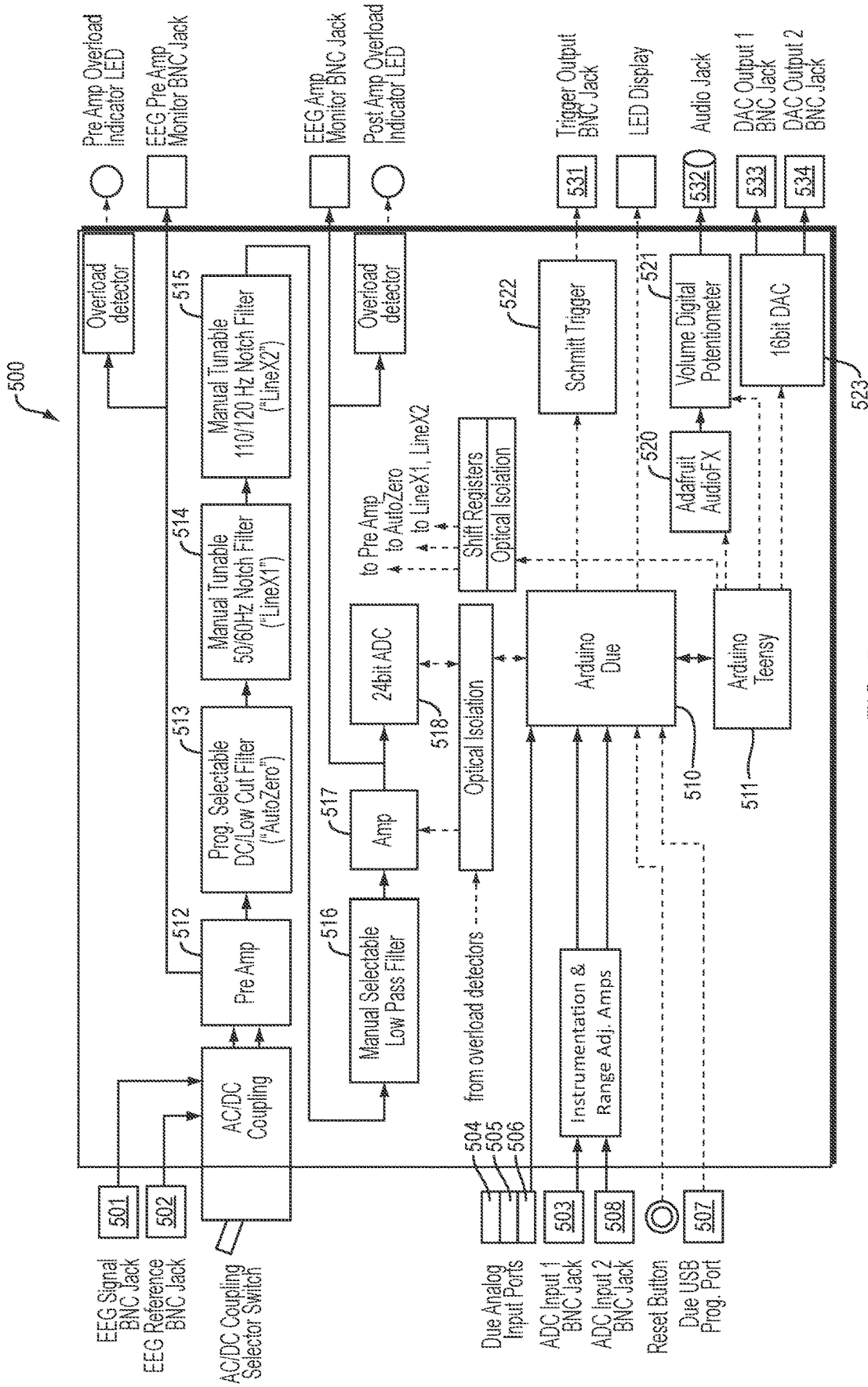

FIG. 5 is a block diagram that shows hardware used to accelerate sleep onset, in some implementations of this invention.

In the example shown in FIG. 5, input to a neuromodulator 500 may be provided via EEG signal BNC (Bayonet Neill-Concelman) jack 501, EEG signal BNC jack 502, Arduino® Due analog input ports 504, 505, 506, ADC input 1 BNC jack 503, ADC input 2 BNC jack 508, or an Arduino® Due USB programming port 507.

In FIG. 5, EEG signals may be processed by, among other things: a pre-amplifier 412; a programmable selectable DC/low cut filter (which we sometimes call the "autozero") 513; a manual tunable 50/60 Hz notch filter 514, a manual tunable 110/120 Hz Notch filter 515, a manual selectable low pass filter 516, and an amplifier 517. In FIG. 5, processed EEG signals may be digitized by a 24 Bit ADC 518. In FIG. 5, a filter is called "selectable" if the filter settings are a relatively small set of discrete values (e.g. a small set of discrete values for bandwidth or cutoff frequencies). In FIG. 5, a filter is called "tunable" if the filter settings are, loosely speaking, continuous. In FIG. 5, a filter is called "manual" if a parameter of the filter may be manually adjusted (e.g., by manually turning a dial).

In FIG. 5, low-cut "Autozero" filter 513 passes high frequencies. The "Autozero" filter 513 has four discrete, selectable settings for its 3 dB cutoff frequency: (a) "off"; (b) 15.9 Hz corresponding to a 10 millisecond time constant; (c) 0.159 Hz corresponding to a 1 second time constant; and (d) 0.00159 Hz corresponding to a 100 second time constant.

In FIG. 5, low-pass filter 516 may filter the EEG signal in the time domain to ensure that the resulting filtered signal is band-limited and that the maximum frequency of the filtered signal is less than one half of the sampling rate.

In FIG. 5, EEG sensing is performed by hardware elements located in the top half of FIG. 5 (above the optical isolation box). In FIG. 5, digital control of phase-locked stimulation is performed by hardware elements located in the bottom half of FIG. 5 (below the optical isolation box).

In FIG. 5, Adafruit® Audio FX 520 is a sound board. The output from the Adafruit® Audio FX 520 sound board is always on during normal operation. The Arduino® Teensy® board 511 controls Volume Digital Potentiometer 521. By adjusting the potentiometer, volume is adjusted. For instance, volume may be ramped in such a way that popping noises (that may otherwise occur due to overly abrupt transitions) are avoided. In FIG. 5, a digital audio signal may be sent to an external audio transducer via headphone jack 532. For instance, headphone jack 532 may be a 3.5 mm headphone jack.

In FIG. 5, output from Arduino® Due board 510 may be sent through a Schmitt trigger 522 to trigger output BNC jack 531. Other output from Arduino® Due board 510 may be sent to an LED display. For instance, the LED display may be a four row character LED display. Digital output from Arduino® Due board 510 may be converted to an analog signal by a 16-bit DAC (digital-to-analog-converter) 523. This 16-bit DAC 523 may output analog signals that are sent to external devices via DAC Output 1 BNC jack 533 and DAC Output 2 BNC jack 534.

Figure 6:
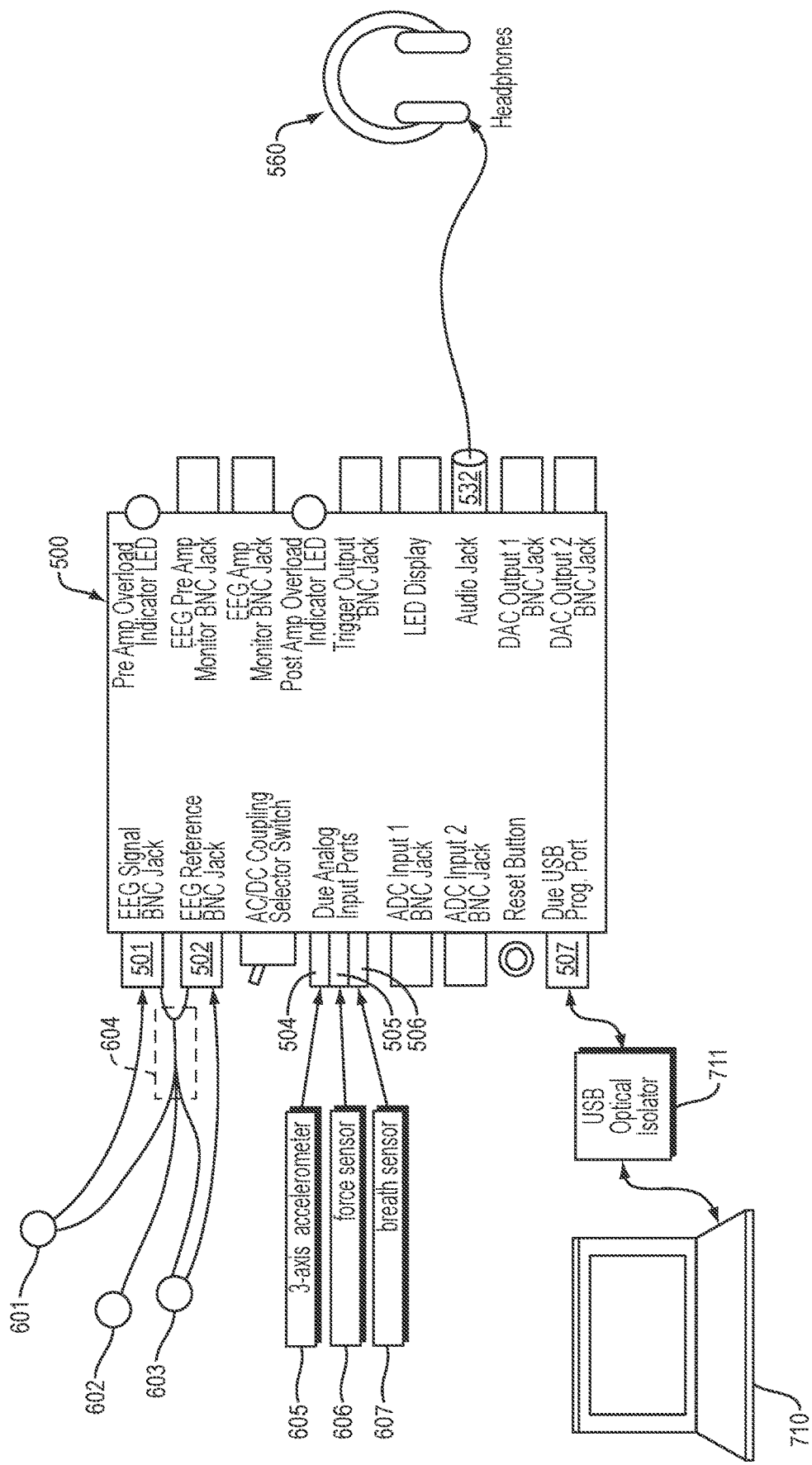

FIG. 6 shows a use scenario, in which a neuromodulator 500 outputs audio stimuli via headphones 560. In FIG. 6, electrodes 601, 602 and 603 may include a reference electrode and ground electrode. Electrodes 601 and 603 may be shielded. Leads for electrodes 601 and 603 may each have a co-axial metal jacket (shield) which is electrically connected to ground. A lead for electrode 602 (as well as certain wires that are electrically connected to electrodes 601 and 603) may be electrically shielded by shielding in region 604.

In FIG. 6, neuromodulator 500 may also receive analog signals that encode measurements taken by a 3-axis accelerometer 605, a force sensor 606 and a breath sensor 607. Measurements taken by these analog sensors may provide additional biomarkers that are indicative of a sleep or wake stage or that are indicative of any state that occurs in the process of falling asleep or being asleep.

Figure 7:
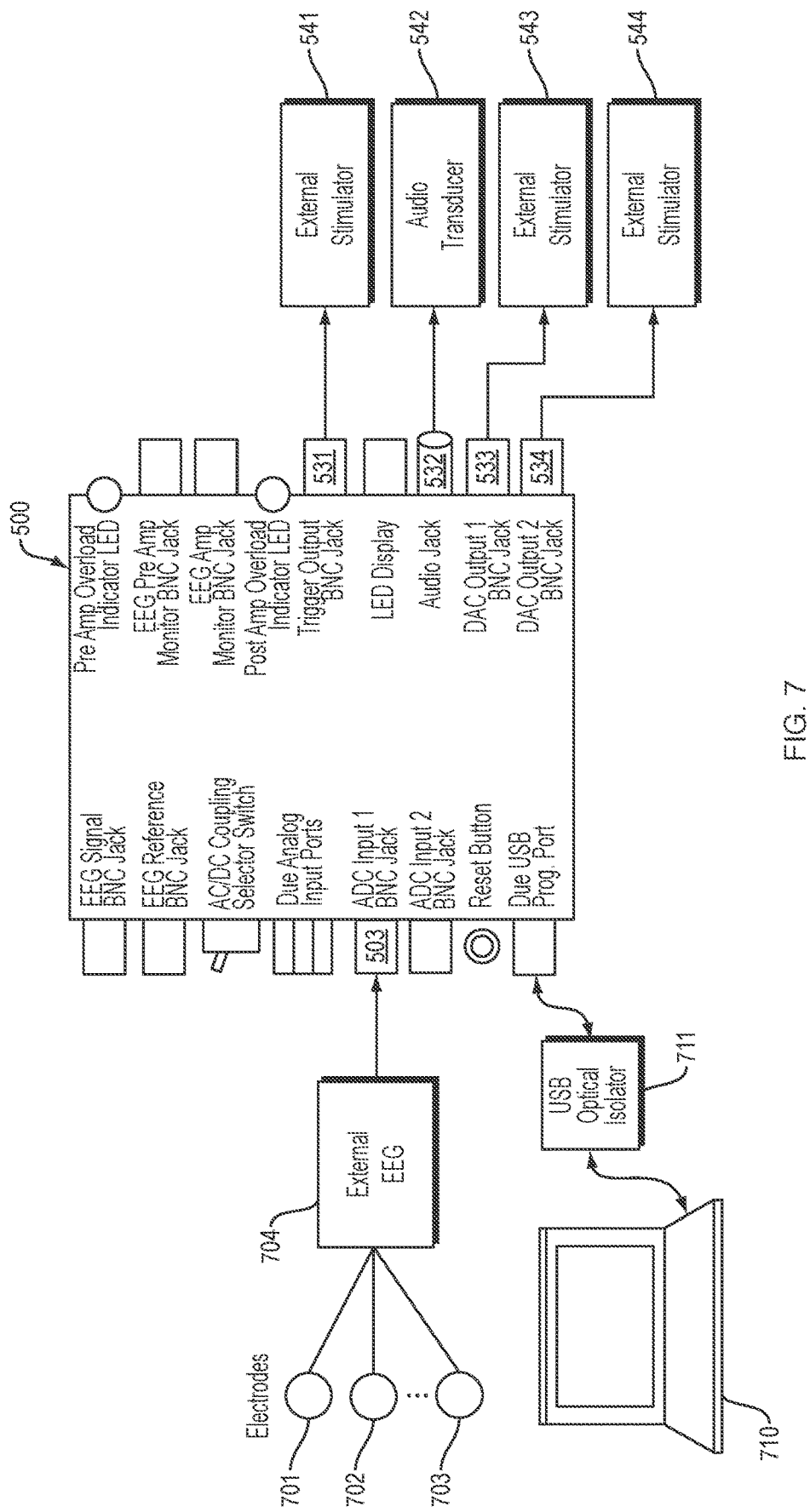

FIG. 7 shows a use scenario, in which a neuromodulator interfaces with an external EEG device and outputs, to multiple external devices, signals that encode phase-locked stimulation. In the example shown in FIG. 7, neuromodulator 500 receives input from external EEG device 704, which takes EEG measurements with multiple electrodes (e.g., electrodes 701, 702, 703). External EEG device 704 may have multi-channel functionality, and may record EEG signals via multiple EEG channels. For instance, each EEG channel may use different electrodes at different positions (e.g., on a user's head). In FIG. 7, a reference electrode and ground electrode may be included in the electrodes (e.g., included in electrodes 701, 702, 703). In FIG. 7, neuromodulator 500 may output signals to external stimulators 541, 543, 544 and to external audio transducer 542. These outputted signals may encode stimulation that is phase-locked with an endogenous neural signal of the user.

In FIGS. 6 and 7, a reference electrode and a ground electrode may each, individually, be positioned in any position on the user's head or in any other portion of the user's body, including on the wrist or behind the ear (e.g., superficial to the mastoid part of the temporal bone).

In the examples shown in FIGS. 6 and 7, computer 710 may include I/O devices (e.g., a keyboard and display screen). A user may input, via computer 710, parameters for neuromodulator 710. For instance, these parameters may include target frequency, amplitude threshold, power threshold, start phase of pulses, end phase of pulses, and whether output is enabled or disabled. The inputted parameters may be sent (e.g., via serial communication) from computer 710 through a USB optical isolator 711 to neuromodulator 500.

Prototype

The following 31 paragraphs describe a prototype of this invention.

FIGS. 8A, 8B, 8C, 8D, 8E, 8F, 8G, 8H, 9A, 9B, 9C, 9D, 9E, 10A, 10B, 10C, 10D, 11A, 11B, 11C, 11D and 11E are each a circuit schematic for a circuit in this prototype.

Figure 8A:
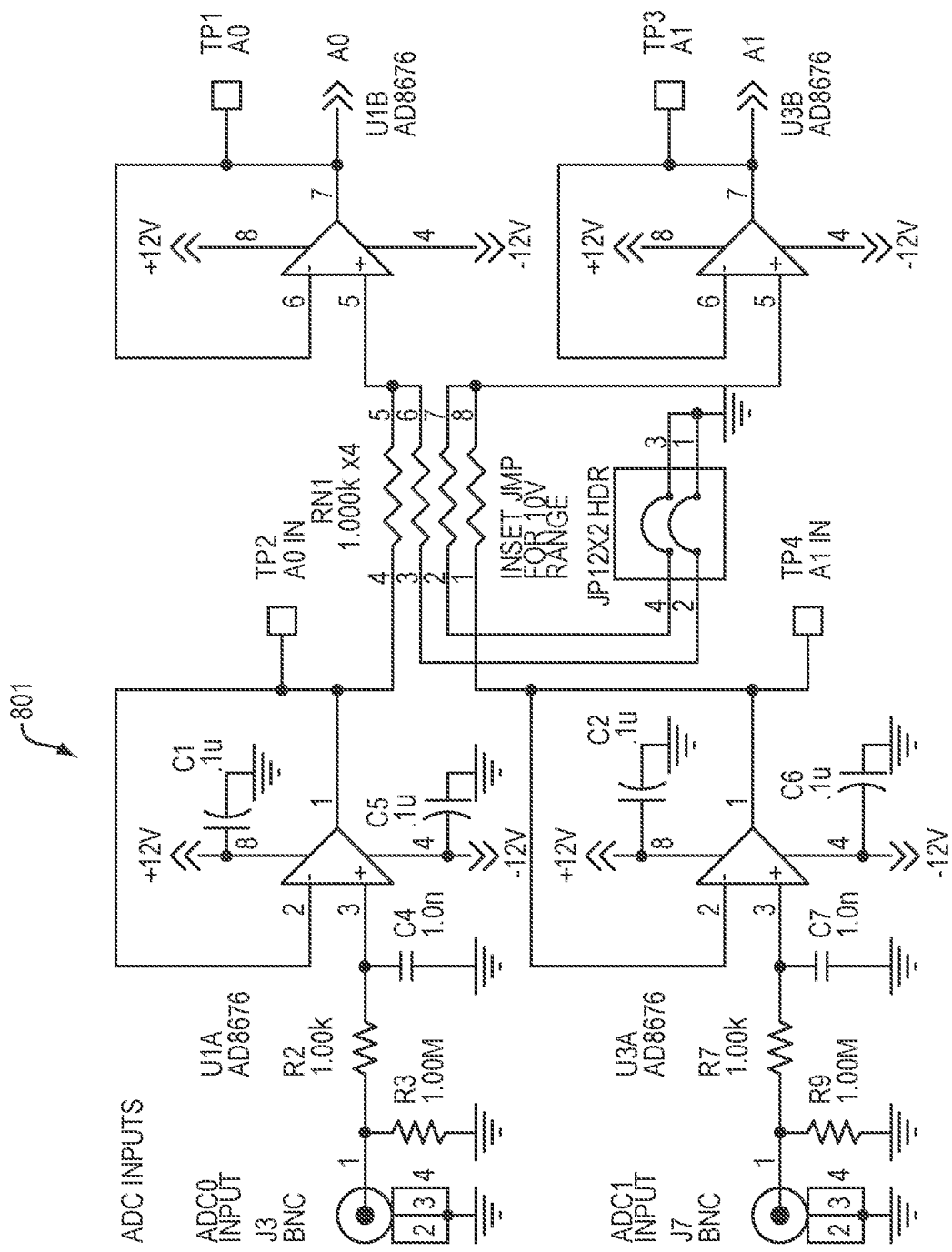

In this prototype, in circuit 801, a pair of BNC Jacks allows the connection of external analog sources such as the analog outputs from an external EEG. Each analog input may range from −10 to 10V. Each analog input is fed through a unity-gain buffer amplifier, a jumper-selectable voltage divider (jumper off=unity gain, jumper on=½ gain), and a secondary unity gain buffer amplifier. The voltage at the end of this sequence, at "A0" or "A1", does not exceed the range −5V to 5V. "A0" and "A1" ultimately connect to a secondary voltage divider before being fed into the 12 bit ADC internal to the Arduino® Due. Circuit 801 is shown in FIG. 8A.

Figure 8B:
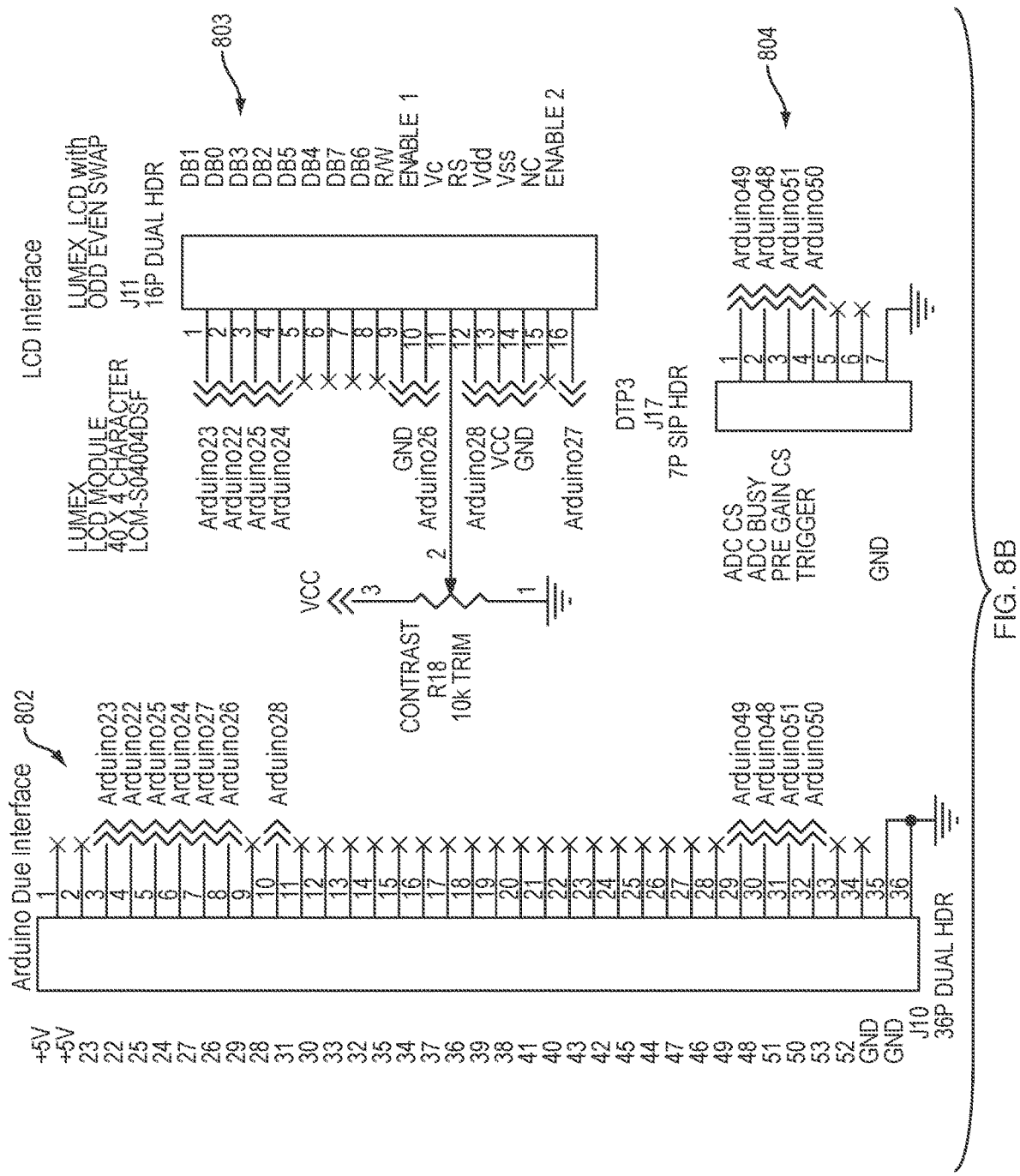

In this prototype, in circuit 802, a 2×18 strip of male header which connects with female header on the Arduino® Due. Circuit 802 is shown in FIG. 8B.

In this prototype, in circuit 803, a 1×16 strip of male header which may connect directly or via a cable to the header on the LCD display. Circuit 803 is shown in FIG. 8B.

In this prototype, in circuit 804, a 1×7 strip of male header as test points to probe signal voltages at their interface to the Arduino® Due. Circuit 804 is shown in FIG. 8B.

Figure 8C:
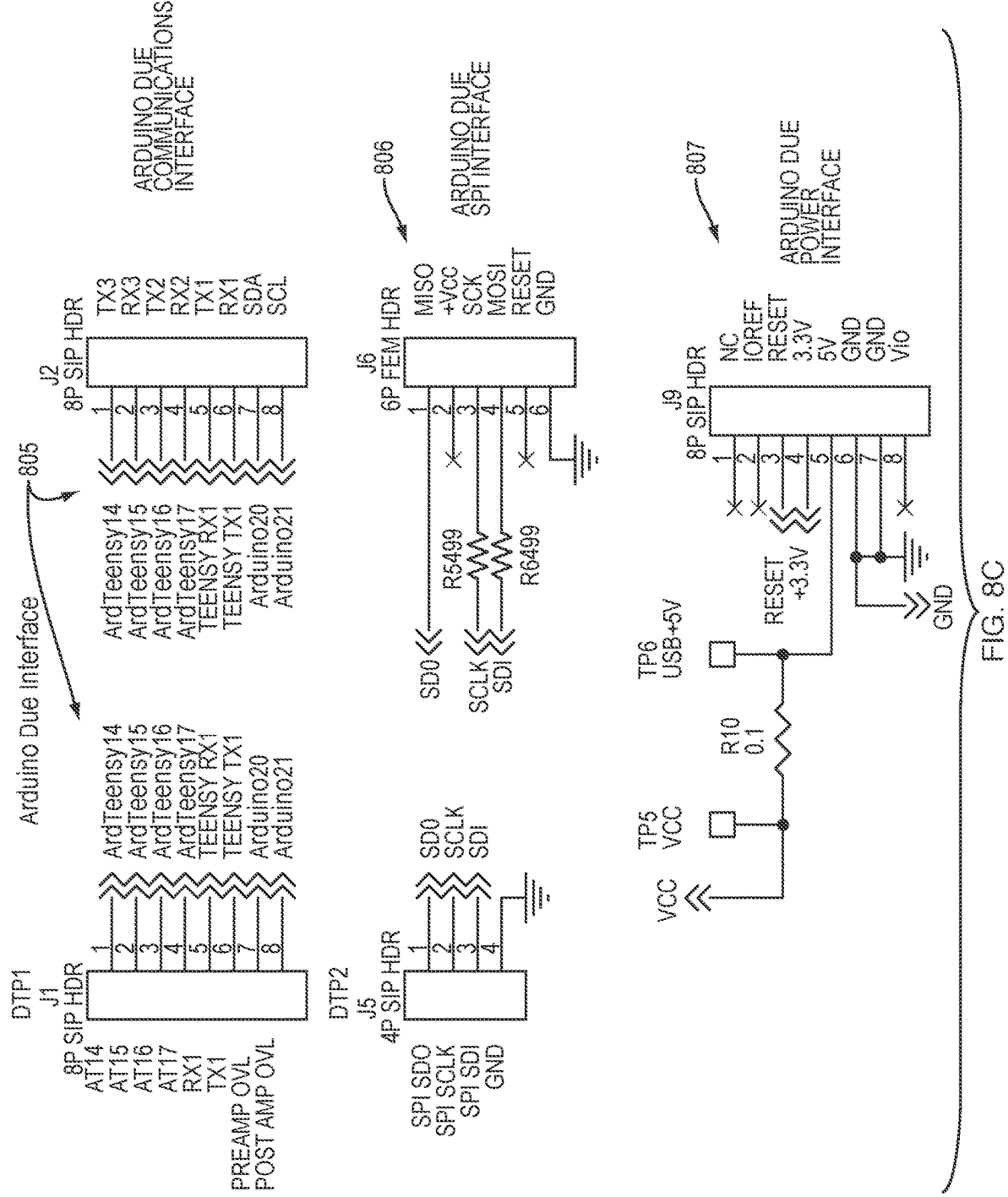

In this prototype, circuit 805 includes the Arduino® Due serial interfaces (read/write by Due) and overload signals (read by Due). (right) is a 1×8 strip of male header which connects with female header on the Arduino® Due. (left) is a 1×8 strip of male header as test points to probe the corresponding signal voltages at their interface to the Arduino® Due. Circuit 805 is shown in FIG. 8C.

In this prototype, circuit 806 supports the Arduino® Due SPI interface. (right) is a 2×3 strip of female header which connects with male header on the Arduino® Due. (left) is a 1×4 strip of male header as test points to probe the SPI signals. Circuit 806 is shown in FIG. 8C.

In this prototype, circuit 807 includes the Arduino® Due power and reset interface. A 1×8 strip of male header connects with the female header on the Arduino® Due. 5V is used to power the Arduino® Due. The Arduino® Due's built-in regulator produces the 3.3V supply used by this system. Circuit 807 is shown in FIG. 8C.

Figure 8D:
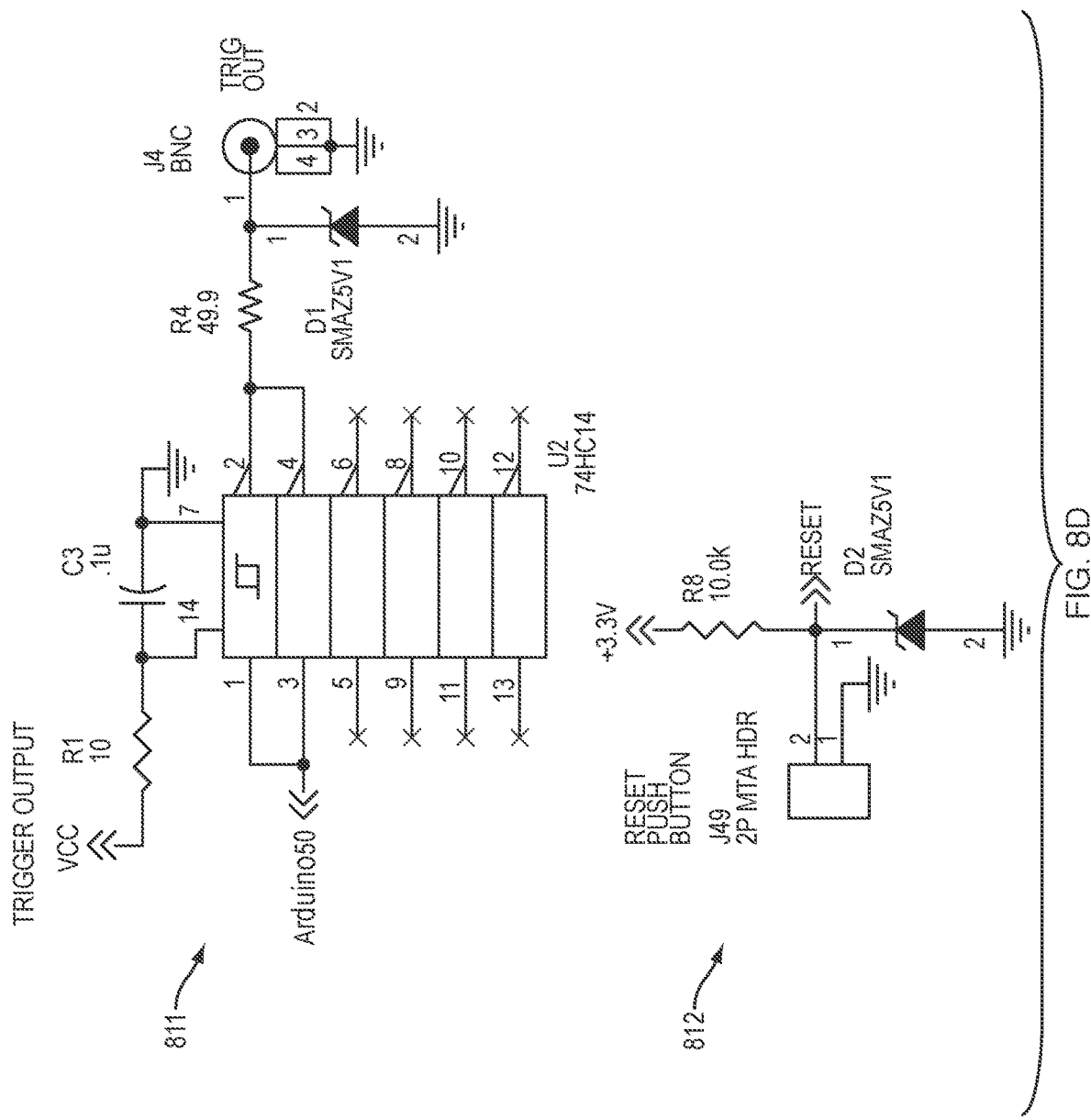
Figure 8E:
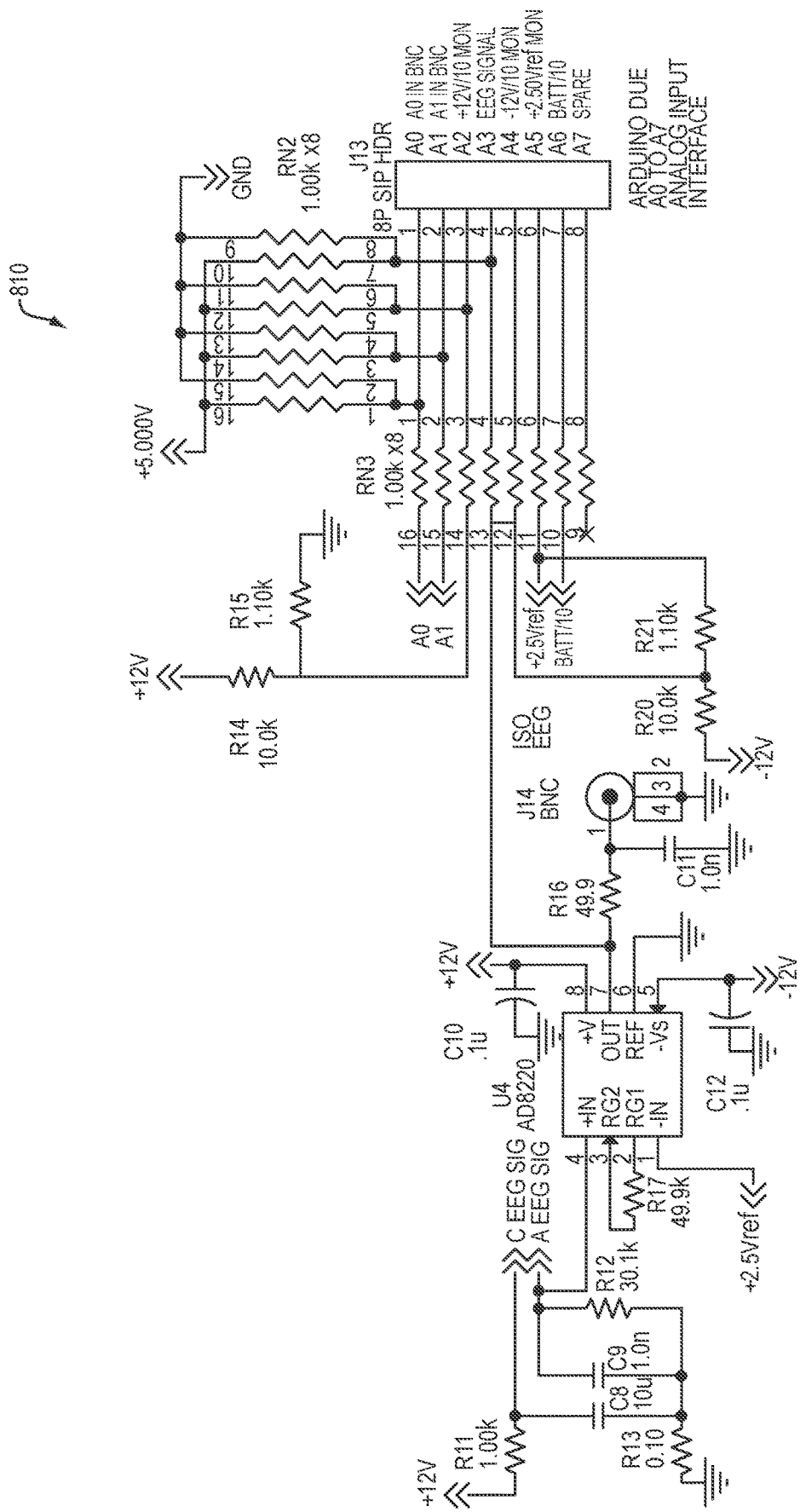

In this prototype, circuit 810 uses the Arduino® Due's built-in 12 bit multi-channel ADC to read analog signals. The signals include 2 external analog sources, +12V supply, EEG monitor, −12V supply, +2.5V supply, and the voltage of the optional 12V battery. (right) is a 1×8 strip of male header which connects with female header on the Due. Resistors arranged as voltage dividers ensure the Arduino® Due's built-in DAC only measures its allowed 0 to 3.3V voltage range. (left) is a BNC jack that allows external monitoring of the internal EEG's post-amplifier signal. An instrumentation amplifier prevents external monitors from loading the EEG. Circuit 810 is shown in FIG. 8E.

In this prototype, in circuit 811, a trigger BNC jack allows external stimulators or data loggers to be notified with a 0-5V digital signal from the Arduino® Due. An inverting Schmitt trigger ensures the digital output switches quickly between 0 and 5V. Circuit 811 is shown in FIG. 8D.

In this prototype, in circuit 812, a 1×2 male header allows the connection of a reset button or switch to reset the Arduino® Due. Circuit 812 is shown in FIG. 8D.

Figure 8F:
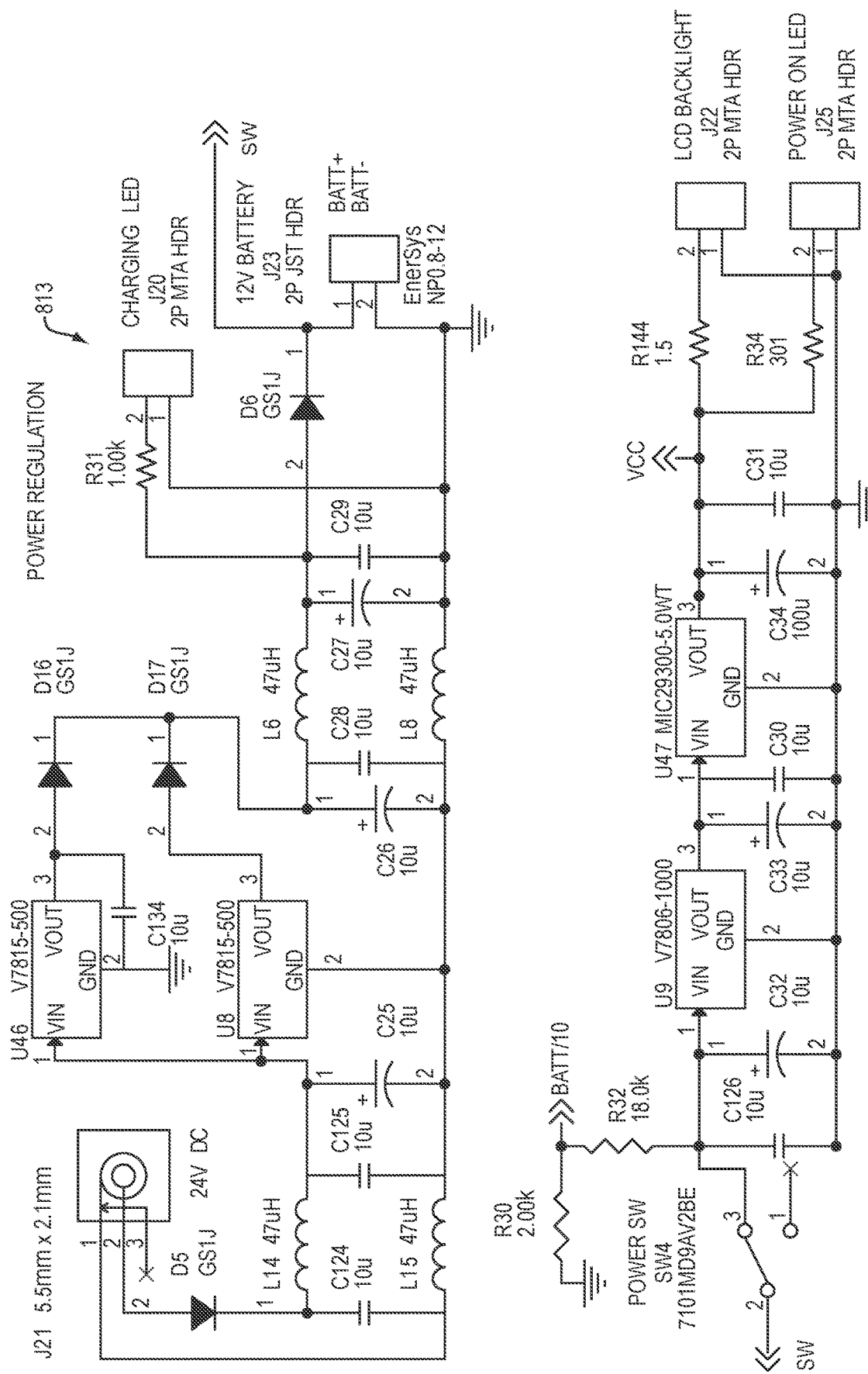

In this prototype, circuit 813 is the first portion of the primary power regulation circuit. Power is supplied via a barrel jack. The supplied voltage must be between 18-24V at 2 amps to run the system and charge an optional 12V lead-acid battery simultaneously. Otherwise, the supplied voltage may be 12-24V at 1.25 amps to run the system without the battery. The supplied voltage is regulated to produce +15V and +5V (labeled as VCC). A medical grade power supply may be connected to the barrel jack (e.g., when using this system with human subjects). LEDs are used as power-on indicators for the various voltages produced. Headers may be used to connect the optional battery, off-board power-on indicator LEDs, and the backlight of the LCD display. Circuit 813 is shown in FIG. 8F.

Figure 8G:
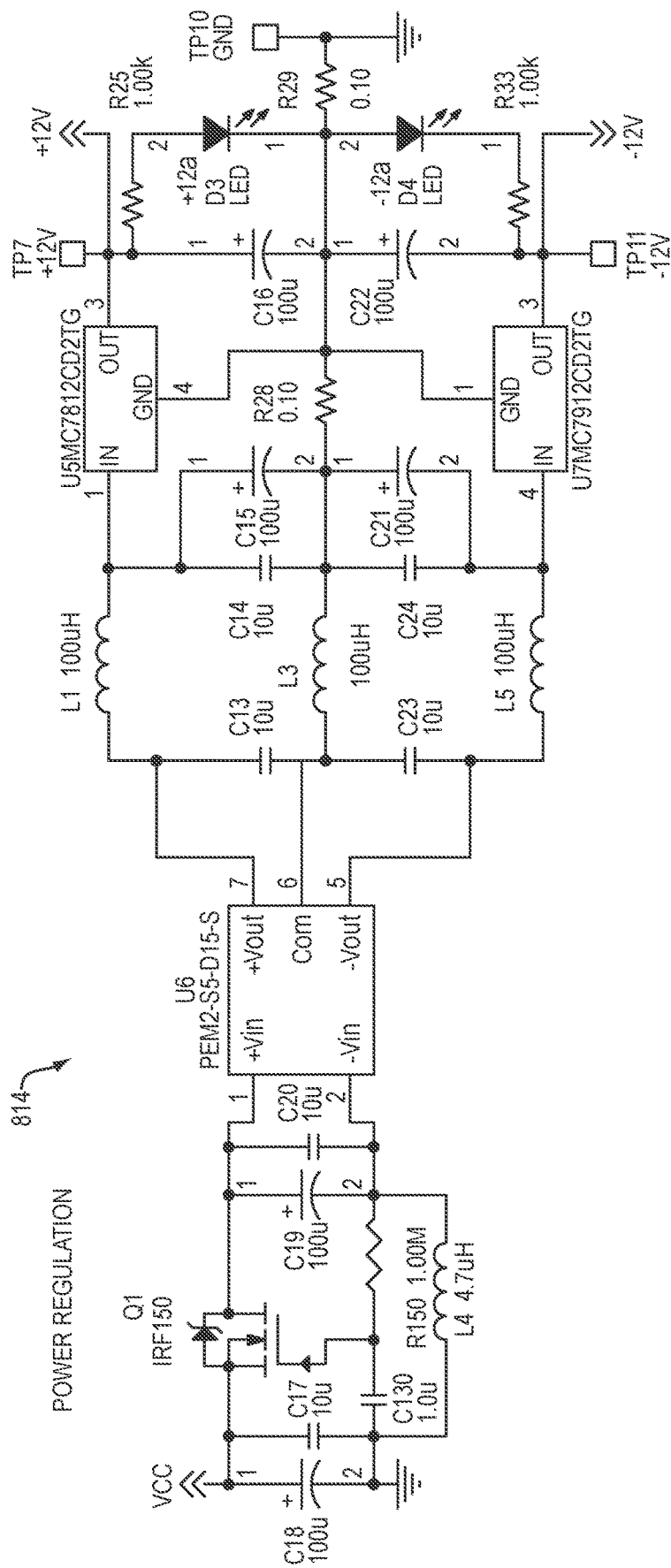

In this prototype, circuit 814 is the second portion of the primary power regulation circuit. VCC (+5V) from circuit 813 is regulated to produce +12V and −12V. LEDs are used as power-on indicators for the voltages produced. Circuit 814 is shown in FIG. 8G.

Figure 8H:
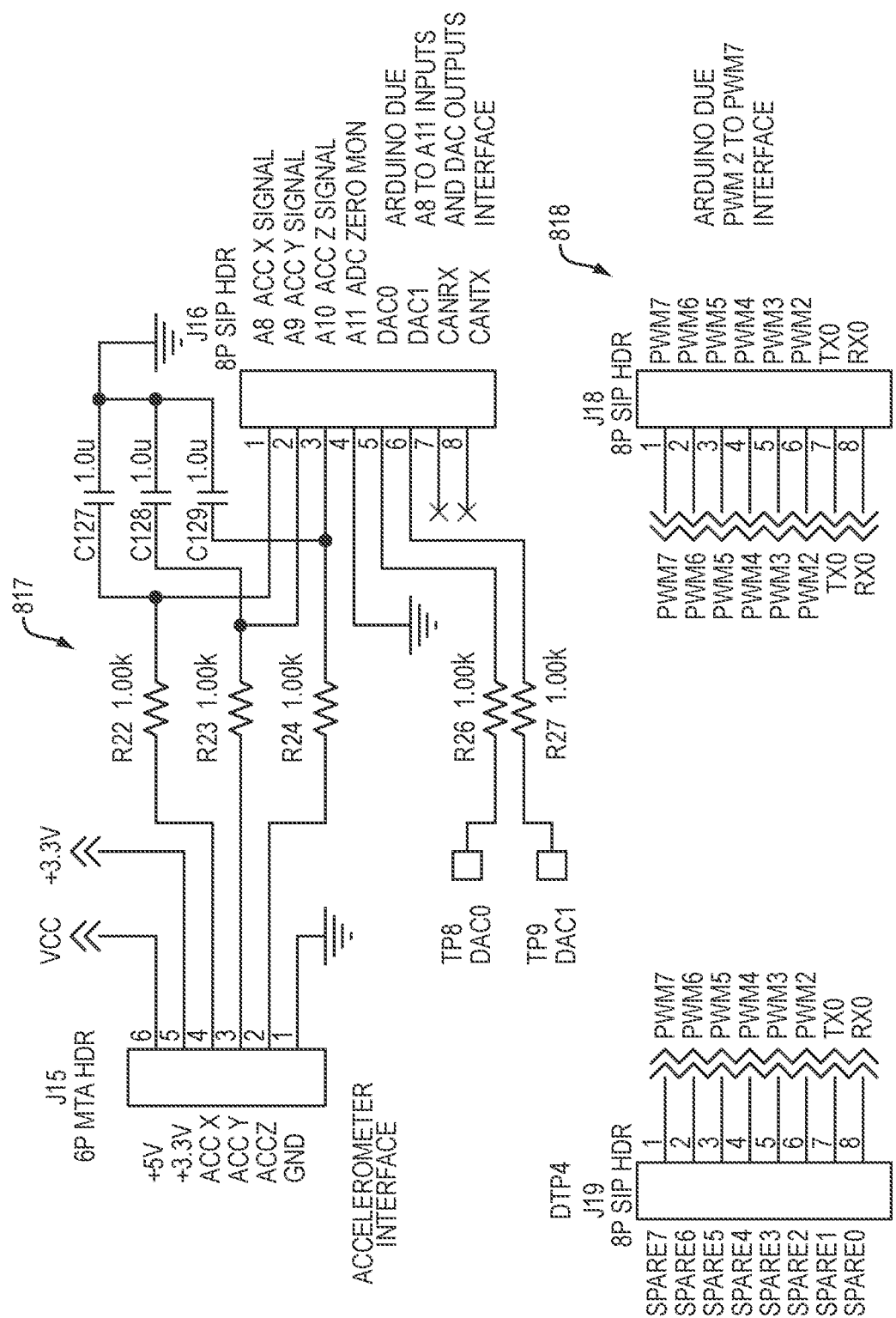

In this prototype, circuit 817 uses the Arduino® Due's built-in 12 bit multi-channel ADC, built-in 12 bit DACs (not used), and CAN bus (not used). (right) is a 1×8 strip of male header which connects with female header on the Arduino® Due. (left) is a 1×6 strip of male header which allows external analog sensors such as accelerometers, pressure, and breath sensors to be read by the Arduino® Due's built-in ADC. Circuit 817 is shown in FIG. 8H.

In this prototype, circuit 818 shows connections to the Arduino® Due that may be used to interface with digital circuits. (right) is a 1×8 strip of male header which connects with female header on the Arduino® Due. (left) is a 1×8 strip of male header as test points to probe the corresponding signal voltages at their interface to the Arduino® Due. Circuit 818 is shown in FIG. 8H.

Figure 9A:
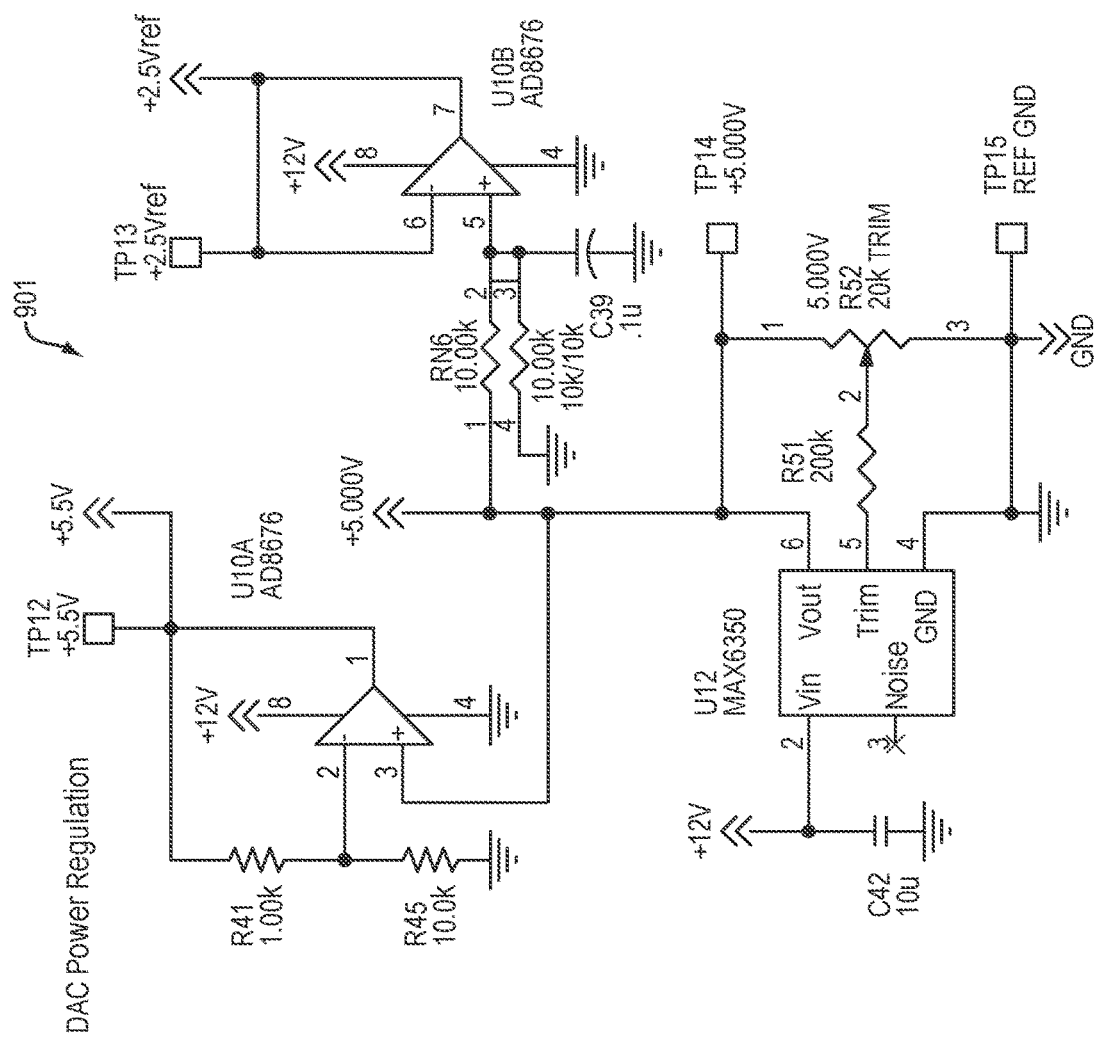

In this prototype, circuit 901 is the power regulation circuit for the 16 bit DAC (circuit 903) and its output scaling (circuit 905). +12V is taken from the primary power regulation circuit and converted to +5.5V, +5V, and +2.5V. The +2.5V is tied to the +2.5V from circuit 1106 to produce the 2.5V reference used across the system. Circuit 901 is shown in FIG. 9A.

Figure 9B:
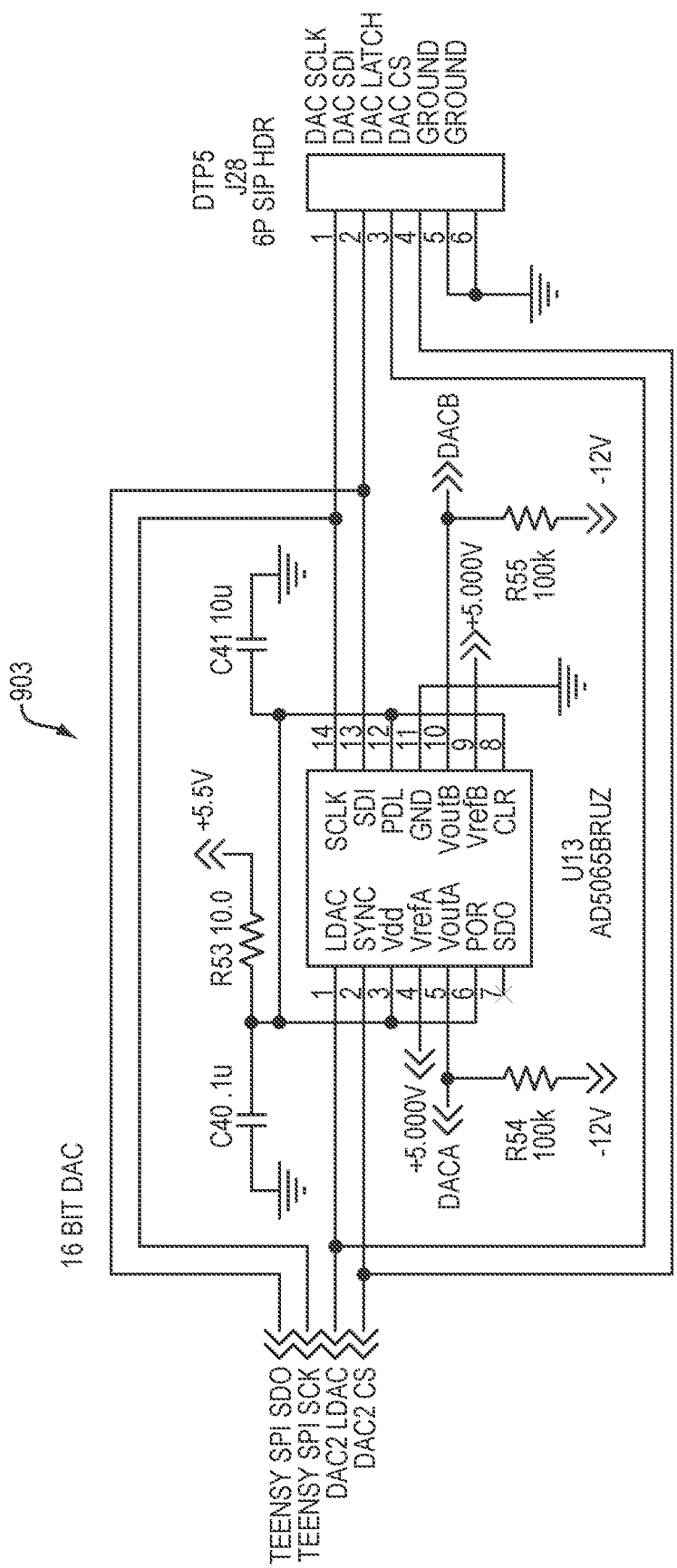

In this prototype, circuit 903 includes a 16 bit DAC, which allows for the control or signaling of external devices such as stimulators. Circuit 903 is shown in FIG. 9B.

Figure 9C:
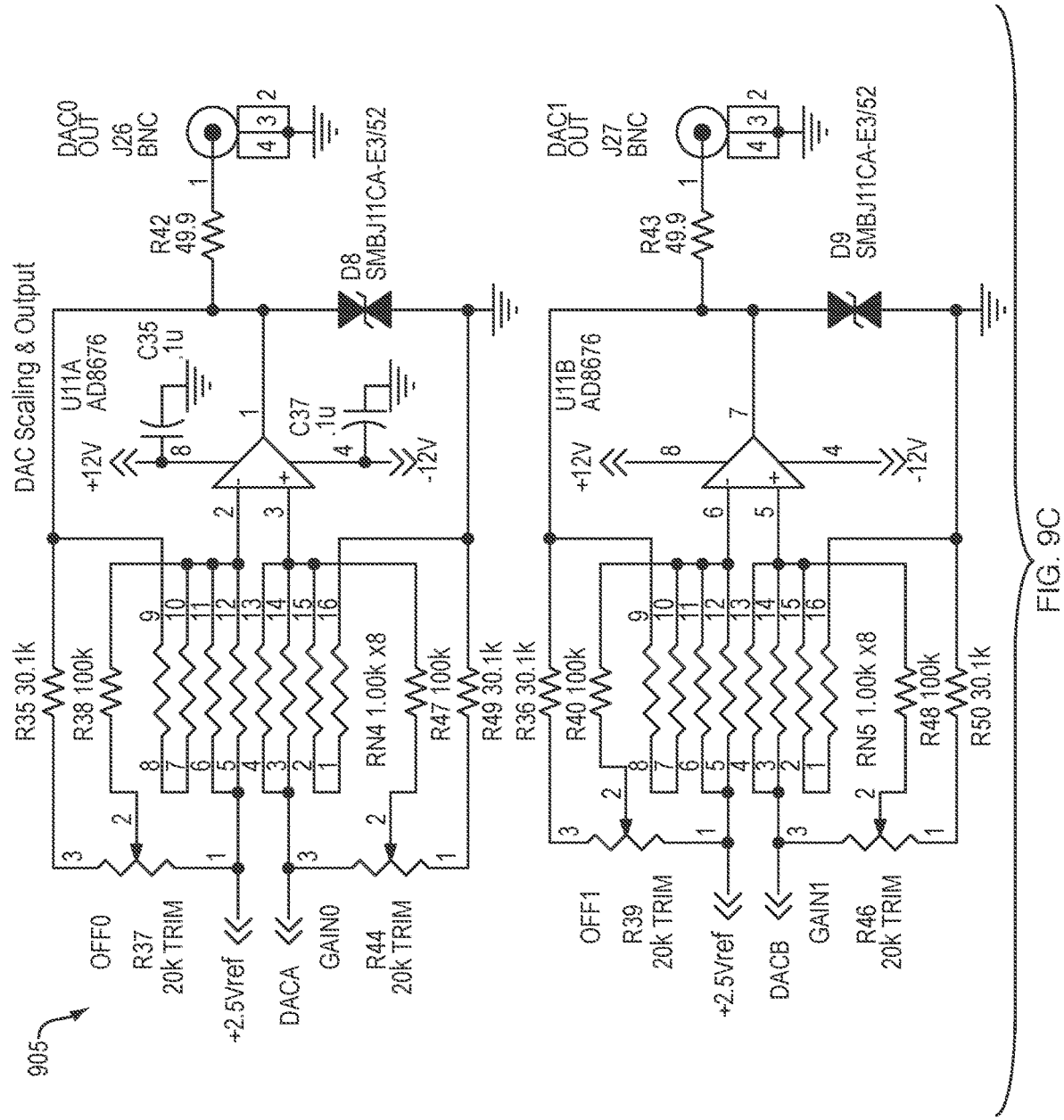

In this prototype, in circuit 905, a pair of amplifiers allow manual trimming of the output voltage of the 16 bit DAC (circuit 903) from 0 to 5V up to −12V to 12V. Circuit 905 is shown in FIG. 9C.

Figure 9D:
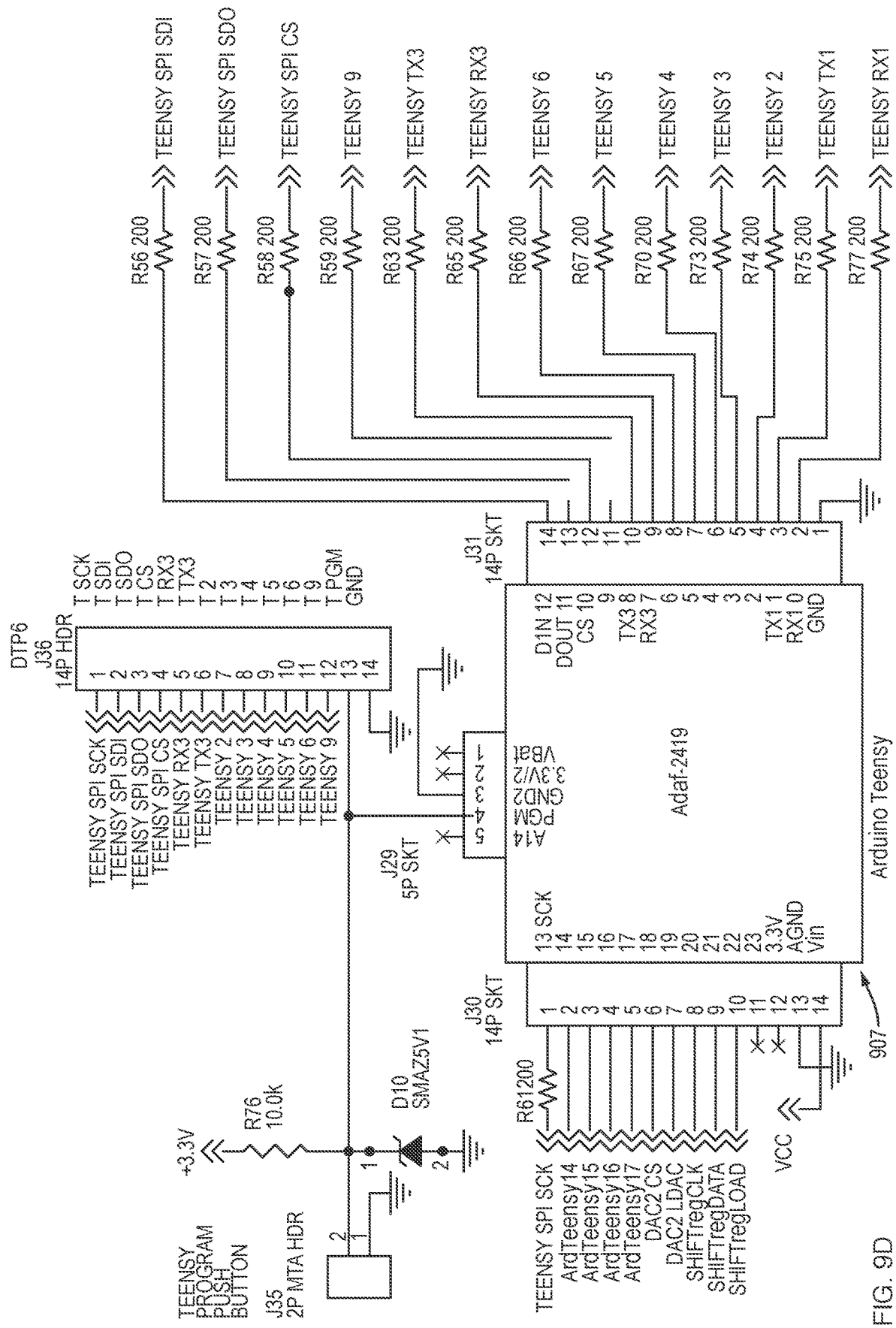

In this prototype, circuit 907 includes the interface for the Arduino® Teensy® and digital test points for the signals interfaced with the Teensy®. Circuit 907 is shown in FIG. 9D.

Figure 9E:
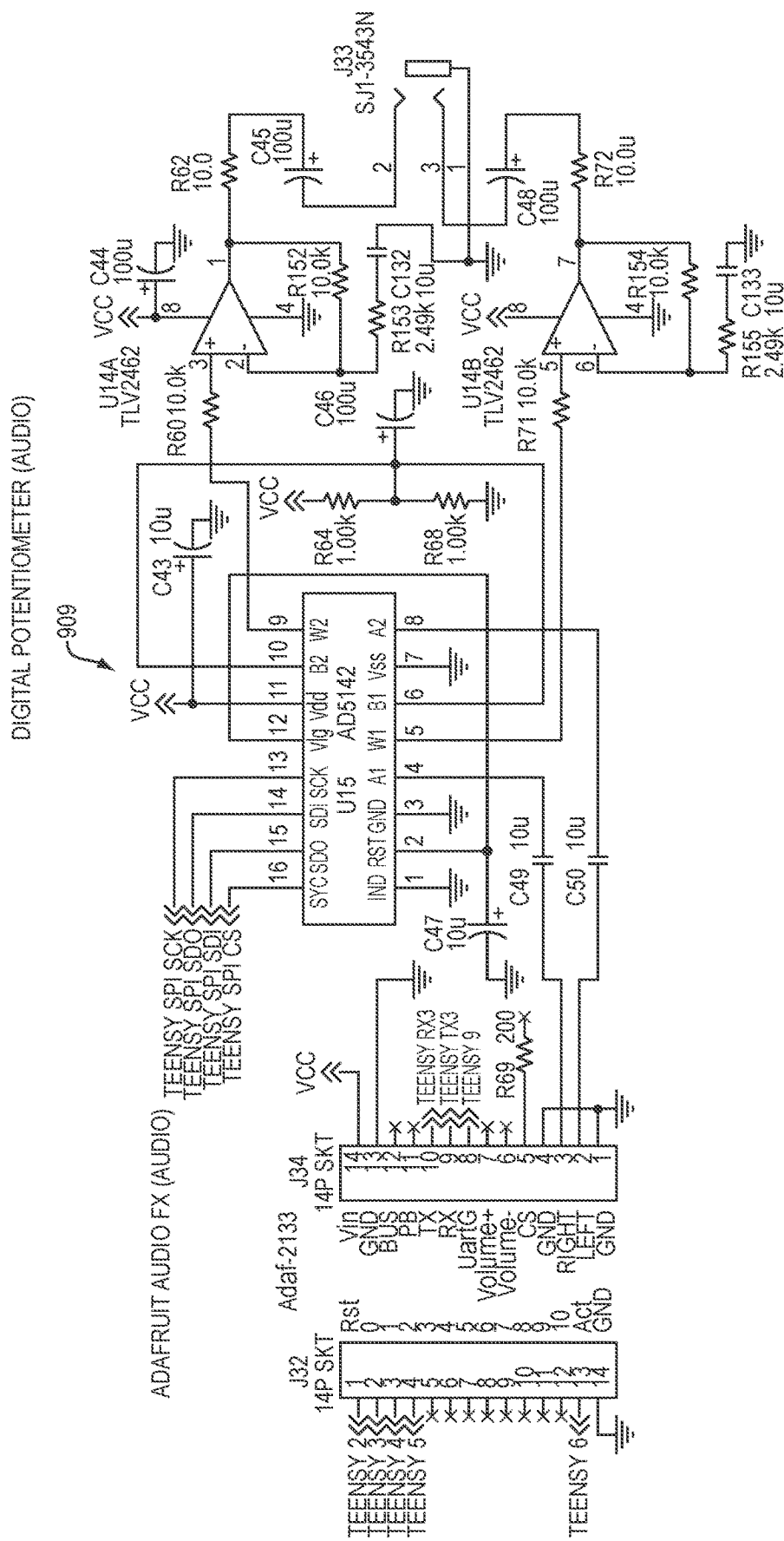

In this prototype, circuit 909 includes the Adafruit® Audio FX interface, a digital potentiometer, unity-gain amplifiers, and a 3.5 mm audio jack. The Adafruit® Audio FX is a programmatically controlled sound card which may play WAV or OGG files pre-loaded onto its internal memory via a USB cable. The stereo (2 signals) output of the sound card is then fed through a digital potentiometer which provides high-speed volume control. The signal is then isolated with amplifiers and connected to an audio jack for interfacing with external analog drivers, such as headphones. Circuit 909 is shown in FIG. 9E.

Figure 10A:
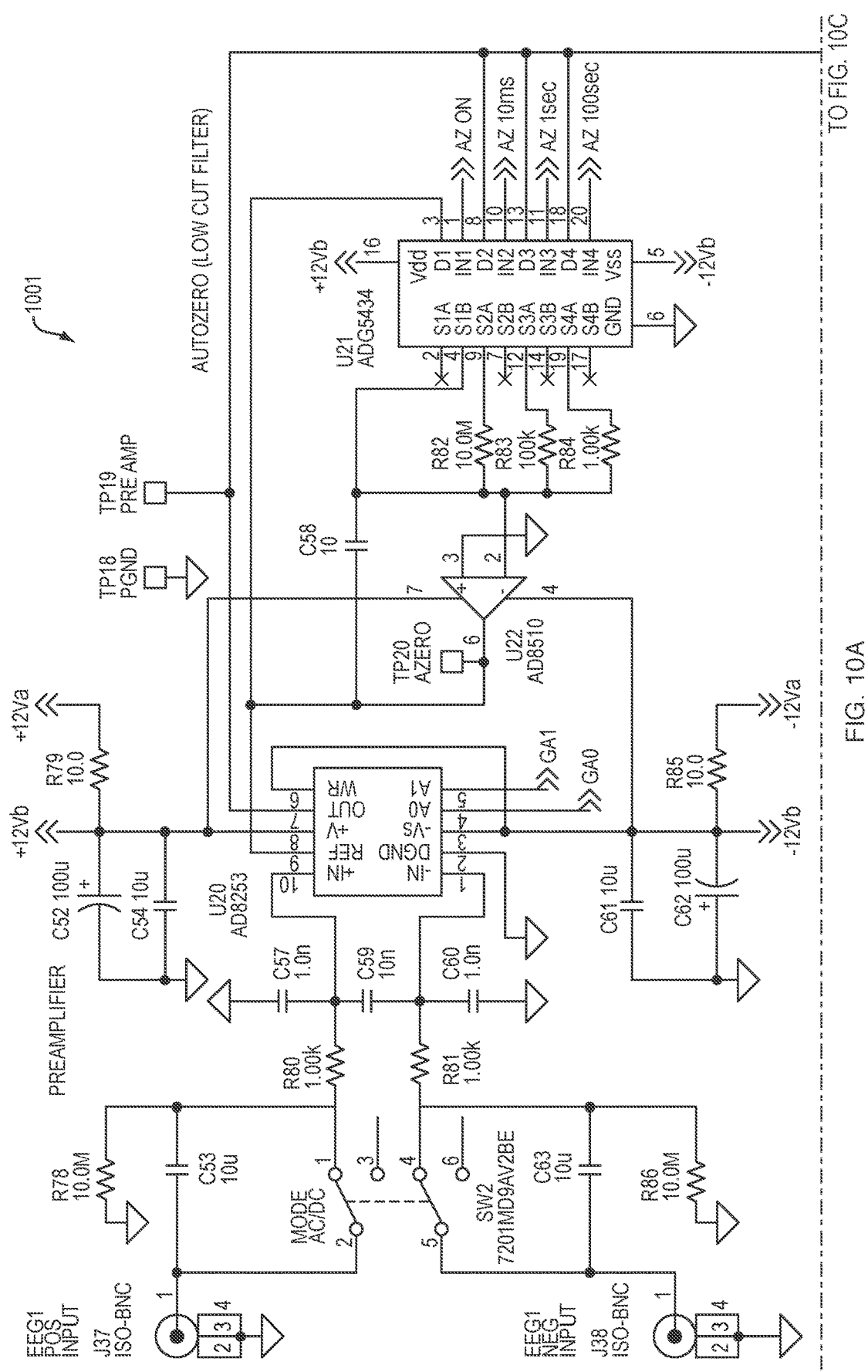

In this prototype, circuit 1001 comprises the first portion of the EEG's analog circuitry. 2 BNC Jacks allows for the connection of a differential pair of electrodes. The Fz electrode is typically connected to the positive BNC jack. The reference electrode is typically connected to the negative BNC jack. An additional ground electrode or any electrode shielding may be connected to analog ground through the coaxial ground provided by the BNC jacks. The input signals are then fed through a preamplifier followed by an auto zero circuit. The preamplifier allows for programmatic selection of gains 1×, 10×, 100×, and 1000×. The auto zero circuit is a low-cut or high-pass filter that allows for programmatic selection between filters with RC time constants of 100 milliseconds, 1 seconds, and 10 seconds. Circuit 1001 is shown in FIG. 10A.

Figure 10B:
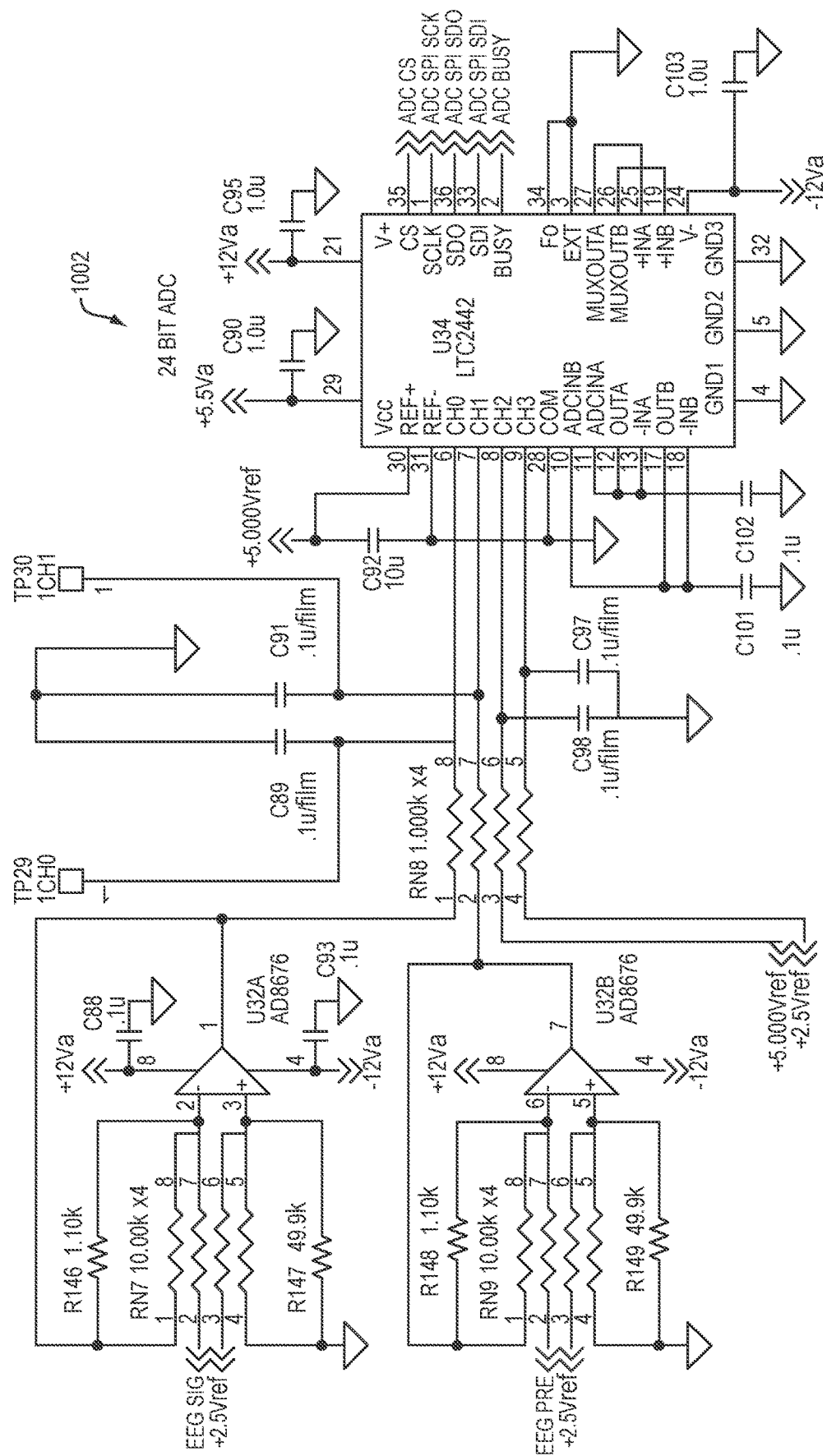

In this prototype, circuit 1002 comprises the fourth portion of the EEG's analog circuitry. The voltage levels coming out of the EEG's preamplifier, the EEG's amplifier, the +5V EEG reference, and +2.5V reference may be read programmatically by a 24 bit DAC. Typically, only the EEG's amplifier voltage is read. Circuit 1002 is shown in FIG. 10B.

In this prototype, circuit 1003 comprises the second portion of the EEG's analog circuitry. The signal from the preamplifier, from circuit 1001, is fed through a sequence of notch filters intended to remove the electrical noise common to operating close to AC power lines. Each filter has a pair of manual trim potentiometers to tune the filter. The "Line X1" filter is configured to filter 50 hz to 60 hz noise. The "Line X2" filter is configured to filter 100 hz to 120 hz noise from the second harmonic. Circuit 1003 is shown in FIG. 10C.

Figure 10D:
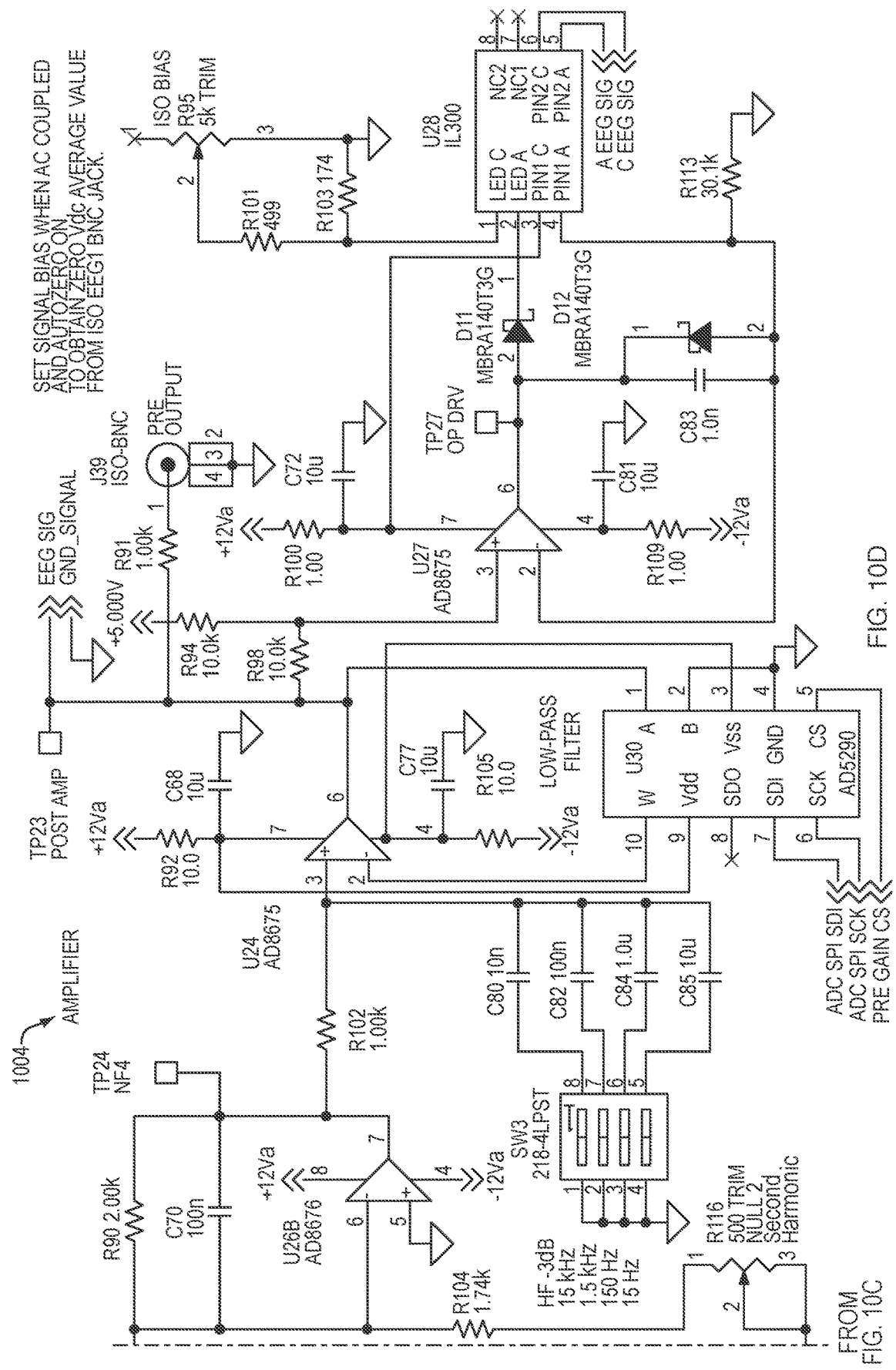

In this prototype, circuit 1004 comprises the third portion of the EEG's analog circuitry. The signal from power line filtering, circuit 1003, is fed into a low-pass filter, the amplifier, and an analog optical isolation circuit. The low-pass filter has a manual switch to allow selection between 15 kHz, 1.5 kHz, 150 Hz, and 15 Hz cut-off frequencies. The amplifier uses a programmatically tunable digital potentiometer to control its gain from 1-10×. The optical isolation circuit allows the amplifier's analog output signal to be measured externally without introducing external noise. Circuit 1004 is shown in FIG. 10D.

Figure 11A:
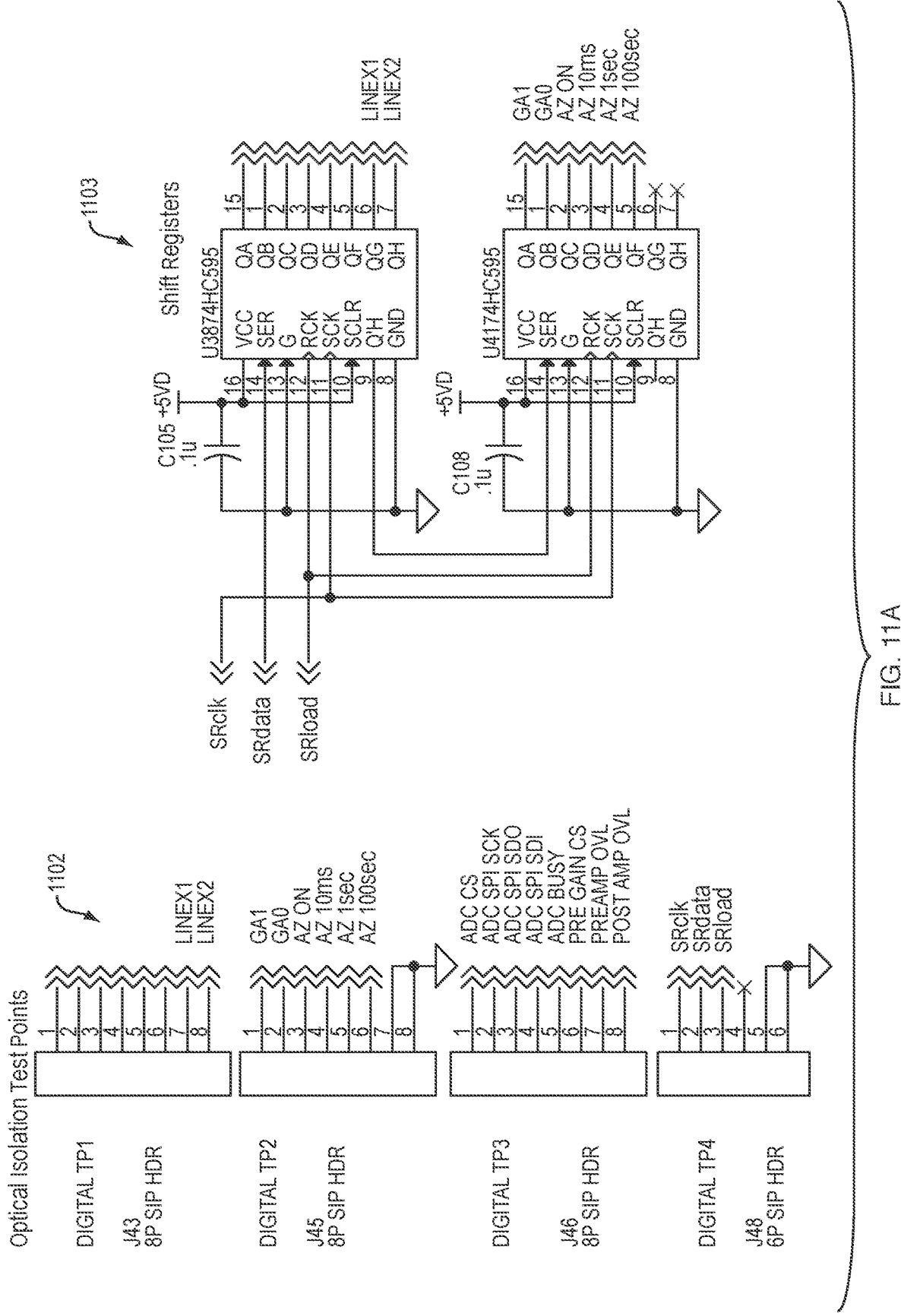
Figure 11B:
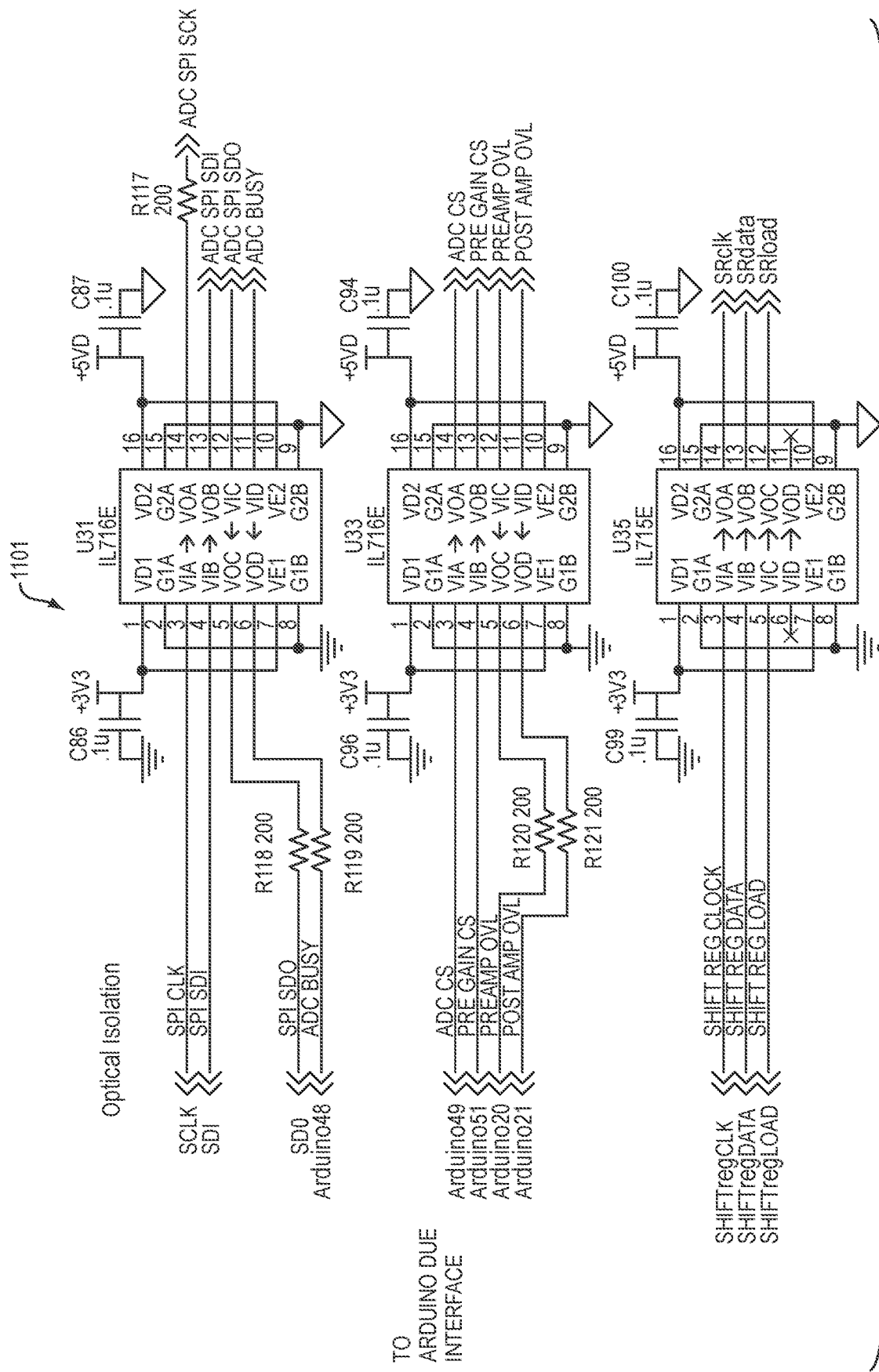

In this prototype, in circuit 1101, a set of three optical isolators provide electrical isolation between the EEG's analog circuitry and the digital processing provided by the Arduino® Due and Arduino® Teensy®. Circuit 1101 is shown in FIG. 11B.

In this prototype, in circuit 1102, a set of single row male header as test points to probe the circuit signals. Circuit 1102 is shown in FIG. 11A.

In this prototype, in circuit 1103, a pair of shift registers, allowing 3 digital lines from the Arduino® Teensy® *SRclk", "SRdata", "SRload" to control 8 digital lines. The shift register reduces the number of optical isolators needed to partition the Teensy® from the analog circuitry. Circuit 1103 is shown in FIG. 11A.

Figure 11C:
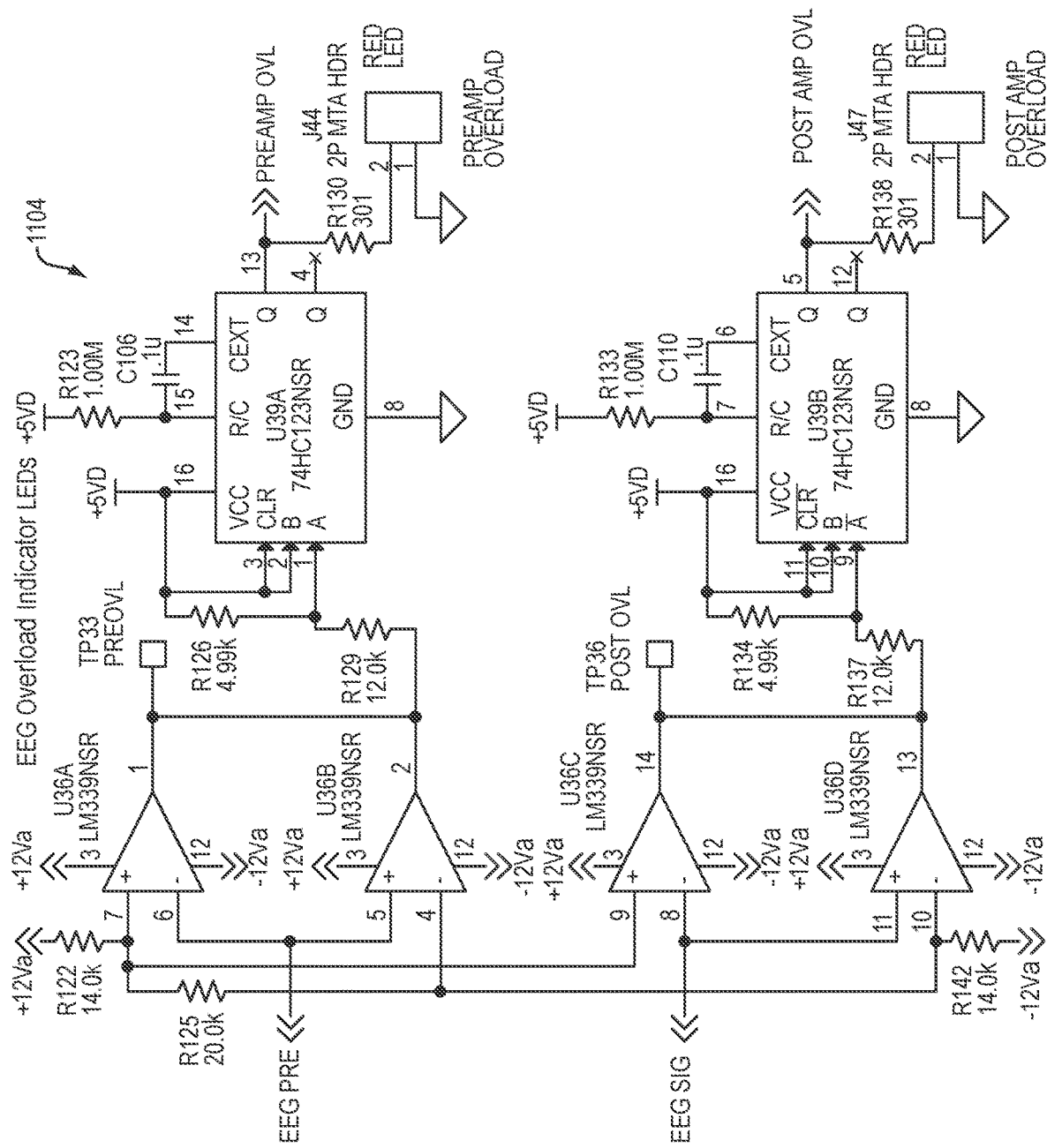

In this prototype, circuit 1104 monitors for overvoltage and undervoltage on two of the EEG's signals: after preamplification and again after amplification. If an overvoltage or undervoltage condition is detected on the signal, a 5V signal is produced which powers an LED indicator through the provided headers and may be measured by circuit 905. Circuit 1104 is shown in FIG. 11C.

Figure 11D:
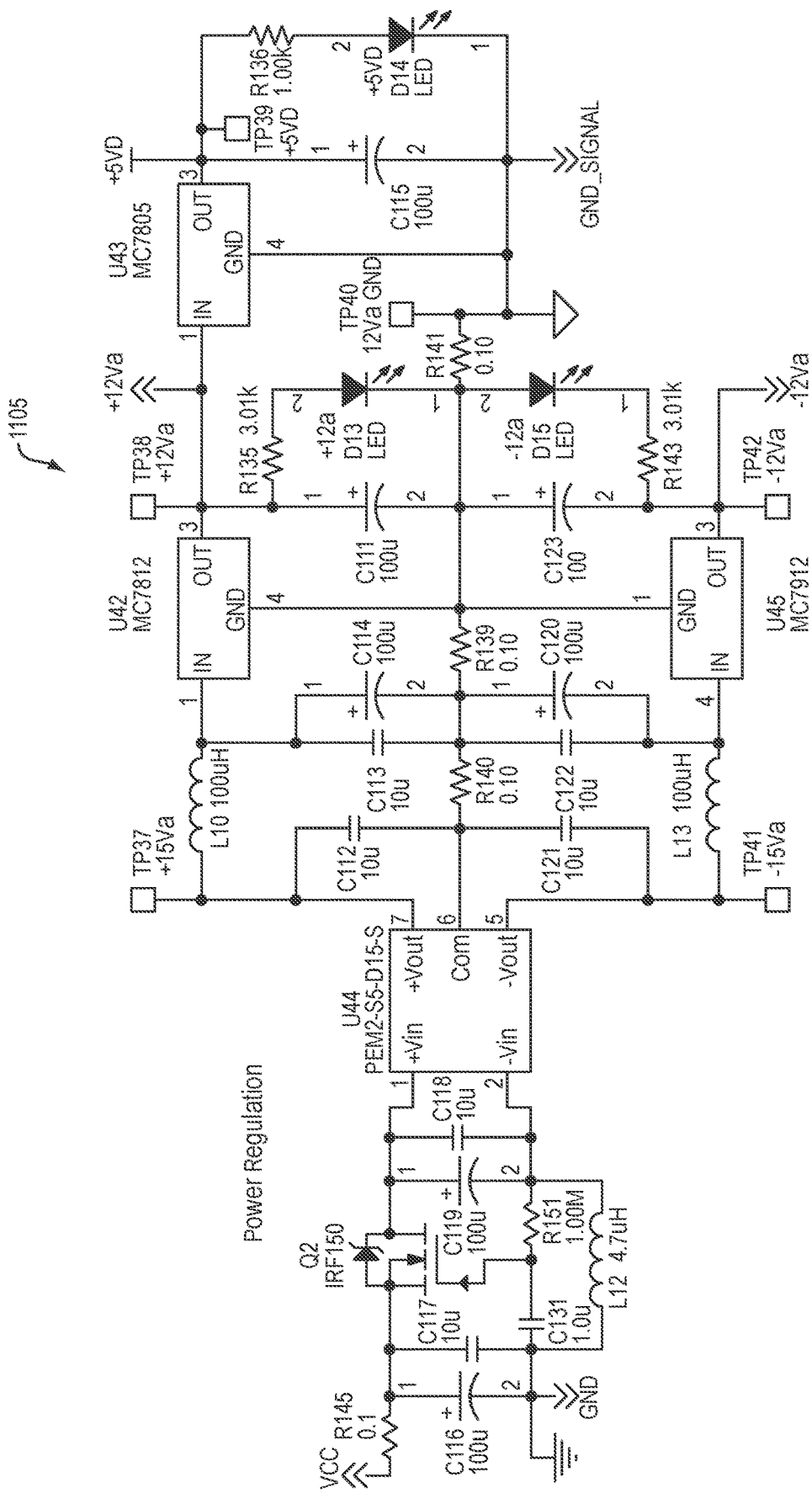

In this prototype, circuit 1105 is one of two power regulation circuits for the analog circuitry of the EEG. VCC (+5V) is taken from the primary power regulation circuit and converted to +12V, −12V, and +5V. Circuit 1105 is shown in FIG. 11D.

Figure 11E:
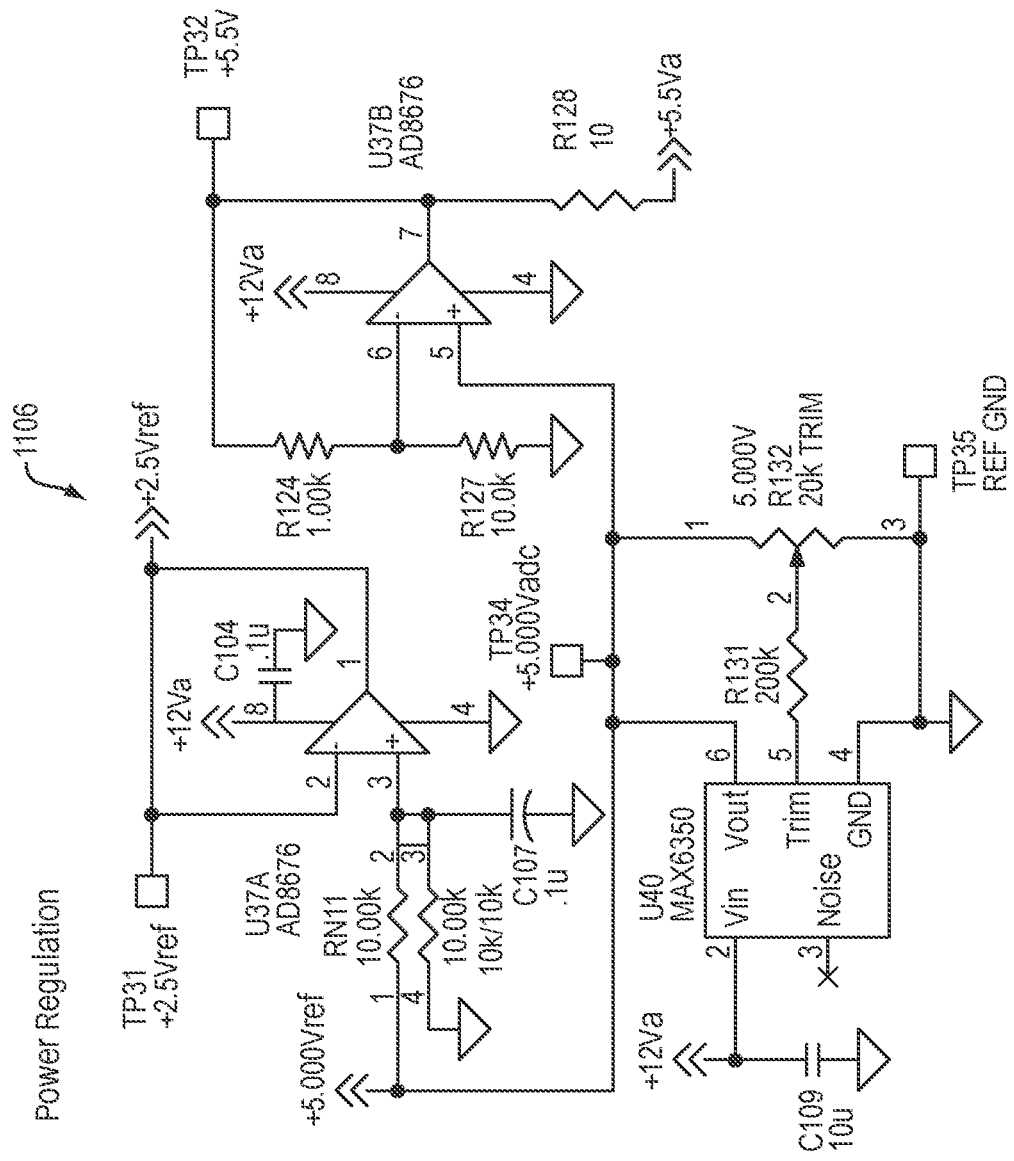

In this prototype, circuit 1106 is one of two power regulation circuits for the analog circuitry of the EEG. +12V is taken from circuit 1105 and converted to +5.5V, +5V, and +2.5V. The +2.5V is tied to the +2.5V from circuit 901 to produce the 2.5V reference used across the system. Circuit 1106 is shown in FIG. 11E.

In the schematics for this prototype, circuit components labeled "DTP" or "Digital TP" stand for "Digital Test Points". These are male header intended for probing and debugging purposes and are not typically connected to another component.

The prototype described in the preceding 31 paragraphs is a non-limiting example of this invention. This invention may be implemented in many other ways.

Endpoint-Corrected Hilbert Transform

In some implementations of this invention, a neuromodulator accurately measures—in real time and over a range of frequencies—the instantaneous phase and amplitude of a natural signal. For example, the natural signal may be an electrical signal produced by neural tissue. The neuromodulator may generate signals that are precisely timed relative to the phase of the natural signal. For example, the neuromodulator may generate stimuli that are phase-locked with the natural signal. Or, for example, the neuromodulator may generate an exogenous signal that comprises short bursts which occur only during a narrow phase range of each period of an oscillating natural signal. The neuromodulator may correct distortions due to Gibbs phenomenon. In some cases, the neuromodulator does so by applying a causal filter to a discrete Fourier transform in the frequency domain, prior to taking an inverse discrete Fourier transform.

This ability to take accurate, real-time measurements of instantaneous phase and amplitude of a natural signal is highly advantageous. It enables the neuromodulator to generate signals ("exogenous signals") that are precisely timed relative to the phase of the natural signal. For example, the neuromodulator may generate an exogenous signal that is phase-locked with the natural signal. Or, for example, the neuromodulator may generate an exogenous signal that comprises short bursts which occur only during a narrow phase range of each period of an oscillating natural signal.

In some implementations of this invention, the neuromodulator (a) detects the instantaneous phase and amplitude of the natural signal in real time and (b) based on that instantaneous phase and amplitude, precisely controls timing of the exogenous signal relative to the phase of the natural signal, in order to achieve a desired neuromodulation effect.

In order to understand why the present invention is able to take accurate real-time measurements of instantaneous phase and amplitude of a sensor signal, it is helpful to consider challenges involved in computing these instantaneous attributes.

The estimation of instantaneous attributes of a real-valued periodic signal (e.g., amplitude, phase and frequency) may be done efficiently with a version of the signal, known as the analytic signal. The analytic signal is complex (in the sense of complex numbers with real and imaginary parts). The real part of the analytic signal is the given real-valued signal and the imaginary part of the analytic signal is its Hilbert transform.

A popular, conventional strategy for computing the analytic signal and the Hilbert transform signal is: (a) to compute a discrete Fourier transform (DFT) of the real-valued signal and thus to represent the signal in the frequency domain; (b) to manipulate the frequency domain representation to remove the negative frequencies; and then (c) to construct the complex analytic signal using the inverse discrete Fourier transform (IDFT).

This popular strategy suffers from distortion, known as the Gibbs phenomenon, at the ends of the sample data resulting in erroneous estimations of the most recent attributes. Specifically, the Gibbs phenomenon distortion in the analytic signal stems from the properties of the DFT-IDFT process that converts the sampled time domain data into its frequency domain representation and then reconstructs a time domain signal. As long as the signal satisfies the Dirichlet conditions (most practical signals), the DFT-IDFT recovers any point of the original signal apart from points of "jump-discontinuity", where the Fourier series converges to the midpoint (average value of the discontinuity). The DFT produces a frequency domain representation of a discrete, finite time signal as if the signal were repeated periodically. Thus, if the last and first time-points of the signal do not have the same phase and are not continuously differentiable, the DFT encounters a jump-discontinuity between the signal ends In the frequency domain, the jump-discontinuity is represented with a spreading out of the spectrum over many frequencies. The result is an analytic signal and a Hilbert transform signal with erroneous amplitude and phase near the last and first sample points.

In some implementations of this invention, the neuromodulator corrects distortion due to the Gibbs phenomenon by performing an algorithm that we loosely call Endpoint-corrected Hilbert transform (ECHT).

In some cases, the neuromodulator corrects the Gibbs phenomenon by performing what we call "frequency domain" ECHT or by performing what we call "front-padded time domain" ECHT. Both of these approaches may correct the Gibbs phenomenon by ensuring that a signal will be continuous and differentiable at the original end of the signal when a replica of the signal is appended to the signal, as occurs in the DFT of a finite signal. In "frequency domain" ECHT, the neuromodulator performs a DFT to calculate a frequency domain representation of a signal. The neuromodulator then applies a causal filter to the frequency domain representation, prior to an IDFT step. In "front-padded time domain" ECHT, the neuromodulator may front-pad the signal with a copy of an end segment of the signal, then apply a causal filter to the padded signal, and then remove the added segment in the time domain, prior to the DFT and IDFT steps. In both of these approaches, the correction is made before the IDFT step that results in an analytic signal. The neuromodulator may selectively deform the beginning of the signal either in the frequency domain (in "frequency domain" ECHT) or in the time domain (in "front-padded time domain" ECHT) and not deform the end of the signal. In both "frequency domain" ECHT and "front-padded time domain" ECHT, the value of the end of the signal is not changed, but the value of the beginning of the signal is changed, such that the value of the signal at the beginning and end of the signal is the same. Thus, in some cases, if a replica of the signal is appended to the signal at the original end of the signal, the appended signal is continuously differentiable at the original end of the signal. By removing the jump discontinuity at that point, the neuromodulator may eliminate (or significantly reduce) the Gibbs phenomenon distortions at the end of the analytic signal that results from taking an IDFT. This may allow a computer to accurately calculate instantaneous phase and instantaneous amplitude at the end of the analytic signal (which corresponds in time to the end of the original signal).

In some cases, the neuromodulator corrects the Gibbs phenomenon by performing what we call "end-padded time domain" ECHT. In this approach, in some cases, the neuromodulator appends a segment of data values (e.g., zeros) of at least one period length to the end of the signal and then applies a causal filter, which has the directionality property, to make the padded signal continuous and differentiable at the endpoint of the original signal without deforming the original end of the signal. By pushing away the end of the padded signal from the original end before the DFT procedure, the neuromodulator may ensure that the Gibbs distortion occurs away from the original end of the signal. Again, this may allow a computer to accurately calculate instantaneous phase and instantaneous amplitude at t_now (the point in the analytic signal that corresponds in time to the end of the original signal).

ECHT may maintain the same complexity class as the Hilbert transform, with worse case running time of O(n log(n)) for n samples. Thus, ECHT is suitable for real-time computation of instantaneous attributes.

Figure 12:
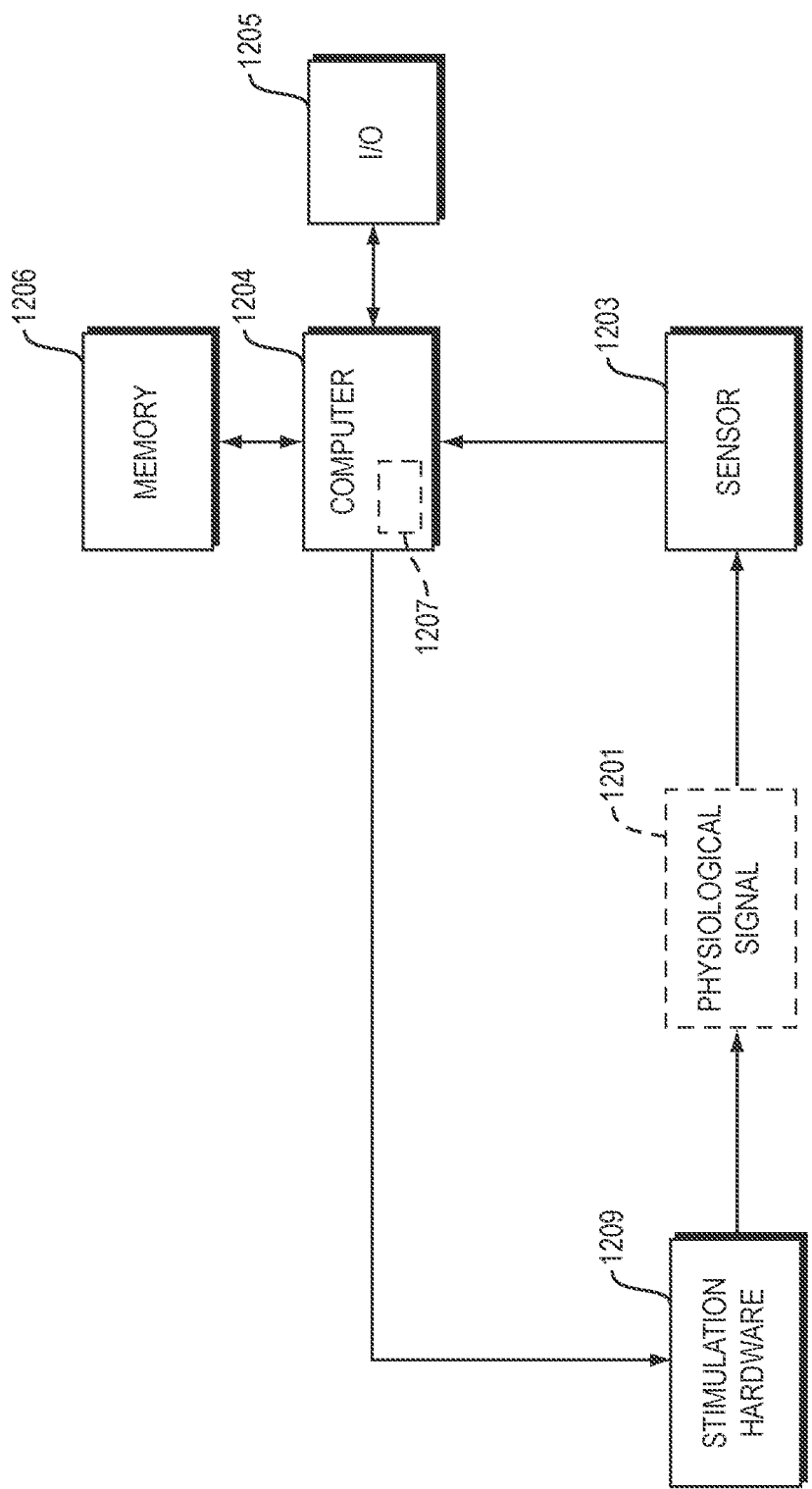
FIG. 12 shows hardware for accelerating sleep onset, using neuromodulation with an endpoint-corrected Hilbert Transform ("ECHT").

FIG. 12 shows hardware for accelerating sleep onset, using neuromodulation with an endpoint-corrected Hilbert Transform ("ECHT"). In the example shown in FIG. 12, a physiological signal 1201 (such as brain neural signal) occurs in a human user. A sensor 1203 takes sensor readings of the physiological activity 3. A computer 1204 performs what we call an Endpoint-Corrected Hilbert Transform (ECHT) calculation. In this ECHT calculation, computer 1204 determines in real time, based on the sensor readings, the instantaneous phase and instantaneous amplitude of the physiological signal. Computer 1204 also performs a control algorithm. In this algorithm, the computer takes the instantaneous phase and amplitude as an input, and outputs signals to control stimulation hardware 1209. This stimulation hardware may output a neuromodulation signal. For example, the neuromodulation signal may comprise an electrical signal, magnetic signal, light signal, ultrasound signal or haptic signal. The neuromodulation signal may directly or indirectly affect neural activity of the human user, and thus modifies the physiological signal 1201. In FIG. 12, a user may enter input and receive output from, computer 1204 via one or more I/O (input/output) devices. For example, in some cases, I/O devices 1205 comprise one or more of the following: touch screens, cameras, microphones, speakers, accelerometers, gyroscopes, magnetometers, inertial measurement units, pressure sensors, touch sensors, capacitive sensors, buttons, dials, sliders, transducers (e.g., haptic transducers), graphical user interfaces, electronic display screens, and projectors. Computer 1204 may store data in, and access data from, memory device 1206. Computer 1204 may include or may interface with a wireless communication device, in order to send or receive wireless communications to or from other devices.

Figure 13:
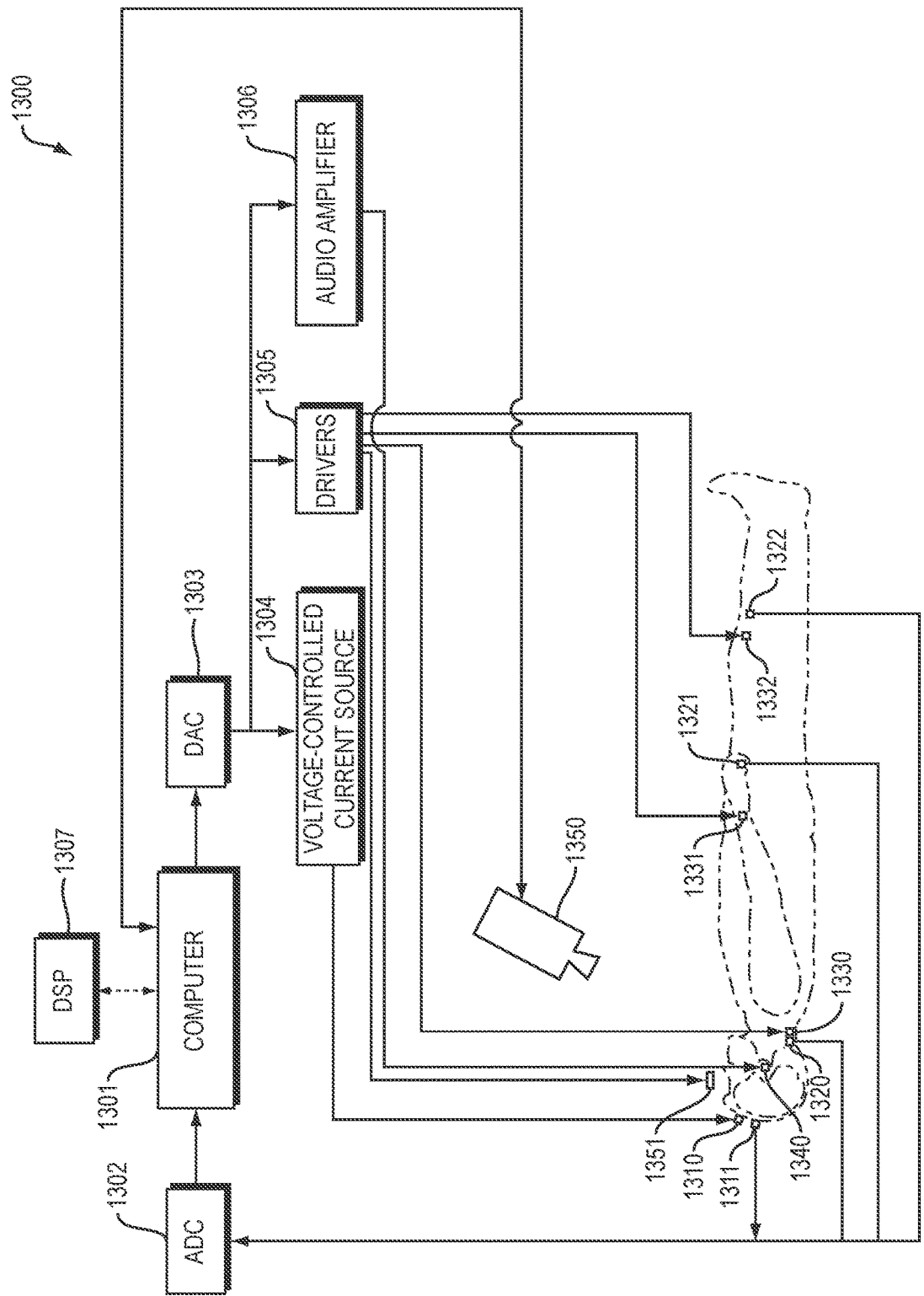
FIG. 13 is a diagram of hardware for neuromodulation using ECHT.

FIG. 13 is a diagram of a neuromodulator 1300, in an illustrative implementation of this invention. In the example shown in FIG. 13, the neuromodulator includes sensors 1310, 1320, 1321, 1322, an ADC (analog-to-digital converter) 1302, a computer 1301, a DSP (digital signal processor) 1307, a DAC (digital-to-analog converter) 1303, a VCCS (voltage controlled current source) 1304, drivers 1305, and an audio amplifier 1306. The DSP is optional. In some cases, computations are performed by a microcontroller, without using a DSP.

In the neuromodulator shown in FIG. 13, sensors record one or more physiological signals. For example: (a) one of more external electrodes 1310 may take EEG (electroencephalography) measurements of neural activity; (b) motion sensors 1320, 1321, 1322 may take measurements of motion of a limb or other body part of the user; and (c) one or more cameras (e.g., 1350) may capture video images of the motion. For example, each of the motion sensors 1320, 1321, 1322 may comprise a three-axis digital gyroscope and three-axis digital accelerometer. In some cases, sensors (such as EEG sensor 1310 and motion sensors 1320, 1321, 1322) may output analog signals that encode measurements taken by the sensors. In some cases, sensors (such as camera 1350) may output digital signals that encode sensor measurements. For the sensors that output analog signals, an ADC (analog-to-digital converter) 1302 may convert these analog signals into digital signals.

In the neuromodulator shown in FIG. 13, a computer 1301 takes sensor readings as an input, in digital form. Computer 1301 may perform an ECHT algorithm to determine the instantaneous phase and amplitude of one or more physiological signals (e.g., neural activity). Computer 1301 may also interface with a DSP (digital signal processor) 1307 that processes incoming and outgoing digital signals. Computer

1301 may output digital signals. A DAC (digital-to-analog converter) 1303 may convert these digital signals to analog signals.

In the neuromodulator shown in FIG. 13, an analog voltage signal produced by a DAC 1303 may control a VCCS (voltage-controlled current source) 1304, which in turn may output an electrical current that is delivered to a user via one or more electrodes. For example, external electrode 1311 may deliver transcranial electrical stimulation to the brain of the user. Electrodes for delivering electrical stimulation may be placed in any position on the head or skin of the user or may be implanted inside a user. The electrical current that is delivered to the user via these one or more electrodes may comprise an electrical neuromodulation signal.

In some cases, the VCCS includes one or more OTAs (operational transconductance amplifiers) or operational amplifiers. In some cases, the VCCS is a component of a bi-phasic current source, such as a Digitimer® DS4 Bi-phasic Stimulus Isolator.

In the neuromodulator shown in FIG. 13, one or more analog signals from a DAC 1303 may control one or more drivers 1305. The drivers 1305 may in turn control one or more transducers that output a signal that affects neural activity in the user. For example, the transducers may include one or more light sources 1351 that display visual neuromodulation signals to a user. For instance, light sources 1351 may comprise (i) a computer screen, virtual reality screen, augmented reality display, or other electronic display screen, or (ii) an array of LEDs (light-emitting diodes). In some cases, the transducers may include one or more haptic transducers 1330, 1331, 1332 for delivering tactile/haptic neuromodulation signals to a user.

In the neuromodulator shown in FIG. 13, one or more analog signals from a DAC 203 may control one or more audio amplifiers 1306. The amplifiers 1306 may in turn control one or more audio transducers (e.g., 1340). For example, the audio transducers may include one or more headphones, earbuds, earphones, bone conduction transducers, or speakers that deliver audible neuromodulation signals.

FIG. 14A shows an electrode 1401 that both delivers a neuromodulation electrical signal to neural tissue and detects electrical activity produced by neural tissue, in an illustrative implementation of this invention. For example, the operation of electrode 1401 may be time-multiplexed, such that electrode 1401 takes sensor readings at different times than when it delivers electrical stimulation.

In FIGS. 14A, 14B, 14C, 15A, 15B and 16: (a) each arrow 1410 signifies that sensor readings are being output by a sensor; and (b) each arrow 1411 signifies that a signal (e.g., an electrical signal from DAC 1303, VCCS 1304, drivers 1305 or audio amplifier 1306) is being delivered to stimulation hardware.

FIG. 14B shows an implantable electrode 1403 and an external recording electrode 1310, in an illustrative implementation of this invention. For example, the implantable electrode 1403 may stimulate brain tissue (cortex or deeper), or record neural activity, or both. The implantable electrode 1403 may be used alone or together with external recording electrode 1310. For example, the recording electrode 1310 may record neural activity that has been affected by stimulation from implantable electrode 1403.

FIG. 14C shows four external electrodes 1431 for transcutaneous stimulation, in an illustrative implementation of this invention. In the example shown in FIG. 14D, the electrodes 1431 are positioned on the skin of the back 1430 of a user.

Figure 15B:
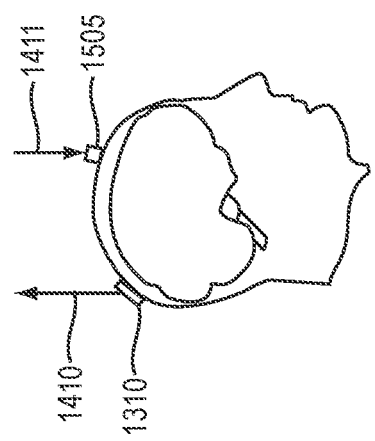
FIG. 15B shows an ultrasound transducer and an external recording electrode.
Figure 15A:
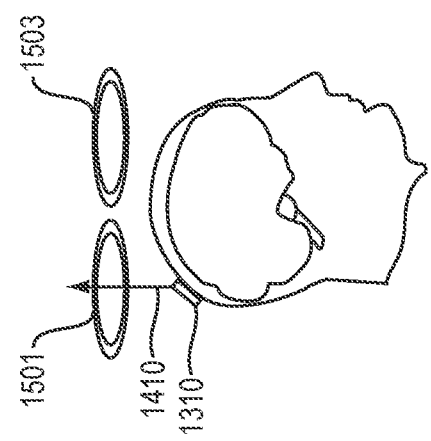
FIG. 15A shows magnetic coils for magnetic stimulation and an external recording electrode.

FIG. 15A shows magnetic coils 1501, 1503 for magnetic stimulation and an external recording electrode 1310, in an illustrative implementation of this invention. In the example shown in FIG. 15A, magnetic coils 1501, 1503 deliver magnetic stimulation to the brain of a user.

FIG. 15B shows an ultrasound transducer 1505 and an external recording electrode 1310, in an illustrative implementation of this invention. In the example shown in FIG. 15B, ultrasound transducer 1505 delivers ultrasound stimulation to the brain of a user.

Figure 16:
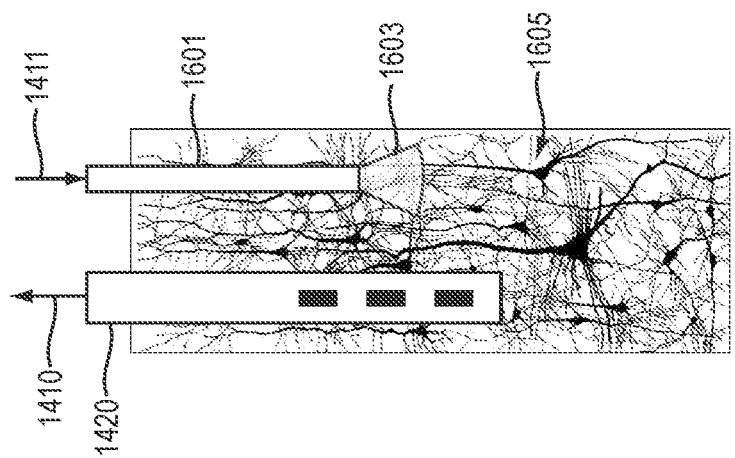
FIG. 16 shows an implantable optic fiber for optogenetic stimulation and an implantable recording electrode.

FIG. 16 shows an implantable optic fiber 1601 for optogenetic stimulation and an implantable recording electrode 1420, in an illustrative implementation of this invention. The optic fiber 1601 delivers light stimulation 1603 to transfected neural tissue (e.g., 1605). The transfected neural tissue has been optogenetically modified in such a way that exposing the transfected neural tissue to certain wavelengths of light triggers a response in the tissue (e.g., stimulation or suppression of activity of the tissue). The recording electrode 1420 may record neural activity that has been affected by light stimulation from optic fiber 1601.

In some implementations of this invention, one or more computers (e.g., in a neuromodulator) perform what we call "Endpoint Corrected Hilbert Transform" or "ECHT". The ECHT algorithm corrects distortion due to Gibbs phenomenon that occurs when calculating instantaneous attributes (e.g. instantaneous phase and amplitude) of a signal using an FFT/IFFT procedure.

Advantageously, ECHT is computationally efficient. This computational efficiency may allow ECHT to compute instantaneous phase and amplitude in real time using inexpensive, off-the-shelf, computer processors.

The runtime complexity of the conventional Hilbert transform (without correction for the Gibbs phenomenon) for n samples is $O(n \log(n))$, which is dominated by the FFT-IFFT operations. Both the FFT (fast Fourier transform) and the IFFT (inverse fast Fourier transform) have a complexity of $O(n \log(n))$. Amelioration of the Gibbs phenomenon using recursive models, such as autoregression or polynomial fitting, may add a parameters estimation operation (e.g. Yule-Walker method) with a runtime complexity of $O(n^3)$ and known theoretical limit of $O(n^{2.81})$. In comparison, in some implementations of this invention, ECHT adds a simple filtering operation with a runtime complexity of $O(n)$, thus maintaining an overall $O(n \log(n))$ complexity of the Hilbert transform.

In some implementations of this invention, one or more computer processors perform an ECHT algorithm, thereby achieving real-time computation of the Hilbert transform with minimal computing power. This in turn allows sophisticated tracking and closed-loop applications in affordable and portable hardware.

The following is a description of three types of ECHT: specifically, what we call (1) "frequency domain" ECHT; (2) "end-padded time domain" ECHT, and (3) "front-padded time domain" ECHT.

"Frequency Domain" ECHT

In some implementations of this invention, one or more computers (e.g., in a neuromodulator) perform what we call "frequency domain" ECHT. In these cases, causal smoothing occurs in the frequency domain.

In some cases, "frequency domain" ECHT corrects the Gibbs phenomenon by ensuring that a signal will be continuous and differentiable at the original end of the signal when a replica of the signal is appended to the signal, as occurs in the DFT of a finite signal. In "frequency domain" ECHT, a computer may apply a causal filter to the frequency domain representation of a signal. This filter may be applied after the DFT that results in the frequency domain representation of the signal, but before the IDFT step that results in an analytic signal. The causal filtering may preserve the values at the end of the signal while selectively deforming the values at the beginning of the signal. Thus, in some cases, if a replica of the signal is appended to the signal at the original end of the signal (as is done during the DFT of a finite signal), the appended replica is continuously differentiable at the original end of the signal. By removing the jump discontinuity at that point, a computer may eliminate (or significantly reduce) the Gibbs phenomenon distortions at the end of the analytic signal that results from taking an IDFT. This may allow a computer to accurately compute instantaneous phase and instantaneous amplitude at the end of the analytic signal (which corresponds in time to the end of the original signal). In "frequency domain" ECHT, the start and end values of the causally smoothed signal in the frequency domain may be the same, and thus, after the IDFT, the start and end values of the Hilbert transform (which is the imaginary component of the analytic signal) may be the same.

Figure 17:
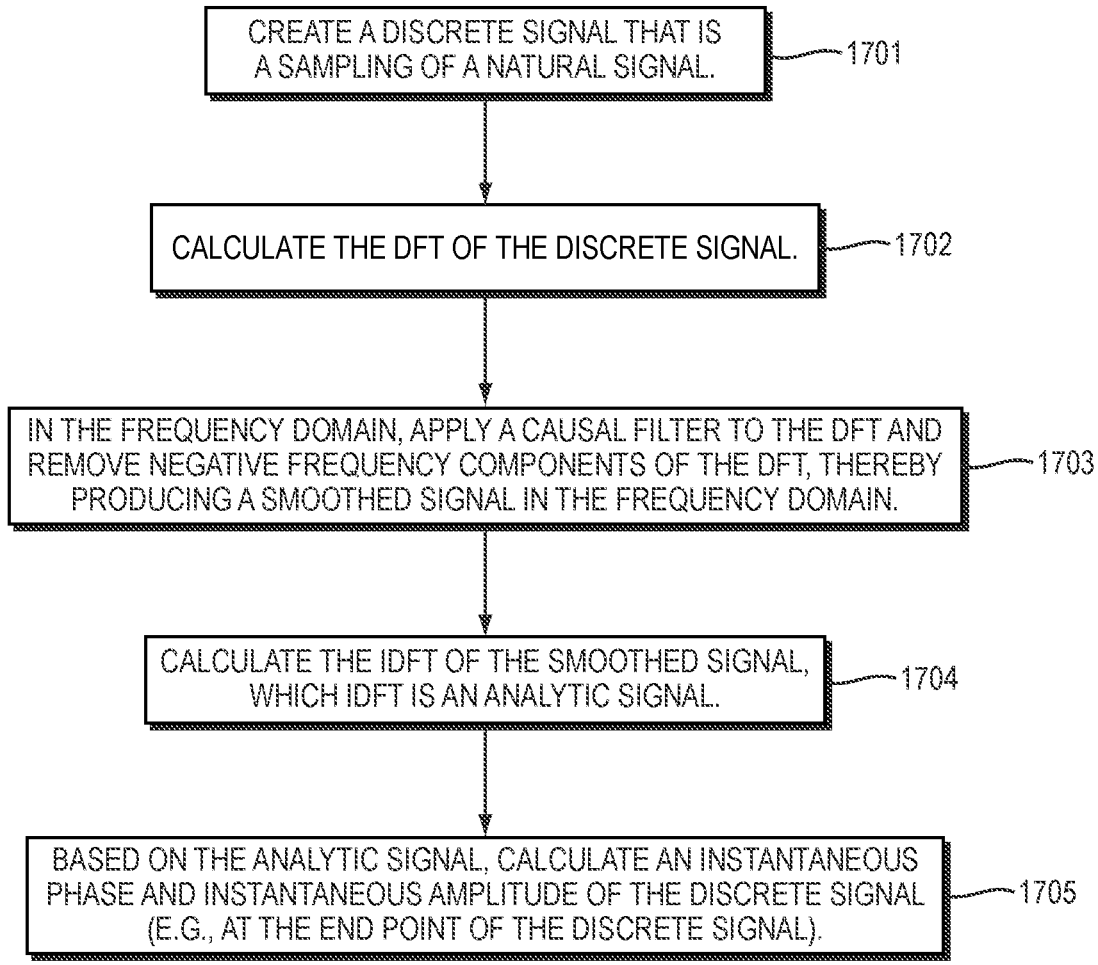
FIG. 17 shows a method of "frequency domain" ECHT.

FIG. 17 shows a method of "frequency domain" ECHT, in an illustrative implementation of this invention. In the example shown in FIG. 17, the method includes the following steps: Create a discrete signal that is a sampling of a natural signal (Step 1701). Calculate the DFT of the discrete signal (Step 1702). In the frequency domain, apply a causal filter to the frequency domain representation of the signal and remove negative frequency components of that representation, thereby producing a smoothed signal in the frequency domain (Step 1703). Calculate the IDFT of the smoothed signal, which results in an analytic signal (Step 1704). Based on the analytic signal, calculate an instantaneous phase and instantaneous amplitude of the discrete signal, such as at the end point of the discrete signal (Step 1705).

In some cases where a "frequency domain smoothing" version of ECHT is employed, a computer calculates a smoothed signal in the frequency domain. The smoothed signal may be the product of three signals: (1) the frequency domain representation of the impulse response of a causal filter, (2) what we call a "scrubber signal" (described in more detail below); and (3) the frequency domain representation of a discrete signal, which discrete single is a sampling of a natural signal of interest. Then the computer may calculate an analytic signal, which is the IDFT of the smoothed signal. Then, based on the analytic signal, the computer may calculate the instantaneous phase and amplitude of the natural signal.

The "scrubber signal" may remove negative frequency components. For instance, a "scrubber signal" may comprise a signal that, when multiplied by a frequency domain representation of a signal, removes negative frequency components from that frequency domain representation. Put differently, the product of a scrubber signal and a frequency domain representation of a signal may be another frequency domain representation that does not have negative frequency components. C[n] (mentioned below) is an example of a "scrubber signal". Removing negative frequency components is desirable in the computation of an analytic signal, which has no negative frequency components.

In some cases, "frequency domain" ECHT involves causal filtering, in the frequency domain, of a spectral spread that results from a jump discontinuity between the two ends of a finite signal in the time domain.

In some cases, "frequency domain" ECHT reduces the spreading out of a spectrum that resulted from a jump discontinuity between the two ends of a finite signal in the time domain. This process of reducing the frequency spreading by reshaping the spectrum may effectively be a filtering process.

In some cases, "frequency domain" ECHT includes the following steps:

Step A: Calculate $\hat{X}[n]$ as follows: $\hat{X}[n]=H[n]C[n]X[n]$, where $$C[n] \text{ is: } C[n] = \begin{cases} 0 & n < 0 \\ 2 & 0 < n < \frac{N}{2} \\ 1 & n = 0, \frac{N}{2} \end{cases}$$

and where X[n] is the DFT (discrete Fourier transform) of a real-valued, discrete signal (for example, the discrete signal may comprise a sampled physiological signal, such as a sampled neural signal), and where H[n] is the DFT of h[n], and where h[n] is the impulse response of an LTI causal filter such that h[n]=0 for n<0, and where N is the sample size, and where n is an integer such that $$-\frac{N}{2} < n \le \frac{N}{2}.$$

Step B: Calculate an analytic signal $\hat{x}[n]$ as follows: $\hat{x}[n]=\text{IDFT}(\hat{X}[n])$, where IDFT is the inverse discrete Fourier transform operator.

Step C: Calculate the instantaneous amplitude A of the real-valued discrete signal x[n] and the instantaneous phase (I) of the real-valued discrete signal x[n] as follows:

$$A[n] = \sqrt{\text{Re}\{\hat{x}[n]\}^2 + \text{Im}\{\hat{x}[n]\}^2}$$

$$\phi[n] = \text{atan}\left(\frac{\text{Im}\{\hat{x}[n]\}}{\text{Re}\{\hat{x}[n]\}}\right)$$

where $\text{Re}\{\hat{x}[n]\}$ and $\text{Im}\{\hat{x}[n]\}$ are the real portion and imaginary portion, respectively, of the complex analytic signal $\hat{x}[n]$.

"End-Padded Time Domain" ECHT

In some cases, one or more computers (e.g., in a neuromodulator) correct the Gibbs phenomenon by performing what we call "end-padded time domain" ECHT.

In some cases, in "end-padded time domain" ECHT, the computer appends a segment of data values (e.g., zeros) of at least one period length to the end of the signal and then applies a causal filter, which has the directionality property, to make the padded signal continuous and differentiable at the endpoint of the original signal without deforming the original end of the signal. By pushing away the end of the padded signal from the original end before the DFT procedure, the computer may ensure that the Gibbs distortion occurs away from the original end of the signal. This may allow a computer to accurately compute instantaneous phase and instantaneous amplitude at t_now (the point in the analytic signal that corresponds in time to the end of the original signal).

Figure 18:
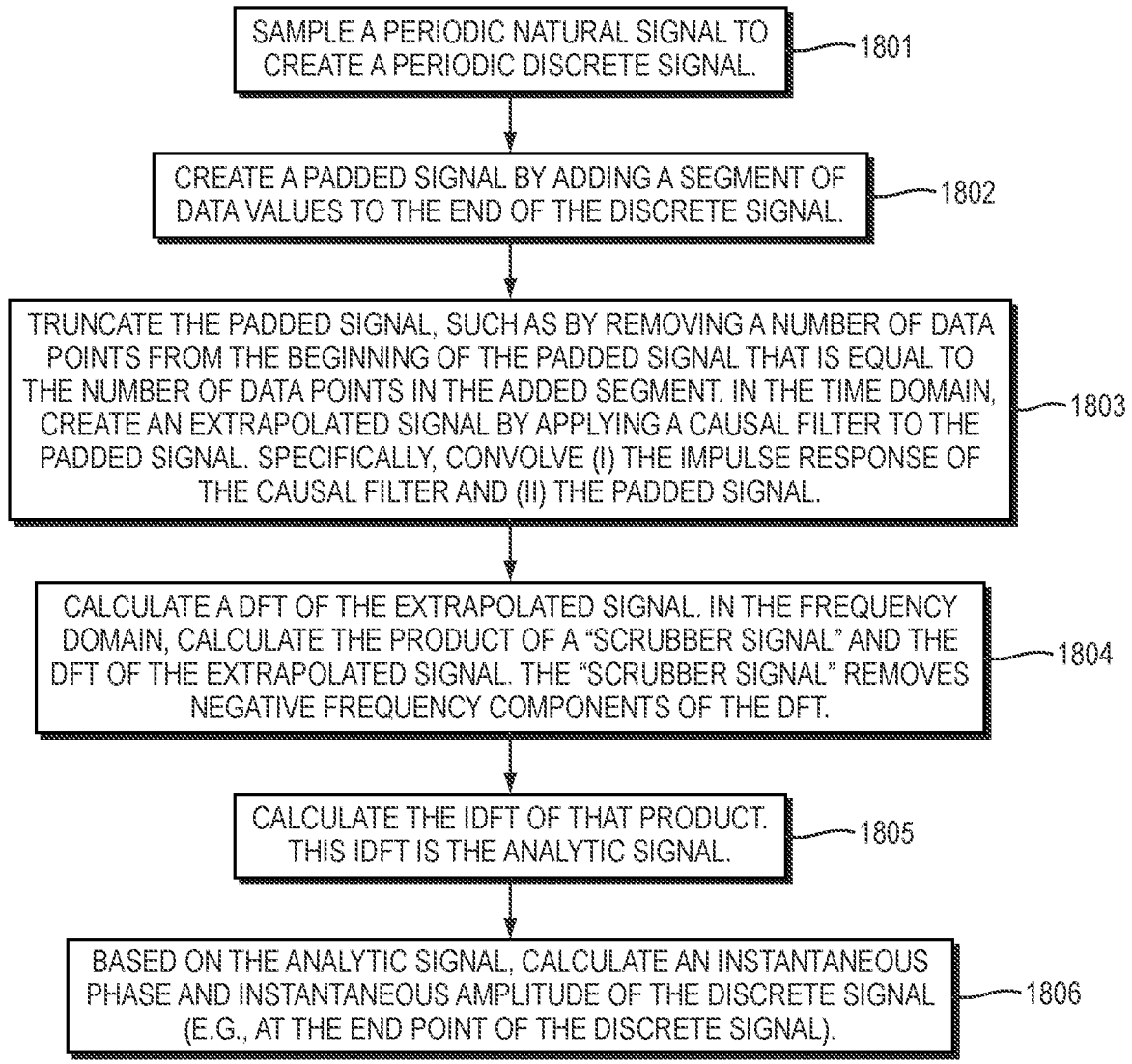
FIG. 18 shows a method of "end-padded time domain" ECHT.

FIG. 18 shows a method of "end-padded time domain" ECHT, in an illustrative implementation of this invention. In the example shown in FIG. 18, the method includes the following steps: Sample a periodic natural signal to create a periodic discrete signal (Step 1801). Create a padded signal by adding a segment of data values to the end of the periodic discrete signal (Step 1802). Truncate the padded signal, such as by removing, from the beginning of the padded signal, a number of data points that is equal to the number of data points in the added segment. In the time domain, create an extrapolated signal by applying a causal filter to the padded signal. Specifically, convolve (i) the impulse response of the causal filter and (ii) the padded signal (Step 1803). Calculate a DFT of the extrapolated signal. In the frequency domain, calculate the product of a "scrubber signal" and the frequency domain representation of the extrapolated signal. Again, the "scrubber signal" removes negative frequency components (Step 1804). Calculate the IDFT of that product. This IDFT is the analytic signal (Step 1805). Based on the analytic signal, calculate the instantaneous phase and instantaneous amplitude of the natural signal. (Step 1806).

In "end-padded time domain" ECHT, a padded discrete signal may be created by adding a segment of data points at the end of a real-valued, discrete, periodic signal. The length of the added segment may be greater than or equal to the length of a period of the original (unpadded) signal. The added segment may consist of zeroes. An advantage of zeroes is that they do not contain prior information. Alternatively, the added segment may include non-zero values. For example, the added segment may include a duplicate of the original signal or a portion of the original signal.

In "end-padded time domain" ECHT, the padded signal may be casually smoothed. This may be done to smooth an abrupt transition that would otherwise be introduced by adding the extra data segment at the end (e.g., by zero padding at the end). For example, if the original signal is sinusoidal and it is zero padded by adding zeroes at the original end, then—in the absence of smoothing—a discontinuity would occur at the original end of the signal, where the padded signal transitions abruptly from a sinusoidal curve to a flat line of zeroes.

In "end-padded time domain" ECHT, casual smoothing may be performed in the time domain, to prevent this problem. Specifically, the padded signal may be causally smoothed, by convolving (i) the impulse response of a causal filter, and (ii) the padded signal. The causal filter may smooth the padded signal, such that a discontinuity does not occur at the data point that was formerly the end of original signal.

In some cases, "end-padded time domain" ECHT includes the following steps:

Step A': Zero-pad a sample, which sample is a real-valued discrete signal x[n]. The zero-padding consists of adding zeros at the end of the sample. For example, x[n] may comprise a sampling of a natural signal (e.g., a neural signal).

Step B': Truncate the sample to sample size N.

Step C': Calculate a convolved signal x'[n]=h[n]*x[n], where h[n] is the impulse response of a causal filter such that h[n]=0 for n<0 and where "*" is convolution operator.

Step D': Calculate $\hat{X}[n]$ as follows: $\hat{X}[n]=C[n]X'[n]$, where $$C[n] \text{ is: } C[n] = \begin{cases} 0 & n < 0 \\ 2 & 0 < n < \frac{N}{2} \\ 1 & n = 0, \frac{N}{2} \end{cases}$$

and where X'[n] is the DFT (discrete Fourier transform) of x'[n], N is the sample size (e.g., number of discrete sampled values in the sample), and n is an integer such that $$-\frac{N}{2} < n \leq \frac{N}{2}.$$

Step E': Calculate an analytic signal $\hat{x}[n]$ as follows: $\hat{x}[n]=\text{IDFT}(\hat{X}[n])$, where IDFT is the inverse discrete Fourier transform operator.

Step F': Calculate the instantaneous amplitude A of the real-valued discrete signal x[n] and the instantaneous phase φ of the real-valued discrete signal x[n] as follows:

$$A[n] = \sqrt{\text{Re}\{\hat{x}[n]\}^2 + \text{Im}\{\hat{x}[n]\}^2}$$

$$\phi[n] = \text{atan}\left(\frac{\text{Im}\{\hat{x}[n]\}}{\text{Re}\{\hat{x}[n]\}}\right)$$

where Re{$\hat{x}[n]$} and Im{$\hat{x}[n]$} are the real portion and imaginary portion, respectively, of the complex analytic signal $\hat{x}[n]$.

In the above example of "end-padded time domain" ECHT, Step B' (truncating) is optional and may be omitted. In some cases, Step B' (truncating) consists of removing the first half of the original signal by removing a number of data values, and Step A' (padding) consists of adding the same number of zeroes at the end of the original sample. Step B' (truncating) has at least two advantages: (a) it reduces the size of the sample window (which would otherwise increase due to the padding), and (b) results in a similar sample window as one would use with conventional Hilbert transform.

"Front-Padded Time Domain" ECHT

In some implementations of this invention, one or more processors (e.g., in a neuromodulator) perform what we call "front-padded time domain" ECHT.

In some cases, "front-padded time domain" ECHT corrects the Gibbs phenomenon by ensuring that a signal will be continuous and differentiable at the original end of the signal when a replica of the signal is appended to the signal, as occurs in the DFT of a finite signal. In "front-padded time domain" ECHT, the neuromodulator may front-pad a sample with a copy of an end segment of the sample, then apply a causal filter to the padded sample, and then remove the added segment in the time domain, prior to the DFT and IDFT steps. The correction may be made before the IDFT step that results in an analytic signal. A computer may selectively deform the beginning of the sample in the time domain and not deform the end of the sample. In some cases, in "front-padded time domain" ECHT, the value of the end of the sample is not changed, but the value of the beginning of the sample is changed, in such a way that the value of the signal at the beginning and end of the signal is the same. Thus, in some cases, if a replica of the sample is appended to the sample at the original end of the sample (as is done during the DFT of a finite sample), the padded sample is continuously differentiable at the original end of the sample. By removing the jump discontinuity at that point, a computer may eliminate (or significantly reduce) the Gibbs phenomenon distortions at the end of the analytic signal that results from taking an IDFT. This may allow a computer to accurately compute instantaneous phase and instantaneous amplitude at the end of the analytic signal (which corresponds in time to the end of the original sample). In "front-padded time domain" ECHT, the start and end values of the causally smoothed signal in the frequency domain may be the same, and thus, after the IDFT, the start and end values of the Hilbert transform (which is the imaginary component of the analytic signal) may be the same.

In front-padded time domain ECHT, in some cases: (a) a signal that starts at t_start is front-padded with a copy of an end segment of the signal, (b) then the padded signal is causally smoothed in the time domain, and (c) then the padded signal is truncated by removing the segment that was added. This procedure may result in a modified signal that, like the original signal, starts at t_start. The modified signal may have the same value at its beginning point (t_start) as at its end point. (This is because the causal smoothing distorts the beginning point of the original signal, such that it fits the added segment that was padded in front of it and which was a copy of the end segment).

Figure 19:
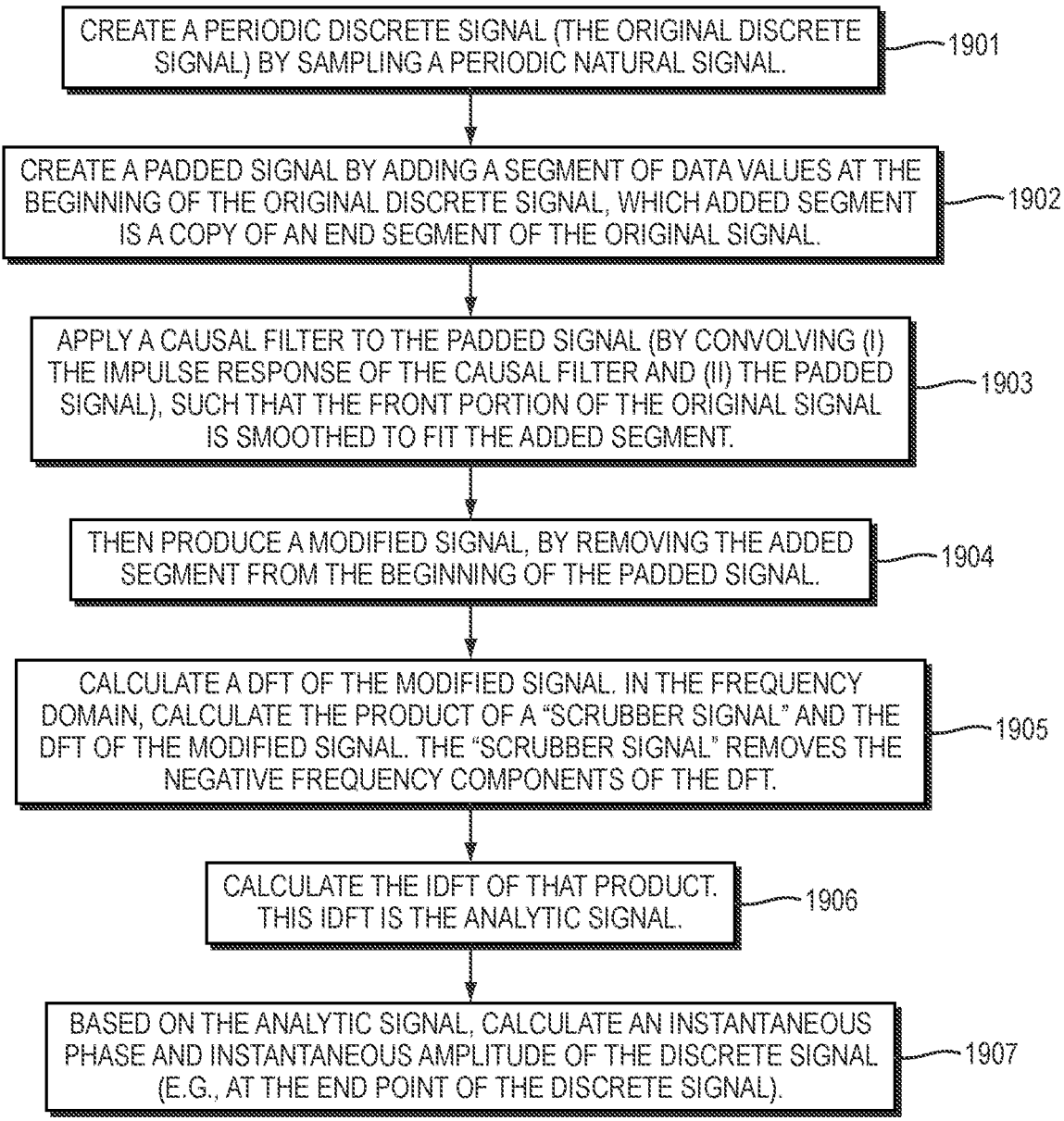
FIG. 19 shows a method of "front-padded time domain" ECHT.

FIG. 19 shows a method of "front-padded time domain" ECHT, in an illustrative implementation of this invention. In the example shown in FIG. 19, the method includes the following steps: Create a periodic discrete signal (the original discrete signal) by sampling a periodic natural signal (Step 1901). Create a padded signal by adding a segment of data values at the beginning of the original discrete signal, which added segment is a copy of an end segment of the original signal (Step 1902). Apply a causal filter to the padded signal (by convolving (i) the impulse response of the causal filter and (ii) the padded signal), such that the front portion of the original signal is smoothed to fit the added segment (Step 1903). Then produce a modified signal, by removing the added segment (at the beginning of the padded signal) before the DFT is performed (Step 1904). Calculate a DFT of the modified signal. In the frequency domain, calculate the product of a "scrubber signal" and the frequency domain representation of the modified signal. The "scrubber signal" removes negative frequency components of the frequency domain representation (Step 1905). Calculate the IDFT of that product. This IDFT is the analytic signal (Step 1906). Based on the analytic signal, calculate the instantaneous phase and instantaneous amplitude of the natural signal. (Step 1907).

More Details Regarding ECHT

A common feature of all three methods discussed above—"frequency domain" ECHT, "end-padded time domain" ECHT, and "front-padded time domain" ECHT—is that a causal filter is applied to a signal. In each of these methods, the causal filter may comprise, for example, a causal IIR (infinite impulse response) filter or causal FIR (finite impulse response) filter. For instance, either the IIR filter or the FIR filter may comprise a causal Butterworth filter, causal Chebyshev filter or causal Bessel filter. The causal filter may be an LTI (linear and time-invariant) bandpass filter.

In some implementations of this invention, the causal filter: (a) reduces distortion of amplitude and phase of the signal inside a passband and (b) suppresses frequencies outside of the passband. The passband may be the range of frequencies of the natural signal.

Figure 20A:
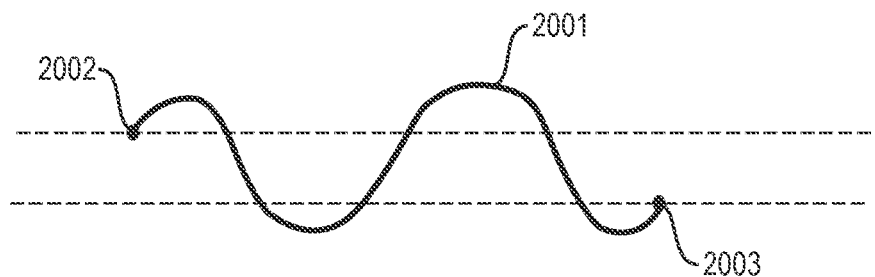
FIG. 20A shows a Hilbert transform signal that has different values at the start point and end point of the signal

FIG. 20A shows a Hilbert transform signal 2001 that has different values at the start point 2002 and end point 2003 of the signal.

Figure 20B:
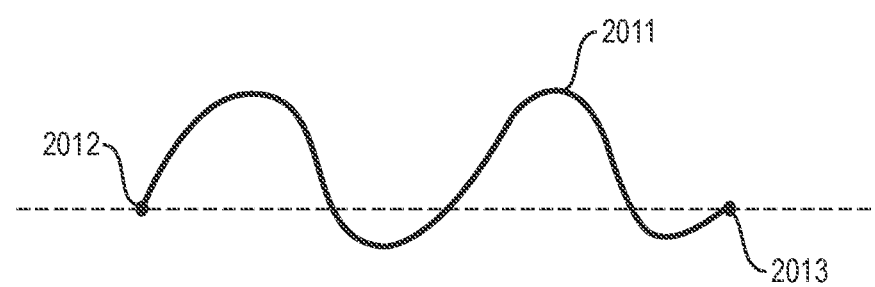
FIG. 20B shows a Hilbert transform signal that has the same values at the start point and end point of a signal.

FIG. 20B shows a Hilbert transform signal 2011 that has the same values at the start point 2012 and end point 2013 of the signal.

In some cases in "frequency domain" ECHT, a causal filter is applied to the frequency domain representation of a signal, before the IDFT step. This correction in the frequency domain is such that the later IDFT step results in an analytic signal, in which the imaginary component (i.e., the Hilbert transform signal) has the same values at its start point and end point (such as the example shown in FIG. 20B).

In some cases in "front-padded time domain" ECHT, corrective steps are taken in the time domain, before the DFT/IDFT process. These corrective steps include (i) front-padding a discrete time signal (the original signal) with an added segment, which added segment is a copy of an end segment of the original discrete signal, (ii) then applying a causal filter that distorts the beginning of the original signal such that it fits the end of the added segment, and (iii) then removing the added segment. These corrective steps in the time domain are such that the later DFT/IDFT process results in an analytic signal, in which the imaginary component (i.e., the Hilbert transform signal) has the same values at its start point and end point (such as the example shown in FIG. 20B).

Figure 20C:
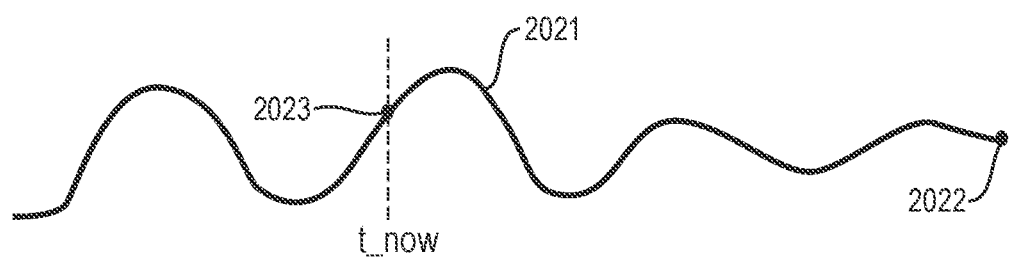
FIG. 20C shows a Hilbert transform signal in which the end of signal has been moved away from the original end of the sample, to a later point.

FIG. 20C shows a Hilbert transform signal 2021 in which the end point 2022 of signal has been moved away from t_now 2023, in an illustrative implementation of this invention. In the example in FIG. 20C, t_now 2023 is the point of the analytic signal (and of the Hilbert transform) that corresponds in time to the endpoint of the original discrete signal from which the analytic signal was derived.

In some cases in "end-padded time domain" ECHT, corrective steps are made in the time domain, before the DFT and IDFT steps. These corrective steps may include (i) end-padding a discrete time signal (the original sample) with an added segment, such as a segment of zeroes, in order to produce a padded sample; and (ii) causal smoothing the padded sample. Due to an abrupt transition between the end of the original sample and the added segment, the causal filter may produce ringing artifacts that smooth the added segment to fit the original sample. These corrective steps in the time domain result in an end-padded, casually smoothed time domain sample, in which the end point of the padded, smoothed sample is located at a distance from (and represents a point in time later than) the end point of the original sample. These corrective steps in the time domain are such that the later DFT/IDFT process results in a Hilbert transform signal in which the end point is at a distance from the end of the original sample (such as the example shown in FIG. 20C). The Hilbert transform is the imaginary part of the analytic signal.

Preferably, in "end-padded time domain" ECHT, the distance between the endpoint of the original sample (that is, t_now 2023) and the end point 2022 of the padded sample is equal to at least a period of the analytic signal. This causes the Gibbs effect to be insignificant at t_now. In some cases, the distance between t_now 2023 and end point 2022 is equal to at least three-quarters of a period of the analytic signal. The analytic signal has the same period as the original signal.

Advantageously, in some implementations, ECHT allows a computer to accurately compute instantaneous phase over a selected range of frequencies. For example, in some cases, ECHT is accurate over a range of frequencies that is centered on, and equal in width to one half of, the main frequency of the natural signal. In some cases, the bandpass of the causal filter in ECHT is selected such that it is the same as that range of frequencies. For example, in some cases, if the main frequency of the natural signal is 8 Hz, then ECHT is accurate in the range of 6-10 Hz.

The ability to accurately measure instantaneous phase over a range of frequencies is helpful where the frequency of the natural signal being measured varies over time. For example, brain signals often have multiple time-varying frequencies with power-law distributions.

In FIGS. 21A-23E, the discrete increments of discrete signals are so small that the signals appear to be continuous. In FIGS. 21A, 21F, 22A, 22F and 23C, horizontal axis 2100 is time and the vertical axis 2110 is the value of the signal (e.g., volts, if the signal is a voltage signal).

FIGS. 21A to 21H illustrate aspects of a conventional method for determining instantaneous phase and amplitude of a natural signal. This conventional method is inaccurate because it does not correct for distortion due to the Gibbs phenomenon.

Figure 21A:
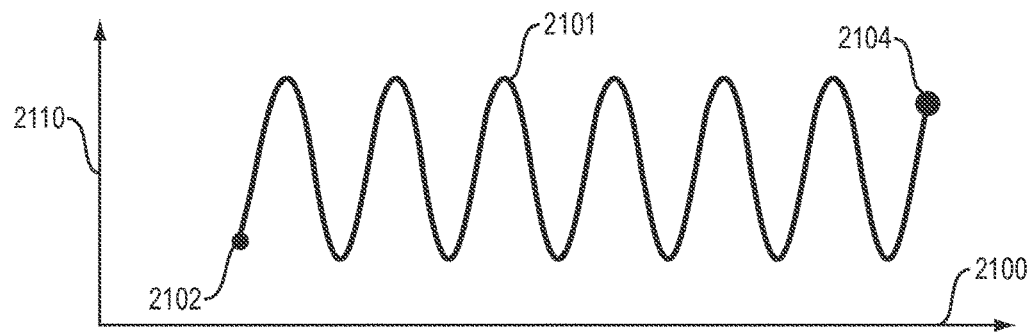
FIGS. 21A, 21B, 21C, 21D, 21E, 21F, 21G and 21H illustrate aspects of a conventional method for determining instantaneous phase and amplitude of a natural signal. This conventional method is inaccurate because it does not correct for distortion due to the Gibbs phenomenon. For this conventional method: (a)

For this conventional (prior art) method, FIG. 21A shows a discrete signal 2101 that is a sampling of a natural signal. Signal 2101 starts at start point 2102 and ends at end point 2104. FIG. 21A illustrates that signal 2101 differs in value at start point 2102 and end point 2104, and thus there is a jump discontinuity between these two points.

Figure 21B:
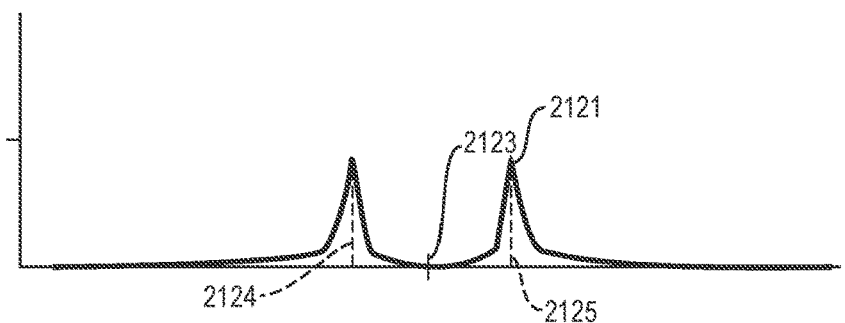
Figure 21C:
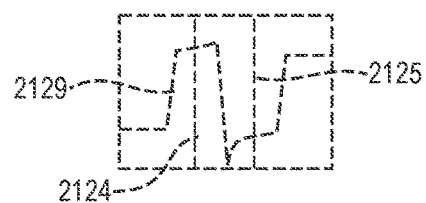
Figure 21D:
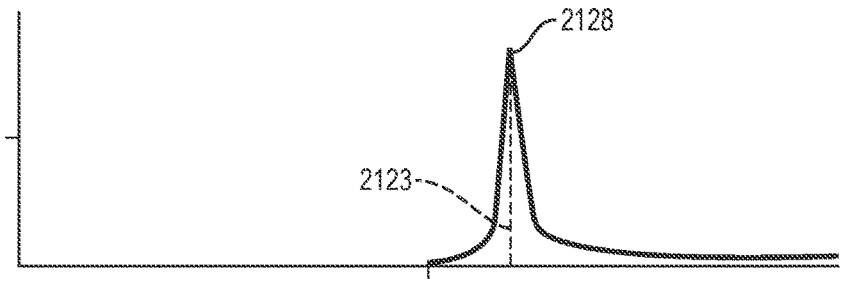
Figure 21E:
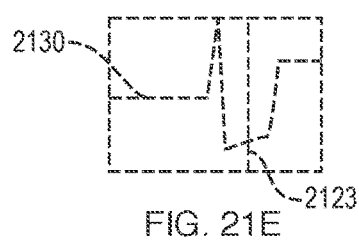

For this conventional method, FIG. 21B and FIG. 21C show the amplitude 2121 and phase 2129, respectively, of the Fourier transform of the discrete signal. FIG. 21D and FIG. 21E show the amplitude 2128 and phase 2130, respectively, of the Fourier transform of the analytic signal. These figures also show center frequency 2123. Frequencies 2124 and 2125 are equal to the center frequency plus or minus, respectively, half of the center frequency.

Figure 21F:
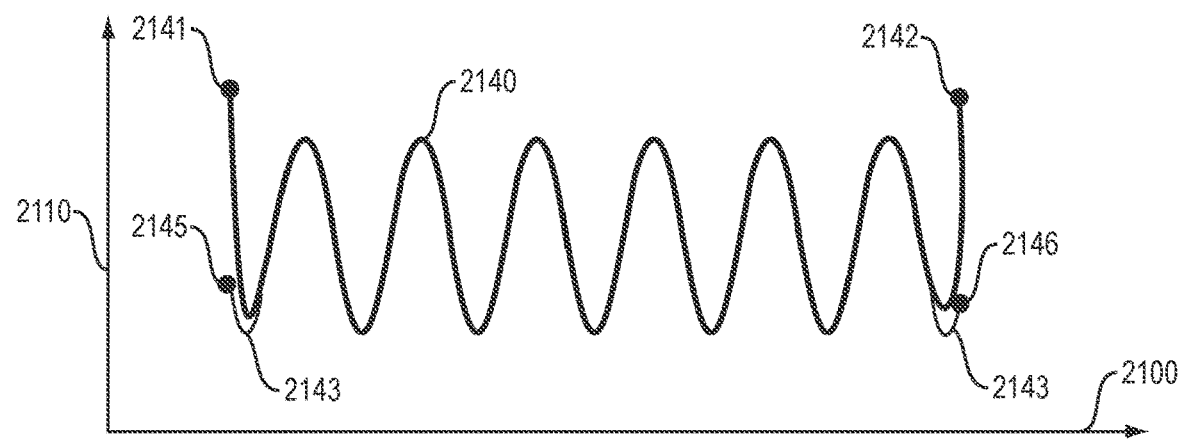

For this conventional method, FIG. 21F shows (a) the correct Hilbert transform signal 2143, which starts at start point 2145 and ends at end point 2146; and (b) the computed Hilbert transform signal 2140, which starts at start point 2141 and ends at end point 2142. Signals 2140 and 2143 overlap over much of their length.

Figure 21G:
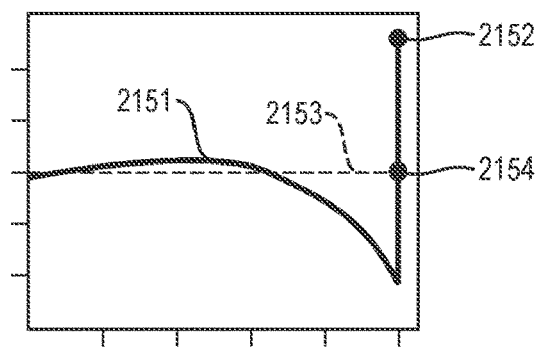

For this conventional (prior art) method, FIG. 21G shows the correct instantaneous amplitude A[n] values 2151 near their endpoint 2154 and the computed instantaneous amplitude A[n] values 2153 near their endpoint 2152. The large difference between the actual endpoint and computed endpoint indicates that instantaneous amplitude is not measured accurately at the end of the signal, in the conventional approach shown in FIG. 21G.

Figure 21H:
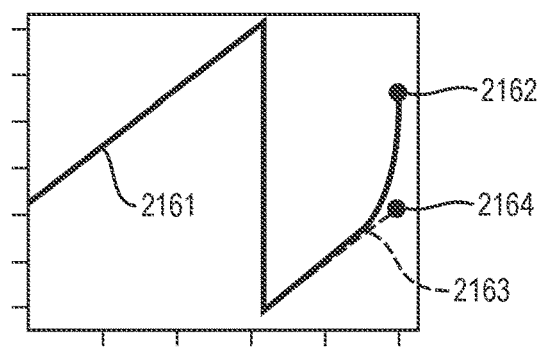

For this conventional (prior art) method, FIG. 21H shows the correct instantaneous phase φ[n] values 2163 near their endpoint 2164 and the computed instantaneous phase φ[n] values 2161 near their endpoint 2162. Curves 2161 and 2163 overlap over much of their length. The large difference between the actual endpoint and computed endpoint indicates that instantaneous phase is not measured accurately at the end of the signal, in the conventional approach shown in FIG. 21H.

FIGS. 22A to 22H illustrate aspects of an "end-padded time domain" version of ECHT, in an implementation of this invention. This version of ECHT accurately measures instantaneous phase and amplitude of a natural signal.

Figure 22A:
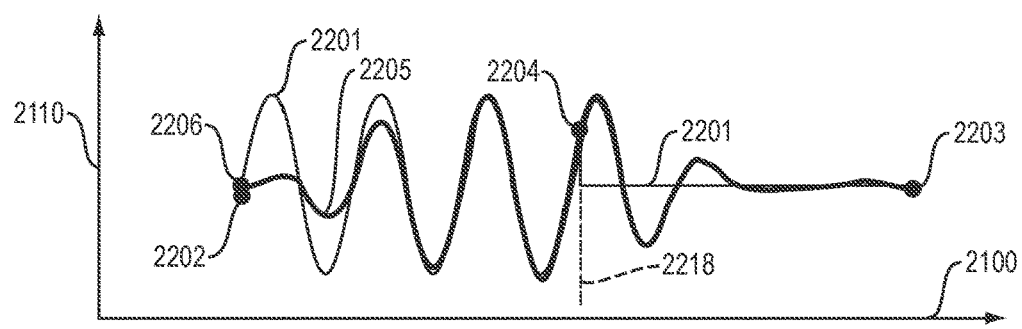
FIGS. 22A, 22B, 22C, 22D, 22E, 22F, 22G and 22H illustrate aspects of an "end-padded time domain" version of ECHT, in an implementation of this invention. This version of ECHT accurately measures instantaneous phase and amplitude of a natural signal. For this "end-padded time domain" version of ECHT: (a)

For this "end-padded time domain" version of ECHT, FIG. 22A shows a zero-padded signal before and after it is smoothed by a causal filter in the time domain (the "before" signal is 2201, the "after" signal is 2205) The signal is zero-padded after point 2204 which occurs at time t_now 2218. Signal 2201 starts at start point 2202 and ends at end point 2203. Signal 2205 starts at start point 2206 and ends at end point 2203.

Figure 22B:
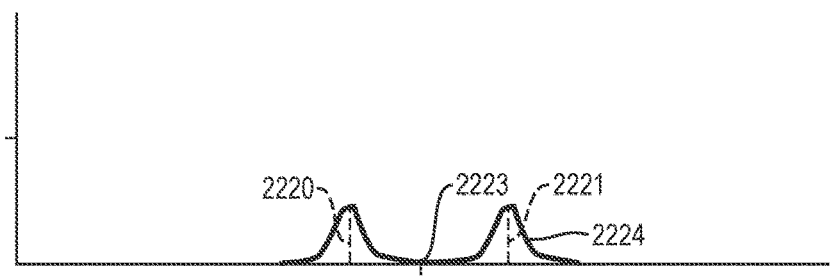
Figure 22C:
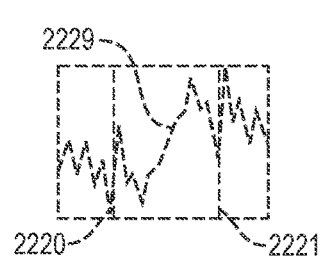
Figure 22D:
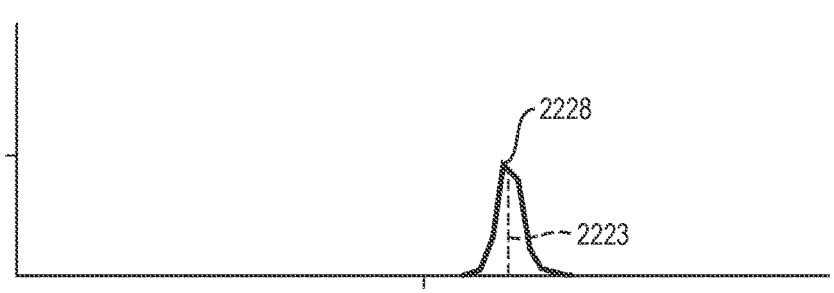
Figure 22E:
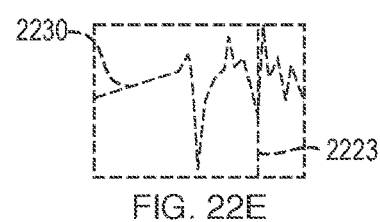

For this "end-padded time domain" version of ECHT, FIG. 22B and FIG. 22C show the amplitude 2224 and phase 2229, respectively, of the Fourier transform of the discrete signal. FIG. 22D and FIG. 22E show the amplitude 2228 and phase 2230, respectively, of the Fourier transform of the analytic signal. These figures also show center frequency 2223. Frequencies 2220 and 2221 are equal to the center frequency plus or minus, respectively, half of the center frequency.

Figure 22F:
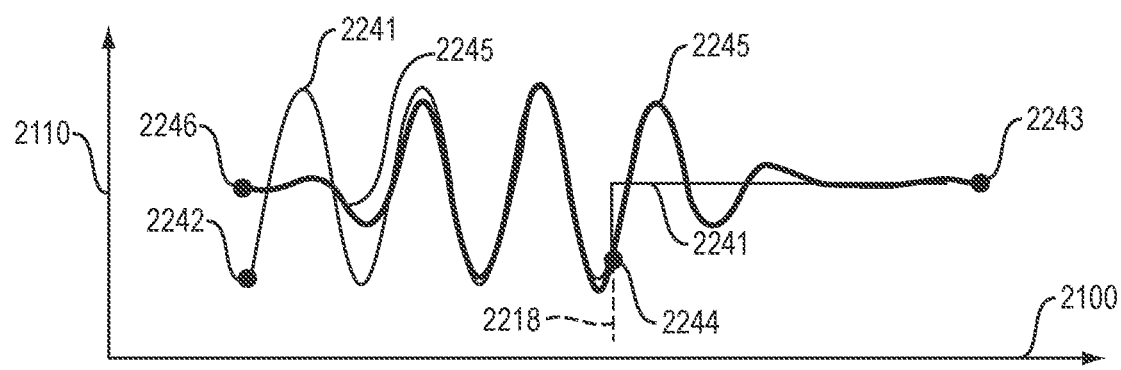

For this "end-padded time domain" version of ECHT, FIG. 22F shows (a) the correct Hilbert transform signal 2241, which starts at start point 2242 and ends at end point 2243; and (b) the computed Hilbert transform signal 2245, which starts at start point 2246 and ends at end point 2243. Signals 2241 and 2245 overlap in some areas. Point t_now 2244 is at time 2218 and corresponds in time to the end of the original signal, before zero-padding.

Figure 22G:
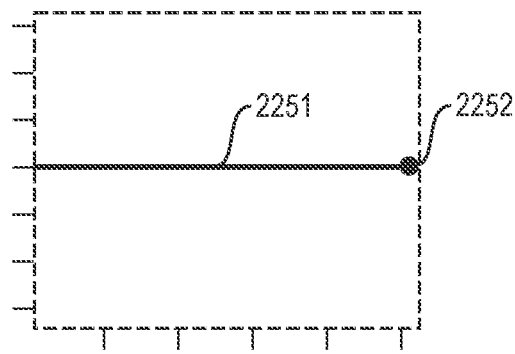

For this "end-padded time domain" version of ECHT, FIG. 22G shows correct instantaneous amplitude A[n] values 2251 near their endpoint 2252. The correct and computed instantaneous amplitude A[n] values overlap with each other, indicating that instantaneous amplitude is measured accurately near endpoint 2252, in "end-padded time domain" ECHT.

Figure 22H:
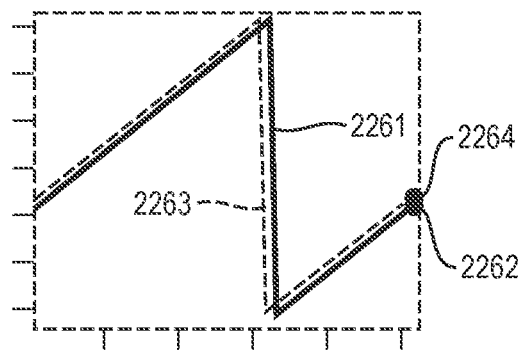

For this "end-padded time domain" version of ECHT, FIG. 22H shows the correct instantaneous phase φ[n] values 2263 near their endpoint 2264 and the computed instantaneous phase φ[n] values 2261 near their endpoint 2262. Curves 2261 and 2263 are close to each other over much of their length. This indicates that instantaneous phase is measured accurately near endpoint 2262, in this example of "end-padded time domain" ECHT.

FIGS. 23A to 23E illustrate aspects of a "frequency domain" version of ECHT, in an implementation of this invention. This version of ECHT accurately measures instantaneous phase and amplitude of a natural signal.

For this "frequency domain" version of ECHT, FIG. 23A and FIG. 23B show the amplitude 2328 and phase 2330, respectively, of the Fourier transform of the analytic signal. These figures also show center frequency 2323.

For this "frequency domain" version of ECHT, FIG. 23C shows (a) the correct Hilbert transform signal 2341, which starts at start point 2342 and ends at end point 2343; and (b) the computed Hilbert transform signal 2345, which starts at start point 2346 and ends at end point 2343. Signals 2341 and 2345 overlap in some areas.

For this "frequency domain" version of ECHT, FIG. 23D shows correct instantaneous amplitude A[n] values 2353 near their endpoint 2354, and shows computed instantaneous amplitude values A[n] 2351 near their endpoint 2352. The correct and computed instantaneous amplitude A[n] values overlap with or are close to each other, indicating that instantaneous amplitude is measured accurately near endpoint 2352.

For this "frequency domain" version of ECHT, FIG. 23E shows the correct instantaneous phase φ[n] values 2363 near their endpoint 2364 and the computed instantaneous phase φ[n] values 2361 near their endpoint 2362. Curves 2361 and 2363 are close to each other. This indicates that instantaneous phase is measured accurately near endpoint 2362, in "frequency domain" ECHT.

In some implementations of this invention, ECHT is not limited to measuring a physiological signal that is indicative of neural tissue activity. Instead, ECHT may be used to accurately measure, in real-time, the instantaneous phase and the instantaneous amplitude of any signal, including any physiological signal, or any seismological signal. For example, the signal that is processed by ECHT may comprise measurements taken by any sensor, including any electrical sensor (e.g., EEG sensor, ECG sensor, voltmeter, or current sensor), motion sensor (e.g., gyroscope, accelerometer or inertial measurement unit) magnetic sensor, light sensor, optical sensor, camera, acoustic sensor (e.g., microphone, geophone, hydrophone), pressure sensor, proximity sensor, or chemical sensor.

More Detail on Neuromodulation

As used herein, to say that stimulation is "phase-locked" with a signal during a time interval means that: (a) the stimulation occurs repeatedly during the time interval; (b) the absolute value of the mean phase difference between a target phase and a second phase for the time interval is less than or equal to 0.872665 radians; and (c) the length of a mean resultant vector for the time interval is greater than or equal to 0.2. For purposes of this paragraph: (a) the target phase is phase of the signal at which a particular feature of the stimulation is targeted to occur; (b) the second phase is phase of the signal at which the particular feature of the stimulation actually occurs; and (c) during repetition of the stimulation, the target phase is fixed while the second phase may but does not necessarily vary. For purposes of this paragraph: (a) the target phase is denoted $\theta_t$, and the second phase for sample i is denoted $\theta_{i2}$;

$$(b)\ \overline{x} = \frac{1}{N}\sum_i \cos(\theta_{i2}) \text{ and } \overline{y}_2 = \frac{1}{N}\sum_i \sin(\theta_{i2});$$

(c) N is the number of samples; (d) the mean resultant vector is a two dimensional vector $\overline{r}=\langle \overline{x},\overline{y}\rangle$; (e) the mean phase difference is $\overline{\theta}_e = \angle(e^{i*\theta_t}/e^{i*\overline{\theta}_2})$, where $\overline{\theta}_2=\arctan 2(\overline{y},\overline{x})$; (f) e is Euler's number, $i=\sqrt{-1}$, and $\angle(w)$ is the phase angle of a complex number w; (g) arctan 2 is the four-quadrant inverse tangent function; and (h) the length of the mean resultant vector is $l=\sqrt{\overline{x}^2+\overline{y}^2}$. For purposes of this paragraph, each of the following is a non-limiting example of a particular feature of a stimulation: (a) start of the stimulation; and (b) end of the stimulation. For purposes of this paragraph, the target phase and second phase are each associated with the same frequency range or frequency bin, which range or bin has a lower frequency bound and an upper frequency bound that do not change throughout the time interval.

As used herein, to say that a sensation is "phase-locked" with a signal during a time interval means that: (a) the sensation occurs repeatedly during the time interval; (b) the absolute value of the mean phase difference between a target phase and a second phase for the time interval is less than or equal to 0.872665 radians; and (c) the length of a mean resultant vector for the time interval is greater than or equal to 0.2. For purposes of this paragraph: (a) the target phase is phase of the signal at which a particular feature of the sensation is targeted to occur; (b) the second phase is phase of the signal at which the particular feature of the sensation actually occurs; and (c) during repetition of the sensation, the target phase is fixed while the second phase may but does not necessarily vary. For purposes of this paragraph: (a) the target phase is denoted $\theta_t$, and the second phase for sample i is denoted $\theta_{i2}$;

$$(b)\ \overline{x} = \frac{1}{N}\sum_i \cos(\theta_{i2}) \text{ and } \overline{y}_2 = \frac{1}{N}\sum_i \sin(\theta_{i2});$$

(c) N is the number of samples; (d) the mean resultant vector is a two dimensional vector $\overline{r}=\langle \overline{x},\overline{y}\rangle$; (e) the mean phase difference is $\overline{\theta}_e = \angle(e^{i*\theta_t}/e^{i*\overline{\theta}_2})$, where $\overline{\theta}_2=\arctan 2(\overline{y},\overline{x})$; (f) e is Euler's number, $i=\sqrt{-1}$, and $\angle(w)$ is the phase angle of a complex number w; (g) arctan 2 is the four-quadrant inverse tangent function; and (h) the length of the mean resultant vector is $$l = \sqrt{\overline{x}^2+\overline{y}^2}.$$

For purposes of this paragraph, each of the following is a non-limiting example of a particular feature of a sensation: (a) start of the sensation; and (b) end of the sensation. For purposes of this paragraph, the target phase and second phase are each associated with the same frequency range or frequency bin, which range or bin has a lower frequency bound and an upper frequency bound that do not change throughout the time interval.

As used herein, to say that stimulation is "phase-tracking" with a signal during a time interval means that: (a) the stimulation occurs repeatedly during the time interval; and (b) throughout the time interval, a target phase lies within a 95% confidence interval for the mean of a second phase. For purposes of this paragraph: (a) the target phase is phase of the signal at which a particular feature of the stimulation is targeted to occur; (b) the second phase is phase of the signal at which the particular feature of the stimulation actually occurs; and (c) during repetition of the stimulation, the target phase is fixed while the second phase may but does not necessarily vary. For purposes of this paragraph, to say that target phase lies within the 95% confidence interval for the mean of the second phase means that $|\angle(e^{i*\theta_t}/e^{i*\overline{\theta}_2})|\le d$ when d is defined. For purposes of this paragraph: (a) the target phase is denoted $\theta_t$, and the second phase for sample i is denoted $\theta_{i2}$; (b) e is Euler's number, $i=\sqrt{-1}$, and $\angle(w)$ is the phase angle of a complex number w;

$$(c)\ \overline{x}_2 = \frac{1}{N}\sum_i \cos(\theta_{i2}), \text{ and } \overline{y}_2 = \frac{1}{N}\sum_i \sin(\theta_{i2}),$$

and N is the number of samples; (d) angle $\overline{\theta}_2=\arctan 2(\overline{y}_2, \overline{x}_2)$; (e) arctan 2 is the four-quadrant inverse tangent function;

$$(f)\ R = \sqrt{\overline{x}_2^2 + \overline{y}_2^2};\text{ and}$$

$$(g)\ d = \begin{cases} \left(\sqrt{\dfrac{2N(2R^2N^2 - N\chi_{\delta,1}^2)}{4N - \chi_{\delta,1}^2}}\middle/ RN\right), & R \le 0.9 \text{ and } R > \sqrt{\chi_{\delta,1}^2/2N} \\ \left(\sqrt{N^2 - (N^2 - R^2N^2)e^{\chi_{\delta,1}^2/N}}\middle/ RN\right), & R > 0.9 \\ \text{undefined}, & \text{otherwise} \end{cases}$$

where $\chi_{\delta,1}^2$ is the inverse of the chi-square cumulative distribution function evaluated at probability δ and 1 degree of freedom, and δ=0.95 for a 95% confidence interval. For purposes of this paragraph, each of the following is a non-limiting example of a particular feature of a stimulation: (a) start of the stimulation; and (b) end of the stimulation. For purposes of this paragraph, the target phase and second phase are each associated with the same frequency range or frequency bin, which range or bin has a lower frequency bound and an upper frequency bound that do not change throughout the time interval.

As used herein, to say that a sensation is "phase-tracking" with a signal during a time interval means that: (a) the sensation occurs repeatedly during the time interval; and (b) throughout the time interval, a target phase lies within a 95% confidence interval for the mean of a second phase. For purposes of this paragraph: (a) the target phase is phase of the signal at which a particular feature of the sensation is targeted to occur; (b) the second phase is phase of the signal at which the particular feature of the sensation actually occurs; and (c) during repetition of the sensation, the target phase is fixed while the second phase may but does not necessarily vary. For purposes of this paragraph, to say that target phase lies within the 95% confidence interval for the mean of the second phase means that $|\angle(e^{i*\theta_t}/e^{i*\overline{\theta}_2})| \leq d$ when d is defined. For purposes of this paragraph: (a) the target phase is denoted $\theta_t$, and the second phase for sample i is denoted $\theta_{i2}$; (b) e is Euler's number, $i=\sqrt{-1}$, and $\angle(w)$ is the phase angle of a complex number w;

$$(c)\,\overline{x}_2 = \frac{1}{N}\sum_i \cos(\theta_{i2}), \text{ and } \overline{y}_2 = \frac{1}{N}\sum_i \sin(\theta_{i2}),$$

and N is the number of samples; (d) angle $\overline{\theta}_2 = \arctan 2\,(\overline{y}_2, \overline{x}_2)$; (e) arctan 2 is the four-quadrant inverse tangent function;

$$(f)\, R = \sqrt{\overline{x}_2^2 + \overline{y}_2^2}\,;\text{ and}$$

(g) d =

$$\begin{cases} \arccos\left(\left(\sqrt{\dfrac{2N(2R^2N^2 - N\chi_{\delta,1}^2)}{4N - \chi_{\delta,1}^2}}\right) \big/ RN\right), & R \leq 0.9 \text{ and } R > \sqrt{\chi_{\delta,1}^2/2N} \\ \arccos\left(\left(\sqrt{N^2 - (N^2 - R^2N^2)e^{\chi_{\delta,1}^2/N}}\right) \big/ RN\right), & R > 0.9 \\ \text{undefined,} & \text{otherwise} \end{cases}$$

where $X_{\delta,1}^2$ is the inverse of the chi-square cumulative distribution function evaluated at probability δ and 1 degree of freedom, and δ=0.95 for a 95% confidence interval. For purposes of this paragraph, each of the following is a non-limiting example of a particular feature of a sensation: (a) start of the sensation; and (b) end of the sensation. For purposes of this paragraph, the target phase and second phase are each associated with the same frequency range or frequency bin, which range or bin has a lower frequency bound and an upper frequency bound that do not change throughout the time interval.

As used herein, to say that stimulation is "phase-correlated" with a signal during a time interval means that: (a) the stimulation occurs repeatedly during the time interval; (b) the absolute value of the mean phase difference between a target phase and a second phase for the time interval is less than or equal to 0.872665 radians; and (c) the circular-circular correlation coefficient between the target phase and the second phase for the time interval is greater than 0.6 with p-value of less than 0.05. For purposes of the preceding sentence: (a) the target phase is phase of the signal at which a particular feature of the stimulation is targeted to occur; (b) the second phase is phase of the signal at which the particular feature of the stimulation actually occurs; and (c) during repetition of the stimulation, the target phase and second phase each may but do not necessarily vary. For purposes of this paragraph: (a) $\theta_{it}$ and $\theta_{i2}$ are the target phase and second phase, respectively, for sample i; (b) the circular-circular correlation coefficient is $$\rho_{cc} = \frac{\sum_i \sin(v_{i2} - \overline{v}_2)\sin(v_{it} - \overline{v}_t)}{\sqrt{\sum_i \sin^2(v_{i2} - \overline{v}_2)\sin^2(v_{it} - \overline{v}_t)}};$$

$$(c)\, v_{it} = \langle \cos(\theta_{it}), \sin(\theta_{it}) \rangle$$

is the unit vector that has angle $\theta_{it}$; (d) $v_{i2} = \langle \cos(\theta_{i2}), \sin(\theta_{i2}) \rangle$ is the unit vector that has angle $\theta_{i2}$; (e) N is the number of samples;

$$(f)\, \overline{v}_t = \frac{1}{N}\sum_i v_{it}$$

is the mean resultant vector of the target phase;

$$(g)\, \overline{v}_2 = \frac{1}{N}\sum_i v_{i2}$$

is the mean resultant vector of the second phase; (h) the p-value of the circular-circular correlation coefficient is $$P = 2\left(1 - \int_{x=-\infty}^{|z|} \frac{e^{-x^2/2}}{\sqrt{2\pi}}\right),$$

where π is Archimedes constant, e is Euler's number, $$z = \rho_{cc}\sqrt{\frac{N\lambda_{20}\lambda_{02}}{\lambda_{22}}}\,,\text{ and } \lambda_{ab}\frac{1}{N}\sum_i \sin^a(v_{i2} - \overline{v}_2)\sin^b(v_{it} - \overline{v}_t);$$

(i) the mean phase difference is $$\overline{\theta}_e = \frac{1}{N}\sum_i \theta_{ie}, \text{ where } \theta_{ie} = \angle(e^{i*\theta_{it}}/e^{i*\theta_{iz}});$$

and (j) e is Euler's number, $i=\sqrt{-1}$ and $\angle(w)$ is the phase angle of a complex number w. For purposes of this paragraph, each of the following is a non-limiting example of a particular feature of a stimulation: (a) start of the stimulation; and (b) end of the stimulation. For purposes of this paragraph, the target phase and second phase are each associated with the same frequency range or frequency bin, which range or bin has a lower frequency bound and an upper frequency bound that do not change throughout the time interval.

As used herein, to say that a sensation is "phase-correlated" with a signal during a time interval means that: (a) the sensation occurs repeatedly during the time interval; (b) the absolute value of the mean phase difference between a target phase and a second phase for the time interval is less than or equal to 0.872665 radians; and (c) the circular-circular correlation coefficient between the target phase and the second phase for the time interval is greater than 0.6 with p-value of less than 0.05. For purposes of the preceding sentence: (a) the target phase is phase of the signal at which a particular feature of the sensation is targeted to occur; (b) the second phase is phase of the signal at which the particular feature of the sensation actually occurs; and (c) during repetition of the sensation, the target phase and second phase each may but do not necessarily vary. For purposes of this paragraph: (a) $\theta_{it}$ and $\theta_{i2}$ are the target phase and second phase, respectively, for sample i; (b) the circular-circular correlation coefficient is $$\rho_{cc} = \frac{\sum_i \sin(v_{i2} - \overline{v}_2)\sin(v_{it} - \overline{v}_t)}{\sqrt{\sum_i \sin^2(v_{i2} - \overline{v}_2)\sin^2(v_{it} - \overline{v}_t)}};$$

$$(c)\ v_{it} = \langle\cos(\theta_{it}), \sin(\theta_{it})\rangle$$

is the unit vector that has angle $\theta_{it}$; (d) $v_{i2}=\langle\cos(\theta_{i2}), \sin(\theta_{i2})\rangle$ is the unit vector that has angle $\theta_{i2}$; (e) N is the number of samples;

$$(f)\ \overline{v}_t = \frac{1}{N}\sum_i v_{it}$$

is the mean resultant vector of the target phase;

$$(g)\ \overline{v}_2 = \frac{1}{N}\sum_i v_{i2}$$

is the mean resultant vector of the second phase; (h) the p-value of the circular-circular correlation coefficient is $$P = 2\left(1 - \int_{x=-\infty}^{|z|} \frac{e^{-x^2/2}}{\sqrt{2\pi}}\right),$$

where $\pi$ is Archimedes constant, e is Euler's number, $$z = \rho_{cc}\sqrt{\frac{N\lambda_{20}\lambda_{02}}{\lambda_{22}}},\ \text{and}\ \lambda_{ab}\frac{1}{N}\sum_i \sin^a(v_{i2} - \overline{v}_2)\sin^b(v_{it} - \overline{v}_t);$$

(i) the mean phase difference is $$\overline{\theta}_e = \frac{1}{N}\sum_i \theta_{ie},\ \text{where}\ \theta_{ie} = \angle(e^{i*\theta_{it}}/e^{i*\theta_{iz}});$$

and (j) e is Euler's number, $i=\sqrt{-1}$, and $\angle(w)$ is the phase angle of a complex number w. For purposes of this paragraph, each of the following is a non-limiting example of a particular feature of a sensation: (a) start of the sensation; and (b) end of the sensation. For purposes of this paragraph, the target phase and second phase are each associated with the same frequency range or frequency bin, which range or bin has a lower frequency bound and an upper frequency bound that do not change throughout the time interval.

As used herein, to say that stimulation is "phase-matched" with a signal during a time interval means that the stimulation occurs repeatedly during the time interval and, for the time interval, the mean difference between a target phase and a second phase has a magnitude that is less than or equal to 0.5 degrees, where: (a) the target phase is a phase of the signal and is constant throughout the time interval; (b) the second phase is phase of the signal at which a particular feature of the stimulation actually occurs; and (c) during repetition of the stimulation, the second phase may but does not necessarily vary. For purposes of the first sentence of this paragraph, each of the following is a non-limiting example of a particular feature of a stimulation: (a) start of the stimulation; and (b) end of the stimulation. For purposes of the first sentence of this paragraph, the target phase and second phase are each associated with the same frequency range or frequency bin, which range or bin has a lower frequency bound and an upper frequency bound that do not change throughout the time interval.

As used herein, to say that a sensation is "phase-matched" with a signal during a time interval means that the sensation occurs repeatedly during the time interval and, for the time interval, the mean difference between a target phase and a second phase has a magnitude that is less than or equal to 0.5 degrees, where: (a) the target phase is a phase of the signal and is constant throughout the time interval; (b) the second phase is phase of the signal at which a particular feature of the sensation actually occurs; and (c) during repetition of the sensation, the second phase may but does not necessarily vary. For purposes of the first sentence of this paragraph, each of the following is a non-limiting example of a particular feature of a sensation: (a) start of the sensation; and (b) end of the sensation. For purposes of the first sentence of this paragraph, the target phase and second phase are each associated with the same frequency range or frequency bin, which range or bin has a lower frequency bound and an upper frequency bound that do not change throughout the time interval.

As used herein, to say that a stimulation is "phase-related" with a signal during a time interval means that the stimulation occurs repeatedly during the time interval and, for the time interval, the mean difference between a target phase and a second phase has a magnitude that is less than or equal to 65 degrees, where: (a) the target phase is a phase of the signal and is constant throughout the time interval; (b) the second phase is phase of the signal at which a particular feature of the stimulation actually occurs; and (c) during repetition of the stimulation, the second phase may but does not necessarily vary. For purposes of the first sentence of this paragraph, each of the following is a non-limiting example of a particular feature of a stimulation: (a) start of the stimulation; and (b) end of the stimulation. For purposes of the first sentence of this paragraph, the target phase and second phase are each associated with the same frequency range or frequency bin, which range or bin has a lower frequency bound and an upper frequency bound that do not change throughout the time interval.

As used herein, to say that a sensation is "phase-related" with a signal during a time interval means that the sensation occurs repeatedly during the time interval and, for the time interval, the mean difference between a target phase and a second phase has a magnitude that is less than or equal to 65 degrees, where: (a) the target phase is a phase of the signal and is constant throughout the time interval; (b) the second phase is phase of the signal at which a particular feature of the sensation actually occurs; and (c) during repetition of the sensation, the second phase may but does not necessarily vary. For purposes of the first sentence of this paragraph, each of the following is a non-limiting example of a particular feature of a sensation: (a) start of the sensation; and (b) end of the sensation. For purposes of the first sentence of this paragraph, the target phase and second phase are each associated with the same frequency range or frequency bin, which range or bin has a lower frequency bound and an upper frequency bound that do not change throughout the time interval.

To say that a specific feature of stimulation is "phase-instant-locked" to a target phase of a signal at a specific time means that, at the specific time, the magnitude of the difference between the target phase and the phase of the signal at which the specific feature occurs is less than or equal to 5 degrees. For purposes of the first sentence of this paragraph, each of the following is a non-limiting example of a specific feature of a stimulation: (a) start of the stimulation; and (b) end of the stimulation. For purposes of the first sentence of this paragraph, the target phase and second phase are each associated with the same frequency range or frequency bin.

To say that a specific feature of sensation is "phase-instant-locked" to a target phase of a signal at a specific time means that, at the specific time, the magnitude of the difference between the target phase and the phase of the signal at which the specific feature occurs is less than or equal to 5 degrees. For purposes of the first sentence of this paragraph, each of the following is a non-limiting example of a specific feature of a sensation: (a) start of the sensation; and (b) end of the sensation. For purposes of the first sentence of this paragraph, the target phase and second phase are each associated with the same frequency range or frequency bin.

As used herein, to say that a first signal is "phase-difference-locked" with a second signal means that the difference between the phase of the first signal and the phase of the second signal is constant. For example, two signals that are anti-phasic relative to each other (i.e., 180 degrees in phase apart from each other) are "phase-difference-locked".

As used herein, to say that a first signal is "phase-coordinated" with a second signal means that the full width at half maximum (FWHM) of a histogram is less than 0.314159 radians, where (i) the histogram is a histogram of the difference, in radians, between (A) the instantaneous phase of the first signal and (B) the instantaneous phase of a shifted version of the second signal, which shifted version is shifted to the extent needed to cause the first signal and shifted signal to have the same phase at the first point in time that is taken into account in the histogram. Thus, loosely speaking, when a first and second signal are "phase-coordinated", the variation in difference in phase between the first and second signals is limited and the drift of the first and second signals relative to each other is limited.

Figure 24:
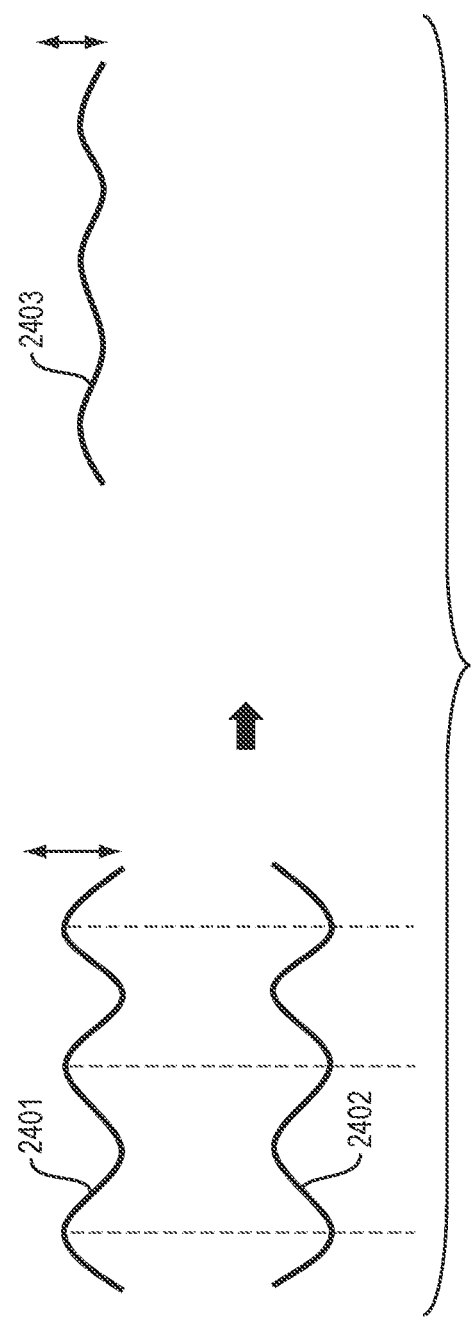
FIG. 24 shows a neuromodulation signal that reduces the amplitude of a physiological signal.

FIG. 24 shows a neuromodulation signal 2402 that is anti-phasic to a physiological signal 2401, in an illustrative implementation of this invention. This reduces the amplitude of physiological signal 2401, resulting in physiological signal 2403.

Figure 25:
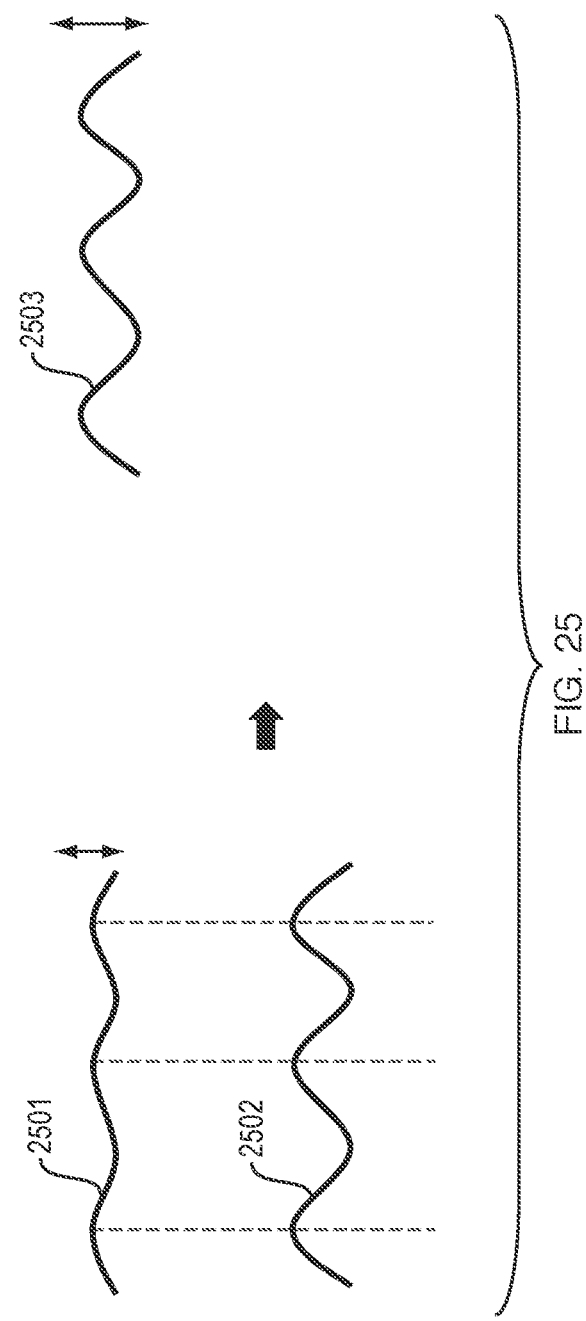
FIG. 25 shows a neuromodulation signal that increases the amplitude of a physiological signal.

FIG. 25 shows a neuromodulation signal 2502 that is phase-locked with a physiological signal 2501, in an illustrative implementation of this invention. This reduces the amplitude of physiological signal 2501, resulting in physiological signal 2503.

Figure 26:
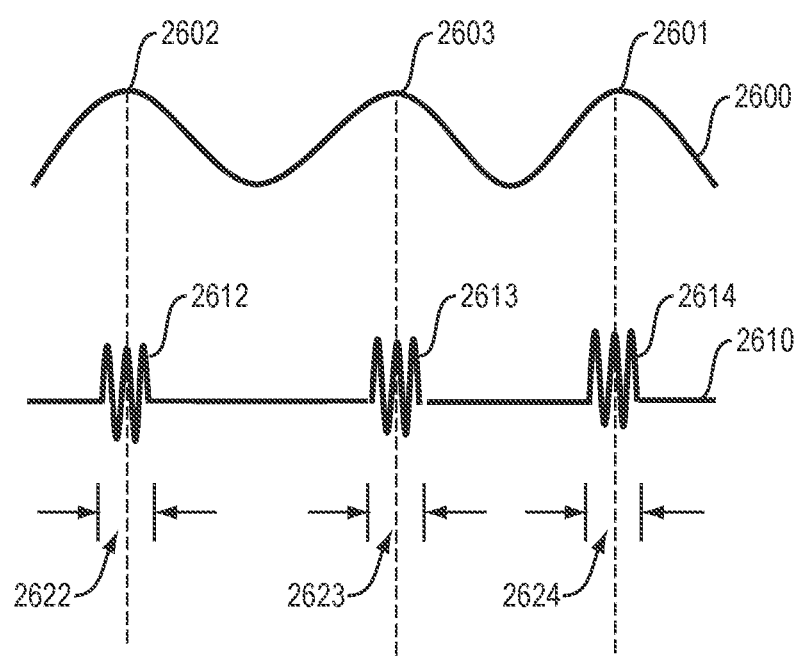
FIG. 26 shows an example of phase coding.

FIG. 26 shows an example of phase coding, in an illustrative implementation of this invention. In FIG. 26, a neuromodulation signal 2610 includes short bursts 2612, 2613, 2614 that are phase-locked with a physiological signal 2600. These short bursts at high frequency occur only during a narrow phase range, e.g., 2622, 2623, 2624, of each period of the physiological signal 2600. In the example shown in FIG. 26, these short bursts occur at the peaks 2602, 2603, 2601 of the physiological signal 2600.

In FIGS. 24, 25 and 26, each neuromodulation signal (2402, 2502, 2610) is phase-coordinated with the physiological signal (2401, 2501, 2600, respectively).

More Details

In some implementations of this invention, the accuracy of ecHT is improved by separately adjusting the time interval between the analog-to-digital sampling (t_ADC) and the interval of ecHT computation (t_ecHT). In some implementations, if the minimal interval of the ecHT computation (t_ecHT_min) is larger than one hundredth of endogenous brain oscillation period (T_brain), i.e., t_ecHT_min>T_brain/100, then t_ecHT is set to t_ecHT_min, t_ADC is set to T_brain/100 or to the closest value that is smaller than T_brain/100, and the size of the ecHT buffer (W_ecHT) is set to 128 or to the power of two value that is closest to T_brain/t_ADC. In some implementations, if t_ecHT_min is equal or smaller than one hundredth of T_brain, then t_ecHT is set to t_ecHT_min or to the closest value that is smaller than T_brain/100, t_ADC is set to t_ecHT, and W_ecHT is set to 128 or to the power of two value that is closest to T_brain/t_ecHT.

Software

The following is a description of the 34 ASCII text files (collectively, the "Source Code") listed in the Computer Program Listing section above.

Out of the 34 software files included in the Source Code, the following 23 files encode software that may be performed by an Arduino® Due board: (1) adc_LTC2442_h.txt; (2) ButterworthBandpass_v2_h.txt; (3) config_table_h.txt; (4) digital_pot_AD5290_h.txt; (5) display_LCM_S04004DSF_h.txt; (6) due_pin_config_h.txt; (7) DueFirmware_ino.txt; (8) DueTimer_cpp.txt; (9) DueTimer_h.txt; (10) EEGRegisterData_h.txt; (11) FFT_C.txt; (12) FFT_H.txt; (13) iir_c.txt; (14) iir_h.txt; (15) InputHandler_h.txt; (16) math_util_h.txt; (17) trigger_h.txt; (18) VarSizeSplitRadixRealP_cpp.txt; (19) VarSizeSplitRadixRealP_h.txt; (20) VirtualLiquidCrystal_h.txt; (21) waveconst_h.txt; (22) window_h.txt; and (23) z_atan2_approximation_h.txt.

Out of the 34 software files included in the Source Code, the following 11 files encode software that is performed by an Arduino® Teensy® board: (1) Adafruit_Soundboard_Mod_cpp.txt; (2) Adafruit_Soundboard_Mod_h.txt; (3) dac_AD5065_h.txt; (4) digital_pot_AD5122_h.txt; (5) EEGRegisterControl_h.txt; (6) EEGRegisterData_h.txt; (7) InputHandler_h.txt; (8) shift_reg_74HC595_h.txt; (9) teensy_pin_config_h.txt; (10) TeensyFirmware_ino.txt; and (11) time_utils_h.txt.

The names of the 34 ASCII files that comprise the Source Code have been modified (a) by replacing each period with an underscore, and (b) by appending the ".txt" extension to each file name. (These modifications were made in order to be able to upload the .txt files to the United States Patent &

Trademark Office website during the patent application process). However, in order for the Source Code to run on Arduino, these modifications to the file names may be reversed, that is: (a) ".txt" may be removed from the end of the file names of the 34 ASCII text files; (b) the last underscore in each file name may be replaced by a period; and (c) in addition, for the file z_atan2_approximation_h.txt, the first underscore in the file name may also be replaced by a period.

Together, the Source Code comprises software used in a prototype of this invention. The Source Code comprises a non-limiting example of software that may be employed in this invention. This invention may be implemented with other software.

Computers

In illustrative implementations of this invention, one or more computers (e.g., servers, network hosts, client computers, integrated circuits, microcontrollers, controllers, field-programmable-gate arrays, personal computers, digital computers, driver circuits, or analog computers) are programmed or specially adapted to perform one or more of the following tasks: (1) to control the operation of, or interface with, hardware components of a neuromodulator, including any transducer or sensor; (2) to control the operation of, or interface with, hardware components of any sensor, including any EEG sensor; (3) to perform any calculation to correct distortion due to Gibbs phenomenon, including to perform any "frequency domain" ECHT algorithm, "end-padded time domain" ECHT algorithm, or any "front-padded time domain" ECHT; (4) to calculate instantaneous phase and instantaneous amplitude (e.g., of the most recent sample of a signal); (5) to control a transducer in such a way that stimulation outputted by the transducer (or sensation caused by the stimulation) is phase-locked with an endogenous neural signal; (6) to control stimulation in such a way that the stimulation causes a user to fall asleep more quickly than the user otherwise would in the absence of the stimulation; (7) to control stimulation in such a way that the stimulation induces or modifies sleep or any behavior or state associated with sleep; (8) to receive data from, control, or interface with one or more sensors; (9) to perform any other calculation, computation, program, algorithm, or computer function described or implied herein; (10) to receive signals indicative of human input; (11) to output signals for controlling transducers for outputting information in human perceivable format; (12) to process data, to perform computations, and to execute any algorithm or software; and (13) to control the read or write of data to and from memory devices (tasks 1-12 of this sentence referred to herein as the "Computer Tasks"). The one or more computers (e.g. 401, 420, 500, 710, 1204, 1301) may, in some cases, communicate with each other or with other devices: (a) wirelessly, (b) by wired connection, (c) by fiber-optic link, or (d) by a combination of wired, wireless or fiber optic links.

In exemplary implementations, one or more computers are programmed to perform any and all calculations, computations, programs, algorithms, computer functions and computer tasks described or implied herein. For example, in some cases: (a) a machine-accessible medium has instructions encoded thereon that specify steps in a software program; and (b) the computer accesses the instructions encoded on the machine-accessible medium, in order to determine steps to execute in the program. In exemplary implementations, the machine-accessible medium may comprise a tangible non-transitory medium. In some cases, the machine-accessible medium comprises (a) a memory unit or (b) an auxiliary memory storage device. For example, in some cases, a control unit in a computer fetches the instructions from memory.

In illustrative implementations, one or more computers execute programs according to instructions encoded in one or more tangible, non-transitory, computer-readable media. For example, in some cases, these instructions comprise instructions for a computer to perform any calculation, computation, program, algorithm, or computer function described or implied herein. For example, in some cases, instructions encoded in a tangible, non-transitory, computer-accessible medium comprise instructions for a computer to perform the Computer Tasks.

Network Communication

In illustrative implementations of this invention, electronic devices (e.g., 401, 420, 500, 541, 542, 543, 544, 605, 606, 607, 710, 1203, 1204, 1209, 1301, 1350) may be configured for wireless or wired communication with other devices in a network.

For example, in some cases, one or more of these electronic devices each include a wireless module for wireless communication with other devices in a network. Each wireless module (e.g., 1207) may include (a) one or more antennas, (b) one or more wireless transceivers, transmitters or receivers, and (c) signal processing circuitry. Each wireless module may receive and transmit data in accordance with one or more wireless standards.

In some cases, one or more of the following hardware components are used for network communication: a computer bus, a computer port, network connection, network interface device, host adapter, wireless module, wireless card, signal processor, modem, router, cables or wiring.

In some cases, one or more computers (e.g., 401, 420, 500, 710, 1204, 1301) are programmed for communication over a network. For example, in some cases, one or more computers are programmed for network communication: (a) in accordance with the Internet Protocol Suite, or (b) in accordance with any other industry standard for communication, including any USB standard, ethernet standard (e.g., IEEE 802.3), token ring standard (e.g., IEEE 802.5), wireless standard (including IEEE 802.11 (wi-fi), IEEE 802.15 (bluetooth/zigbee), IEEE 802.16, IEEE 802.20 and including any mobile phone standard, including GSM (global system for mobile communications), UMTS (universal mobile telecommunication system), CDMA (code division multiple access, including IS-95, IS-2000, and WCDMA), or LTE (long term evolution)), or other IEEE communication standard.

Definitions

The terms "a" and "an", when modifying a noun, do not imply that only one of the noun exists. For example, a statement that "an apple is hanging from a branch": (i) does not imply that only one apple is hanging from the branch; (ii) is true if one apple is hanging from the branch; and (iii) is true if multiple apples are hanging from the branch.

"AASM" means the American Academy of Sleep Medicine.

"AASM Manual" means the AASM Manual for the Scoring of Sleep and Associated Events, version 2.1.

"Alpha band" means a band of frequencies that is greater than 7.5 Hz and less than or equal to 12 Hz.

"Alpha signal" or "alpha wave" means a signal in the alpha band.

"Archimedes' constant" means the ratio of a circle's circumference to its diameter. Archimedes' constant is sometimes called "pi" or "π". Archimedes' constant is an irrational number that is approximately equal to 3.14159.

Unless the context clearly indicates otherwise, a variable with a straight horizontal line accent mark over it denotes an average value of that variable. For instance, $\bar{c}$ denotes an average value of c.

Unless the context clearly indicates otherwise, each of the following is a non-limiting example of an "association": (a) an organization; or (b) a non-human entity that exists under law and that has legal rights.

"Beta band" means a band of frequencies that is greater than 12 Hz and less than or equal to 30 Hz.

"Beta signal" or "beta wave" means a signal in the beta band.

To compute "based on" specified data means to perform a computation that takes the specified data as an input.

The term "comprise" (and grammatical variations thereof) shall be construed as if followed by "without limitation". If A comprises B, then A includes B and may include other things.

The term "computer" includes any computational device that performs logical and arithmetic operations. For example, in some cases, a "computer" comprises an electronic computational device, such as an integrated circuit, a microprocessor, a mobile computing device, a laptop computer, a tablet computer, a personal computer, or a mainframe computer. In some cases, a "computer" comprises: (a) a central processing unit, (b) an ALU (arithmetic logic unit), (c) a memory unit, and (d) a control unit that controls actions of other components of the computer so that encoded steps of a program are executed in a sequence. In some cases, a "computer" also includes peripheral units including an auxiliary memory storage device (e.g., a disk drive or flash memory), or includes signal processing circuitry. However, a human is not a "computer", as that term is used herein.

To "correct" means (i) to correct, (ii) to prevent, (iii) to mitigate or ameliorate, or (iv) to compensate for. A non-limiting example of correcting a distortion is to compensate for the distortion before, after or concurrently with the distortion.

To say that a first data point of a first signal "corresponds in time" to a second data point of a second signal means that the first and second data points are associated with the same moment in time. For example, if a first signal is x(t) and a second signal is y(t), where t is time, and both signals start at the same time and have the same unit of time, then x(3) and y(3) "correspond in time" to each other.

"Defined Term" means a term or phrase that is set forth in quotation marks in this Definitions section.

"Delta band" means a band of frequencies that is greater than 0.1 Hz and less than or equal to 3.5 Hz.

"Delta signal" or "delta wave" means a signal in the delta band.

"Delta/total spectrum ratio" of a signal means the ratio of the absolute power of the theta band of the signal over the absolute power of the total spectrum of the signal.

"DFT" means discrete Fourier transform.

For an event to occur "during" a time period, it is not necessary that the event occur throughout the entire time period. For example, an event that occurs during only a portion of a given time period occurs "during" the given time period.

"ECHT" means endpoint-correct Hilbert transform. "ecHT" means endpoint-correct Hilbert transform.

The term "e.g." means for example.

"Endogenous signal" or "endogenous wave" means a signal that is produced by human tissue.

To "end-pad" a signal which has a given point that is the endpoint of the signal means to add one or more data values to the signal after the given point, such that the given point is no longer the endpoint of the signal.

The "endpoint" of a discrete signal means the final data value in the signal.

An "end-segment" of a discrete signal means a segment of the signal that includes the endpoint of the signal.

The fact that an "example" or multiple examples of something are given does not imply that they are the only instances of that thing. An example (or a group of examples) is merely a non-exhaustive and non-limiting illustration.

"Euler's number" means the unique number whose natural logarithm is equal to one. Euler's number is a constant that is approximately equal to 2.71828

"Exogenous signal" means a signal that is produced by a machine.

"FFT" means Fast Fourier Transform.

The following is a non-limiting example of "filtering" a signal: digitally applying a filter to the signal in the time domain, by convolving (i) an impulse response of the filter and (ii) the signal. The following is another non-limiting example of "filtering" a signal: digitally applying a filter to the signal in the Fourier frequency domain, by multiplying (i) a Fourier transform of the impulse response of the filter and (ii) a Fourier transform of the signal. The following is another non-limiting example of "filtering" a signal: filtering the signal with an analog filter.

The following is a non-limiting example of "casually filtering" or "casually smoothing" a signal: (a) reversing the order of data values in the signal, such that the start of the signal becomes the end of the signal and the end of the signal becomes the start of the signal, and then (b) applying an anti-causal filter to the reversed signal. Likewise, any description of an algorithm that involves applying a causal filter shall be construed as also describing an alternative version in which: (a) the signal is reversed and an anti-causal filter is applied, as described in the preceding sentence; and (b) the algorithm is modified, mutatis mutandis, to accommodate the reversed order, such as, for example, by replacing end-padding with front-padding.

Unless the context clearly indicates otherwise: (1) a phrase that includes "a first" thing and "a second" thing does not imply an order of the two things (or that there are only two of the things); and (2) such a phrase is simply a way of identifying the two things, respectively, so that they each may be referred to later with specificity (e.g., by referring to "the first" thing and "the second" thing later). For example, unless the context clearly indicates otherwise, if an equation has a first term and a second term, then the equation may (or may not) have more than two terms, and the first term may occur before or after the second term in the equation. A phrase that includes a "third" thing, a "fourth" thing and so on shall be construed in like manner.

"For instance" means for example.

To "front-pad" a signal which has a given point that is the start point of the signal means to add one or more data values to the signal before the given point, such that the given point is no longer the start point of the signal.

A "front-segment" of a discrete signal means a segment of the signal that includes the start point of the signal.

"Gamma band" means a band of frequencies that is greater than 30 Hz and less than or equal to 100 Hz.

"Gamma signal" or "gamma wave" means a signal in the gamma band.

To say a "given" X is simply a way of identifying the X, such that the X may be referred to later with specificity. To say a "given" X does not create any implication regarding X. For example, to say a "given" X does not create any implication that X is a gift, assumption, or known fact.

"Herein" means in this document, including text, specification, claims, abstract, and drawings.

As used herein: (1) "implementation" means an implementation of this invention; (2) "embodiment" means an embodiment of this invention; (3) "case" means an implementation of this invention; and (4) "use scenario" means a use scenario of this invention.

The term "include" (and grammatical variations thereof) shall be construed as if followed by "without limitation".

To say that a second point of a signal is "later" than a first point of the signal means that the second point is closer to the endpoint of the signal than the first point is.

"LTI" means linear and time-invariant.

To "multiply" includes to multiply by an inverse. Thus, to "multiply" includes to divide.

The term "or" is inclusive, not exclusive. For example, A or B is true if A is true, or B is true, or both A and B are true. Also, for example, a calculation of A or B means a calculation of A, or a calculation of B, or a calculation of A and B.

A parenthesis is simply to make text easier to read, by indicating a grouping of words. A parenthesis does not mean that the parenthetical material is optional or may be ignored.

The term "phase-coordinated" is defined elsewhere in this document.

The term "phase-correlated" is defined elsewhere in this document.

The term "phase-difference-locked" is defined elsewhere in this document.

The term "phase-instant-locked" is defined elsewhere in this document.

The term "phase-locked" is defined elsewhere in this document.

The term "phase-tracking" is defined elsewhere in this document.

As used herein, the term "set" does not include a group with no elements.

Unless the context clearly indicates otherwise, "some" means one or more.

As used herein, a "subset" of a set consists of less than all of the elements of the set.

"Stage N1" means Stage N1, as defined in the AASM Manual.

"Stage N2" means Stage N2, as defined in the AASM Manual.

"Stage N3" means Stage N3, as defined in the AASM Manual.

"Stage R" means Stage R, as defined in the AASM Manual.

"Stage W" means Stage W, as defined in the AASM Manual.

"Standard-scored sleep onset" means sleep onset as defined in the AASM Manual.

The "start point" of a discrete signal means the beginning data value in the signal.

"Stimulation" means a physical phenomenon that triggers a response. As a non-limiting example, "stimulation" may trigger a response that comprises increasing the frequency or intensity of a behavior, or may trigger a response that comprises suppressing a behavior.

A "substantial increase" in X means a change in value of X from a first value $X_1$ to a second value $X_2$, where $X_2 > X_1$ and $|X_2 - X_1| \geq |0.2 X_1|$ The term "such as" means for example.

"Theta band" means a band of frequencies that is greater than 3.5 Hz and less than or equal to 7.5 Hz.

"Theta signal" or "theta wave" means a signal in the theta band.

"Theta/alpha ratio" of a signal means the ratio of the absolute power of the theta band of the signal over the absolute power of the alpha band of the signal.

To say that a machine-readable medium is "transitory" means that the medium is a transitory signal, such as an electromagnetic wave.

Except to the extent that the context clearly requires otherwise, if steps in a method are described herein, then the method includes variations in which: (1) steps in the method occur in any order or sequence, including any order or sequence different than that described herein; (2) any step or steps in the method occur more than once; (3) any two steps occur the same number of times or a different number of times during the method; (4) any combination of steps in the method is done in parallel or serially; (5) any step in the method is performed iteratively; (6) a given step in the method is applied to the same thing each time that the given step occurs or is applied to different things each time that the given step occurs; (7) one or more steps occur simultaneously, or (8) the method includes other steps, in addition to the steps described herein.

Headings are included herein merely to facilitate a reader's navigation of this document. A heading for a section does not affect the meaning or scope of that section.

This Definitions section shall, in all cases, control over and override any other definition of the Defined Terms. The Applicant or Applicants are acting as his, her, its or their own lexicographer with respect to the Defined Terms. For example, the definitions of Defined Terms set forth in this Definitions section override common usage or any external dictionary. If a given term is explicitly or implicitly defined in this document, then that definition shall be controlling, and shall override any definition of the given term arising from any source (e.g., a dictionary or common usage) that is external to this document. If this document provides clarification regarding the meaning of a particular term, then that clarification shall, to the extent applicable, override any definition of the given term arising from any source (e.g., a dictionary or common usage) that is external to this document. Unless the context clearly indicates otherwise, any definition or clarification herein of a term or phrase applies to any grammatical variation of the term or phrase, taking into account the difference in grammatical form. For example, the grammatical variations include noun, verb, participle, adjective, and possessive forms, and different declensions, and different tenses.

Variations

This invention may be implemented in many different ways. Here are some non-limiting examples:

In some implementations, this invention is a method comprising: (a) taking electroencephalography measurements of an endogenous electrical signal that originates in a brain of a user; (b) calculating a set of one or more estimates of (i) instantaneous phase of the endogenous signal and (ii) instantaneous amplitude of the endogenous signal; (c) producing stimulation in such a way that the stimulation causes the user to undergo, more quickly than the user would in the absence of the stimulation, a transition from wakefulness of the user to sleep onset of the user, which transition (i) starts when the user closes his or her eyes while awake, and (ii) ends with the sleep onset; and (d) controlling, based on the set of one or more estimates of instantaneous phase and instantaneous amplitude, timing of one or more changes in the stimulation. In some cases, each estimate in the set of one or more estimates of instantaneous phase and instantaneous amplitude is calculated based on a specific sample in a specific sample window of the measurements in such a way that: (a) the specific sample window is different than that for any other estimate in the set; and (b) the specific sample is more recent than any other sample in the specific sample window. In some cases, the specific sample window comprises multiple samples of the measurements. In some cases, the stimulation comprises audio stimulation. In some cases, the stimulation comprises visual stimulation. In some cases, each estimate of instantaneous phase and instantaneous amplitude is computed in less than ten milliseconds. In some cases, time elapsed between taking a particular measurement and outputting stimulation based at least in part on the particular measurement is less than ten milliseconds. In some cases, the stimulation causes the user to perceive binaural beats. In some cases, for each specific estimate in the set of estimates of instantaneous phase and instantaneous amplitude: (a) the calculating of the specific estimate is based on a specific sample window of the measurements that is different than that for each other estimate in the set; (b) the calculating of the specific estimate is not based on any sample window of the measurements other than the specific sample window; and (c) the calculating includes performing an inverse discrete Fourier transform that reconstructs only a single sample, which single sample is in the specific sample window and is more recent than other sample in the specific sample window. In some cases, for each specific estimate in the set of estimates of instantaneous phase and instantaneous amplitude, the calculating includes: (a) reconstructing, by an inverse discrete Fourier transform, a single sample of the measurements; and (b) computing the specific estimate based on the single sample and not based on any other sample. In some cases, the calculating of each estimate of instantaneous phase and instantaneous amplitude includes applying a causal filter in a frequency domain. In some cases, for each specific estimate in the set of one or more estimates of instantaneous phase and instantaneous amplitude, the method further includes: (a) padding and filtering a specific sample window for the specific estimate to create a padded and filtered sample window, in such a way that a difference in value between data points at each end of the padded and filtered sample window is less than a difference in value between data points at each end of the sample window before padding and filtering; and (b) performing a discrete Fourier transform and Hilbert transform to calculate an analytic representation of the padded and filtered sample window. In some cases, for each specific estimate in the set of one or more estimates of instantaneous phase and instantaneous amplitude, the method further includes: (a) adding padding to a specific sample window for the specific estimate and then filtering the specific sample window to create a padded and filtered sample window; and (b) performing a discrete Fourier transform and Hilbert transform to calculate an analytic representation of the padded and filtered sample window. In some cases, the transition from wakefulness to sleep onset involves an increase in absolute theta band power of the endogenous signal. In some cases, the transition from wakefulness to sleep onset involves an increase in theta/alpha ratio of the endogenous signal. In some cases, the transition from wakefulness to sleep onset involves an increase in absolute theta band power of the endogenous signal and an increase in theta/alpha ratio of the endogenous signal. In some cases, the sleep onset comprises standard-scored sleep onset. In some cases, the sleep onset is the first 30-second epoch, after the start of the transition, in which theta/alpha ratio of the endogenous signal during the epoch is greater than or equal to one. In some cases: (a) the measurements are taken by frontal cortex electroencephalography; and (b) the sleep onset is the first 30-second epoch, after the start of the transition, in which theta/alpha ratio of the endogenous signal during the epoch is greater than or equal to one. In some cases, the sleep onset is the first 30-second epoch, after the start of the transition, in which: (a) average absolute theta power of the endogenous signal during the epoch is at least 50% greater than an initial absolute theta power; and (b) average theta/alpha ratio of the endogenous signal during the epoch is at least 50% greater than an initial theta/alpha ratio, where the initial absolute theta power and the initial theta/alpha ratio are absolute theta power of the endogenous signal and theta/alpha ratio of the endogenous signal, respectively, during an initial 30-second period that starts at the beginning of the transition. In some cases, the sleep onset is the first 30-second epoch of Stage N–1 sleep after the start of the transition. In some cases, the sleep onset is the first 30-second epoch of Stage N–2 sleep after the start of the transition. In some cases, the sleep onset occurs at the beginning of the first three consecutive 30-second epochs of non-rapid-eye-movement (NREM) sleep after the start of the transition. In some cases, the sleep onset occurs at the beginning of the first ten consecutive 30-second epochs of non-rapid-eye-movement (NREM) sleep after the start of the transition. In some cases, the stimulation is phase-locked with the endogenous signal. In some cases, the stimulation is phase-tracking with the endogenous signal. In some cases, the stimulation is phase-tracking with the endogenous signal. In some cases, the stimulation is phase-matched with the endogenous signal. In some cases, the stimulation is phase-related with the endogenous signal. In some cases, a feature of the stimulation is phase-instant-locked to a target phase of the endogenous signal at a specific time. In some cases, the stimulation is phase-difference-locked with the endogenous signal. In some cases, the stimulation is phase-coordinated with the endogenous signal. In some cases, time of peaks of the stimulation is positively correlated with time of peaks of the endogenous signal. In some cases, time of peaks of the stimulation is negatively correlated with time of peaks of the endogenous signal. In some cases, the stimulation produces sensation in the user, which sensation is phase-locked with the endogenous signal. In some cases, the stimulation produces sensation in the user, which sensation is phase-tracking with the endogenous signal. In some cases, the stimulation produces sensation in the user, which sensation is phase-correlated with the endogenous signal. In some cases, the stimulation produces a sensation in the user, which sensation is phase-matched with the endogenous signal. In some cases, the stimulation produces a sensation in the user, which sensation is phase-related with the endogenous signal. In some cases, the stimulation produces a sensation in the user, in such a way that a feature of the sensation is phase-instant-locked to a target phase of the endogenous signal at a specific time. In some cases, the stimulation produces a sensation in the user, which sensation is phase-difference-locked with the endogenous signal. In some cases, the stimulation produces a sensation in the user, which sensation is phase-coordinated with the endogenous signal. In some cases: (a) the stimulation produces a sensation in the user; and (b) time of peaks of the sensation is positively correlated with time of peaks of the endogenous signal. In some cases: (a) the stimulation produces a sensation in the user; and (b) time of peaks of the sensation is negatively correlated with time of peaks of the endogenous signal. In some cases, the stimulation causes one or more changes in behavior of the user, which changes are positively correlated with a process of falling asleep, and which behavior is a behavior other than neural activity. In some cases, the stimulation causes changes in one or more physiological states of the user, which changes are positively correlated with a process of falling asleep, and which physiological states comprise respiration, beating of the heart, movement of an eye, or movement of a limb or head of the user. In some cases, the stimulation is anti-phasic to the endogenous signal. In some cases: (a) the stimulation produces a sensation in the user; and (b) the stimulation is anti-phasic to the endogenous signal. In some cases, the stimulation is periodic. In some cases, the endogenous signal is periodic. In some cases, the stimulation is periodic and the endogenous signal is periodic. In some cases, greatest power of the endogenous signal occurs in the theta band, during a least a portion of the transition. In some cases, greatest power of the endogenous signal occurs in the alpha band, during a least a portion of the transition. In some cases, amplitude of the stimulation is greater during refractory neural periods than during other periods. In some cases, amplitude of the stimulation is greater during excitable neural periods than during other periods. In some cases: (a) the endogenous signal is periodic and is a theta signal; and (b) a pulse of the stimulation (i) starts when phase of the endogenous signal is less than or equal to zero degrees, and (ii) stops when the endogenous signal has a phase that is greater than or equal to zero degrees, zero degrees phase being phase at which the endogenous signal peaks during a period of the endogenous signal. In some cases: (a) the endogenous signal is periodic and is a theta signal; and (b) a pulse of the stimulation (i) starts when phase of the endogenous signal is less than or equal to 180 degrees, and (ii) stops when the endogenous signal has a phase that is greater than or equal to 180 degrees, zero degrees phase being phase at which the endogenous signal peaks during a period of the endogenous signal. In some cases: (a) the endogenous signal is periodic and is an alpha signal; and (b) a pulse of the stimulation (i) starts when phase of the endogenous signal is less than or equal to zero degrees, and (ii) stops when the endogenous signal has a phase that is greater than or equal to zero degrees, zero degrees phase being phase at which the endogenous signal peaks during a period of the endogenous signal. In some cases: (a) the endogenous signal is periodic and is an alpha signal; and (b) a pulse of the stimulation (i) starts when phase of the endogenous signal is less than or equal to 180 degrees, and (ii) stops when the endogenous signal has a phase that is greater than or equal to 180 degrees, zero degrees phase being phase at which the endogenous signal peaks during a period of the endogenous signal. In some cases: (a) the endogenous signal is periodic and is a delta signal, gamma signal or beta signal; and (b) a pulse of the stimulation (i) starts when phase of the endogenous signal is less than or equal to zero degrees, and (ii) stops when the endogenous signal has a phase that is greater than or equal to zero degrees, zero degrees phase being phase at which the endogenous signal peaks during a period of the endogenous signal. In some cases: (a) the endogenous signal is periodic and is a delta signal, gamma signal or beta signal; and (b) a pulse of the stimulation (i) starts when phase of the endogenous signal is less than or equal to 180 degrees, and (ii) stops when the endogenous signal has a phase that is greater than or equal to 180 degrees, zero degrees phase being phase at which the endogenous signal peaks during a period of the endogenous signal. In some cases: (a) the endogenous signal is periodic and is a theta signal; and (b) a pulse of the stimulation (i) starts when phase of the endogenous signal is less than or equal to 90 degrees, and (ii) stops when the endogenous signal has a phase that is greater than or equal to 90 degrees, zero degrees phase being phase at which the endogenous signal peaks during a period of the endogenous signal. In some cases: (a) the endogenous signal is periodic and is an alpha signal; and (b) a pulse of the stimulation (i) starts when phase of the endogenous signal is less than or equal to 90 degrees, and (ii) stops when the endogenous signal has a phase that is greater than or equal to 90 degrees, zero degrees phase being phase at which the endogenous signal peaks during a period of the endogenous signal. In some cases: (a) the endogenous signal is periodic and is a delta signal, gamma signal or beta signal; and (b) a pulse of the stimulation (i) starts when phase of the endogenous signal is less than or equal to 90 degrees, and (ii) stops when the endogenous signal has a phase that is greater than or equal to 90 degrees, zero degrees phase being phase at which the endogenous signal peaks during a period of the endogenous signal. In some cases: (a) the endogenous signal is periodic and is a theta signal; and (b) a pulse of the stimulation (i) starts when phase of the endogenous signal is less than or equal to −10 degrees, and (ii) stops when the endogenous signal has a phase that is greater than or equal to zero degrees, zero degrees phase being phase at which the endogenous signal peaks during a period of the endogenous signal. In some cases: (a) the endogenous signal is periodic and is a theta signal; and (b) a pulse of the stimulation (i) starts when phase of the endogenous signal is less than or equal to 170 degrees, and (ii) stops when the endogenous signal has a phase that is greater than or equal to 180 degrees, zero degrees phase being phase at which the endogenous signal peaks during a period of the endogenous signal. In some cases: (a) the endogenous signal is periodic and is an alpha signal; and (b) a pulse of the stimulation (i) starts when phase of the endogenous signal is less than or equal to −10 degrees, and (ii) stops when the endogenous signal has a phase that is greater than or equal to zero degrees, zero degrees phase being phase at which the endogenous signal peaks during a period of the endogenous signal. In some cases: (a) the endogenous signal is periodic and is an alpha signal; and (b) a pulse of the stimulation (i) starts when phase of the endogenous signal is less than or equal to 170 degrees, and (ii) stops when the endogenous signal has a phase that is greater than or equal to 180 degrees, zero degrees phase being phase at which the endogenous signal peaks during a period of the endogenous signal. In some cases: (a) the endogenous signal is periodic and is a delta signal, gamma signal or beta signal; and (b) a pulse of the stimulation (i) starts when phase of the endogenous signal is less than or equal to −10 degrees, and (ii) stops when the endogenous signal has a phase that is greater than or equal to zero degrees, zero degrees phase being phase at which the endogenous signal peaks during a period of the endogenous signal. In some cases: (a) the endogenous signal is periodic and is a delta signal, gamma signal or beta signal; and (b) a pulse of the stimulation (i) starts when phase of the endogenous signal is less than or equal to 170 degrees, and (ii) stops when the endogenous signal has a phase that is greater than or equal to 180 degrees, zero degrees phase being phase at which the endogenous signal peaks during a period of the endogenous signal. In some cases: (a) the endogenous signal is periodic and is a theta signal; and (b) pulses of the stimulation (i) start, on average, when phase of the endogenous signal is less than or equal to zero degrees, and (ii) stop, on average, when the endogenous signal has a phase that is greater than or equal to zero degrees, zero degrees phase being phase at which the endogenous signal peaks during a period of the endogenous signal. In some cases: (a) the endogenous signal is periodic and is a theta signal; and (b) pulses of the stimulation (i) start, on average, when phase of the endogenous signal is less than or equal to 180 degrees, and (ii) stop, on average, when the endogenous signal has a phase that is greater than or equal to 180 degrees, zero degrees phase being phase at which the endogenous signal peaks during a period of the endogenous signal. In some cases: (a) the endogenous signal is periodic and is an alpha signal; and (b) pulses of the stimulation (i) start, on average, when phase of the endogenous signal is less than or equal to zero degrees, and (ii) stop, on average, when the endogenous signal has a phase that is greater than or equal to zero degrees, zero degrees phase being phase at which the endogenous signal peaks during a period of the endogenous signal. In some cases: (a) the endogenous signal is periodic and is an alpha signal; and (b) pulses of the stimulation (i) start, on average, when phase of the endogenous signal is less than or equal to 180 degrees, and (ii) stop, on average, when the endogenous signal has a phase that is greater than or equal to 180 degrees, zero degrees phase being phase at which the endogenous signal peaks during a period of the endogenous signal. In some cases: (a) the endogenous signal is periodic and is a delta signal, gamma signal or beta signal; and (b) pulses of the stimulation (i) start, on average, when phase of the endogenous signal is less than or equal to zero degrees, and (ii) stop, on average, when the endogenous signal has a phase that is greater than or equal to zero degrees, zero degrees phase being phase at which the endogenous signal peaks during a period of the endogenous signal. In some cases: (a) the endogenous signal is periodic and is a delta signal, gamma signal or beta signal; and (b) pulses of the stimulation (i) start, on average, when phase of the endogenous signal is less than or equal to 180 degrees, and (ii) stop, on average, when the endogenous signal has a phase that is greater than or equal to 180 degrees, zero degrees phase being phase at which the endogenous signal peaks during a period of the endogenous signal. In some cases: (a) the endogenous signal is periodic and is a theta signal; and (b) pulses of the stimulation (i) start, on average, when phase of the endogenous signal is less than or equal to 90 degrees, and (ii) stop, on average, when the endogenous signal has a phase that is greater than or equal to 90 degrees, zero degrees phase being phase at which the endogenous signal peaks during a period of the endogenous signal. In some cases: (a) the endogenous signal is periodic and is an alpha signal; and (b) pulses of the stimulation (i) start, on average, when phase of the endogenous signal is less than or equal to 90 degrees, and (ii) stop, on average, when the endogenous signal has a phase that is greater than or equal to 90 degrees, zero degrees phase being phase at which the endogenous signal peaks during a period of the endogenous signal. In some cases: (a) the endogenous signal is periodic and is a delta signal, gamma signal or beta signal; and (b) pulses of the stimulation (i) start, on average, when phase of the endogenous signal is less than or equal to 90 degrees, and (ii) stop, on average, when the endogenous signal has a phase that is greater than or equal to 90 degrees, zero degrees phase being phase at which the endogenous signal peaks during a period of the endogenous signal. In some cases: (a) the endogenous signal is periodic and is a theta signal; and (b) pulses of the stimulation (i) start, on average, when phase of the endogenous signal is less than or equal to −10 degrees, and (ii) stop, on average, when the endogenous signal has a phase that is greater than or equal to zero degrees, zero degrees phase being phase at which the endogenous signal peaks during a period of the endogenous signal. In some cases: (a) the endogenous signal is periodic and is a theta signal; and (b) pulses of the stimulation (i) start, on average, when phase of the endogenous signal is less than or equal to 170 degrees, and (ii) stop, on average, when the endogenous signal has a phase that is greater than or equal to 180 degrees, zero degrees phase being phase at which the endogenous signal peaks during a period of the endogenous signal. In some cases: (a) the endogenous signal is periodic and is an alpha signal; and (b) pulses of the stimulation (i) start, on average, when phase of the endogenous signal is less than or equal to −10 degrees, and (ii) stop, on average, when the endogenous signal has a phase that is greater than or equal to zero degrees, zero degrees phase being phase at which the endogenous signal peaks during a period of the endogenous signal. In some cases: (a) the endogenous signal is periodic and is an alpha signal; and (b) pulses of the stimulation (i) start, on average, when phase of the endogenous signal is less than or equal to 170 degrees, and (ii) stop, on average, when the endogenous signal has a phase that is greater than or equal to 180 degrees, zero degrees phase being phase at which the endogenous signal peaks during a period of the endogenous signal. In some cases: (a) the endogenous signal is periodic and is a delta signal, gamma signal or beta signal; and (b) pulses of the stimulation (i) start, on average, when phase of the endogenous signal is less than or equal to −10 degrees, and (ii) stop, on average, when the endogenous signal has a phase that is greater than or equal to zero degrees, zero degrees phase being phase at which the endogenous signal peaks during a period of the endogenous signal. In some cases: (a) the endogenous signal is periodic and is a delta signal, gamma signal or beta signal; and (b) pulses of the stimulation (i) start, on average, when phase of the endogenous signal is less than or equal to 170 degrees, and (ii) stop, on average, when the endogenous signal has a phase that is greater than or equal to 180 degrees, zero degrees phase being phase at which the endogenous signal peaks during a period of the endogenous signal. In some cases: (a) the stimulation comprises stimulation pulses; and (b) the stimulation pulses start at points of the endogenous signal that differ in phase from peaks of the endogenous signal by no more than 30 degrees. In some cases: (a) the stimulation comprises stimulation pulses; and (b) the stimulation pulses start at points of the endogenous signal that, on average, differ in phase from peaks of the endogenous signal by no more than 30 degrees. In some cases: (a) the stimulation comprises stimulation pulses; and (b) the stimulation pulses start at points of the endogenous signal that differ in phase from peaks of the endogenous signal by no more than 60 degrees. In some cases: (a) the stimulation comprises stimulation pulses; and (b) the stimulation pulses start at points of the endogenous signal that, on average, differ in phase from peaks of the endogenous signal by no more than 60 degrees. In some cases, throughout the transition, the user is sitting or is lying down. In some cases, the stimulation causes the user to perceive phosphenes. In some cases, the stimulation: (a) is electrical; and (b) causes the user to perceive phosphenes. In some cases: (a) the stimulation causes the use to experience a sensation; and (b) the sensation comprises phosphenes. In some cases: (a) the stimulation is electrical and causes the use to experience a sensation; and (b) the sensation comprises phosphenes. In some cases: (a) the stimulation comprises sound and causes the use to experience a sensation; and (b) the sensation comprises binaural beats. In some cases, the stimulation comprises light and causes the user to experience a visual sensation. In some cases, the stimulation comprises sound and causes the user to experience an audible sensation. Each of the cases described above in this paragraph is an example of the method described in the first sentence of this paragraph, and may be combined with one or more other embodiments of this invention.

In some implementations, this invention is a method comprising: (a) taking electroencephalography measurements of an endogenous electrical signal that originates in a brain of a user; (b) calculating a set of one or more estimates of (i) instantaneous phase of the endogenous signal and (ii) instantaneous amplitude of the endogenous signal; (c) producing stimulation in such a way that the stimulation causes delta/total spectrum ratio of the endogenous signal to increase more rapidly than would occur in the absence of the stimulation; and (d) controlling, based on the set of one or more estimates of instantaneous phase and instantaneous amplitude, timing of one or more changes in the stimulation. In some cases, each estimate in the set of one or more estimates of instantaneous phase and instantaneous amplitude is calculated based on a specific sample in a specific sample window of the measurements in such a way that: (a) the specific sample window is different than that for any other estimate in the set; and (b) the specific sample is more recent than any other sample in the specific sample window. In some cases, the stimulation causes the user to perceive binaural beats. In some cases, for each specific estimate in the set of estimates of instantaneous phase and instantaneous amplitude: (a) the calculating of the specific estimate is based on a specific sample window of the measurements that is different than that for each other estimate in the set; (b) the calculating of the specific estimate is not based on any sample window of the measurements other than the specific sample window; and (c) the calculating includes performing an inverse discrete Fourier transform that reconstructs only a single sample, which single sample is a specific sample that is in the specific sample window and that is more recent than other sample in the specific sample window. In some cases, for each specific estimate in the set of estimates of instantaneous phase and instantaneous amplitude, the calculating includes: (a) reconstructing, by an inverse discrete Fourier transform, a single sample of the measurements; and (b) computing the specific estimate based on the single sample and not based on any other sample. In some cases, for each specific estimate in the set of one or more estimates of instantaneous phase and instantaneous amplitude, the method further includes: (a) padding and filtering a specific sample window for the specific estimate to create a padded and filtered sample window, in such a way that a difference in value between data points at each end of the padded and filtered sample window is less than a difference in value between data points at each end of the sample window before padding and filtering; and (b) performing a discrete Fourier transform and Hilbert transform to calculate an analytic representation of the padded and filtered sample window. In some cases, for each specific estimate in the set of one or more estimates of instantaneous phase and instantaneous amplitude, the method further includes: (a) adding padding to a specific sample window for the specific estimate and then filtering the specific sample window to create a padded and filtered sample window; and (b) performing a discrete Fourier transform and Hilbert transform to calculate an analytic representation of the padded and filtered sample window. Each of the cases described above in this paragraph is an example of the method described in the first sentence of this paragraph, and may be combined with one or more other embodiments of this invention.

In some implementations, this invention is an apparatus comprising: (a) one or more sensors that are configured to take electroencephalography measurements of an endogenous electrical signal that originates in a brain of a user; (b) one or more transducers that are configured to produce stimulation; and (c) one or more computers that are programmed (i) to calculate a set of one or more estimates of (A) instantaneous phase of the endogenous signal and (B) instantaneous amplitude of the endogenous signal, (ii) to control the one or more transducers in such a way that the stimulation causes the user to undergo, more quickly than the user would in the absence of the stimulation, a transition from wakefulness of the user to sleep onset of the user, which transition (A) starts when the user closes his or her eyes while awake, and (B) ends with the sleep onset, and (iii) to control, based on the set of one or more estimates of instantaneous phase and instantaneous amplitude, timing of one or more changes in the stimulation. In some cases, the one or more computers are programmed to calculate each estimate, in the set of one or more estimates of instantaneous phase and instantaneous amplitude, based on a specific sample in a specific sample window of the measurements in such a way that: (a) the specific sample window is different than that for any other estimate in the set; and (b) the specific sample is more recent than any other sample in the specific sample window. In some cases, the specific sample window comprises multiple samples of the measurements. In some cases, the stimulation comprises audio stimulation. In some cases, the stimulation comprises visual stimulation. In some cases, the one or more computers are configured to compute each estimate of instantaneous phase and instantaneous amplitude in less than ten milliseconds. In some cases, the apparatus is configured to output stimulation based at least in part on a particular measurement, less than ten milliseconds after taking the particular measurement. In some cases, the apparatus is configured to output the stimulation in such a way that the stimulation causes the user to perceive binaural beats. In some cases, the one or more computers are programmed to calculate each specific estimate, in the set of estimates of instantaneous phase and instantaneous amplitude, by a calculation that: (a) is based on a specific sample window of the measurements that is different than that for each other estimate in the set; (b) is not based on any sample window of the measurements other than the specific sample window; and (c) includes performing an inverse discrete Fourier transform that reconstructs only a single sample, which single sample is in the specific sample window and is more recent than other sample in the specific sample window. In some cases, the one or more computers are programmed to calculate each specific estimate, in the set of estimates of instantaneous phase and instantaneous amplitude, by a calculation that includes: (a) reconstructing, by an inverse discrete Fourier transform, a single sample of the measurements; and (b) computing the specific estimate based on the single sample and not based on any other sample. In some cases, the one or more computers are programmed to calculate each estimate of instantaneous phase and instantaneous amplitude by a calculation that includes applying a causal filter in a frequency domain. In some cases, the one or more computers are programmed to calculate each specific estimate, in the set of one or more estimates of instantaneous phase and instantaneous amplitude, by a calculation that includes: (a) padding and filtering a specific sample window for the specific estimate to create a padded and filtered sample window, in such a way that a difference in value between data points at each end of the padded and filtered sample window is less than a difference in value between data points at each end of the sample window before padding and filtering; and (b) performing a discrete Fourier transform and Hilbert transform to calculate an analytic representation of the padded and filtered sample window. In some cases, the one or more computers are programmed to calculate each specific estimate, in the set of one or more estimates of instantaneous phase and instantaneous amplitude, by a calculation that includes: (a) adding padding to a specific sample window for the specific estimate and then filtering the specific sample window to create a padded and filtered sample window; and (b) performing a discrete Fourier transform and Hilbert transform to calculate an analytic representation of the padded and filtered sample window. In some cases, the transition from wakefulness to sleep onset involves an increase in absolute theta band power of the endogenous signal. In some cases, the transition from wakefulness to sleep onset involves an increase in theta/alpha ratio of the endogenous signal. In some cases, the transition from wakefulness to sleep onset involves an increase in absolute theta band power of the endogenous signal and an increase in theta/alpha ratio of the endogenous signal. In some cases, the sleep onset comprises standard-scored sleep onset. In some cases, the sleep onset is the first 30-second epoch, after the start of the transition, in which theta/alpha ratio of the endogenous signal during the epoch is greater than or equal to one. In some cases, the apparatus is configured in such a way that: (a) the measurements are taken by frontal cortex electroencephalography; and (b) the sleep onset is the first 30-second epoch, after the start of the transition, in which theta/alpha ratio of the endogenous signal during the epoch is greater than or equal to one. In some cases, the sleep onset is the first 30-second epoch, after the start of the transition, in which: (a) average absolute theta power of the endogenous signal during the epoch is at least 50% greater than an initial absolute theta power; and (b) average theta/alpha ratio of the endogenous signal during the epoch is at least 50% greater than an initial theta/alpha ratio, where the initial absolute theta power and the initial theta/alpha ratio are absolute theta power of the endogenous signal and theta/alpha ratio of the endogenous signal, respectively, during an initial 30-second period that starts at the beginning of the transition. In some cases, the sleep onset is the first 30-second epoch of Stage N−1 sleep after the start of the transition. In some cases, the sleep onset is the first 30-second epoch of Stage N−2 sleep after the start of the transition. In some cases, the sleep onset occurs at the beginning of the first three consecutive 30-second epochs of non-rapid-eye-movement (NREM) sleep after the start of the transition. In some cases, the sleep onset occurs at the beginning of the first ten consecutive 30-second epochs of non-rapid-eye-movement (NREM) sleep after the start of the transition. In some cases, the apparatus is configured to output the stimulation in such a way that the stimulation is phase-locked with the endogenous signal. In some cases, the apparatus is configured to output the stimulation in such a way that the stimulation is phase-tracking with the endogenous signal. In some cases, the apparatus is configured to output the stimulation in such a way that the stimulation is phase-correlated with the endogenous signal. In some cases, the apparatus is configured to output the stimulation in such a way that the stimulation is phase-matched with the endogenous signal. In some cases, the apparatus is configured to output the stimulation in such a way that the stimulation is phase-related with the endogenous signal. In some cases, the apparatus is configured to output the stimulation in such a way that a feature of the stimulation is phase-instant-locked to a target phase of the endogenous signal at a specific time. In some cases, the apparatus is configured to output the stimulation in such a way that the stimulation is phase-difference-locked with the endogenous signal. In some cases, the apparatus is configured to output the stimulation in such a way that the stimulation is phase-coordinated with the endogenous signal. In some cases, the apparatus is configured to output the stimulation in such a way that time of peaks of the stimulation is positively correlated with time of peaks of the endogenous signal. In some cases, the apparatus is configured to output the stimulation in such a way that time of peaks of the stimulation is negatively correlated with time of peaks of the endogenous signal. In some cases, the apparatus is configured to output the stimulation in such a way that the stimulation produces sensation in the user, which sensation is phase-locked with the endogenous signal. In some cases, the apparatus is configured to output the stimulation in such a way that the stimulation produces sensation in the user, which sensation is phase-tracking with the endogenous signal. In some cases, the apparatus is configured to output the stimulation in such a way that the stimulation produces sensation in the user, which sensation is phase-correlated with the endogenous signal. In some cases, the apparatus is configured to output the stimulation in such a way that the stimulation produces a sensation in the user, which sensation is phase-matched with the endogenous signal. In some cases, the apparatus is configured to output the stimulation in such a way that the stimulation produces a sensation in the user, which sensation is phase-related with the endogenous signal. In some cases, the apparatus is configured to output the stimulation in such a way that the stimulation produces a sensation in the user, in such a way that a feature of the sensation is phase-instant-locked to a target phase of the endogenous signal at a specific time. In some cases, the apparatus is configured to output the stimulation in such a way that the stimulation produces a sensation in the user, which sensation is phase-difference-locked with the endogenous signal. In some cases, the apparatus is configured to output the stimulation in such a way that the stimulation produces a sensation in the user, which sensation is phase-coordinated with the endogenous signal. In some cases, the apparatus is configured to output the stimulation in such a way that: (a) the stimulation produces a sensation in the user; and (b) time of peaks of the sensation is positively correlated with time of peaks of the endogenous signal. In some cases, the apparatus is configured to output the stimulation in such a way that: (a) the stimulation produces a sensation in the user; and (b) time of peaks of the sensation is negatively correlated with time of peaks of the endogenous signal. In some cases, the apparatus is configured to output the stimulation in such a way that the stimulation causes one or more changes in behavior of the user, which changes are positively correlated with a process of falling asleep, and which behavior is a behavior other than neural activity. In some cases, the apparatus is configured to output the stimulation in such a way that the stimulation causes changes in one or more physiological states of the user, which changes are positively correlated with a process of falling asleep, and which physiological states comprise respiration, beating of the heart, movement of an eye, or movement of a limb or head of the user. In some cases, wherein the apparatus is configured to output the stimulation in such a way that the stimulation is anti-phasic to the endogenous signal. In some cases, the apparatus is configured to output the stimulation in such a way that: (a) the stimulation produces a sensation in the user; and (b) the stimulation is anti-phasic to the endogenous signal. In some cases, the apparatus is configured to output the stimulation in such a way that the stimulation is periodic. In some cases, the endogenous signal is periodic. In some cases: (a) the endogenous signal is periodic; and (b) the apparatus is configured to output the stimulation in such a way that the stimulation is periodic. In some cases, greatest power of the endogenous signal occurs in the theta band, during a least a portion of the transition. In some cases, greatest power of the endogenous signal occurs in the alpha band, during a least a portion of the transition. In some cases, the apparatus is configured to output the stimulation in such a way that amplitude of the stimulation is greater during refractory neural periods than during other periods. In some cases, the apparatus is configured to output the stimulation in such a way that amplitude of the stimulation is greater during excitable neural periods than during other periods. In some cases: (a) the endogenous signal is periodic and is a theta signal; and (b) the apparatus is configured to output the stimulation in such a way that a pulse of the stimulation (i) starts when phase of the endogenous signal is less than or equal to zero degrees, and (ii) stops when the endogenous signal has a phase that is greater than or equal to zero degrees, zero degrees phase being phase at which the endogenous signal peaks during a period of the endogenous signal. In some cases: (a) the endogenous signal is periodic and is a theta signal; and (b) the apparatus is configured to output the stimulation in such a way that a pulse of the stimulation (i) starts when phase of the endogenous signal is less than or equal to 180 degrees, and (ii) stops when the endogenous signal has a phase that is greater than or equal to 180 degrees, zero degrees phase being phase at which the endogenous signal peaks during a period of the endogenous signal. In some cases: (a) the endogenous signal is periodic and is an alpha signal; and (b) the apparatus is configured to output the stimulation in such a way that a pulse of the stimulation (i) starts when phase of the endogenous signal is less than or equal to zero degrees, and (ii) stops when the endogenous signal has a phase that is greater than or equal to zero degrees, zero degrees phase being phase at which the endogenous signal peaks during a period of the endogenous signal. In some cases: (a) the endogenous signal is periodic and is an alpha signal; and (b) the apparatus is configured to output the stimulation in such a way that a pulse of the stimulation (i) starts when phase of the endogenous signal is less than or equal to 180 degrees, and (ii) stops when the endogenous signal has a phase that is greater than or equal to 180 degrees, zero degrees phase being phase at which the endogenous signal peaks during a period of the endogenous signal. In some cases: (a) the endogenous signal is periodic and is a delta signal, gamma signal or beta signal; and (b) the apparatus is configured to output the stimulation in such a way that a pulse of the stimulation (i) starts when phase of the endogenous signal is less than or equal to zero degrees, and (ii) stops when the endogenous signal has a phase that is greater than or equal to zero degrees, zero degrees phase being phase at which the endogenous signal peaks during a period of the endogenous signal. In some cases: (a) the endogenous signal is periodic and is a delta signal, gamma signal or beta signal; and (b) the apparatus is configured to output the stimulation in such a way that a pulse of the stimulation (i) starts when phase of the endogenous signal is less than or equal to 180 degrees, and (ii) stops when the endogenous signal has a phase that is greater than or equal to 180 degrees, zero degrees phase being phase at which the endogenous signal peaks during a period of the endogenous signal. In some cases: (a) the endogenous signal is periodic and is a theta signal; and (b) the apparatus is configured to output the stimulation in such a way that a pulse of the stimulation (i) starts when phase of the endogenous signal is less than or equal to 90 degrees, and (ii) stops when the endogenous signal has a phase that is greater than or equal to 90 degrees, zero degrees phase being phase at which the endogenous signal peaks during a period of the endogenous signal. In some cases: (a) the endogenous signal is periodic and is an alpha signal; and (b) the apparatus is configured to output the stimulation in such a way that a pulse of the stimulation (i) starts when phase of the endogenous signal is less than or equal to 90 degrees, and (ii) stops when the endogenous signal has a phase that is greater than or equal to 90 degrees, zero degrees phase being phase at which the endogenous signal peaks during a period of the endogenous signal. In some cases: (a) the endogenous signal is periodic and is a delta signal, gamma signal or beta signal; and (b) the apparatus is configured to output the stimulation in such a way that a pulse of the stimulation (i) starts when phase of the endogenous signal is less than or equal to 90 degrees, and (ii) stops when the endogenous signal has a phase that is greater than or equal to 90 degrees, zero degrees phase being phase at which the endogenous signal peaks during a period of the endogenous signal. In some cases: (a) the endogenous signal is periodic and is a theta signal; and (b) the apparatus is configured to output the stimulation in such a way that a pulse of the stimulation (i) starts when phase of the endogenous signal is less than or equal to −10 degrees, and (ii) stops when the endogenous signal has a phase that is greater than or equal to zero degrees, zero degrees phase being phase at which the endogenous signal peaks during a period of the endogenous signal. In some cases: (a) the endogenous signal is periodic and is a theta signal; and (b) the apparatus is configured to output the stimulation in such a way that a pulse of the stimulation (i) starts when phase of the endogenous signal is less than or equal to 170 degrees, and (ii) stops when the endogenous signal has a phase that is greater than or equal to 180 degrees, zero degrees phase being phase at which the endogenous signal peaks during a period of the endogenous signal. In some cases: (a) the endogenous signal is periodic and is an alpha signal; and (b) the apparatus is configured to output the stimulation in such a way that a pulse of the stimulation (i) starts when phase of the endogenous signal is less than or equal to −10 degrees, and (ii) stops when the endogenous signal has a phase that is greater than or equal to zero degrees, zero degrees phase being phase at which the endogenous signal peaks during a period of the endogenous signal. In some cases: (a) the endogenous signal is periodic and is an alpha signal; and (b) the apparatus is configured to output the stimulation in such a way that a pulse of the stimulation (i) starts when phase of the endogenous signal is less than or equal to 170 degrees, and (ii) stops when the endogenous signal has a phase that is greater than or equal to 180 degrees, zero degrees phase being phase at which the endogenous signal peaks during a period of the endogenous signal. In some cases: (a) the endogenous signal is periodic and is a delta signal, gamma signal or beta signal; and (b) the apparatus is configured to output the stimulation in such a way that a pulse of the stimulation (i) starts when phase of the endogenous signal is less than or equal to −10 degrees, and (ii) stops when the endogenous signal has a phase that is greater than or equal to zero degrees, zero degrees phase being phase at which the endogenous signal peaks during a period of the endogenous signal. In some cases: (a) the endogenous signal is periodic and is a delta signal, gamma signal or beta signal; and (b) the apparatus is configured to output the stimulation in such a way that a pulse of the stimulation (i) starts when phase of the endogenous signal is less than or equal to 170 degrees, and (ii) stops when the endogenous signal has a phase that is greater than or equal to 180 degrees, zero degrees phase being phase at which the endogenous signal peaks during a period of the endogenous signal. In some cases: (a) the endogenous signal is periodic and is a theta signal; and (b) the apparatus is configured to output the stimulation in such a way that pulses of the stimulation (i) start, on average, when phase of the endogenous signal is less than or equal to zero degrees, and (ii) stop, on average, when the endogenous signal has a phase that is greater than or equal to zero degrees, zero degrees phase being phase at which the endogenous signal peaks during a period of the endogenous signal. In some cases: (a) the endogenous signal is periodic and is a theta signal; and (b) the apparatus is configured to output the stimulation in such a way that pulses of the stimulation (i) start, on average, when phase of the endogenous signal is less than or equal to 180 degrees, and (ii) stop, on average, when the endogenous signal has a phase that is greater than or equal to 180 degrees, zero degrees phase being phase at which the endogenous signal peaks during a period of the endogenous signal. In some cases: (a) the endogenous signal is periodic and is an alpha signal; and (b) the apparatus is configured to output the stimulation in such a way that pulses of the stimulation (i) start, on average, when phase of the endogenous signal is less than or equal to zero degrees, and (ii) stop, on average, when the endogenous signal has a phase that is greater than or equal to zero degrees, zero degrees phase being phase at which the endogenous signal peaks during a period of the endogenous signal. In some cases: (a) the endogenous signal is periodic and is an alpha signal; and (b) the apparatus is configured to output the stimulation in such a way that pulses of the stimulation (i) start, on average, when phase of the endogenous signal is less than or equal to 180 degrees, and (ii) stop, on average, when the endogenous signal has a phase that is greater than or equal to 180 degrees, zero degrees phase being phase at which the endogenous signal peaks during a period of the endogenous signal. In some cases: (a) the endogenous signal is periodic and is a delta signal, gamma signal or beta signal; and (b) the apparatus is configured to output the stimulation in such a way that pulses of the stimulation (i) start, on average, when phase of the endogenous signal is less than or equal to zero degrees, and (ii) stop, on average, when the endogenous signal has a phase that is greater than or equal to zero degrees, zero degrees phase being phase at which the endogenous signal peaks during a period of the endogenous signal. In some cases: (a) the endogenous signal is periodic and is a delta signal, gamma signal or beta signal; and (b) the apparatus is configured to output the stimulation in such a way that pulses of the stimulation (i) start, on average, when phase of the endogenous signal is less than or equal to 180 degrees, and (ii) stop, on average, when the endogenous signal has a phase that is greater than or equal to 180 degrees, zero degrees phase being phase at which the endogenous signal peaks during a period of the endogenous signal. In some cases: (a) the endogenous signal is periodic and is a theta signal; and (b) the apparatus is configured to output the stimulation in such a way that pulses of the stimulation (i) start, on average, when phase of the endogenous signal is less than or equal to 90 degrees, and (ii) stop, on average, when the endogenous signal has a phase that is greater than or equal to 90 degrees, zero degrees phase being phase at which the endogenous signal peaks during a period of the endogenous signal. In some cases: (a) the endogenous signal is periodic and is an alpha signal; and (b) the apparatus is configured to output the stimulation in such a way that pulses of the stimulation (i) start, on average, when phase of the endogenous signal is less than or equal to 90 degrees, and (ii) stop, on average, when the endogenous signal has a phase that is greater than or equal to 90 degrees, zero degrees phase being phase at which the endogenous signal peaks during a period of the endogenous signal. In some cases: (a) the endogenous signal is periodic and is a delta signal, gamma signal or beta signal; and (b) the apparatus is configured to output the stimulation in such a way that pulses of the stimulation (i) start, on average, when phase of the endogenous signal is less than or equal to 90 degrees, and (ii) stop, on average, when the endogenous signal has a phase that is greater than or equal to 90 degrees, zero degrees phase being phase at which the endogenous signal peaks during a period of the endogenous signal. In some cases: (a) the endogenous signal is periodic and is a theta signal; and (b) the apparatus is configured to output the stimulation in such a way that pulses of the stimulation (i) start, on average, when phase of the endogenous signal is less than or equal to −10 degrees, and (ii) stop, on average, when the endogenous signal has a phase that is greater than or equal to zero degrees, zero degrees phase being phase at which the endogenous signal peaks during a period of the endogenous signal. In some cases: (a) the endogenous signal is periodic and is a theta signal; and (b) the apparatus is configured to output the stimulation in such a way that pulses of the stimulation (i) start, on average, when phase of the endogenous signal is less than or equal to 170 degrees, and (ii) stop, on average, when the endogenous signal has a phase that is greater than or equal to 180 degrees, zero degrees phase being phase at which the endogenous signal peaks during a period of the endogenous signal. In some cases: (a) the endogenous signal is periodic and is an alpha signal; and (b) the apparatus is configured to output the stimulation in such a way that pulses of the stimulation (i) start, on average, when phase of the endogenous signal is less than or equal to −10 degrees, and (ii) stop, on average, when the endogenous signal has a phase that is greater than or equal to zero degrees, zero degrees phase being phase at which the endogenous signal peaks during a period of the endogenous signal. In some cases: (a) the endogenous signal is periodic and is an alpha signal; and (b) the apparatus is configured to output the stimulation in such a way that pulses of the stimulation (i) start, on average, when phase of the endogenous signal is less than or equal to 170 degrees, and (ii) stop, on average, when the endogenous signal has a phase that is greater than or equal to 180 degrees, zero degrees phase being phase at which the endogenous signal peaks during a period of the endogenous signal. In some cases: (a) the endogenous signal is periodic and is a delta signal, gamma signal or beta signal; and (b) the apparatus is configured to output the stimulation in such a way that pulses of the stimulation (i) start, on average, when phase of the endogenous signal is less than or equal to −10 degrees, and (ii) stop, on average, when the endogenous signal has a phase that is greater than or equal to zero degrees, zero degrees phase being phase at which the endogenous signal peaks during a period of the endogenous signal. In some cases: (a) the endogenous signal is periodic and is a delta signal, gamma signal or beta signal; and (b) the apparatus is configured to output the stimulation in such a way that pulses of the stimulation (i) start, on average, when phase of the endogenous signal is less than or equal to 170 degrees, and (ii) stop, on average, when the endogenous signal has a phase that is greater than or equal to 180 degrees, zero degrees phase being phase at which the endogenous signal peaks during a period of the endogenous signal. In some cases, the apparatus is configured to output the stimulation in such a way that: (a) the stimulation comprises stimulation pulses; and (b) the stimulation pulses start at points of the endogenous signal that differ in phase from peaks of the endogenous signal by no more than 30 degrees. In some cases, the apparatus is configured to output the stimulation in such a way that: (a) the stimulation comprises stimulation pulses; and (b) the stimulation pulses start at points of the endogenous signal that, on average, differ in phase from peaks of the endogenous signal by no more than 30 degrees. In some cases, the apparatus is configured to output the stimulation in such a way that: (a) the stimulation comprises stimulation pulses; and (b) the stimulation pulses start at points of the endogenous signal that differ in phase from peaks of the endogenous signal by no more than 60 degrees. In some cases, the apparatus is configured to output the stimulation in such a way that: (a) the stimulation comprises stimulation pulses; and (b) the stimulation pulses start at points of the endogenous signal that, on average, differ in phase from peaks of the endogenous signal by no more than 60 degrees. In some cases, throughout the transition, the user is sitting or is lying down. In some cases, the apparatus is configured to output the stimulation in such a way that the stimulation causes the user to perceive phosphenes. In some cases, the apparatus is configured to output the stimulation in such a way that the stimulation: (a) is electrical; and (b) causes the user to perceive phosphenes. In some cases, the apparatus is configured to output the stimulation in such a way that: (a) the stimulation causes the use to experience a sensation; and (b) the sensation comprises phosphenes. In some cases, the apparatus is configured to output the stimulation in such a way that: (a) the stimulation is electrical and causes the use to experience a sensation; and (b) the sensation comprises phosphenes. In some cases, the apparatus is configured to output the stimulation in such a way that: (a) the stimulation comprises sound and causes the use to experience a sensation; and (b) the sensation comprises binaural beats. In some cases, the apparatus is configured to output the stimulation in such a way that the stimulation comprises light and causes the user to experience a visual sensation. In some cases, the apparatus is configured to output the stimulation in such a way that the stimulation comprises sound and causes the user to experience an audible sensation. Each of the cases described above in this paragraph is an example of the apparatus described in the first sentence of this paragraph, and may be combined with one or more other embodiments of this invention.

In some implementations, this invention is an apparatus comprising: (a) one or more sensors that are configured to take electroencephalography measurements of an endogenous electrical signal that originates in a brain of a user; (b) one or more transducers that are configured to produce stimulation; and (c) one or more computers that are programmed (i) to calculate a set of one or more estimates of (A) instantaneous phase of the endogenous signal and (B) instantaneous amplitude of the endogenous signal, (ii) to control the one or more transducers in such a way that the stimulation causes delta/total spectrum ratio of the endogenous signal to increase more rapidly than would occur in the absence of the stimulation, and (iii) to control, based on the set of one or more estimates of instantaneous phase and instantaneous amplitude, timing of one or more changes in the stimulation. In some cases, the one or more computers are programmed in such a way that each estimate in the set of one or more estimates of instantaneous phase and instantaneous amplitude is calculated based on a specific sample in a specific sample window of the measurements in such a way that: (a) the specific sample window is different than that for any other estimate in the set; and (b) the specific sample is more recent than any other sample in the specific sample window. In some cases, the apparatus is configured to output the stimulation in such a way that the stimulation causes the user to perceive binaural beats. In some cases, the one or more computers are programmed to calculate each specific estimate, in the set of estimates of instantaneous phase and instantaneous amplitude, by a calculation that: (a) is based on a specific sample window of the measurements that is different than that for each other estimate in the set; (b) is not based on any sample window of the measurements other than the specific sample window; and (c) includes performing an inverse discrete Fourier transform that reconstructs only a single sample, which single sample is in the specific sample window and is more recent than other sample in the specific sample window. In some cases, the one or more computers are programmed to calculate each specific estimate, in the set of estimates of instantaneous phase and instantaneous amplitude, by a calculation that includes: (a) reconstructing, by an inverse discrete Fourier transform, a single sample of the measurements; and (b) computing the specific estimate based on the single sample and not based on any other sample. In some cases, the one or more computers are programmed to calculate each specific estimate, in the set of one or more estimates of instantaneous phase and instantaneous amplitude, by a calculation that includes: (a) padding and filtering a specific sample window for the specific estimate to create a padded and filtered sample window, in such a way that a difference in value between data points at each end of the padded and filtered sample window is less than a difference in value between data points at each end of the sample window before padding and filtering; and (b) performing a discrete Fourier transform and Hilbert transform to calculate an analytic representation of the padded and filtered sample window. In some cases, the one or more computers are programmed to calculate each specific estimate, in the set of one or more estimates of instantaneous phase and instantaneous amplitude, by a calculation that includes: (a) adding padding to a specific sample window for the specific estimate and then filtering the specific sample window to create a padded and filtered sample window; and (b) performing a discrete Fourier transform and Hilbert transform to calculate an analytic representation of the padded and filtered sample window. Each of the cases described above in this paragraph is an example of the apparatus described in the first sentence of this paragraph, and may be combined with one or more other embodiments of this invention.

In some implementations, this invention is a method comprising: (a) taking electroencephalography measurements of an endogenous electrical signal that originates in a brain of a user; (b) calculating a set of one or more estimates of (i) instantaneous phase of the endogenous signal and (ii) instantaneous amplitude of the endogenous signal; (c) producing stimulation in such a way that the stimulation causes the user to undergo, more quickly than the user would in the absence of the stimulation, a transition from wakefulness of the user to sleep onset of the user; and (d) controlling, based on the set of one or more estimates of instantaneous phase and instantaneous amplitude, timing of one or more changes in the stimulation.

In some implementations, this invention is a method comprising: (a) taking electroencephalography measurements of an endogenous electrical signal that originates in a brain of a user; (b) calculating a set of one or more estimates of (i) instantaneous phase of the endogenous signal and (ii)

instantaneous amplitude of the endogenous signal; (c) producing stimulation in such a way that the stimulation causes absolute theta power of the endogenous signal to increase more rapidly than would occur in the absence of the stimulation; and (d) controlling, based on the set of one or more estimates of instantaneous phase and instantaneous amplitude, timing of one or more changes in the stimulation.

In some implementations, this invention is a method comprising: (a) taking electroencephalography measurements of an endogenous electrical signal that originates in a brain of a user; (b) calculating a set of one or more estimates of (i) instantaneous phase of the endogenous signal and (ii) instantaneous amplitude of the endogenous signal; (c) producing stimulation in such a way that the stimulation causes theta/alpha ratio of the endogenous signal to increase more rapidly than would occur in the absence of the stimulation; and (d) controlling, based on the set of one or more estimates of instantaneous phase and instantaneous amplitude, timing of one or more changes in the stimulation.

In some implementations, this invention is a method comprising: (a) taking electroencephalography measurements of an endogenous electrical signal that originates in a brain of a user; (b) calculating a set of one or more estimates of (i) instantaneous phase of the endogenous signal and (ii) instantaneous amplitude of the endogenous signal; (c) producing stimulation in such a way that the stimulation causes number of sleep spindles in the endogenous signal to increase more rapidly than would occur in the absence of the stimulation; and (d) controlling, based on the set of one or more estimates of instantaneous phase and instantaneous amplitude, timing of one or more changes in the stimulation.

In some implementations, this invention is a method comprising: (a) taking electroencephalography measurements of an endogenous electrical signal that originates in a brain of a user; (b) calculating a set of one or more estimates of (i) instantaneous phase of the endogenous signal and (ii) instantaneous amplitude of the endogenous signal; (c) producing stimulation in such a way that the stimulation causes number of K-complexes in the endogenous signal to increase more rapidly than would occur in the absence of the stimulation; and (d) controlling, based on the set of one or more estimates of instantaneous phase and instantaneous amplitude, timing of one or more changes in the stimulation.

In some implementations, this invention is a method comprising: (a) taking electroencephalography measurements of an endogenous electrical signal that originates in a brain of a user; (b) calculating a set of one or more estimates of (i) instantaneous phase of the endogenous signal and (ii) instantaneous amplitude of the endogenous signal; (c) producing stimulation in such a way that the stimulation causes number of electroencephalography vertex waves in the endogenous signal to increase more rapidly than would occur in the absence of the stimulation; and (d) controlling, based on the set of one or more estimates of instantaneous phase and instantaneous amplitude, timing of one or more changes in the stimulation.

In some implementations, this invention is a method comprising: (a) taking electroencephalography measurements of an endogenous electrical signal that originates in a brain of a user; (b) calculating a set of one or more estimates of (i) instantaneous phase of the endogenous signal and (ii) instantaneous amplitude of the endogenous signal; (c) producing stimulation in such a way that the stimulation causes physiological changes in the user to occur more rapidly than would occur in the absence of the stimulation, which physiological changes (A) are positively correlated with falling asleep and (B) comprise changes in one or more of respiration, heart contractions, and movement of a limb or head of the user; and (d) controlling, based on the set of one or more estimates of instantaneous phase and instantaneous amplitude, timing of one or more changes in the stimulation.

In some implementations, this invention is a method comprising: (a) taking electroencephalography measurements of an endogenous electrical signal that originates in a brain of a user; (b) calculating a set of one or more estimates of (i) instantaneous phase of the endogenous signal and (ii) instantaneous amplitude of the endogenous signal; (c) producing stimulation in such a way that the stimulation causes behavioral changes in the user to occur more rapidly than would occur in the absence of the stimulation, which behavioral changes (A) are positively correlated with falling asleep and (B) comprise changes in a behavior other than neural activity; and (d) controlling, based on the set of one or more estimates of instantaneous phase and instantaneous amplitude, timing of one or more changes in the stimulation.

Each of the methods described in the preceding eight paragraphs may be combined with one or more other embodiments of this invention.

In some implementations, this invention is an apparatus comprising: (a) one or more sensors that are configured to take electroencephalography measurements of an endogenous electrical signal that originates in a brain of a user; (b) one or more transducers that are configured to produce stimulation; and (c) one or more computers that are programmed (i) to calculate a set of one or more estimates of (A) instantaneous phase of the endogenous signal and (B) instantaneous amplitude of the endogenous signal, and (ii) to control the one or more transducers in such a way that the stimulation causes the user to undergo, more quickly than the user would in the absence of the stimulation, a transition from wakefulness of the user to sleep onset of the user; and (iii) to control, based on the set of one or more estimates of instantaneous phase and instantaneous amplitude, timing of one or more changes in the stimulation.

In some implementations, this invention is an apparatus comprising: (a) one or more sensors that are configured to take electroencephalography measurements of an endogenous electrical signal that originates in a brain of a user; (b) one or more transducers that are configured to produce stimulation; and (c) one or more computers that are programmed (i) to calculate a set of one or more estimates of (A) instantaneous phase of the endogenous signal and (B) instantaneous amplitude of the endogenous signal, (ii) to control the one or more transducers in such a way that the stimulation causes absolute theta power of the endogenous signal to increase more rapidly than would occur in the absence of the stimulation, and (iii) to control, based on the set of one or more estimates of instantaneous phase and instantaneous amplitude, timing of one or more changes in the stimulation.

In some implementations, this invention is an apparatus comprising: (a) one or more sensors that are configured to take electroencephalography measurements of an endogenous electrical signal that originates in a brain of a user; (b) one or more transducers that are configured to produce stimulation; and (c) one or more computers that are programmed (i) to calculate a set of one or more estimates of (A) instantaneous phase of the endogenous signal and (B) instantaneous amplitude of the endogenous signal, (ii) to control the one or more transducers in such a way that the stimulation causes theta/alpha ratio of the endogenous signal to increase more rapidly than would occur in the absence of the stimulation, and (iii) to control, based on the set of one or more estimates of instantaneous phase and instantaneous amplitude, timing of one or more changes in the stimulation.

In some implementations, this invention is an apparatus comprising: (a) one or more sensors that are configured to take electroencephalography measurements of an endogenous electrical signal that originates in a brain of a user; (b) one or more transducers that are configured to produce stimulation; and (c) one or more computers that are programmed (i) to calculate a set of one or more estimates of (A) instantaneous phase of the endogenous signal and (B) instantaneous amplitude of the endogenous signal, (ii) to control the one or more transducers in such a way that the stimulation causes number of sleep spindles in the endogenous signal to increase more rapidly than would occur in the absence of the stimulation, and (iii) to control, based on the set of one or more estimates of instantaneous phase and instantaneous amplitude, timing of one or more changes in the stimulation.

In some implementations, this invention is an apparatus comprising: (a) one or more sensors that are configured to take electroencephalography measurements of an endogenous electrical signal that originates in a brain of a user; (b) one or more transducers that are configured to produce stimulation; and (c) one or more computers that are programmed (i) to calculate a set of one or more estimates of (A) instantaneous phase of the endogenous signal and (B) instantaneous amplitude of the endogenous signal, (ii) to control the one or more transducers in such a way that the stimulation causes number of K-complexes in the endogenous signal to increase more rapidly than would occur in the absence of the stimulation, and (iii) to control, based on the set of one or more estimates of instantaneous phase and instantaneous amplitude, timing of one or more changes in the stimulation.

In some implementations, this invention is an apparatus comprising: (a) one or more sensors that are configured to take electroencephalography measurements of an endogenous electrical signal that originates in a brain of a user; (b) one or more transducers that are configured to produce stimulation; and (c) one or more computers that are programmed (i) to calculate a set of one or more estimates of (A) instantaneous phase of the endogenous signal and (B) instantaneous amplitude of the endogenous signal, (ii) to control the one or more transducers in such a way that the stimulation causes number of electroencephalography vertex waves in the endogenous signal to increase more rapidly than would occur in the absence of the stimulation, and (iii) to control, based on the set of one or more estimates of instantaneous phase and instantaneous amplitude, timing of one or more changes in the stimulation.

In some implementations, this invention is an apparatus comprising: (a) one or more sensors that are configured to take electroencephalography measurements of an endogenous electrical signal that originates in a brain of a user; (b) one or more transducers that are configured to produce stimulation; and (c) one or more computers that are programmed (i) to calculate a set of one or more estimates of (A) instantaneous phase of the endogenous signal and (B) instantaneous amplitude of the endogenous signal, (ii) to control the one or more transducers in such a way that the stimulation causes physiological changes in the user to occur more rapidly than would occur in the absence of the stimulation, which physiological changes (A) are positively correlated with falling asleep and (B) comprise changes in one or more of respiration, heart contractions, and movement of a limb or head of the user, and (iii) to control, based on the set of one or more estimates of instantaneous phase and instantaneous amplitude, timing of one or more changes in the stimulation.

In some implementations, this invention is an apparatus comprising: (a) one or more sensors that are configured to take electroencephalography measurements of an endogenous electrical signal that originates in a brain of a user; (b) one or more transducers that are configured to produce stimulation; and (c) one or more computers that are programmed (i) to calculate a set of one or more estimates of (A) instantaneous phase of the endogenous signal and (B) instantaneous amplitude of the endogenous signal, (ii) to control the one or more transducers in such a way that the stimulation causes behavioral changes in the user to occur more rapidly than would occur in the absence of the stimulation, which behavioral changes (A) are positively correlated with falling asleep and (B) comprise changes in a behavior other than neural activity, and (iii) to control, based on the set of one or more estimates of instantaneous phase and instantaneous amplitude, timing of one or more changes in the stimulation.

Each of the apparatuses described in the preceding eight paragraphs may be combined with one or more other embodiments of this invention.

In some implementations, this invention is a method comprising: (a) performing a set of one or more iterations, in such a way that each specific iteration in the set includes (i) taking electroencephalography measurements of an endogenous electrical signal produced in a brain of a user, (ii) computing an estimate of instantaneous phase and instantaneous amplitude of a specific sample in a sample window of the measurements, which specific sample is a sample of the signal taken at a time that is more recent than that for any other sample in the window, and (ii) based on the estimate, computing timing of stimulation; and (b) producing the stimulation in such a way that (i) the stimulation is, or a sensation of the user caused by the stimulation is, phase-locked with the signal during a time interval, and (ii) the stimulation, during one or more of the iterations, causes the user to undergo standard-scored sleep onset more quickly than the user would in the absence of the stimulation. In some cases, the stimulation comprises audio stimulation. In some cases, the stimulation comprises visual stimulation. In some cases, the estimate in each iteration is computed in less than ten milliseconds. In some cases, time elapsed between taking a particular measurement and outputting stimulation based at least in part on the particular measurement is less than ten milliseconds. In some cases, the stimulation causes the user to perceive binaural beats. In some cases, the computing in each specific iteration includes performing an inverse discrete Fourier transform that reconstructs only a single sample in the sample window, which single sample is the specific sample taken at a time more recent than that for any other sample in the window of the specific iteration. In some cases, the computing in each iteration includes computing the instantaneous phase and instantaneous amplitude based on the single sample reconstructed by the inverse discrete Fourier transform. In some cases, the computing in each specific iteration includes applying a causal filter in a frequency domain. In some cases, the computing in each specific iteration includes (a) padding and filtering the sample window for the specific iteration to create a padded and filtered sample window, in such a way that a difference in value between data points at each end of the padded and filtered sample window is less than a difference in value between data points at each end of the sample window before padding and filtering; and (b)

performing a discrete Fourier transform and Hilbert transform to calculate an analytic representation of the padded and filtered sample window. In some cases, the computing in each specific iteration includes (a) adding padding to the sample window for the specific iteration and then filtering the sample window to create a padded and filtered sample window; and (b) performing a discrete Fourier transform and Hilbert transform to calculate an analytic representation of the padded and filtered sample window. Each of the cases described above in this paragraph is an example of the method described in the first sentence of this paragraph, and is also an example of an embodiment of this invention that may be combined with other embodiments of this invention.

In some implementations, this invention is an apparatus comprising: (a) a sensor; (b) a transducer; and (c) one or more computers that are programmed (i) to cause a set of one or more iterations to occur, in such a way that each specific iteration in the set includes (A) the sensor taking electroencephalography measurements of an endogenous electrical signal produced in a brain of a user, (B) the one or more computers (I) computing an estimate of instantaneous phase and instantaneous amplitude of a specific sample in a sample window of the measurements, which specific sample is a sample of the signal taken at a time that is more recent than that for any other sample in the window, and (II) based on the estimate, computing timing of stimulation; and (i) to cause the transducer to output the stimulation in such a way that (A) the stimulation is, or a sensation of the user caused by the stimulation is, phase-locked with the signal during a time interval, and (B) the stimulation, during one or more of the iterations, causes the user to undergo standard-scored sleep onset more quickly than the user would in the absence of the stimulation. In some cases, the transducer is configured to output audio stimulation. In some cases, the transducer is configured to output visual stimulation. In some cases, the computing in each specific iteration includes performing an inverse discrete Fourier transform that reconstructs only a single sample in the sample window, which single sample is the specific sample taken at a time more recent than that for any other sample in the window of the specific iteration. In some cases, 16. The apparatus of claim 15, wherein the computing in each iteration includes computing the instantaneous phase and instantaneous amplitude based on the single sample reconstructed by the inverse discrete Fourier transform. In some cases, the computing in each specific iteration includes applying a causal filter in a frequency domain. In some cases, the computing in each specific iteration includes (a) padding and filtering the sample window for the specific iteration to create a padded and filtered sample window, in such a way that a difference in value between data points at each end of the padded and filtered sample window is less than a difference in value between data points at each end of the sample window before padding and filtering; and (b) performing a discrete Fourier transform and Hilbert transform to calculate an analytic representation of the padded and filtered sample window. In some cases, the computing in each specific iteration includes (a) adding padding to the sample window for the specific iteration and then filtering the sample window to create a padded and filtered sample window; and (b) performing a discrete Fourier transform and Hilbert transform to calculate an analytic representation of the padded and filtered sample window. Each of the cases described above in this paragraph is an example of the apparatus described in the first sentence of this paragraph, and is also an example of an embodiment of this invention that may be combined with other embodiments of this invention.

Each description herein (or in the Provisional or '022 Application) of any method, apparatus or system of this invention describes a non-limiting example of this invention. This invention is not limited to those examples, and may be implemented in other ways.

Each description herein (or in the Provisional or '022 Application) of any prototype of this invention describes a non-limiting example of this invention. This invention is not limited to those examples, and may be implemented in other ways.

Each description herein (or in the Provisional or '022 Application) of any feature, implementation, embodiment, or case of this invention (or any use scenario for this invention) describes a non-limiting example of this invention. This invention is not limited to those examples, and may be implemented in other ways.

Each Figure herein (or in the Provisional or '022 Application) that illustrates any feature of this invention shows a non-limiting example of this invention. This invention is not limited to those examples, and may be implemented in other ways.

Each time that stimulation is described above in this document as "phase-locked" with a signal, the stimulation may be phase-locked with the signal during a time interval and for a target phase. Each time that stimulation is described above in this document as "phase-locked" with a signal, the stimulation may be phase-tracking with the signal during a time interval and for a target phase. Each time that stimulation is described above in this document as "phase-locked" with a signal, the stimulation may be phase-correlated with the signal during a time interval and for a target phase. Each time that stimulation is described above in this document as "phase-locked" with a signal, the stimulation may be phase-matched with the signal during a time interval and for a target phase. Each time that stimulation is described above in this document as "phase-locked" with a signal, the stimulation may be phase-related with the signal during a time interval and for a target phase. Each time that stimulation is described above in this document as "phase-locked" with a signal, a specific feature of the stimulation may be phase-instant-locked with the signal at a specific time. Each time that stimulation is described above in this document as "phase-locked" with a signal, the stimulation may be phase-coordinated with the signal during a time interval.

Each time that a sensation is described above in this document as "phase-locked" with a signal, the sensation may be phase-locked with the signal during a time interval and for a target phase. Each time that a sensation is described above in this document as "phase-locked" with a signal, the sensation may be phase-tracking with the signal during a time interval and for a target phase. Each time that a sensation is described above in this document as "phase-locked" with a signal, the sensation may be phase-correlated with the signal during a time interval and for a target phase. Each time that a sensation is described above in this document as "phase-locked" with a signal, the sensation may be phase-matched with the signal during a time interval and for a target phase. Each time that a sensation is described above in this document as "phase-locked" with a signal, the sensation may be phase-related with the signal during a time interval and for a target phase. Each time that a sensation is described above in this document as "phase-locked" with a signal, a specific feature of the sensation may be phase-instant-locked with the signal at a specific time.

For purposes of the preceding two paragraphs: (a) any specific phase may be targeted as the target phase; (b) the time interval may have any specific, finite, non-zero, positive length; and (c) the specific time may be any particular time.

The above description (including without limitation any attached drawings and figures) describes illustrative implementations of the invention. However, the invention may be implemented in other ways. The methods and apparatus which are described herein are merely illustrative applications of the principles of the invention. Other arrangements, methods, modifications, and substitutions by one of ordinary skill in the art are also within the scope of the present invention. Numerous modifications may be made by those skilled in the art without departing from the scope of the invention. Also, this invention includes without limitation each combination and permutation of one or more of the items (including hardware, hardware components, methods, processes, steps, software, algorithms, features, or technology) that are described herein.

What is claimed:

1. A method comprising:
   (a) taking electroencephalography measurements of an endogenous electrical signal that originates in a brain of a user;
   (b) calculating a set of one or more estimates of (i) instantaneous phase of the endogenous signal and (ii) instantaneous amplitude of the endogenous signal including, for each estimate of the set of one or more estimates:
      reconstructing, by an inverse discrete Fourier transform, a single sample of the electroencephalography measurements; and
      computing that estimate based on the single sample and not based on any other sample;
   (c) producing stimulation in such a way that the stimulation causes the user to undergo, more quickly than the user would in the absence of the stimulation, a transition from wakefulness of the user to sleep onset of the user, which transition
      (i) starts when the user closes his or her eyes while awake, and
      (ii) ends with the sleep onset; and
   (d) controlling, based on the set of one or more estimates of instantaneous phase and instantaneous amplitude, timing of one or more changes in the stimulation.

2. The method of claim 1, wherein each estimate in the set of one or more estimates of instantaneous phase and instantaneous amplitude is calculated based on a specific sample in a specific sample window of the measurements in such a way that:
   (a) the specific sample window is different than that for any other estimate in the set; and
   (b) the specific sample is more recent than any other sample in the specific sample window.

3. The method of claim 1, wherein the stimulation comprises audio stimulation.

4. The method of claim 1, wherein the stimulation comprises visual stimulation.

5. The method of claim 1, wherein each estimate of instantaneous phase and instantaneous amplitude is computed in less than ten milliseconds.

6. The method of claim 1, wherein the stimulation causes the user to perceive binaural beats.

7. The method of claim 1, wherein, for each specific estimate in the set of estimates of instantaneous phase and instantaneous amplitude:
   (a) the calculating of the specific estimate is based on a specific sample window of the measurements that is different than that for each other estimate in the set;
   (b) the calculating of the specific estimate is not based on any sample window of the measurements other than the specific sample window; and
   (c) the calculating includes performing an inverse discrete Fourier transform that reconstructs only a single sample, which single sample is in the specific sample window and is more recent than any other sample in the specific sample window.

8. The method of claim 1, wherein the calculating of each estimate of instantaneous phase and instantaneous amplitude includes applying a causal filter in a frequency domain.

9. The method of claim 1, wherein, for each specific estimate in the set of one or more estimates of instantaneous phase and instantaneous amplitude, the method further includes:
   (a) padding and filtering a specific sample window for the specific estimate to create a padded and filtered sample window, in such a way that a difference in value between data points at each end of the padded and filtered sample window is less than a difference in value between data points at each end of the sample window before padding and filtering; and
   (b) calculating an analytic signal of the padded and filtered sample window.

10. The method of claim 1, wherein, for each specific estimate in the set of one or more estimates of instantaneous phase and instantaneous amplitude, the method further includes:
    (a) adding padding to a specific sample window for the specific estimate and then filtering the specific sample window to create a padded and filtered sample window; and
    (b) calculating an analytic signal of the padded and filtered sample window.

11. The method of claim 1, wherein the stimulation causes one or more of the following:
    a number of K-complexes in the endogenous signal to increase more rapidly than would occur in the absence of the stimulation;
    a number of electroencephalography vertex waves in the endogenous signal to increase more rapidly than would occur in the absence of the stimulation;
    a number of sleep spindles in the endogenous signal to increase more rapidly than would occur in the absence of the stimulation;
    a theta/alpha ratio of the endogenous signal to increase more rapidly than would occur in the absence of the stimulation; or
    an absolute theta power of the endogenous signal to increase more rapidly than would occur in the absence of the stimulation.

12. An apparatus comprising:
    (a) one or more sensors that are configured to take electroencephalography measurements of an endogenous electrical signal that originates in a brain of a user;
    (b) one or more transducers that are configured to produce stimulation; and
    (c) one or more computers that are programmed
       (i) to calculate a set of one or more estimates of (A) instantaneous phase of the endogenous signal and (B) instantaneous amplitude of the endogenous signal by:

reconstructing, by an inverse discrete Fourier transform, a single sample of the electroencephalography measurements; and computing the specific estimate based on the single sample and not based on any other sample, (ii) to control the one or more transducers in such a way that the stimulation causes the user to undergo, more quickly than the user would in the absence of the stimulation, a transition from wakefulness of the user to sleep onset of the user, which transition
(A) starts when the user closes his or her eyes while awake, and
(B) ends with the sleep onset, and (iii) to control, based on the set of one or more estimates of instantaneous phase and instantaneous amplitude, timing of one or more changes in the stimulation.

13. The apparatus of claim 12, wherein the one or more computers are programmed to calculate each estimate, in the set of one or more estimates of instantaneous phase and instantaneous amplitude, based on a specific sample in a specific sample window of the measurements in such a way that:
(a) the specific sample window is different than that for any other estimate in the set; and
(b) the specific sample is more recent than any other sample in the specific sample window.

14. The apparatus of claim 12, wherein the stimulation comprises audio stimulation.

15. The apparatus of claim 12, wherein the stimulation comprises visual stimulation.

16. The apparatus of claim 12, wherein the one or more computers are programmed to calculate each estimate of instantaneous phase and instantaneous amplitude by a calculation that includes applying a causal filter in a frequency domain.

17. The apparatus of claim 12, wherein the one or more computers are programmed to calculate each specific estimate, in the set of one or more estimates of instantaneous phase and instantaneous amplitude, by a calculation that includes:
(a) padding and filtering a specific sample window for the specific estimate to create a padded and filtered sample window, in such a way that a difference in value between data points at each end of the padded and filtered sample window is less than a difference in value between data points at each end of the sample window before padding and filtering; and
(b) calculating an analytic signal of the padded and filtered sample window.

18. The apparatus of claim 12, wherein the one or more computers are programmed to calculate each specific estimate, in the set of one or more estimates of instantaneous phase and instantaneous amplitude, by a calculation that includes:
(a) adding padding to a specific sample window for the specific estimate and then filtering the specific sample window to create a padded and filtered sample window; and
(b) calculating an analytic signal of the padded and filtered sample window.

19. An apparatus comprising:
(a) one or more sensors that are configured to take electroencephalography measurements of an endogenous electrical signal that originates in a brain of a user;
(b) one or more transducers that are configured to produce stimulation; and
(c) one or more computers that are programmed
(i) to calculate a set of one or more estimates of (A) instantaneous phase of the endogenous signal and (B) instantaneous amplitude of the endogenous signal by:
reconstructing, by an inverse discrete Fourier transform, a single sample of the electroencephalography measurements; and
computing the specific estimate based on the single sample,
(ii) to control the one or more transducers in such a way that the stimulation causes delta/total spectrum ratio of the endogenous signal to increase more rapidly than would occur in the absence of the stimulation, and
(iii) to control, based on the set of one or more estimates of instantaneous phase and instantaneous amplitude, timing of one or more changes in the stimulation.

20. The apparatus of claim 19, wherein the calculation includes computing the specific estimate based on the single sample and not based on any other sample.

* * * * *